US007524937B2

(12) United States Patent
Carter et al.

(10) Patent No.: US 7,524,937 B2
(45) Date of Patent: Apr. 28, 2009

(54) WSX RECEPTOR AGONIST ANTIBODIES

(75) Inventors: Paul J. Carter, San Francisco, CA (US); Nancy Y. Chiang, San Francisco, CA (US); Kyung Jin Kim, Los Altos, CA (US); William Matthews, Woodside, CA (US); Maria L. Rodrigues, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 11/439,325

(22) Filed: May 22, 2006

(65) Prior Publication Data

US 2006/0280737 A1  Dec. 14, 2006

Related U.S. Application Data

(63) Continuation of application No. 10/921,710, filed on Aug. 18, 2004, now abandoned, which is a continuation of application No. 08/779,457, filed on Jan. 7, 1997, now abandoned, and a continuation-in-part of application No. 08/667,197, filed on Jun. 20, 1996, now Pat. No. 7,074,397.

(60) Provisional application No. 60/064,855, filed on Jan. 8, 1996.

(51) Int. Cl.
    *C07K 16/00* (2006.01)
(52) U.S. Cl. .................................. 530/387.9; 530/388.1
(58) Field of Classification Search ........................ None
    See application file for complete search history.

(56) References Cited

U.S. PATENT DOCUMENTS

| | | | |
|---|---|---|---|
| 5,116,951 A | 5/1992 | Druez et al. |
| 5,264,416 A | 11/1993 | Park et al. |
| 5,349,053 A | 9/1994 | Landolfi |
| 5,378,808 A | 1/1995 | D'Andrea et al. |
| 5,453,491 A | 9/1995 | Takatsu et al. |
| 5,455,165 A | 10/1995 | Capon et al. |
| 5,521,283 A | 5/1996 | DiMarchi et al. |
| 5,525,705 A | 6/1996 | DiMarchi et al. |
| 5,532,336 A | 7/1996 | DiMarchi et al. |
| 5,543,320 A | 8/1996 | Park et al. |
| 5,552,522 A | 9/1996 | DiMarchi et al. |
| 5,552,523 A | 9/1996 | Basinski et al. |
| 5,552,524 A | 9/1996 | Basinski et al. |
| 5,554,727 A | 9/1996 | Basinski et al. |
| 5,559,208 A | 9/1996 | Basinski et al. |
| 5,563,243 A | 10/1996 | DiMarchi et al. |
| 5,563,244 A | 10/1996 | DiMarchi et al. |
| 5,563,245 A | 10/1996 | DiMarchi et al. |
| 5,567,678 A | 10/1996 | DiMarchi et al. |
| 5,567,803 A | 10/1996 | Basinski et al. |
| 5,569,743 A | 10/1996 | DiMarchi et al. |
| 5,569,744 A | 10/1996 | Basinski et al. |
| 5,571,513 A | 11/1996 | Burstein |
| 5,574,133 A | 11/1996 | DiMarchi et al. |
| 5,580,954 A | 12/1996 | DiMarchi et al. |
| 5,594,101 A | 1/1997 | Becker et al. |
| 5,594,104 A | 1/1997 | Basinski et al. |
| 5,599,905 A | 2/1997 | Mosley et al. |
| 5,605,886 A | 2/1997 | Basinski et al. |
| 5,614,379 A | 3/1997 | MacKellar |
| 5,635,177 A | 6/1997 | Bennett et al. |
| 5,635,388 A | 6/1997 | Bennett et al. |
| 5,639,605 A | 6/1997 | Kitamura et al. |
| 5,643,748 A | 7/1997 | Snodgrass et al. |
| 5,670,373 A | 9/1997 | Kishimoto et al. |
| 5,691,309 A | 11/1997 | Basinski et al. |
| 5,698,389 A | 12/1997 | de la Brousse et al. |
| 5,739,277 A | 4/1998 | Presta et al. |
| 5,763,211 A | 6/1998 | Snodgrass et al. |
| 5,827,734 A | 10/1998 | Weigle et al. |
| 5,856,098 A | 1/1999 | Snodgrass et al. |
| 5,858,967 A | 1/1999 | Weigle et al. |
| 5,869,610 A | 2/1999 | Snodgrass et al. |
| 5,882,860 A | 3/1999 | Snodgrass et al. |
| 5,912,123 A * | 6/1999 | Snodgrass et al. ............... 435/6 |
| 5,935,810 A | 8/1999 | Friedman et al. |
| 5,968,779 A | 10/1999 | Campfield et al. |
| 5,969,109 A | 10/1999 | Bona et al. |
| 5,972,621 A | 10/1999 | Tartaglia et al. |
| 5,980,893 A | 11/1999 | Avraham et al. |

(Continued)

FOREIGN PATENT DOCUMENTS

CA      2195955      8/1995

(Continued)

OTHER PUBLICATIONS

Van Regenmortel, A Companion to Methods of Enzymology, 1996, vol. 9:465-472, 1996, pages.*
Rudikoff et al., Proc Natl Acad Sci USA 1982 vol. 79 p. 1979.*
Knappik et al., Journal of Molecular Biology, 2000, vol. 296, p. 57-86.*
Ellis et al., J of Immunology, 1995, vol. 155, pp. 925-937.*
Owens et al J of Immunol. Method, vol. 168, pp. 149-165, 1994.*
Allen, T.M., *Trends Pharmaceutical Science*, 515(7):215-220 (1994).
"Antibodies. A Laboratory Manual," Harlow and Lane, Cold Spring Harbor Laboratory, p. 341 (1988).
Arai et al., *Bioassay* 5(4), pp. 166-171 (1986__.
Ashkenazi et al., "Protection Against Endotoxic Shock by a Tumor Necrosis Factor Receptor Immunoadhesin," *Proc. Natl. Acad. Sci.* 88:10535-10539 (Dec. 1991).

(Continued)

*Primary Examiner*—Michail A Belyavskyi
(74) *Attorney, Agent, or Firm*—Knobbe Martens Olson & Bear LLP

(57) ABSTRACT

Methods for identifying antibodies that decrease body weight, fat depot weight or food intake in an obese animal are provided, as well as antibodies. Preferred antibodies bind to a reactor having a WSX motif and the extracellular domain sequence within SEQ ID NO:2.

18 Claims, 83 Drawing Sheets

U.S. PATENT DOCUMENTS

| | | | |
|---|---|---|---|
| 6,001,968 | A | 12/1999 | Friedman et al. |
| 6,005,080 | A | 12/1999 | Snodgrass et al. |
| 6,025,325 | A | 2/2000 | Campfield et al. |
| 6,124,439 | A | 9/2000 | Friedman et al. |
| 6,355,237 | B1 | 3/2002 | Snodgrass et al. |
| 6,506,877 | B1 | 1/2003 | Tartaglia et al. |
| 6,620,413 | B1 | 9/2003 | DeSauvage et al. |
| 7,074,397 | B1 | 7/2006 | Matthews |
| 2002/0037553 | A1 | 3/2002 | Al-Barazanji et al. |
| 2003/0203837 | A1 | 10/2003 | Pelleymounter et al. |

FOREIGN PATENT DOCUMENTS

| | | |
|---|---|---|
| CA | 2224646 | 6/1996 |
| EP | 372752 | 6/1990 |
| EP | 0 396 387 A2 | 11/1990 |
| EP | 0 396 387 A3 | 11/1990 |
| EP | 0 741 187 A2 | 11/1996 |
| EP | 0 956 862 A1 | 11/1999 |
| JP | 07-313152 | 5/1995 |
| WO | WO 91/01004 | 1/1991 |
| WO | WO 91/01743 | 2/1991 |
| WO | WO 91/06646 | 5/1991 |
| WO | WO 94/04690 | 3/1994 |
| WO | WO 94/05332 | 3/1994 |
| WO | WO 9404689 | 3/1994 |
| WO | WO 94/11404 | 5/1994 |
| WO | WO 95/11987 | 5/1995 |
| WO | PCT/GB96/01388 | 6/1995 |
| WO | WO 95/14930 | 6/1995 |
| WO | WO 95/21864 | 8/1995 |
| WO | WO 96/03438 | 2/1996 |
| WO | WO 96/05309 | 2/1996 |
| WO | WO 96/08510 | 3/1996 |
| WO | WO 96/23517 | 8/1996 |
| WO | WO 96/24670 | 8/1996 |
| WO | WO 96/31526 | 10/1996 |
| WO | WO 96/34885 A2 | 11/1996 |
| WO | WO 96/34885 A3 | 11/1996 |
| WO | WO 96/35787 | 11/1996 |
| WO | WO 97/00319 | 1/1997 |
| WO | WO 97/12037 | 4/1997 |
| WO | WO 97/18833 | 5/1997 |
| WO | WO 97/19952 | 6/1997 |
| WO | WO 97/25424 | 7/1997 |
| WO | WO 97/26272 | 7/1997 |
| WO | WO 97/26335 | 7/1997 |
| WO | WO 97/26370 | 7/1997 |
| WO | WO 97/26523 | 7/1997 |
| WO | WO 97/27286 | 7/1997 |
| WO | WO 97/41217 | 11/1997 |
| WO | WO 97/41263 | 11/1997 |
| WO | WO 97/48419 | 12/1997 |
| WO | WO 97/48806 | 12/1997 |
| WO | WO 98/18486 | 5/1998 |
| WO | WO 98/28427 | 7/1998 |

OTHER PUBLICATIONS

Ashkenazi and Chamow, "Immunoadhesins: An Alternative to Human Monoclonal Antibodies. Methods: A Companion to Methods in Enzymology," 8:104-115 (1995).

Barinaga, Marcia, "'Obese' protein slims mice," *Science* 269:475-476 (1995).

Barinaga, M., "Obesity: Leptin Receptor Weighs In," *Science* 271:29(Jan. 5, 1996).

Baumann et al., "Multiple regions within the cytoplasmic domains of the leukemia inhibitory factor receptor and gp 130 cooperate in signal transduction in hepatic and neuronal cells," *Molecular & Cellular Biology*, 14(1):138-146 (1994).

Beck et al., "Generation of soluble interleukin-1 receptor from an immunoadhesive by specific cleavage," *Molecular Immunology* 31(17):1335-1344 (1994).

Bell-Anderson et al., "Leptin as a Potential Treatment for Obesity." *Treat Endocrinol.* 3(1) 11-18 (2003).

Bennett et al., "A role for leptin and its cognate receptor in hematopoiesis," *Current Biology*, vol. 6, No. 9, pp. 1170-1180 (1996).

Bennett et al., "Extracellular Domain-lgG Fusion Proteins for Three Human Natriuretic Peptide Receptors. Hormone Pharmacology and Application to Solid Phase Screening of Synthetic Peptide Antisera," *The Journal of Biological Chemistry* 26 (34):23060-23067 (Dec. 5, 1991).

Bruno et al.,"Effect of Recombinant and Purified Hematopoietic Growth Factors on Human Megakaryocyte Colony Formation," *Exp Dematol* 16, pp. 371-377 (1988).

Calandra et al., "The role of leptin in the etiopathogenesis of anorexia nervosa and bulimia," *Eat Weight Disorder*, 8(2): 130-7 (Jun. 2003) (abstract).

Campfield et al., "Recombinant mouse ob protein: evidence for a peripheral signal linking adiposity and central neural networks," *Science* 269:546-549 (1995).

Campfield et al., "Strategies and Potential Molecular Targets for Obesity Treatment", *Science*, 280:1383-1387 (May 1998).

Carter et al., Mutagenesis. A Practical Approach. Mcpherson, ed., Oxford, UK:IRL Press vol. Ch. 1:1-25 (1991).

Carter et al., "Engineering Subtilisin BPN' for Site-Specific Proteolysis," *Proteins: Struct. Funct. Genet.* 6:240-248 (1989).

Carter et al., "Humanization of an anti-p1185.sup.HER2 antibody for human cancer therapy," *Proc. Natl. Acad. Sci.* 89:4285-4289 (1992).

Chen et al., "Evidence That the Diabetes Gene Encodes the Leptin Receptor: Identification of a Mutation in the Leptin Receptor Gene in db/db Mice," *Cell*, 84:491-495 (Feb. 1996).

Cioffi et al., "Novel B219/OB receptor isoforms: possible role of leptin in hematopoiesis and reproduction," *Nature* 2(5):585-589 (1996).

Colditz, G.A., "Economic costs of obesity," *Am. J. Clin. Nutr.*, 55:503S-507S (1992).

Coleman, et al., "Obese and Diabetes: Two Mutant Genes Causing Diabetes-Obesity Syndromes in Mice," *Diabetologia*, 14:141-148 (1978).

Coleman, D.L., "Effects of parabiosis of obese with diabetes and normal mice," *Diabetol* 9:294-298 (1973).

Coleman and Hummel, "Effects of parabiosis of normal with genetically diabetic mice," *Am. J. Physiol.* 217:1298-1304 (1969).

Considine et al., "Serum immunoreactive-leptin concentrations in normal-weight and obese humans," *The New England Journal of Medicine*, pp. 292-295 (Feb. 1, 1996).

Cosman et al., *TIBS* 15, pp. 265-270 (Jul. 1990).

D'Andrea, A.D., "Cytokine receptors in congenital hematopoietic disease," *New England J. of Medicine* 330(12):839-846 (1994).

Dexter et al., "Growth and Differentiation in the Hemopoietic System," *Ann. Rev. Cell Biol.* 3:423-441 (1987).

Eisenberg, R., "Structure and Function in Gene Patenting," *Nature Genetics* 15:125-129 (1997).

Francis, G.E., *Focus on Growth Factors*, vol. 3, pp. 4-10 (1997).

Friedman et al., "Molecular mapping of the mouse ob mutation" *Genomics* 11:1054-1062 (1991).

Fukunaga et al., "Functional domains of the granulocyte colony-stimulating factor receptor," *EMBO Journal* 10(10):2855-2865 (1991).

Gainsford et al., "Leptin can induce proliferation, differentiation, and functional activation of hemopoietic cells," *PNAS* vol. 93, pp. 14564-14568 (1996).

Gale et al., "Energy Homeostasis, Obesity and Eating Disorders: Recent Advances in Endocrinology," *J Nutr.* 134:295-298 (2004).

Ganong, "Endocrine Functions of the Pancreas and the Regulation of Carbohydrate Metabolism," *Review of Medical Physiology*, 299-300 (1989).

Genbank, "Release 100" Homosapiens cDNA clone 84708 5' (Mar. 2, 1995).

Griffiths et al., "Isolation of High Affinity Human Antibodies Directly from Large Synthetic Repertoires," *EMBO Journal* 13:3245-3260 (1994).

Grupe et al., "Transgenic Knockouts Reveal a Critical Requirement for Pancreatic Beta Cell Glucokinase in Maintaining Glucose Homeostasis," *Cell* 83:69-78 (1995).

Halaas et al., "Weight-reducing effects of the plasma protein encoded by the obese gene," *Science* 269:543-546 (1995).

Hardy et al., "Resolution and characterization of pro-B and pre-pro-B cell stages in normal mouse bone marrow," *Journal of Experimental Medicine* 173:1213-1225 (1991).

Harlow et al., "Antibodies: A Laboratory Manual," Cold Spring Harbor (1988).

Herpertz et al., Plasma concentrations of leptons in a bulimic patient. *Int J Eat Disord.* 23 (4): 459-463 (May 1998).

Hillier et al. "WashU-Merck EST Project," GenBank (1995).

Hirsch, J., "The search for new ways to treat obesity," *PNAS*, 99(14): 9096-9097 (Jul. 9, 2002).

Hollenbaugh et al., *Current Protocols in Immunology*, vol. 2, pp. 10.19.1-10.19.11.

Holmes et al., "Structure and Functional Expression of a Human Interleukin-8 Receptor," *Science* 253(5125):1278-1280 (Sep. 13, 1991).

Humphries et al., "Self-Renewal of Hemopoietic Stem Cells During Mixed Colony Formation in Vitro," *Proc. Natl. Acad. Sci.* 78;3629-3633 (1981).

Ishizaka et al., "Preferential Differentiation of Inflammatory Cells by Recombinant Human Interleukins," *Int. Arch Allergy Appll Immunol* vol. 88, pp. 46-49 (1989).

Kim et al., "Detection of Human Leukemia Inhibitory Factor by Monoclonal Antibody Based ELISA," *Journal of Immunological Methods* 156:9-17 (1992).

Kishimoto, "Cytokine Signal Transcution," *Cell* 76:253-262 (Jan. 28, 1994).

Koike et al., "Synergism of BSF-2/interleukin 6 and interleukin 3 on development of multipotential hemopoietic progenitors in serum-free culture," *J. Exp Med* vol. 168, pp. 879-890 (Sep. 1988).

Kuczmarski et al., "Increasing prevalence of overweight among US adults," *J. Am. Med. Assoc.* 272(3):205-211 (1994).

Laskov et al., "Extinction of B-cell surface differentiation markers in hybrids between murine B-lymphoma and myeloma cells," *Cellular Immunology* 55(2):251-264 (1980).

Lee et al., "Abnormal splicing of the leptin in diabetic mice," *Nature* 379:632-635 (Feb. 1996).

Levin et al., "Decreased Food Intake Does Not Completely Account for Adiposity Reduction After ob Protein Infusion," *Proc. Natl. Acad. Sci.* 93:1726-1730 (1996).

Maffei et al., "Increased expression in adiopocytes of ob RNA in mice with lesions of the hypothalamus and with mutations at the db locus" *Proc. Natl. Acad. Sci.* 92:6957-6960 (1995).

Mark et al., "rse, a Novel Receptor-type Tyrosine Kinase with Homology to Ax1/Ufo, Is Expressed at High Levels in the Brain," *Journal of Biological Chemistry* 269(14) :10720-10728 (Apr. 8, 1994).

McNiece et al., "The Role of recombinant stem cell factor in early B cell development. Synergistic interaction with IL-7" *J. Immunol.* 146:3785-3790 (1991).

Migliaccio et al., "Effect of recombinant hematopoietic growth factors on proliferation of human marrow progenitor cells in serum-deprived liquid culture," *Blood* 72(4) p. 1387-1392 (1988).

Miyajima et al., "Receptors for Granulocyte-Macrophage Colony-Stimulating Factor, Interleukin-3, and Interleukin-5" *Blood* 82(7):1960-1974 (Oct. 1, 1993).

Murakami et al., "Critical cytoplasmic region of the interleukin 6 signal transducer gp130 is conserved in the cytokine receptor family," *Proc. Natl. Acad. Sci. USA* 88:11349-11353 (Dec. 1991).

Nicola, N., "Cytokine Pleiotrophy and Redundancy: A View From the Receptor," *Stem Cells* 12 (Suppl.1):3-14 (1994).

Pelleymounter et al., "Effects of the obese gene product on body weight regulation in ob/ob mice," *Science* 269:540-543 (1995).

Pi-Sunyer, F.X., "Medical Hazards of Obesity," *Anns. Int. Med.* 119:655-660 (1993).

"Polyethylene glycol and derivatives" Catalog Shearwater Polymers, Inc. Functionalized Biocompatible Polymers for Research (Jan. 1994).

Rink, Timothy J., "In search of a satiety factor," *Nature* 372:406-407.

Rudikoff et al., Single amino acid substitution altering antigen-binding specificity. *Proc Natl Acad Sci USA*, 79: 1979-1983, Mar. 1992.

Shin et al., "Hybrid Antibodies," *Intern Rev Immunol* 10:177-186 (1993).

Stewart et al., "Introduction of Type 1 Diabetes by Interferon-A in Transgenic Mice" *Science* 260:1942-1946 (1993).

Suva et al., "A parathyroid hormone-related protein implicated in malignant hypercalcemia: cloning and expression" *Science* 237(4817):893-896 (Aug. 1987).

Tartaglia et al., "Identification and expression cloning of a leptin receptor, ob-r" *Cell* 83:1263-1271 (1995).

Tavassoli, M., "Lodegment of haemopoietic cells in the course of haemopoiesis on cellulose ester membrane: an experimental model for haemopoietic cell trapping," *Brit. J. Haematology* 57:71-80 (1984).

Vaisse et al., "Leptin Activation of Stat3 in the Hypothalamus of Wild-Type and ob/ob Mice But Not db/db Mice" *Nature Genetics* 14:95-97 (1996).

Vaughan et al., "Human Antibodies With Sub-nanomolar Affinities Isolated From a Large Non-immunized Phage Display Library" *Nature Biotechnology* 14:309-314 (1996).

Wells, J., "Structural and functional basis for hormone binding and receptor oligomerization" *Cell Biology* 6:163-173 (1994).

Woods et al., "Signals That Regulate Food Intake and Energy Homeostasis," *Science* 280: 1378-1383 (May 29, 1998).

Zaghouani et al., *Intern. Rev. Immunol.* 10(2-3):265-278 (1993).

Zeigler et al., "Cellular and Molecular Characterization of the Role of the FLK-2/FLT-3 Receptor Tyrosine Kinase in Hematopoietic Stem Cells" *Blood* (8) :2422-2430 (1994).

Zhang et al., "Positional cloning of the mouse obese gene and its human homologue," *Nature* 372:425-431 (1994).

Batra et al., "Insertion of Constant Region Domains of Human IgG1 Into CD4-PE40 Increases Its Plasma Half-Life," *Mol. Immunol.* 30(4):379-385 (1993).

NCBI Entrez Protein Record for Accession No. AAD38158. Immunoglobulin G1 Fc fragment [Homo sapiens]. 2 pages. Jun. 10, 1998.

NCBI Entrez Protein Record for Accession No. AAG00910. Recombinant IgG2 heavy chain [Homo sapiens]. 2 pages. May 10, 2001.

NCBI Entrez Protein Record for Accession No. AAG00912. Recombinant IgG4 heavy chain [Homo sapiens]. 2 pages. May 11, 2001.

NCBI Entrez Protein Record for Accession No. AAW65947. Immunoglobulin gamma heavy chain 3 [Homo sapiens]. 2 pages. Jan. 31, 2005.

Hollenbaugh et al., *Current Protocols in Immunology*, vol. 2, pp. 10.19.1-10.19.11, 1992.

Batra et al., "Insertion of Constant Region Domains of Human $IgG_1$ Into CD4-PE40 Increases Its Plasma Half-Life," *Mol. Immunol.* 30(4):379-386 (1993).

Baumann et al., "The full-length leptin receptor has signaling capabilities of interleukin 6-type cytokine receptors," *Proc. Natl. Acad. Sci USA*, vol. 93, pp. 8374-8378 (Aug. 1996).

Bennett et al., "Extracellular Domain-IgG Fusion Proteins for Three Human Natriuretic Peptide Receptors," *Journal of Biological Chemistry*, 266(34):23060-23067 (1991).

Bickel et al., "Pharmacologic Effects in vivo in Brain by Vector-Mediated Peptide Drug Delivery," *Proc. Natl. Acad. Sci. USA* vol. 90, pp. 2618-2622 (1993).

Bjork, et al. "a Preliminary Gene Map for the Van der Woude Syndrome Critical Region Derived from 900 kb of Genomic Sequence at 1q32-q41," *Genome Research* 10:81-94 (2000).

Bork, P., "Powers and Pitfalls in Sequence Analysis: The 70% Hurdle," *Genome Research*, 10:398-400 (2000).

Bork and Bairoch, "Go hunting in sequence databases but watch out for the traps" *Trends in Genetics* 12(10):425 (Oct. 1996).

Brenner, "Errors in genome annotation," *Trends in Genetics* 15(4):132 (Apr. 1999).

Brewerton et al., "Reduced plasma leptin concentrations in bulimia nervosa," *Psychoneuroendocrinology*, 25:649-658 (2000).

Burguera et al., "The Long form of the Leptin Receptor (OB-Rb) is Widely Expressed in the Human Brain," *Neuroendocrinology*, vol. 61, pp. 187-195 (2000).

Chua et al., "Phenotypes of Mouse diabetes and Rat fatty Due to Mutations in the OB (Leptin) Receptor," *Science*, vol. 271, pp. 994-996 (Feb. 16, 1996).

Corwin et al., "Behavioral models of binge-type eating," Physiology and Behavior, 82:123-130 (2004).

Cosman, D., "The Hematopoietin Receptor Superfamily," *Cytokine* 5(2):95-106 (Mar. 1993).

De Vas et al., *JBC* 270(7) p. 15958 (1995).

Doerks et al., "Protein annotation: detective work for function prediction," *Trends in Genetics* 14(6):248 (Jun. 1998).

Farooqi et al., "Effects of Recombinant Leptin Therapy in a Child with Congenital Leptin Deficiency," *New England J Med*, 341(12):879-884 (Sep. 1999).

Grunfeld et al., "LPS, TNF and IL-1 Induce Expression of Leptin, the OB Gene Product, in Hamsters: A Role for Leptin in the Anorexia of Infection," *Eur Cytokine Netw.* vol. 7, p. 258 (1996).

Hanaki et al., "Leptin Before and After Insulin Therapy in Children with New-Onset Type 1 Diabetes," *J Clin Endo & Metab*, 84(5):1524-1526 (1999).

Hardy, J. and Selkoe, D.J., "The Amyloid Hypothesis of Alzheimer's Disease: Progress and Problems on the Road to Therapeutics," *Science* vol. 297 pp. 353-356 (Jul. 2002).

Heymsfield et al., "Recombinant Leptin for Weight Loss in Obese and Lean Adults," *JAMA*, 282(16):1568-1575 (Oct. 1999).

Hoggard et al., "Ontogeny of the expression of leptin and its receptor in the murine fetus and placenta," *British Journal of Nutrition*, vol. 83, pp. 317-326 (2000).

Hukshorn et al., "Weekly Subcutaneous Pegylated Recombinant Native Human Leptin (PEG-OB) Adminstration in Obese Men," *J Clin Endo & Metab*, 85(11):4003-4008 (2000).

Jimerson et al., "Decreased Serum Leptin in Bulimia Nervosa", *J Clin Endo & Metab* 85(12):4511-4514 (2000).

Kaczmarski et al., "The cytokine receptor superfamily," *Blood Reviews* 5(3):193-203 (1991).

Katre et al. "Chemical modification of recombinant interleukin 2 by polyethylene glycol increases its potency in the murine Meth A sarcoma model," *Proc Natl. Acad. Sci. USA*, vol. 84 p. 1487-1491 (1987).

Koike et al., "Synergism of BSF-2/interleukin 6 and interleukin 3 on development of multipotential hemopoietic progenitors in serum-free culture," *J. Exp Med* vol. 168, pp. 879-890 (Sep. 1988).

Luoh et al., "Cloning and characterization of human leptin receptor using a biologically active leptin immunoadhesin," *Journal of Molecular Endocrinology*, vol. 17, pp. 77-85 (1997).

Ma et al., "Obese Gene Expression in Acutely Regulated by Tumor Necrosis Factor During Sublethal Endotoxemia in Mice," *Surgical Forum, 82nd Annual Clinical Congress*, vol. XLVII, pp. 17-20 (1996).

Ngo et al. "The Protein Folding Problem and Tertiary Structure Prediction, Chapter 14: Computational Complexity Protein Structure Prediction, and the Levinthal Paradox," pp. 492-495.

Patrick, L., "Eating Disorders: A Review of the Literature with Emphasis on Medical Complications and Clinical Nutrition," *Alternative Medicine Review*, 7(3), pp. 183-202 (2000).

Reddy et al., "Immunohistochemical demonstration of leptin in pancreatic islets of non-obese diabetic and CD-1 mice: Co-localization in glucagon cells and its attenuation at the onset of diabetes," *J Mol Histology*, 35:511-519 (2004).

Rosenbaum et al., "Low dose leptin administration reverses effects of sustained weight-reduction on energy expenditure and circulating concentrations of thyroid hormones," *J Clin Endo & Metab*, 87(5):2391-2394 (May 2002).

Shields et al., "The Evolution of Haematopoietic Cytokine Receptor Complexes," *Cytokine* vol. 7, No. 7, pp. 679-680 (Oct. 1995).

Shin et al., "Transferrin-antibody fusion proteins are effective in brain targeting," *Proc. Natl Acad Sci USA*, 92:2820-2824.

Shisslak et al., "Body Weight and Bulimia as Discriminators of Psychological Characteristics Among Anorexic, Bulimic, and Obese Women," *Journal of Abnormal Psychology*, 99(4):380-384 (1990).

Skolnick and Fetrow, "From genes to structure: novel applications of computational approaches in the genomic era," *Trends in Biotech* (2000) 18(1): 34.

Smith and Zhang, "The challenges of genome sequence annotation or 'The devil is in the details'" *Nature Biotechnology* 15:1222 (Nov. 1997).

Taylor et al., "Impact of Binge Eating on Metabolic and Leptin Dynamics in Normal Young Women," *J Clin Endo & Metab*, 84(2):428-434 (1999).

Wells, "Additivity of Mutational Effects in Protein," *Biochemistry* 29(37):8509-8517 (Sep. 1990).

* cited by examiner

FIG. 1A

```
                                                                xmnI
                                                                tfII
                                                                hinfI
                                                    pleI        truI9
                                                    hinfI       mseI asp700       sau96I
                  truI9                                                           avaII
       bsrI       bsmAI mseI                                                      asuI
501 AAACTGAAAC ATACAGTGCT AGACTAAAAG GGCTAAAAGG TTATTCATCT GTTATGTGGA TCAGGAATTA TAACTATAAG
    TTTGACCTTG TATGTCACGA TCTGATTTTC CCGATTTTCC AATAAGTAGA CAATACACCT CAGTATATAA AGTCCTTAAT ATTGATATTC
126  N  W  N    I  Q  C  W    L  K  G    D  L  K    L  F  I  C    Y  V  E    S  L  F    F  K  N  L  F    R  N  Y   N  Y  X nlaIII
                    tfII                                                                          rcaI
                    hinfI    mnlI          bslI                                        muNI       bspHI
       eco57I       mboII    hphI          nlaIV
601 GTCCATCTTT TATATGTTCT GCCTGAAGTG TTAGAAGATT CACCTCTGGT TCCCCAAAAA GGCAGTTTTC AGATGGTTCA CTGCAATTGC AGTGTTCATG
    CAGGTAGAAA ATATACAAGA CGGACTTCAC AATCTTCTAA GTGGAGACCA AGGGGTTTTT CCGTCAAAAG TCTACCAAGT GACGTTAACG TCACAAGTAC
159  V  H  L   L  Y  V  L    P  E  V    L  E  D  S    P  L  V    P  Q  K    G  S  F    Q  M  V  H    C  N  C    S  V  H  E hphI
                                                                                                         maeIII
                                                                                                 bsrI    mnlI
701 AATGTTGTGA ATGTCTTGTG CCTGTGCCAA CAGCCAAACT CTCCTTAGTT GTTTGAAAAT CACATCTGGT GGAGTAATTT TCCAGTCACC
    TTACAACACT TACAGAACAC GGACACGGTT GTCGGTTTGA GAGGAATCAA CAAACTTTTA GTGTAGACCA CCTCATTAAA AGGTCAGTGG
193  C  C  E   C  L  V    P  V  P  T    A  K  L   N  D  T    L  L  M  C    L  K  I    T  S  G    G  V  I  F    Q  S  P bslI
             sau3AI
             mboI/ndeII[dam-]
             dpnI[dam+]                                                                       xcmI
             dpnII[dam-]                                                              truI9   sau96I
             alwI[dam-]                                                               mseI    avaII
       bstXI     hphI                                       ndeI                      ahaIII/draI asuI
801 TCTAAATGTCA GTTCAGCCCA TAAATATGGT GAAGCCTGAT CCACCATTAG GTTTGCATAT GGAAATCACA GATGATGGTA ATTTAAAGAT TTCTTGGTCC
    AGATTACAGT CAAGTCGGGT ATTTATACCA CTTCGGACTA GGTGGTAATC CAAACGTATA CCTTTAGTGT CTACTACCAT TAAATTTCTA AAGAACCAGG
226  L  M  S   V  Q  P  I    N  M  V    K  P  D    P  P  L  G    L  H  M    E  I  T    D  D  G  N    L  K  I   S  W  S
```

```
                                                      sau3AI
                                                      mboI/ndeII[dam-]
                                                      dpnI[dam+]
                                                      dpnII[dam-]
                                                      alwI[dam-]                                          rmaI     pleI
                        ppu10I                        manI[dam-]                                          maeI     hinfI
                        nsiI/avaIII             mboII  bsaBI[dam-]        draIII
                        bsmI
1601 GTGATGGTTT TTATGAATGC ATTTTCCAGC CAATCTTCCT ATTATCTGGC TACACAATGT GGATTAGGAT CAATCACTCT CTAGGTTCAC TTGACTCTCC
     CACTACCAAA AATACTTACG TAAAAGGTCG GTTAGAAGGA TAATAGACCG ATGTGTTACA CCTAATCCTA GTTAGTGAGA GATCCAAGTG AACTGAGAGG
 493  D  G  F   Y  E  C   I  F  Q  P    I  F  L    L  S  G   Y  T  M  W    I  R  I    N  H  S    L  G  S  L    D  S  P
                                ^begin13-2 nlaIII
                  nspI
                  nspHI             tfiI                       fokI
                  aflIII            hinfI    hphI              mnlI   bsrI
1701 ACCAACATGT GTCCTTCCTG ATTCTGTGGT GAAGCCACTG CCTCCATCCA GTGTGAAAGC AGAAATTACT ATAAACATTG GATTATTGAA AATATCTTGG
     TGGTTGTACA CAGGAAGGAC TAAGACACCA CTTCGGTGAC GGAGGTAGGT CACACTTTCG TCTTTAATGA TATTTGTAAC CTAATAACTT TTATAGAACC
 526  P  T  C    V  L  P  D   S  V  V   K  P  L    P  P  S  S    V  K  A    E  I  T    I  N  I  G    L  L  K    I  S  W tfiI
                                       hinfI          tru9I    rsaI
              bsrI                      xcmI          maeI      csp6I    mboII      mnlI       sfaNI
1801 GAAAGCCAG TCTTTCCAGA CAATTCCAGA TTCGCTATGG TTTAAGTGGA AAAGAAGTAC AATGGAAGAT GTAGGAGGTT TATGATGCAA
     CTTTCGGGTC AGAAAGGTCT GTTAAGGTCT AAGCGATACC AAATTCACCT TTTCTTCATG TTACCTTCTA CATCCTCCAA ATACTACGTT
 559  E  K  P  V    E  F  P    N  N  L    Q  F  Q  I    R  Y  G    L  S  G    K  E  V  Q    W  K  M    Y  E  V  Y  D  A  K hinPI
                 bsmAI bsrI                                  hhaI/cfoI mnlI maeI         bsrI
1901 AATCAAAATC TGTCAGTCTC CCAGTTCCAG ACTTGTGTGC AGTCATGCT GTTCAGGTGG GCTGTAGATG GCTAGATGGA CTGGGATATT GGAGTAATTG
     TTAGTTTTAG ACAGTCAGAG GGTCAAGGTC TGAACACACG TCAGTACGA CAAGTCCACC CGACATCTAC CGATCTACCT GACCCTATAA CCTCATTAAC
 593  S  K  S    V  S  L    P  V  P  D    L  C  A    V  V  A    V  Q  V  R    C  K  R    L  D  G    L  G  Y  W    G  N  W sau96I
                                                 avaII
                                                 asuI                             tru9I
                                                 ppuMI                            mseI
                                nlaIII      econI ecoO109I/draII  apoI            aseI/asnI/vspI
2001 GAGCAATCCA GCCTACACAG TTGTCATGGA TATAAAGTT CCTATGAGAG GACCTGAATT TGGAGAATA ATTAATGGAG ATACTATGAA AAAGGAGAAA
     CTCGTTAGGT CGGATGTGTC AACAGTACCT ATATTTTCAA GGATACTCTC CTGGACTTAA ACCTCTTAT TAATTACCTC TATGATACTT TTTCCTCTTT
 626  S  N  P   A  T  T  V    V  M  D    I  K  V    P  M  R  G   P  E  F    W  R  I   I  N  G  D    T  M  K    K  E  K

FIG. 1E
```

```
                       maeIII                                              pleI
                                                                           hinfI
2101 AATGTCACTT TACTTTGGAA GCCCCTGATG AAAAATGACT CATTGTGCAG TGTTCAGAGA TATGTGATAA ACCATCATAC TTCCTGCAAT GGAACATGGT
     TTACAGTGAA ATGAAACCTT CGGGGACTAC TTTTTACTGA GTAACACGTC ACAAGTCTCT ATACACTATT TGGTAGTATG AAGGACGTTA CCTTGTACCA
659    N  V  T  L   L  W  K   P  L  M   K  N  D   S  L  C  S   V  Q  R   Y  V  I  N   H  H  T   S  C  N   G  T  W  S haeIII/palI
                                                              mscI/balI
                                                               haeI
                       mboII                                    eaeI                                              scrFI
                        apoI                                     cfrI     maeIII                       munI       mvaI
                                                                                                                 ecoRII
2201 CAGAGAGATGT GGGAAATCAC ACGAAAATTCA CTTTCCTGTG GACAGAGCAA GCACATACTG TTACGGTTCT GGCCATCAAT TCAATTGGTG CTTCTGTTGC
     GTCTCTCTACA CCCTTTAGTG TGCTTTTAAGT GAAAGGACAC CTGTCTCGTT CGTGTATGAC AATGCCAAGA CCGGTAGTTA AGTTAACCAC GAAGACAACG
693    E  D  V  G  N  H   T  K  F  T   F  L  W   T  E  Q   A  H  T  V   L  T  V   L  A  I  N   S  I  G   A  S  V  A bslI      haeIII/palI
     truI9 truI9         haeI
      apoI msel          nlaIII                    ddeI                                                         xmnI
                                                    draIII                                                       tfiI
                                                     maeIII                                                       hinfI mboII
                                                                                                                  asp700
2301 AAATTTTAAT TTAACTTTT CATGGCCTAT GAGCAAAGTA AATATCGTGC TGCTTATCCT TTAAACAGA AGTCACTCAG GTGTGTGAT TGTTTCCTGG
     TTTAAAATTA AATTGAAAA GTACCGGATA CTCGTTTCAT TTATAGCACG ACGAATAGGA AATTTGTCGT TCAGTGAGTC CACACACTA ACAAAGGACC
726    M  F  N   L  T  F  S   W  P  M   S  K  V   N  I  V  Q   S  L  S   A  Y  P   L  N  S  S   C  V  I   V  S  W ddeI  earI/xsp632I
         draIII                        truI9                  truI9                                       hinfI
          hphI bsrI      aluI           msel                   msel  mboII hphI
2401 ATACCATCAC CCAGTGATTA CAAGCTAAATG TATTTTATTA TTTGAGTGGAA AAATCTTAAT GAAGATGGTG AAATAAAATG GCTTAGAATC TCTTCATCTG
     TATGGTAGTG GGTCACTAAT GTTCGATTAC ATAAAATAAT AAACTCACCTT TTTAGAATTA CTTCTACCAC TTTATTTTAC CGAATCTTAG AGAAGTAGAC
759    I  L  S  P   S  D  Y   K  L  M   Y  F  I  I   E  W  K   N  L  N   E  D  G   E  I  K  W   L  R  I   S  S  S  V
```

FIG. 1F

```
                                                                                                              tru9I
                                                                                                              mseI
                sau3AI                                                                                        aseI/asnI/vspI
                mboI/ndeII[dam-]
                dpnI[dam+]
                dpnII[dam-]                     bsrI
                bclI[dam-]                      rsaI                          sspI
     tru9I      nlaIII                          csp6I                                     tatggaagga gtgggaaaac caaagataat
     mseI
2501 TTAAGAAGTA TTATATCCAT GATCATTTTA TCCCATTGA GAAGTACCAG TTCAGTCTTT ACCCAATAAT TATGGAAGGA GTGGGAAAAC CAAAGATAAT
     AATTCTTCAT AATATAGGTA CTAGTAAAAT AGGGTAACT CTTCATGGTC AAGTCAGAAA TGGGTATTA ATACCTTCCT CACCCTTTTG GTTTCTATTA
 793   K  K  Y   Y  I  H   D  H  F  I   P  I  E   K  Y  Q   F  S  L  Y   P  I  F   M  E  G   V  G  K  P   K  I  I mboII
                                                 bspMI                         earI/ksp632I
                                                 sfaNI                         mnlI            bsrI
2601 TAATAGTTTC ACTCAAGATG ATATTGAAAA ACACCAGAGT GATGACAGGTT TATATGTAAT TGTGCCAGTA ATTATTCCT CTTCCATCTT ATTGCTTGGA
     ATTATCAAAG TGAGTTCTAC TATAACTTTT TGTGGTCTCA CTACTGCCAA ATATACATTA ACACGGTCAT TAATAAAGGA GAAGTAGAA TAACGAACCT
 826   N  S  F   T  Q  D  D   I  E  K   H  Q  S   D  A  G  L   Y  V  I   V  P  V   I  I  S  S   I  L  L  L  G bsp1286
                                                                                bmyI
                                                                                scrFI
                                                                                mvaI
                                                                                ecoRII
                                                                                dsaV
                                                       xmnI                     bstNI                    tru9I
                                                       mboII                    bsaJI                    mseI
     tru9I                                             asp700                   apyI[dcm+]
     mseI                                  aluI                                 CCTGGGCACA AGGACTTAAT TTTCAGAAGC
     aseI/asnI/vspI                                    GGGAAGATGT TCCGAACCCC AAGAATTGTT CCTGGGCACA AGGACTTAAT TTTCAGAAGC
2701 ACATTATTAA TATCACACCA AAGAATGAAA AGCTATTTTT TTCGATAAAT TTCTTACTTT CCCTTGGGG TTCTTAACAA GGACCCGTGT TCCTGAATTA AAAGTCTTCG
     TGTAATAATT ATAGTGTGGT TTCTTACTTT ATAGTGTTCG
 859   T  L  L  I   S  H  Q   R  M  K   K  L  F  W   E  D  V   P  N  P   K  N  C  S   W  A  Q   G  L  N   F  Q  K  P nlaIII
                                                 nspI    earI/ksp632I
                                                 nspHI   sau96I
                                                 aflIII  avaII
                                                 eam1105I mnlI                              ecoRV
                       maeII                     maeIII  asuI mboII       nlaIV             mboII
     maeII             sfaNI                     sfaNI   maeIII AGTGACATGT GGTCCCTCTC TTTTGGAGCC TGAAACAATT TCAGAAGATA TCAGTGTTGA
     psp1406I          TGAGCCATCT TTTATCAGCC ATACAGCATC AGTGACATGT GGTCCCTCTC TTTTGGAGCC TGAAACAATT TCAGAAGATA TCAGTGTTGA
2801 CAGAAACGTT TGAGCCATCT TTTATCAGCC ATACAGCATC AGTGACATGT GGTCCCTCTC TTTTGGAGCC TGAAACAATT TCAGAAGATA TCAGTGTTGA
     GTCTTTGCAA ACTCGGTAGA AAATAGTCGG TATGTCGTAG TCACTGTACA CCAGGAGAAG AAAACCTCGG ACTTTGTTAA AGTCTTCTAT AGTCACAACT
 893   E  T  F   E  H  L   F  I  K  H   T  A  S   V  T  C   G  P  L  L   E  P   E  T  I   S  E  D  I   S  V  D
```

FIG. 1G

```
                                                                sau3AI
                                                                mboI/ndeII[dam-]
                                                                dpnI[dam+]
                                                                dpnII[dam-]                                    sau3AI
                                                                bstYI/xhoII                           bsrI     mboI/ndeII[dam+]
                                          bsmAI                 bglII                                maeIII   dpnI[dam+]
                                  sfaNI   bsaI                                                                dpnII[dam-]
         nlaIII                                                                                               bclI[dam-]
2901 TACATCATGG AAAAATAAAG ATGAGATGAT GCCAACAACT GTGTTCTCTC TACTTTCAAC AACAGATCTT GAAAAGGGTT CTGTTTGTAT TAGTGACCAG
     ATGTAGTACC TTTTTATTTC TACTCTACTA CGGTTGTTGA CACCAGAGAG ATGAAAGTTG TTGTCTAGAA CTTTTCCCAA GACAAACATA ATCACTGGTC
 926  T  S  W  K  N  K  D  E  M  M  P  T  T  V  V  S  L  S  T  T  D  L  E  K  G  S  V  C  I  S  D  Q tru9I
               mseI                                                                tru9I
          hpaI       ddeI  ddeI                                           bsmAI    mseI
          hincII/hindIII mnlI mnlI csp6I bstEII        mnlI
3001 TTCAACAGTG TTAACTTCTC TGAGGCTGAG GGTACTGAGG TAACCTATGA CAGAGACAAC CCTTTGTTAA ATACGCCACG CTGATCAGCA
     AAGTTGTCAC AATTGAAGAG ACTCCGACTC CCATGACTCC ATTGGATACT GTCTCTGTTG GGAAACAATT TATGCGGTGC GACTAGTCGT
 959  F  N  S  V  N  F  S  E  A  E  G  T  E  V  *  T  Y  E  D  E  S  Q  R  Q  P  F  V  K  Y  A  T  L  I  S  N draIII
                              hphI                       hphI                           rmaI                tfiI
                              bsrI    mboII              maeIII                         maeI    apoI        hinfI
3101 ACTTCAAACC AAGTGAAACT GGTGAAGAAC AAGGGCTTAT TTCCCGAATA TTTATCAAGT CAGTGGTTCA CGAAGAGATC GTTTTTAAGA GGCAACTTCC TAAGAAAGAG
     TGAGAGTTGG TTCACTTTGA CCACTTCTTG TTCCCGAATA AAATAGTTCA AAATAGTTCA GTCACCAAGT GCTTCTCTAG CAAAAATTCT CCGTTGAAGG ATTCTTCTC
 993  S  K  P  S  E  T  G  E  E  Q  G  L  I  N  S  S  V  T  K  C  F  S  S  K  N  S  P  L  K  D  S  F  S scrFI
                                  mvaI
                                  ecoRII
                                  dsaV
                                  bstNI          sfaNI
                                  apyI[dcm+]     sau3AI foki
                                  sau96I         mboI/ndeII[dam-]
                                  haeIII/palI    dpnI[dam+]
                                  asuI           dpnII[dam-]
         nlaIII                                  bsaBI[dam-]
         aluI       mnlI bsaJI                                                          hphI                  ddeI      foki
3201 TAATAGTTCA TGGGAGATCA AGGCCCAGGC ATTTTTTATA TTATCAGATC AGCATCCCAA CATAATTTCA CCACACCTCA CATTCTGAGA AGGATTGGAT
     ATTATCGAGT ACCCTCTAGT TCCGGGTCCG TAAAAAATAT AATAGTCTAG TCGTAGGGTT GTATTAAAGT GGTGTGGAGT GTAAGAGTCT TCCTAACCTA
1026  N  S  S  W  E  I  E  A  Q  A  F  F  I  L  S  D  Q  H  P  N  I  I  S  P  H  L  T  F  S  E  G  L  D
```

FIG. 1H

```
                                                                          mnlI
                                                                          hphI
                                                                          maeIII
                                                 mboII                    bstEII
                    mnlI   apoI   eco57I
3301 GAACTTTTGA AATTGGAGGG AAATTTCCCT GAAGAAAATA ATGGATAAAAA GTCTATCTAT TATTTAGGGG TCAACCTCAAT CAAAAAGAGA GAGAGTGGTG
     CTTGAAAACT TTAACCTCCC TTTAAAGGGA CTTCTTTTAT TACTATTTTT CAGATAGATA ATAAATCCCC AGTGGAGTTA GTTTTTCTCT CTCTCACCAC
1059  E  L  L  K   L  E  G   N  F  P   E  E  N  N   D  K  K   V  Y  L   G  V  T   S  I  K   K  R  E   S  G  V scrFI
                                                                                             mvaI
                                                                                             ecoRII
                                                                                             dsaV
                                                                                             bstNI
                                                                                             apyI[dcm+]
                   bsp1286                                                                   gsuI/bpmI
                   bmyI
3401 TGCTTTTGAC TGACAAGTCA AGGGTATCGT GCCCATTCCC AGCCCCCTGT TTATTCACGG ACATCAGAGT TCTCCAGGAC AGTTGCTCAC AGTTGTAGA
     ACGAAAACTG ACTGTTCAGT TCCCATAGCA CGGGTAAGGG TCGGGGACA AATAAGTGCC TGTAGTCTCA AGAGGTCCTG TCAACGAGTG TGAAACATCT
1093  L  L  T  D   K  S  R   V  S  C   P  F  P   A  P  C   L  F  T  D   I  R  V   L  Q  D   S  C  S  H   F  V  E nlaIII
                                                                                                         sau3AI
                                                                                                         mboI/ndeII[dam-]
                                                                                             pleI        dpnI[dam+]
                                                                                             hinfI       dpnII[dam-]
                       mboII          nlaIII
                       bpuAI          nspI
              rmaI     bbsI           sfaNI nspHI mnlI                                    ddeI
              maeI
3501 AAATAATATC AACTTAGGAA CTTCTAGTAA CTTCTGAAAA GCATCCTACA TGCCTCAATT CCAAACTTGT TCTCATAAGAT CCTACTACGA CATGGAAAAC
     TTTATTATAG TTGAATCCTT GAAGATCATT GAAGACTTTT CGTAGGATGT ACGGAGTTAA GGTTTGAACA AGAGTAGTCT GGATGATGCT GTACCTTTTG
1126  N  N  I  N   L  G  T   F  A  S   Y  M  P   Q  F   A  S  Y  M  P   Q  F  Q   T  C  S   T  Q  T   H  K  I  M  E  N mboII
                              eco57I
3601 AAGATGTGTG ACCTAACTGT GTAATTTCAC TGAAGAAACC TTCAGATTTG TGTTATAAATG GGTAATATAA AGTGTAATAG ATTATAGTTG TGGGTGGGAG
     TTCTACACAC TGGATTGACA CATTAAAGTG ACTTCTTTGG AAGTCTAAAC ACAATATTAC CCATTATATT TCACATTATC TAATATCAAC ACCCACCCTC
1159  K  M  C  D   L  T  V xmnI
             pleI                                                 ddeI  maeIII                       asp700
             hinfI  apoI
3701 AGAGAAAAGA AACCAGAGTC AAATTTGAAA ATAATTGTTC CAAATGAATG GTTTACTTAC AACAGACAAA TCATTGTATC TGTTTTTTAA ACTCTTTCGG
     TCTCTTTTCT TTGGTCTCAG TTTAAACTTT TATTAACAAG GTTTACTTAC AACAGACAAA TCATTGTATC TGTTTTTTAA ACTCTTTCGG
```

FIG. 1I

```
                                                                sau96I
                                                                nlaIV
                                                                avaII
                                           rmaI                 asuI       rmaI
                                mboII      maeI                 ppuMI      maeI
                      earI/ksp632I         aluI         ecoO109I/draII     aluI
           accI       sapI
3801 TTCATAAGCC TACCAATGTA GACACGCTCT TCTATTTTAT TCCGAAGCTC TAGTGGGAAG GTCCCTTGTT TCCAGCTAGA AATAAGCCCA ACAGACACCA
     AAGTATTCGG ATGGTTACAT CTGTGCGAGA AGATAAAATA AGGCTTCGAG ATCACCCTTC CAGGGAACAA AGGTCGATCT TTATTCGGGT TGTCTGTGGT nspI
                                                                                                      nspHI
                                                           rsaI                                       tru9I nlaIII
                                     mnlI                  csp6I                                      maeI aflIII
3901 TCTTTTGTGA GATGTAATTG GGGCGTGTTG TTTTACCTCA AGTTTTTGTT TGTACCAAAC ACACACACAC ACACACATTC TTAACACATG
     AGAAAACACT CTACATTAAC CCCGCACAAC AAAATGGAGT TCAAAAACAA AACATGGTTG TGTGTGTGTG TGTGTGTAAG AATTGTGTAC sfuI
                                                                                                      bstBI
                                                                                                      bsiCI
                                                                                                      asuII
                                scfI                                                       tru9I      ecoRI
                                                                                           maeI       apoI
4001 TCCTTGTGTG TTTTGAGAGT ATATATGTA TTTATATTTT GTGCTATACAG ACTGTAGGAT TTGAAGTAGG ACTTTCCTAA ATGTTAAGA TAAACAGAAT
     AGGAACACAC AAAACTCTCA TATAATACAT AAATATAAAA CACGATAGTC TGACATCCTA AACTTCATCC TGAAAGGATT TACAAATTCT ATTTGTCTTA taqI
4101 TC
     AG length: 4102
```

SEQ ID NO: 3
SEQ ID NO: 4
SEQ ID NO: 2

```
                    1   M I C Q K F C V V L L H W E F I Y V I T A F N L S Y P I T P W R F K L S C M P P N S T Y D Y F L L P
wsxfull.6.4.variant 1   M I C Q K F C V V L L H W E F I Y V I T A F N L S Y P I T P W R F K L S C M P P N S T Y D Y F L L P
wsxfull.12.1.variant 1  M I C Q K F C V V L L H W E F I Y V I T A F N L S Y P I T P W R F K L S C M P P N S T Y D Y F L L P
wsxfull.13.2.variant wsxfull.6.4.variant  51  A G L S K N T S N S N G H Y E T A V E P K F N S S G T H F S N L S K T T F H C C F R S E Q D R N C S
wsxfull.12.1.variant 51  A G L S K N T S N S N G H Y E T A V E P K F N S S G T H F S N L S K T T F H C C F R S E Q D R N C S
wsxfull.13.2.variant 51  A G L S K N T S N S N G H Y E T A V E P K F N S S G T H F S N L S K T T F H C C F R S E Q D R N C S wsxfull.6.4.variant  101 L C A D N I E G K T F V S T V N S L V F Q Q I D A N W N I Q C W L K G D L K L F I C Y V E S L F K N
wsxfull.12.1.variant 101 L C A D N I E G K T F V S T V N S L V F Q Q I D A N W N I Q C W L K G D L K L F I C Y V E S L F K N
wsxfull.13.2.variant 101 L C A D N I E G K T F V S T V N S L V F Q Q I D A N W N I Q C W L K G D L K L F I C Y V E S L F K N wsxfull.6.4.variant  151 L F R N Y N Y K V H L L Y V L P E V L E D S P L V P Q K G S F Q M V H C N C S V H E C C E C L V P V
wsxfull.12.1.variant 151 L F R N Y N Y K V H L L Y V L P E V L E D S P L V P Q K G S F Q M V H C N C S V H E C C E C L V P V
wsxfull.13.2.variant 151 L F R N Y N Y K V H L L Y V L P E V L E D S P L V P Q K G S F Q M V H C N C S V H E C C E C L V P V wsxfull.6.4.variant  201 P T A K L N D T L L M C L K I T S G G V I F Q S P L M S V Q P I N M V K P D P P L G L H M E I T D D
wsxfull.12.1.variant 201 P T A K L N D T L L M C L K I T S G G V I F Q S P L M S V Q P I N M V K P D P P L G L H M E I T D D
wsxfull.13.2.variant 201 P T A K L N D T L L M C L K I T S G G V I F Q S P L M S V Q P I N M V K P D P P L G L H M E I T D D wsxfull.6.4.variant  251 G N L K I S W S S P P L V P F P L Q Y Q V K Y S E N S T T V I R E A D K I V S A T S L L V D S I L P
wsxfull.12.1.variant 251 G N L K I S W S S P P L V P F P L Q Y Q V K Y S E N S T T V I R E A D K I V S A T S L L V D S I L P
wsxfull.13.2.variant 251 G N L K I S W S S P P L V P F P L Q Y Q V K Y S E N S T T V I R E A D K I V S A T S L L V D S I L P
```

| | | |
|---|---|---|
| wsxfull.6.4.variant | 301 | G S S Y E V Q V R G K R L D G P G I W S D W S T P R V F T T Q D V I Y F P P K I L T S V G S N V S F |
| wsxfull.12.1.variant | 301 | G S S Y E V Q V R G K R L D G P G I W S D W S T P R V F T T Q D V I Y F P P K I L T S V G S N V S F |
| wsxfull.13.2.variant | 301 | G S S Y E V Q V R G K R L D G P G I W S D W S T P R V F T T Q D V I Y F P P K I L T S V G S N V S F |
| wsxfull.6.4.variant | 351 | H C I Y K K E N K I V P S K E I V W W M N L A E K I P Q S Q Y D V V S D H V S K V T F F N L N E T K |
| wsxfull.12.1.variant | 351 | H C I Y K K E N K I V P S K E I V W W M N L A E K I P Q S Q Y D V V S D H V S K V T F F N L N E T K |
| wsxfull.13.2.variant | 351 | H C I Y K K E N K I V P S K E I V W W M N L A E K I P Q S Q Y D V V S D H V S K V T F F N L N E T K |
| wsxfull.6.4.variant | 401 | P R G K F T Y D A V Y C C N E H E C H H R Y A E L Y V I D V N I N I S C E T D G Y L T K M T C R W S |
| wsxfull.12.1.variant | 401 | P R G K F T Y D A V Y C C N E H E C H H R Y A E L Y V I D V N I N I S C E T D G Y L T K M T C R W S |
| wsxfull.13.2.variant | 401 | P R G K F T Y D A V Y C C N E H E C H H R Y A E L Y V I D V N I N I S C E T D G Y L T K M T C R W S |
| wsxfull.6.4.variant | 451 | T S T I Q S L A E S T L Q L R Y H R S S L Y C S D I P S I H P I S E P K D C Y L Q S D G F Y E C I F |
| wsxfull.12.1.variant | 451 | T S T I Q S L A E S T L Q L R Y H R S S L Y C S D I P S I H P I S E P K D C Y L Q S D G F Y E C I F |
| wsxfull.13.2.variant | 451 | T S T I Q S L A E S T L Q L R Y H R S S L Y C S D I P S I H P I S E P K D C Y L Q S D G F Y E C I F |
| wsxfull.6.4.variant | 501 | Q P I F L L S G Y T M W I R I N H S L G S L D S P P T C V L P D S V V K P L P P S S V K A E I T I N |
| wsxfull.12.1.variant | 501 | Q P I F L L S G Y T M W I R I N H S L G S L D S P P T C V L P D S V V K P L P P S S V K A E I T I N |
| wsxfull.13.2.variant | 501 | Q P I F L L S G Y T M W I R I N H S L G S L D S P P T C V L P D S V V K P L P P S S V K A E I T I N |
| wsxfull.6.4.variant | 551 | I G L L K I S W E K P V F P E N N L Q F Q I R Y G L S G K E V Q W K M Y E V Y D A K S K S V S L P V |
| wsxfull.12.1.variant | 551 | I G L L K I S W E K P V F P E N N L Q F Q I R Y G L S G K E V Q W K M Y E V Y D A K S K S V S L P V |
| wsxfull.13.2.variant | 551 | I G L L K I S W E K P V F P E N N L Q F Q I R Y G L S G K E V Q W K M Y E V Y D A K S K S V S L P V |

FIG. 2B

```
wsxfull.6.4.variant    601  P D L C A V Y Y A V Q V R C K R L D G L G Y W S N W S N P A Y T V V M D I K V P M R G P E F W R I I N
wsxfull.12.1.variant   601  P D L C A V Y Y A V Q V R C K R L D G L G Y W S N W S N P A Y T V V M D I K V P M R G P E F W R I I N
wsxfull.13.2.variant   601  P D L C A V Y Y A V Q V R C K R L D G L G Y W S N W S N P A Y T V V M D I K V P M R G P E F W R I I N wsxfull.6.4.variant    651  G D T M K K E K N V T L L W K P L M K N D S L C S V Q R Y V I N H H T S C N G T W S E D V G N H T K
wsxfull.12.1.variant   651  G D T M K K E K N V T L L W K P L M K N D S L C S V Q R Y V I N H H T S C N G T W S E D V G N H T K
wsxfull.13.2.variant   651  G D T M K K E K N V T L L W K P L M K N D S L C S V Q R Y V I N H H T S C N G T W S E D V G N H T K wsxfull.6.4.variant    701  F T F L W T E Q A H T V T V L A I N S I G A S V A N F N L T F S W P M S K V N I V Q S L S A Y P L N
wsxfull.12.1.variant   701  F T F L W T E Q A H T V T V L A I N S I G A S V A N F N L T F S W P M S K V N I V Q S L S A Y P L N
wsxfull.13.2.variant   701  F T F L W T E Q A H T V T V L A I N S I G A S V A N F N L T F S W P M S K V N I V Q S L S A Y P L N wsxfull.6.4.variant    751  S S C V I V S W I L S P S D Y K L M Y F I I E W K N L N E D G E I K W L R I S S S V K K Y Y I H D H
wsxfull.12.1.variant   751  S S C V I V S W I L S P S D Y K L M Y F I I E W K N L N E D G E I K W L R I S S S V K K Y Y I H D H
wsxfull.13.2.variant   751  S S C V I V S W I L S P S D Y K L M Y F I I E W K N L N E D G E I K W L R I S S S V K K Y Y I H D H ┌─Trans─
wsxfull.6.4.variant    801  F I P I E K Y Q F S L Y P I F M E G V G K P K I I N S F T Q D D I E K H Q S D A G L Y V I V P V I
wsxfull.12.1.variant   801  F I P I E K Y Q F S L Y P I F M E G V G K P K I I N S F T Q D D I E K H Q S D A G L Y V I V P V I
wsxfull.13.2.variant   801  F I P I E K Y Q F S L Y P I F M E G V G K P K I I N S F T Q D D I E K H Q S D A G L Y V I V P V I ├──membrane Domain──┤├────────Box 1────────┤
wsxfull.6.4.variant    851  S S S I L L L G T L L I S H Q R M K K L F W E D V P N P K N C S W A Q G L N F Q K . . . . . M F .
wsxfull.12.1.variant   851  S S S I L L L G T L L I S H Q R M K K L F W E D V P N P K N C S W A Q G L N F Q K . . . . . M F .
wsxfull.13.2.variant   851  S S S I L L L G T L L I S H Q R M K K L F W E D V P N P K N C S W A Q G L N F Q K P E T F E H L F I
```

```
wsxfull.6.4.variant   351 CTTCCTTTTGCCTGCTGGACTCTCAAAGAATACTTCAAATTCGAATGGAC
wsxfull.12.1.variant  264 CTTCCTTTTGCCTGCTGGACTCTCAAAGAATACTTCAAATTCGAATGGAC
wsxfull.13.2.variant  264 CTTCCTTTTGCCTGCTGGACTCTCAAAGAATACTTCAAATTCGAATGGAC wsxfull.6.4.variant   401 ATTATGAGACAGCTGTTGAACCTAAGTTTAATTCAAGTGGTACTCACTTT
wsxfull.12.1.variant  314 ATTATGAGACAGCTGTTGAACCTAAGTTTAATTCAAGTGGTACTCACTTT
wsxfull.13.2.variant  314 ATTATGAGACAGCTGTTGAACCTAAGTTTAATTCAAGTGGTACTCACTTT wsxfull.6.4.variant   451 TCTAACTTATCCAAAACAACTTTCCACTGTTGCTTTCGGAGTGAGCAAGA
wsxfull.12.1.variant  364 TCTAACTTATCCAAAACAACTTTCCACTGTTGCTTTCGGAGTGAGCAAGA
wsxfull.13.2.variant  364 TCTAACTTATCCAAAACAACTTTCCACTGTTGCTTTCGGAGTGAGCAAGA wsxfull.6.4.variant   501 TAGAAACTGCTCCTTATGTGCAGACAACATTGAAGGAAAGACATTTGTTT
wsxfull.12.1.variant  414 TAGAAACTGCTCCTTATGTGCAGACAACATTGAAGGAAAGACATTTGTTT
wsxfull.13.2.variant  414 TAGAAACTGCTCCTTATGTGCAGACAACATTGAAGGAAAGACATTTGTTT wsxfull.6.4.variant   551 CNACAGTAAAATTCTTTAGTTTTTCAACAAAATAGATGCAAACTGGAACATA
wsxfull.12.1.variant  464 CAACAGTAAAATTCTTTAGTTTTTCAACAAAATAGATGCAAACTGGAACATA
wsxfull.13.2.variant  464 CAACAGTAAAATTCTTTAGTTTTTCAACAAAATAGATGCAAACTGGAACATA wsxfull.6.4.variant   601 CAGTGCTGGCTAAAAGGAGACTTAAAAATTATTCATCTGTTATGTGGAGTC
wsxfull.12.1.variant  514 CAGTGCTGGCTAAAAGGAGACTTAAAATTATTCATCTGTTATGTGGAGTC
wsxfull.13.2.variant  514 CAGTGCTGGCTAAAAGGAGACTTAAAATTATTCATCTGTTATGTGGAGTC
```

FIG. 3B

| | | |
|---|---|---|
| wsxfull.6.4.variant | 651 | ATTATTTAAGAATCTATTTCAGGAATTATAACTATAAGGTCCATCTTTTAT |
| wsxfull.12.1.variant | 564 | ATTATTTAAGAATCTATTTCAGGAATTATAACTATAAGGTCCATCTTTTAT |
| wsxfull.13.2.variant | 564 | ATTATTTAAGAATCTATTTCAGGAATTATAACTATAAGGTCCATCTTTTAT |
| wsxfull.6.4.variant | 701 | ATGTTCTGCCTGAAGTGTTAGAAGATTCACCTCTGGTTCCCCAAAAAGGC |
| wsxfull.12.1.variant | 614 | ATGTTCTGCCTGAAGTGTTAGAAGATTCACCTCTGGTTCCCCAAAAAGGC |
| wsxfull.13.2.variant | 614 | ATGTTCTGCCTGAAGTGTTAGAAGATTCACCTCTGGTTCCCCAAAAAGGC |
| wsxfull.6.4.variant | 751 | AGTTTTCAGATGGTTCACTGCAATTGCAGTGTTCATGAATGTTGTGAATG |
| wsxfull.12.1.variant | 664 | AGTTTTCAGATGGTTCACTGCAATTGCAGTGTTCATGAATGTTGTGAATG |
| wsxfull.13.2.variant | 664 | AGTTTTCAGATGGTTCACTGCAATTGCAGTGTTCATGAATGTTGTGAATG |
| wsxfull.6.4.variant | 801 | TCTTGTGCCTGTGCCAACAGCCAAACTCAACGACACTCTCCTTATGTGTT |
| wsxfull.12.1.variant | 714 | TCTTGTGCCTGTGCCAACAGCCAAACTCAACGACACTCTCCTTATGTGTT |
| wsxfull.13.2.variant | 714 | TCTTGTGCCTGTGCCAACAGCCAAACTCAACGACACTCTCCTTATGTGTT |
| wsxfull.6.4.variant | 851 | TGAAAATCACATCTGGTGGAGTAATTTTTCCAGTCACCTCTAATGTCAGTT |
| wsxfull.12.1.variant | 764 | TGAAAATCACATCTGGTGGAGTAATTTTTCCAGTCACCTCTAATGTCAGTT |
| wsxfull.13.2.variant | 764 | TGAAAATCACATCTGGTGGAGTAATTTTTCCAGTCACCTCTAATGTCAGTT |
| wsxfull.6.4.variant | 901 | CAGCCCATAAATATGGTGAAGCCTGATCCACCATTAGGTTTGCATATGGA |
| wsxfull.12.1.variant | 814 | CAGCCCATAAATATGGTGAAGCCTGATCCACCATTAGGTTTGCATATGGA |
| wsxfull.13.2.variant | 814 | CAGCCCATAAATATGGTGAAGCCTGATCCACCATTAGGTTTGCATATGGA |

FIG. 3C

```
wsxfull.6.4.variant    951   AATCACAGATGATGGTAATTTAAAGATTTCTTGGTCCAGCCCACCATTGG
wsxfull.12.1.variant   864   AATCACAGATGATGGTAATTTAAAGATTTCTTGGTCCAGCCCACCATTGG
wsxfull.13.2.variant   864   AATCACAGATGATGGTAATTTAAAGATTTCTTGGTCCAGCCCACCATTGG wsxfull.6.4.variant    1001  TACCATTTCCACTTCAATATCAAGTGAAATATTCAGAGAATTCTACAACA
wsxfull.12.1.variant   914   TACCATTTCCACTTCAATATCAAGTGAAATATTCAGAGAATTCTACAACA
wsxfull.13.2.variant   914   TACCATTTCCACTTCAATATCAAGTGAAATATTCAGAGAATTCTACAACA wsxfull.6.4.variant    1051  GTTATCAGAGAAGCTGACAAGATTGTCTCAGCTACATCCCTGCTAGTAGA
wsxfull.12.1.variant   964   GTTATCAGAGAAGCTGACAAGATTGTCTCAGCTACATCCCTGCTAGTAGA
wsxfull.13.2.variant   964   GTTATCAGAGAAGCTGACAAGATTGTCTCAGCTACATCCCTGCTAGTAGA wsxfull.6.4.variant    1101  CAGTATACTTCCTGGGTCTTCGTATGAGGTTCAGGTGAGGGGCAAGAGAC
wsxfull.12.1.variant   1014  CAGTATACTTCCTGGGTCTTCGTATGAGGTTCAGGTGAGGGGCAAGAGAC
wsxfull.13.2.variant   1014  CAGTATACTTCCTGGGTCTTCGTATGAGGTTCAGGTGAGGGGCAAGAGAC wsxfull.6.4.variant    1151  TGGATGGGCCCAGGAATCTGGAGTGACTGGAGTACTCCTCGTGTCTTTACC
wsxfull.12.1.variant   1064  TGGATGGGCCCAGGAATCTGGAGTGACTGGAGTACTCCTCGTGTCTTTACC
wsxfull.13.2.variant   1064  TGGATGGGCCCAGGAATCTGGAGTGACTGGAGTACTCCTCGTGTCTTTACC wsxfull.6.4.variant    1201  ACACAAGATGTCATATACTTTCCACCTAAAATTCTGACAAGTGTTGGGTC
wsxfull.12.1.variant   1114  ACACAAGATGTCATATACTTTCCACCTAAAATTCTGACAAGTGTTGGGTC
wsxfull.13.2.variant   1114  ACACAAGATGTCATATACTTTCCACCTAAAATTCTGACAAGTGTTGGGTC
```

| | | |
|---|---|---|
| wsxfull.6.4.variant 1551 | TTGCAGATGGTCAAACCAGTACAATCCAGTCACTTGCGGAAAGCACTTTGC |
| wsxfull.12.1.variant 1464 | TTGCAGATGGTCAAACCAGTACAATCCAGTCACTTGCGGAAAGCACTTTGC |
| wsxfull.13.2.variant 1464 | TTGCAGATGGTCAAACCAGTACAATCCAGTCACTTGCGGAAAGCACTTTGC |
| wsxfull.6.4.variant 1601 | AATTGAGGTATCATAGGAGCAGCCCTTTACTGTTCTGATATTCCATCTATT |
| wsxfull.12.1.variant 1514 | AATTGAGGTATCATAGGAGCAGCCCTTTACTGTTCTGATATTCCATCTATT |
| wsxfull.13.2.variant 1514 | AATTGAGGTATCATAGGAGCAGCCCTTTACTGTTCTGATATTCCATCTATT |
| wsxfull.6.4.variant 1651 | CATCCCATATCTGAGCCCAAAGATTGCTATTTGCTATTTCCTATTATCTA |
| wsxfull.12.1.variant 1564 | CATCCCATATCTGAGCCCAAAGATTGCTATTTGCTATTTCCTATTATCTA |
| wsxfull.13.2.variant 1564 | CATCCCATATCTGAGCCCAAAGATTGCTATTTGCTATTTCCTATTATCTA |
| wsxfull.6.4.variant 1701 | TGAATGCATTTTTCCAGCCAATCACTCTCTAGGTTCACTTGACTTCACTTCA |
| wsxfull.12.1.variant 1614 | TGAATGCATTTTTCCAGCCAATCACTCTCTAGGTTCACTTGACTTCACTTCA |
| wsxfull.13.2.variant 1614 | TGAATGCATTTTTCCAGCCAATCACTCTCTAGGTTCACTTGACTTCACTTCA |
| wsxfull.6.4.variant 1751 | TTAGGATCAATCACTCTGTGGTGAAGCCACTGCCTCCACCAACATCCAGTGTC |
| wsxfull.12.1.variant 1664 | TTAGGATCAATCACTCTGTGGTGAAGCCACTGCCTCCACCAACATCCAGTGTC |
| wsxfull.13.2.variant 1664 | TTAGGATCAATCACTCTGTGGTGAAGCCACTGCCTCCACCAACATCCAGTGTC |
| wsxfull.6.4.variant 1801 | CTTCCTGATTCTGTGGTGAAGCCACTGCCTCCATCCAGTGTGAAAGCAGA |
| wsxfull.12.1.variant 1714 | CTTCCTGATTCTGTGGTGAAGCCACTGCCTCCATCCAGTGTGAAAGCAGA |
| wsxfull.13.2.variant 1714 | CTTCCTGATTCTGTGGTGAAGCCACTGCCTCCATCCAGTGTGAAAGCAGA |

FIG. 3F

| | | |
|---|---|---|
| wsxfull.6.4.variant | 1851 | AATTACTATAAACATTGGATTATTGAAAATATCTTGGGAAAAAGCCAGTCT |
| wsxfull.12.1.variant | 1764 | AATTACTATAAACATTGGATTATTGAAAATATCTTGGGAAAAAGCCAGTCT |
| wsxfull.13.2.variant | 1764 | AATTACTATAAACATTGGATTATTGAAAATATCTTGGGAAAAAGCCAGTCT |
| | | |
| wsxfull.6.4.variant | 1901 | TTCCAGAGAATAACCTTCAATTCCAGATTCGCTATGGTTTAAGTGGAAAA |
| wsxfull.12.1.variant | 1814 | TTCCAGAGAATAACCTTCAATTCCAGATTCGCTATGGTTTAAGTGGAAAA |
| wsxfull.13.2.variant | 1814 | TTCCAGAGAATAACCTTCAATTCCAGATTCGCTATGGTTTAAGTGGAAAA |
| | | |
| wsxfull.6.4.variant | 1951 | GAAGTACAATGGAAGATGTATGAGGTTTATGATGCAAAATCAAAATCTGT |
| wsxfull.12.1.variant | 1864 | GAAGTACAATGGAAGATGTATGAGGTTTATGATGCAAAATCAAAATCTGT |
| wsxfull.13.2.variant | 1864 | GAAGTACAATGGAAGATGTATGAGGTTTATGATGCAAAATCAAAATCTGT |
| | | |
| wsxfull.6.4.variant | 2001 | CAGTCTCCCAGTTCCAGACTTGTGTGTGCAGTCTATGCTGTTCAGGTGCGCT |
| wsxfull.12.1.variant | 1914 | CAGTCTCCCAGTTCCAGACTTGTGTGTGCAGTCTATGCTGTTCAGGTGCGCT |
| wsxfull.13.2.variant | 1914 | CAGTCTCCCAGTTCCAGACTTGTGTGTGCAGTCTATGCTGTTCAGGTGCGCT |
| | | |
| wsxfull.6.4.variant | 2051 | GTAAGAGGCTAGATGGACTGGGATATTGGAGTAATTGGAGCAATCCAGCC |
| wsxfull.12.1.variant | 1964 | GTAAGAGGCTAGATGGACTGGGATATTGGAGTAATTGGAGCAATCCAGCC |
| wsxfull.13.2.variant | 1964 | GTAAGAGGCTAGATGGACTGGGATATTGGAGTAATTGGAGCAATCCAGCC |
| | | |
| wsxfull.6.4.variant | 2101 | TACACAGTTGTCATGGATATAAAAGTTCCTATGAGAGGACCTGAATTTTG |
| wsxfull.12.1.variant | 2014 | TACACAGTTGTCATGGATATAAAAGTTCCTATGAGAGGACCTGAATTTTG |
| wsxfull.13.2.variant | 2014 | TACACAGTTGTCATGGATATAAAAGTTCCTATGAGAGGACCTGAATTTTG |

```
wsxfull.13.2.variant  3514  TTAGGAACTTCTAGTAAGAAGACTTTTGCATCTTACATGCCTCAATTCCA
wsxfull.13.2.variant  3564  AACTTGTTCTACTCAGACTCATAAGATCATGGAAAACAAGATGTGACC
wsxfull.13.2.variant  3614  TAACTGTGTAATTTCACTGAAGAAACCTTCAGATTTGTGTTATAATGGGT
wsxfull.13.2.variant  3664  AATATAAAGTGTAATTATAGTTGTGGGTGGGAGAGAAAAGAAAC
wsxfull.13.2.variant  3714  CAGAGTCAAATTTGAAAATAAATTGTTCCAAATGAATGTTGTCTGTTTGTT
wsxfull.13.2.variant  3764  CTCTCTTAGTAACACGGTCTTCTATTTTATTCCAAGCTCATAAGCCTAC
wsxfull.13.2.variant  3814  CAATGTAGACATAGACAAAATAAGCCCAACAGACACCATCTTTTGTGAGGTC
wsxfull.13.2.variant  3864  CCTTGTTTCCAGCTAGAAATAAGCCCAACAGACACCATCTTTTGTGAGAT
wsxfull.13.2.variant  3914  GTAATTTGTTTTTTCAGAGGGCGTGTTTACCTCAAGTTTTGTTTTG
wsxfull.13.2.variant  3964  TACCAAACACACACACACACACACACATTCTTAACATGTCCTTGTGTTT
wsxfull.13.2.variant  4014  TGAGAGTATATTATGTATTTATTTTTGCTATCAGACTGTAGGATTTG
wsxfull.13.2.variant  4064  AAGTAGGACTTTCCTAAATGTTTAAGATAAACAGAATTC
```

```
wsxfull.13.2.variant  601  PDLCAVYYAVQVRCKRLDGLGYWSNPAYTVVMDIKVPMRGPEFWRIIN
mu.wsx.ecd            599  SDLCAYYYVQVRCRRLDGLGYWSNSPAYTLVMDVKVPMRGPEFWRKMD wsxfull.13.2.variant  651  GDTMKKENVTLLWKPLMKNDSLCSVQRYVINHHTSCNGTWSEDVGNHTK
mu.wsx.ecd            649  GDVTKKERNVTLLWKPLTKNDSLCSVRRYVKHRTAHNGTWSEDVGNRTN wsxfull.13.2.variant  701  FTFLWTEQAHTVTVLAIN

```
wsxfull.13.2.variant   901  KHTASVTCGPLLLEPETISEDISVDTSWKNKDEMMPTTVVSLLSTTDLEK wsxfull.13.2.variant   951  GSVCISDQFNSVNFSEAEGTEVTYEDESQRQPFVKYATLISNSKPSETGE wsxfull.13.2.variant  1001  EQGLINSSVTKCFSSKNSPLKDSFSNSSWEIEAQAFFILSDQHPNIISPH wsxfull.13.2.variant  1051  LTFSEGLDELLKLEGNFPEENNDKKSIYYLGVTSIKKRESGVLLTDKSRV wsxfull.13.2.variant  1101  SCPFPAPCLFTDIRVLQDSCSHFVENNINLGTSSKKTFASYMPQFQTCST wsxfull.13.2.variant  1151  QTHKIMENKMCDLTV
```

FIG. 4D

```
mu.wsx.ecd      1  GGGCCCCCCCTCGAAGTCGACGGTATCGATAAGCTTGATATCGAATTCCG
         SEQ ID NO: 8
mu.wsx.ecd     51  GCCGGGACACAGGTGGGACACTCTTTTAGTCCTCAATCCCTGGCGCGAGG mu.wsx.ecd    101  CCACCCAAGGCAACGCAGGACGCAGGGCGTTTGGGGACCAGGCAGCAGAC mu.wsx.ecd    151  TGGGGCGGGTACCTGCGGAGAGCCACGCAACTTCTCCAGGCCTCTGACTAC mu.wsx.ecd    201  TTTGGAAACTGCCCCGGGGCTGCGACATCAACCCCTTAAGTCCCGAGGCG mu.wsx.ecd    251  GAAAGAGGGTGGGTTTGGTTTGAAAGACACAAGGAAGAAAAATGTGTGTG mu.wsx.ecd    301  GGGCGGGGTTAAGTTTCCCACCCTCTTCCCCCCTTCCCGAGCAAAATTAGAAAA mu.wsx.ecd         351  CAAAACAAATAGAAAAGCCAGCCCTCCGGCCAACC······GAATTCTCGGAC
   SEQ ID NO: 1
wsxfull.13.2.variant  1  ···································GAATCTCGAGTCGAC
```

```
mu.wsx.ecd              2794 ACCTGATGATTATATCTGGTTATTATTGAATGGAAGAGATCCTTA
wsxfull.13.2.variant    2409 ACCCAGTGATTACAAGCTATTGTATTTATTATTGAGTGGAAAATCTTA mu.wsx.ecd              2844 ATGAAGATGATGGAATGAAGTGGCT
wsxfull.13.2.variant    2459 ATGAAGATGGTGAAATAAATGGCTTAGAATCTCTTCATCTGTTAAGAAG wsxfull.13.2.variant    2509 TATTTATATCCATGATCATTTTATGGAAGGAGTGGGAAAAACACCAGTTCAGTCT wsxfull.13.2.variant    2559 TTACCCAATATTTATGGAAGGAGTGGGAAAAACACCAGAGTGATGCAGGTTTATGTA wsxfull.13.2.variant    2609 TCACTCAAGATGATATTGAAAAACACCAGAGTGATGCAGGTTTATGTA wsxfull.13.2.variant    2659 ATTGTGCCAGTAATTATTCCTCTTATTGCTTGGAACATTATT wsxfull.13.2.variant    2709 AATATCACACCAAAGAATGAAAAAGCTATTTTGGGAAGATGTTCCGAACC wsxfull.13.2.variant    2759 CCAAGAATTGTTCCTGGGCACAAGGACTTAATTTTCAGAAGCCAGAAACG
```

FIG. 5J

```
wsxfull.13.2.variant  2809  TTTGAGCATCTTTTTATCAAGCATACAGCATCAGTGACATGTGGTCCTCT
wsxfull.13.2.variant  2859  TCTTTTTGGAGCCTGAAACAATTTCAGAAGATATCAGTGTTGATACATCAT
wsxfull.13.2.variant  2909  GGAAAAATAAAGATGAGATGATGCCAACAACTGTGGTCTCTCTACTTTCA
wsxfull.13.2.variant  2959  ACAAACAGATCTTGAAAAGGGTTCTGTTTGTATTAGTGACCAGTTCAACAG
wsxfull.13.2.variant  3009  TGTTAACTTCTCTGAGGCTGAGGGTACTGAGGTAACCTATGAGGACGAAA
wsxfull.13.2.variant  3059  GCCAGAGACAACCCTTTGTTAAATACGCCACGCTGATCAGCAACTCTAAA
wsxfull.13.2.variant  3109  CCAAGTGAAACTGGTGAAGAACAAGGGCTTATAAATAGTTCAGTCACCAA
wsxfull.13.2.variant  3159  GTGCTTCTCTAGCAAAAATTCTCCGTTGAAGGATTCTTTCTAATAGCT
wsxfull.13.2.variant  3209  CATGGGAGATAGAGGCCCAGGCATTTTTTATATTATCAGATCAGCATCCC
```

FIG. 5K

```
wsxfull.13.2.variant  3259  AACATAATTTCACCACACCTCACATTCTCAGAAGGATTGGATGAACTTTT
wsxfull.13.2.variant  3309  GAAATTGGAGGGAAATTTCCCTGAAGAAAATAATGATAAAAGTCTATCT
wsxfull.13.2.variant  3359  ATTATTTAGGGGTCACCCTCAATCAAAAAGAGAGAGTGGTGTGCTTTTG
wsxfull.13.2.variant  3409  ACTGACAAGTCAAGGGTATCGTGCCCATTCCCAGCCCCTGTTTATTCAC
wsxfull.13.2.variant  3459  GGACATCAGAGTTCTCCAGGACAGTTGCTCACACTTTGTAGAAAATAATA
wsxfull.13.2.variant  3509  TCAACTTAGGAACTTCTAGTAAGAAGACTTTTGCATCTTACATGCCTCAA
wsxfull.13.2.variant  3559  TTCCAAACTTGTTCTACTCAGACTCATAAGATCATGGAAAACAAGATGTG
wsxfull.13.2.variant  3609  TGACCTAACTGTGTAATTTCACTGAAGAAACCTTCAGATTTGTGTTATAA
wsxfull.13.2.variant  3659  TGGGTAATATAAAGTGTAATAGATTATAGTTGTGGGTGGGAGAGAAAA
```

FIG. 5L

```
wsxfull.13.2.variant  3709  GAAACCAGAGTCAAATTTGAAAATAATTGTTCCAAATGAATGTTGTCTGT wsxfull.13.2.variant  3759  TTGTTCTCTCTTAGTAACATAGACAAAAAATTTGAGAAAGCCTTCATAAG wsxfull.13.2.variant  3809  CCTACCAATGTAGACACGGCTCTTCTATTTTATTCCCAAGCTCTAGTGGGA wsxfull.13.2.variant  3859  AGGTCCCTTGTTTCCAGCTAGAAATAAGCCCAACAGACACCATCTTTTGT wsxfull.13.2.variant  3909  GAGATGTAATTGTTTTTTCAGAGGGCGTGTTTTACCTCAAGTTTTTG wsxfull.13.2.variant  3959  TTTTGTACCAACACACACACACACATTCTTAACACATGTCCTTGTG wsxfull.13.2.variant  4009  TGTTTTGAGAGTATATTATGTATTTATTTGTGCTATCAGACTGTAGG wsxfull.13.2.variant  4059  ATTTGAAGTAGGACTTTCCTAAATGTTTAAGATAAACAGAATTC
```

FIG. 5M

Murine

| | | | |
|---|---|---|---|
| -213 | Sense: | GGGTTAAGTTTCCCACCC | (SEQ ID NO:9) |
| | Antisense: | GGGTGGGAAACTTAACCC | (SEQ ID NO:10) |
| | Scrambled: | AGGATACAGTGGGATCCC | (SEQ ID NO:11) |
| -99 | Sense: | GCCCGAGCACTCCTTTAA | (SEQ ID NO:12) |
| | Antisense: | TTAAAGGAGTGCTCCCGC | (SEQ ID NO:13) |
| | Scrambled: | GAGCGGCCCTGTTAGATA | (SEQ ID NO:14) |
| -20 | Sense: | GTATACACCTCTGAAGAA | (SEQ ID NO:15) |
| | Antisense: | TTCTTCAGAGGTGTACAC | (SEQ ID NO:16) |
| | Scrambled: | ATGCGAGGCTACTTCTAT | (SEQ ID NO:17) |
| +84 | Sense: | CTCTCCCTGGAAATTTAA | (SEQ ID NO:18) |
| | Antisense: | TTAAATTTCCAGGGAGAG | (SEQ ID NO:19) |
| | Scrambled: | ATTTGAAGGAGTTAAGCC | (SEQ ID NO:20) |
| +211 | Sense: | AATTTAATTCAAGTGGTA | (SEQ ID NO:21) |
| | Antisense: | TACCAGTTGAATTAAATT | (SEQ ID NO:22) |
| | Scrambled: | GTATCACTTCATAATATA | (SEQ ID NO:23) |

Human

| | | | |
|---|---|---|---|
| 5L | Sense: | GATGGTCAGGGTGAACTG | (SEQ ID NO:24) |
| | Antisense: | CAGTTCACCCTGACCATC | (SEQ ID NO:25) |
| | Scrambled: | GAGGCGAATGTGCGGATT | (SEQ ID NO:26) |
| +85 | Sense: | CTTAAATCTCCAAGGAGT | (SEQ ID NO:27) |
| | Antisense: | ACTCCTTGGAGATTTAAG | (SEQ ID NO:28) |
| | Scrambled: | AAGTCTTAAGCCAGACTT | (SEQ ID NO:29) |
| -47 | Sense: | TCTAAGGCACATCCCAGC | (SEQ ID NO:30) |
| | Antisense: | GCTGGGATGTGCCTTAGA | (SEQ ID NO:31) |
| | Scrambled: | CGCAATGAATTGACCCCC | (SEQ ID NO:32) |
| -20 | Sense: | TACTTCAGAGAAGTACAC | (SEQ ID NO:33) |
| | Antisense: | GTGTACTTCTCTGAAGTA | (SEQ ID NO:34) |
| | Scrambled: | GAATCACGGTAACTATCA | (SEQ ID NO:35) |
| +185 | Sense: | CAGCTGTCTCATAATGTC | (SEQ ID NO:36) |
| | Antisense: | GACATTATGAGACAGCTG | (SEQ ID NO:37) |
| | Scrambled: | TTCGTCAAGCCATCTGAT | (SEQ ID NO:38) |

FIG. 7

```
> sites: std
> length: 7127 (circular)

aluI
            sstI
            sacI
            hgiJII
            hgiAI/aspHI
            ecl136II
            bspl286
            bsiHKAI
            bmyI
            banII                                                                                                            thaI
            taqI          rmaI    tru9I                                                                                      fnuDII/mvnI
                          maeI    mseI                                                                                       bstUI
                          speI    aseI/asnI/vspI                                                           bslI              bshl236I
                                                                                                                             aclI maeIII
  1 TTCGAGCTCG CCCGACATTG ATTATTGACT AGTAATCAAT TACGGGGTCA TTAGTTCATA GCCCATATAT GGAGTTCCGC GTTACATAAG
    AAGCTCGAGC GGGCTGTAAC TAATAACTGA TCATTAGTTA ATGCCCCAGT AATCAAGTAT CGGGTATATA CCTCAAGGCG CAATGTATTG scrFI
              mvaI
              ecoRII
              dsaV
              aclI
              bglI bstNI                                    maeII
              sau96I                                        hinlI/acyI
              haeIII/palI aclI                              ahaII/bsaHI                      maeIII
              asuI apyI[dcm+]         sclI                  aatII          maeII
101 TTACGGTAAA TGGCCCGCCT GGGTGACGGC CCAACCACCC ACGTCAATAA TGACGTATGT TCCCATAGTA ACGGCAATAG GGACTTTCCA
    AATGCCATTT ACCGGGCGGA CCCACTGCCG GGTTGCTGGG TGCAGTTATT ACTGCATACA AGGGTATCAT TGCCGTTATC CCTGAAAGGT maeII
    hinlI/acyI                                                                     maeII
    ahaII/bsaHI                rsaI                                                hinlI/acyI
    aatII                      csp6I              bglI             ndeI            ahaII/bsaHI
                                                                   rsaI            aatII
                                                                   csp6I
201 TTGACGTCAA TGGGTGGAGT ATTTACGGTA AACTGCCCAC TTGGCAGTAC ATCAAGTGTA TCATATGCCA AGTACGCCCC CTATTGACGT CAATGACGGT
    AACTGCAGTT ACCCACCTCA TAAATGCCAT TTGACGGGTG AACCGTCATG TAGTTCACAT AGTATACGGT TCATGCGGGG GATAACTGCA GTTACTGCCA
```

FIG. 16A

```
                                                                                      nlaIII
                                                                                       ncoI
                              acII                                                    dsaI hphI  acII
                        bglI  dsaV                                             styI   bsaJI     sfaNI
                  sau96I bstNI       rsaI                                rsaI  maeII
                  haeIII/palI        csp6I                              csp6I  snaBI
           asuI   apyI(dcm+)   bsrI  nlaIII                                    bsaAI
301 AAATGGCCCG CCTGGCATTA TGCCCAGTAC ATGACCTTAT GGGACTTTCC TACTTGGCAG TACATCTACG TATTAGTCAT CGCTATTACC ATGGTGATGC
    TTTACCGGGC GGACCGTAAT ACGGGTCATG TACTGGAATA CCCTGAAAGG ATGAACCGTC ATGTAGATGC ATAATCAGTA GCGATAATGG TACCACTACG maeII
                                                            hinII/acyI                         nlaIV
                rsaI                          pleI          ahaII/bsaHI                        hgiCI
                csp6I          acII           hinfI         aatII                              banI
401 CGTTTTGGCA GTACATCAAT GGGCGTGGAT AGCGGTTTGA CTCACGGGGA TTTCCAAGTC TCCACCCCAT TGACGTCAAT GGGAGTTTGT TTTGGCACCA
    GCAAAACCGT CATGTAGTTA CCCGCACCTA TCGCCAAACT GAGTGCCCCT AAAGGTTCAG AGGTGGGGTA ACTGCAGTTA CCCTCAAACA AAACCGTGGT bsmAI                               aluI
                                                                                               sstI
                                                                                               sacI
                                                                                               hgiJII
                                                                                               hgiAI/aspHI
                                                                                               ecl136II
                                                                                               bsp1286
                                                           rsaI                                bs1HKAI
                                   acII                    csp6I          mnlI                 bmyI
                       maeIII      hgaI      acII                                              banII
501 AAATCAACGG GACTTTCCAA AATGTCGTAA CAACTCCGCC CCATTGACGC AAATGGGCGG TAGGCGTGTA CGGTGGGAGG TCTATATAAG CAGAGCTCGT
    TTTAGTTGCC CTGAAAGGTT TTACAGCATT GTTGAGGCGG GGTAACTGCG TTTACCCGCC ATCCGCACAT GCCACCCTCC AGATATATTC GTCTCGAGCA
```

```
                                                                                        eaml1051
                                                                                        sau96I
                                                         scrFI
                                                         mvaI   avaII
                                                                ecoRII
                                                                dsaV
                                                         bstNI  asuI          mboII  mboII
         scrFI                                           bsaJI  nlaIV         bpuAI  earI/ksp632I
         mvaI                                            apyI[dcm+]           bsrI   mnlI
         ecoRII
         dsaV
         bstNI                                  bspI286
         bsaI                    hphI     nlaIII    bspI286
         bsaJI                   maeIII   nspI     bmyI alwNI
         ddeI apyI[dcm+]         maeIII   nspHI
         mnlI bsaJI aciI bstEII
1401 GACCTCAGCC CTGGGTGCGG GACCACGCC CCAGTGGCTG TTTTGAGTGT GTACGGGTGG CACGGGTCGT GGACTTGAGG ACCCCCCTGG CAGTCAGAAG GAGAAGGGGG
162  AspLeuSerP roGlyCysGl yValThrAsp LysThrHisT hrCysProPr oCysProAla ProGluLeuL euGlyGlyPr oServalPhe LeuPheProPro
                            ^Insertion of a gly
                            "START OF HUMAN IgG1 CH2CH3
                                          sau96I
                                          nlaIV
                                   mspI
                                   hpaII
                                   scrFI
                                   ncII
                                   dsaV
                           sau3AI  avaII
                           mboI/ndeII(dam-)
                           nlaIII  cauII              nlaIII
                           rcaI dpnI[dam-]   mnlI     nspI                               drdI     mnlI         maeII
                    styI   bspHI[dam-]   ddeI  nspHI                              mboII  ddeI                  rsaI
                    bsaJI  mnlI dpnII[dam-] asuI ecoBII maeIII                    bpuAI  ecoBII                csp6I
                                              bsu36I/mstII/sauI           maeII   bbsI   bsu36I/mstII/sauI     bsrI bsaAI
1501 CAAAACCCAA GGACACCCTC ATGATCTCCC GGACCCCTGA GGTCACATGC GTGGTGGTGG ACGTGAGCCA CGAAGACCCT GAGGTCAAGT TCAACTGGTA
196  LysProLy  sAspThrLeu MetIleSerA rgThrProGl uValThrCys ValValValA spValSerHi sGluAspPro GluValLysP heAsnTrpTyr
```

```
                                                                                    scrFI
                                                                                    ncII
                                                                                    mspI
                                                                  mnII               hpaII
                                                                  scfI               dsaV
                              mspI                        pleI    mnII  mnII         dsaI
                              hpaII                       hinfI   mboII scfI         hphI
                              fnu4HI                mnII  pleI    nlaIV mboII scfI   aluI bsaJI
                              bbvI                                GGACTCCGAC CTCCCGTGCT GGCTCCTTCT TCCTCTACAG CAAGCTCACC
1901 CGTGGAGTGG GAGAGCAATG GGCAGCCCGG GAACAACTAC AAGACCACGC CTCCCGTGCT GACTCCGAC CCTGAGGCTG CCGAGGAAGA AGGAGATGTC GTTCGAGTGG
     GCACCTCACC CTCTCGTTAC CGTCGGGCC  CTTGTTGATG TTCTGGTGCG GAGGGCACGA                 GGACTCCGAC CCTGAGGCTG CCGAGGAAGA AGGAGATGTC GTTCGAGTGG
329  ValGluTrp GluSerAsnG lyGlnProGl uAsnAsnTyr LysThrThrP roProValLe uAspSerAsp GlySerPheP heLeuTyrSe rLysLeuThr mboII           nlaIII
                                          bpuAI           ppu10I                                 sapI
                              fnu4HI      maeII           nsiI/avaII                              mboII mnII        bsmAI
                              bbvI   xmnI bbsI     nlaIII sfaNI  mnII                            earI/ksp632I bsII cauII
                   bspMI      bbvI   asp700               nlaIII                    ctgcacaacc actacacgca gaagagcctc tccctgtctc
2001 GTGGACAGAA GCAGGTGGCA GCAGGGGAAC GTCTCTCAT GCTCCGTGAT GCATGAGGCT CTGCACAACC ACTACACGCA GAAGAGCCTC TCCCTGTCTC
     CACCTGTCTT CGTCCACCGT CGTCCCCTTG CAGAGAGTA CGAGGCACTA CGTACTCCGA CGTGTTGCTT TGATGTGCGT CTTCTCGGAG AGGGACAGAG
362  ValAspLysS erArgTrpGl nGlnGlyAsn ValPheSerC ysSerValMe tLeuHisAsnH isGluAla LeuHisAsnH isTyrThrGl nLysSerLeu SerLeuSerPro sau96I
                                                                                          nlaIII
                                                                                          fnu4HI haeIII/paII
                              taqI                                                        bgII styI                aluI
                              saII                                  pleI    scfI          sfII ncoI                fnu4HI
                              pleI       scfI                       rmaI    saII pstI     eaeI dsaI                bbvI
                        rmaI hincII/hindII  pstI                    xbaI    hincII/hindII cfrI bsaJI
                        sau96I hinfI     bsgI     aluI maeI accI bsgMI      hindIII hinfI bspMI      asuI
                        haeII/paII       hindIII  hinfI bspMI               hindIII acII bspMI
                  asuI maeI accI bspMI                                      aluI haeIII/paII
2101 CGGGTAAATG AGTGCGACGG CCCTAGAGTC CACCTGCAGA AGCTTTCTAGA GTCGACCTGC AGAAGCTTGG CCGCCATGGC CCAACTGTT TATTGCAGCT
     GCCCATTTAC TCACGCTGCC GGGATCTCAG GTGGACGTCT TCGAAGATCT CAGCTGGACG TCTTCGAACC GGCGGTACCG GGTTGAACAA ATAACGTCGA
396  GlyLys maeIII                                                                          rmaI
                               sfaNI   apoI                                                   bsmI maeI                      ~sv40 early poly A
2201 TATAATGGTT ACAAATGGTT ACAAATTTCA CAAATAAGC CAATAGCCATC ACAAATTCA CTGCATTCTA CTTCTGTGTT GTCCAAACTC ATCAATGTAT
     ATATTACCAA TGTTTACCAA TGTTTATTTC GTTATCGTAG TGTTTAAAGT TAAAAAAAGT GACGTAAGAT GAAGACACAA CAGGTTTGAG TAGTTACATA
```

```
                    scrFI
                    ncII             sau3AI
                    mspI             mboI/ndeII[dam-]
                    hpaII            dpnI[dam+]
                    dsaV             dpnII[dam-]                                                                        fnu4HI           sau3AI
                    cauII            bstYI/xhoII                                                                        fnu4HI           mboI/ndeII[dam-]
                    bsaJI            alwI[dam-]       hphI                                                              acII             dpnI[dam+]
                                                                                              rsaI            nlaIII   fnu4HI           dpnII[dam-]
                                                                                              csp6I           sfaNI    acII    bbvI     alwI[dam-]
3201 TTGGGGGAAG TGCCGGGGCA GGATCTCCTG TCATCCACC TTGCTCCTGC CGAGAAGTA TCCATCATGG CTGATGCAAT GCGGGGGCTG CATACGGTTG
     AACCCCCTTC ACGGCCCCGT CCTAGAGGAC AGTAGGAGTGG AACGAGGACG GCTCTTTCAT AGGTAGTACC GACTACGTTA CGCCCCCGAC GTATGCCAAC sau3AI
                                                                          bsaAI                                         mboI/ndeII[dam-]
                                                                          hgiAI/aspHI                                   dpnI[dam+]             sapI
                                                                          bsp1286                              fokI     dpnII[dam-]            mboI
                                              taqI     sfaNI    bmyI maeII      foKI       mspI    cfr10I      sau3AI   dpnII[dam-]  dpnII[dam-]  earI/ksp632I
     mspI                                                      bsiHKAI                    hpaII                mboI/ndeII[dam-] taqI[dam-] dpnII[dam-]
     hpaII bspMI   taqI                                                                                        dpnII[dam-]
3301 ATCGGGGTAC CTGCCCATTC GACCACCAAG CGAAACATCG CATCGAGCGA GCACGTACTC GGTCTCTGTC GATCAGGATG ATCTGGACGA
     TAGCCCCATG GACGCGGTAAG CTGGTGGTTC GCTTTGTAGC GTAGCTCGCT CGTGCATGAG CCAGAACAG CTAGTCCTAC TAGACCTGCT sphI
                                      nspI                                      sau3AI
                                      nspHI                                     mboI/ndeII[dam-]
                                      hinPI                                     dpnI[dam+]              styI
                                      hhaI/cfoI                                 dpnII[dam-]   ncoI
                     hinPI            thaI                scrFI    fnuDII/mvnI                bstYI/xhoII  dsaI
                     thaI             fnuDII/mvnI  mvaI   ecoRII   bsh1236I                   alwI[dam-]           bsaJI    sfaNI
                     bstUI            bstUI               dsaV    hinPI   nlaIII              mnII       maeIII    nlaIII
                hgiJII                bmyI         bsp1286 bstNI  hhaI/cfoI  bssHII
        sfaNI   banII  hhaI/cfoI      banII  hhaI/cfoI     apyI[dcm+]
3401 AGACCATCAG GGGCTCGCGC CAGCCGAACT GTTCGGACGC CTCAAGGGCC GCATGCCCGA CGGCGAGGAT CTCGTCGTGA CCATGGCGA TGCCTGCTTG
     TCTGGTAGTC CCCGAGCGCG GTCGGCTTGA CAAGCCTGCG GAGTTCCCGG CGTACGGGCT GCCGCTCCTA GAGCAGCACT GGTACCGCT ACGGACGAAC
```

FIG. 16L

```
                                                            mspI
                                                            hpaII                    bsII
                                                            naeI                     sau96I
                                          acII              cfr10I                   avaII
                                          fnu4HI            haeIII/palI              asuI
                                          haeIII/palI       eaeI                     rsrII/cspI
                         eaeI   tfII      cfrI              cfrI                     cpoI                         hinPI
             nlaIII      cfrI   hinfI     taqI                                       acII acII                    hhaI/cfoI
3501 CCGAATATCA TGGTGGAAAA TCGCCGGCTTT TCTGGATTCA TCGACTGTGG CCGGCTCGGT GTGGGCTGGA CATAGGGTTG GCTACCCGTG
     GGCTTATAGT ACCACCTTTT AGCGGCCGAAA AGACCTAAGT AGCTGACACC GGCCGAGCCA CACCCGACCT GTATCCCAAC CGATGGGCAC sapI
         mboII  fnu4HI                                                              bsrBI                    hinfI bbvI sfaNI
         earI/ksp632I                                                               acII    tfII fnu4HI
         eco57I aluI acII                             acrI    mnlI                  fnu4HI  hinfI
3601 ATATTGCTGA AGAGCTGGCC CTGCCGGCTT CCTCGTGCTT TACGGTATCG CCGCTCCCGA TTCGCAGCGC ATCGCCTTCT ATCGCCTTCT
     TATAAGCACT TCTCGACCGG GACGGCCGAA GGAGCACGAA ATGCCATAGC GGCGAGGGCT AAGCGTCGCG TAGCGGAAGA TAGCGGAAGA taqI
                              sfuI
                   acII       bstBI        hinII/acyI
             ddeI  pleI       bsiCI        hgaI bspMI                                              tfII   acII
         mboII bsrBI hinfI    asuII        ahaII/bsaHI                                             hinfI  fnu4HI
                                                                                                   taqI  acII
3701 TGACGAGTTC TTCTGAGCGG GACTCTGGGG TTCGAAATGA CCGACCAAGC CTGCCATCAC GAGATTTCGA TTCCACCGCC GCCTTCTATG
     ACTGCTCAAG AAGACTCGCC CTGAGACCCC AAGCTTTACT GGCTGGTTCG GACGGTAGTG CTCTAAAGCT AAGGTGGCGG CGGAAGATAC

```
                                                                                                          aciI
                                                                                                          thaI
                                                                                                          fnuDII/mvnI
                                                                                                          bstUI
                                                                                                          sacII/sstII
                                                                                haeIII/palI bshI236I
                                                                                    mcrI      nspBII
                                                                                    dsaI      kspI
                                                                                    bsaJI     dsaI
                                                                            hphI eagI/xmaIII/eclXI
                                                                            maeII eaeI    bsaJI
                                                                            bstEII cfrI   aciI
                              mnlI   hinPI
                              rsaI   hhaI/cfoI
                     mboII    cspGI  haeI   eco47III
     mspI                                                                                                           hinPI  mspI
     hpaII                                                                                                          hhaI/cfoI
     aciI     bsII    sfaNI                                                                                         hpaII
     fnu4HI                                                                                                         fnuDII/mvnI
                                                                                                                    bstUI  bsaWI
                                                                                                     thaI           bshI236I
                                                                                              mboII                 aciI bslI
                                                                                              bpuAI          fnu4HI
                                                                                              bbsI          aciI bcgI  nlaIII          alu I
                                                                nlaIII
4401 GCGGCCGGAC GAACTAAACC TGACTACGGC ATCTCTGCCC CTTCTTCGCT GGTACGAGGA GCGCTTTTGT TTTGTATTGG TCACCACGGC CGAGTTTCCG
     CGCCGGCCTG CTTGATTTGG ACTGATGCCG TAGAGACGGG GAAGAAGCGA CCATGCTCCT CGCGAAAACA AAACATAACC AGTGGTGCCG GCTCAAAGGC
        scrFI    nlaIV
        ncII     hgiCI
        dsaV     scrFI
                 mvaI
        cauII
        bslI     ecoRII
        bslI     dsaV
        bsaJI    bstNI
     sau96I      bsaJI
     nlaIV haeIII/palI
     avaII eaeI
     asuI cfrI   bspI286
     ppuMI mspI apyI(dcm+)
     nlaIV hpaII bmyI
     eco0109I/dzaII banI
                                                                          mboII
                                                                          bpuAI
                                                                          bbsI                           fnu4HI
                                                                 nlaIII                                  aciI bcgI   nlaIII         aluI
4501 CGGGACCCCG GCCAGGGCAC CTGTCCTACG AGTTGCATGA TAAAGAAGAC AGTCATAAGT GCGGCGACGA TAGTCATGCC CCGGCGCCAC CGGAAGGAGC
     GCCCTGGGGC CGGTCCCGTG GACAGGATGC TCAACGTACT ATTTCTTCTG TCAGTATTCA CGCCGCTGCT ATCAGTACGG GGCCGCGGTG GCCTTCCTCG
     ~pBR322 sequence
```

```
                                                                                      thaI
                                                                                      fnuDII/mvnI
                                          tru9I                              tru9I    apoI tru9I
                                          mseI                               mseI     mseI bstUI  mseI
                         haeIII/palI               alu1         tru9I        apoI     bsh1236I   sspI
5001 GGGCTATTCT TTTGATTTAT AAGGGATTTT GCCGATTTCG TAAAAAATGA GCTGATTTAA CAAAAATTTA ACGGAATTG TAACAAAATA
     CCCGATAAGA AAACTAATAA TTCCCTAAAA CGGCTAAAGC ATTTTTTACT CGACTAAATT GTTTTTAAAT TGCCTTAAC ATTGTTTTAT
     maeII
     psp1406I              mnlI                                                       maeII
     tru9I                 haeIII/palI                                                hinII/acyI
     mseI          stuI                             tru9I   rcaI                      ahaII/bsaHI
                   haeI                             mseI    bspHI            ddeI  aatII
5101 TTAACGTTTA CAATTTATG GTGCAGGCCT CGTGATAAGC CTATTTTTAT AGTTAATGT CATGATAATA ATGGTTTCTT AGACGTCAGG TGGCACTTTT
     AATTGCAAAT GTTAAAATAC CACGTCCGGA GCACTATGCG GATAAAAATA TCCAATTACA GTACTATTAT TACCAAAGAA TCTGCAGTCC ACCGTGAAAA
                       "delta 2a"
          nlaIV
          aciI
          thaI
          fnuDII/mvnI
          bstUI
          bsh1236I                                                           rcaI
          hinPI                                                              bspHI                         sspI
          hhaI/cfoI                                                   bsrBI  bsmAI
                                                                      aciI  nlaIII
5201 CGGGGAAATG TGCGCGGAAC CCCTATTGT TTATTTTCT AAATATGTAT CCGCTCATGA GACAATAACC CTGATAAATG CTTCAATAAT
     GCCCCTTTAC ACGCGCCTTG GGGATAACA AATAAAAGA TTTATACATA GGCGAGTACT CTGTTATTGG GACTATTTAC GAAGTATTA
                                                                     fnu4HI
                                                                     aciI                hphI
     mboII
     earI/xsp632I
5301 ATTGAAAAAG GAAGAGTATG AGTATTCAAC ATTTCCGTGT CGCCCTTATT CCCTTTTTG CGGCATTTTG CCTTCCTGTT TTTGCTCACC CAGAAACGCT
     TAACTTTTTC CTTCTCATAC TCATAAGTTG TAAAGGCACA GCGGGAATAA GGGAAAAAAC GCCGTAAAAC GGAAGGACAA AAACGAGTGG GTCTTTGCGA
                                 hgiAI/aspHI
                                 bsp1286
                                 bsiHKAI                             sau3AI
                    sau3AI                                           mboI/ndeII[dam-]   sau3AI
                    mboI/ndeII[dam-]                                 dpnI[dam+]         mboI/ndeII[dam-]
                    dpnI[dam+]                                       dpnII[dam-]        dpnI[dam+]
                    dpnII[dam-]                                      bstYI/xhoII        dpnII[dam-]
                             apaLI/snoI                              bsrI   nspBI      alwI[dam-]
          eco57I             alw44I/snoI     maeIII   taqI     alwI[dam-]  aciI        bstYI/xhoII       mboII
     bphI       sfaNI mboII[dam-]                                                                        mboII
5401 GGTGAAAGTA AAAGATGCTG AAGATCAGTT GGGTGCACGA GTGGGTTACA TCGAACTGGA TCTCAACAGC GGTAAGATCC TTGAGAGTTT TCGCCCCGAA AGCGGGGCTT
     CCACTTTCAT TTTCTACGAC TTCTAGTCAA CCCACGTGCT CACCCAATGT AGCTTGACCT AGAGTTGTCG CCATTCTAGG AACTCTCAAA AGCGGGGCTT
```

```
                                                                scrPI
                                                                ncII
                                                                mspI
                                                  acII          hpaII
                                                  thaI          dsaV
                                                  fnuDII/mvnI   cauII
                              hglAI/aspHI         bstUI         hinII/acyI
         maeII                bspl286   tru9I     bshl236I      hgaI                        acII
         psp1406I             bsiHKAI   mseI      hinPI         ahaII/bsaHI   bcgI   mcrI   fnu4HI
         xmnI                 bmyI      ahaII/draI hhaI/cfoI                                                    fnu4HI
         asp700                                                                                                 bbvI          nlaIII
5501 GAAGGTTTC CAATGATGAG GTTCTGCTAT GTGGCGCGG ATTATCCCGT GATGACGCCG GCAAGAGCA ACTCGGTCGC CGCATACACT
     CTTGCAAAAG GTACTACTC CAAGACGATA CACCGCGCCA TAATAGGGCA CTACTGCGGC CCGTTCTCGT TGAGCCAGCG GCGTATGTGA rsaI
                    csp6I  bsrI                                                                    fnu4HI
             ddeI   scaI   hphI  maeIII                    sfaNI     fokI nlaIII                   bbvI           nlaIII
5601 ATTCTCAGAA TGACTCGGTT GAGTACTCAC CAGTCACAGA AAAGCATCTT ACGGATGGCA TGACAGTGGA AGAATTATGC AGTGCTGCCA TAACCATGAG
     TAAGAGTCTT ACTGAACCAA CTCATGAGTG GTCAGTGTCT TTTCGTAGAA TGCCTACCGT ACTGTCATTC TCTTAATACG TCACGACGGT ATTGGTACTC sau96I
                                              avaII
                                              asuI
                                     sau3AI
                                     mboI/ndeII[dam-]                                                    nlaIII
                          haeIII/palI dpnI[dam+]                                                         sau3AI maeIII            sau3AI
                          eaeI        dpnII[dam-]                                                        mboI/ndeII[dam-]         mboI/ndeII[dam-]
                          cfrI        pvuI/bspCI                                                         dpnI[dam+]               dpnI[dam+]
                          fnu4HI      mcrI   mnlI                         alui  acII                     alwI[dam-]               dpnII[dam-]
                          acII                                                                           nlaIII dpnII[dam-]       dpnII[dam-]
5701 TGATAACACT GGGCCAACTT TACTTCTGAC AACGATCGGA GGACCGAAGG AGCTTACCGC TTTTTTGCAC ATCATGTAAC TCGCCTTGAT
     ACTATTGTGA CCCGGTTGAA ATGAAGACTG TTGCTAGCCT CCTGGCTTCC TCGAATGGCG AAAAAACGTG TAGTACATTG AGCGGAACTA hinPI
                                                                                                   mstI
         nspI                                                                                      aviII/fspI    bsrI
         hpaII                                                                                     maeII hhaI/cfoI tru9I
         bsaWI    aluI                                        maeIII              fnu4HI           psp1406I      mseI
         nlaIV                                                                    bbvI
5801 CCTTGGCAAC TGAAGCCATA CCAAACGACC ACCGTGACAC CGGCAATGCCA CAGCAATGCC AACAACGTT GGCAAACTA TTAACTGGGG
     GGAACCGTTG ACTTCGGTAT GGTTTGCTGG TGGCACTGTG GCCGTTACC GTCGTTACGG CGTTGTTGCAA CCGTTTGAT AATTGACCGC
```

FIG. 16T

```
                                                              sau3AI
                                                              mboI/ndeII(dam-)
                                                   dpnI(dam+)   sau3AI             thaI
                                                   dpnII(dam-)  mboI/ndeII(dam-)
                                         bstYI/xhoI            dpnI(dam+)          fnuDII/mvnI
                                 sau3AI  alwI(dam-)            dpnII(dam-)         bstUI                fnu4HI
                                 mboI/ndeII(dam-)              alwI(dam-)          bsh1236I            bbvI
                                 dpnI(dam+) mboI(dam-)                              hinPI
                    ddeI bgaI    dpnII(dam-)                   bstYI/xhoI          hhaI/cfoI 6301 TTCGTTCCAC TGAGCGTCAG ACCCGTAGA AAGATCAAA GGATCTCTT GAGATCCTTT TTTTCTGCGC GTAATCTGCT GCTTGCAAAC AAAAAAACCA
     AAGCAAGGTG ACTCGCAGTC TGGGCCATCT TTTCTAGTTT CCTAGAGAA CTCTAGGAAA AAAAGACGCG CATTAGACGA CGAACGTTTG TTTTTTTGGT sau3AI
                                 mboI/ndeII(dam-)
                                 dpnI(dam+)
                                 dpnII(dam-)
                                 alwI(dam-)
              mspI                                                                                                rmaI
     acII     hpaII   aluI                                                              bsrI      hinPI           maeI
     acII  nspBII                                                             maeIII   eco57I   hhaI/cfoI 6401 CGGCTACCGG CGGTGGTTTG TTTGCCGGAT CAAGAGCTAC CAACTCTTTT TCCGAAGGTA ACTGGCTTCA GCAGAGCGCA GATACCAAAT ACTGTCCTTC
     GCCGATGGCC GCCACCAAAC AAACGGCCTA GTTCTCGATG GTTGAGAAAA AGGCTTCCAT TGACCGAAGT CGTCTCGCGT CTATGGTTTA TGACAGGAAG fnu4HI
                                                                                        alwNI      bbvI
              haeIII/palI                                                               bsrI      fnu4HI          bsrI
     bslI    haeI                       scfI      aciI     mnlI                         maeIII    bbvI          bsrI 6501 TAGTGTAGCC GTAGTTAGGC CACCACTTCA AGAACTCTGT AGCACCGCCT ACATACCTCG CTCTGCTAAT CCTGTTACCA GTGGCTGCTG CCAGTGGCGA
     ATCACATCGG CATCAATCCG GTGGTGAAGT TCTTGAGACA TCGTGGCGGA TGTATGGAGC GAGACGATTA GGACAATGGT CACCGACGAC GGTCACCGCT mcrI                                 hglAI/aspHI
                  scrFI                                    nspBII                               bsp1286
                  ncII                          mspI       fnu4HI                               bsiHKAI
                  mspI                          hpaII      bbvI                                 bmyI
                  hpaII           bsaWI                    hinPI  aciI                          apaLI/snoI
                  dsaV            maeII                    hhaI/cfoI                            alw44I/snoI   aluI
                  cauII   pleI                                                                                
                          hinfI 6601 TAAGTCGTGT CTTACGGGGT TGGACTCAAG ACGATAGTTA CCGGATAAGG CCGACGGGTC GGGCTGAACG GGGGTTCGTG CCACACAGCC CAGCTTGGAG
     ATTCAGCACA GAATGCCCCA ACCTGAGTTC TGCTATCAAT GGCCTATTCC GGCTGCCCAG CCCGACTTGC CCCCAAGCAC GGTGTGTCGG GTCGAACCTC
```

FIG. 16U

```
                                                             hinPI                                              mspI
                                                      ddeI   hhaI/cfoI                                          hpaII
                                                      scfI   haeII                              acII            bsII       fnu4HI
6701 CGAACGACCT ACACGGAACT GAGATACCTA CAGGGTGAGC ATTGAGAAAG CGCCACGCTT CCCGAAGGGA GAAAGGGGGA CAGTATCCG GTAAGGGCA
     GCTTGCTGGA TGTGCCTTGA CTCTATGGAT GTCCCACTCG TAACTCTTTC GCGGTGCGAA GGGCTTCCCT CTTTCCCCCT GTCCATAGGC CATTCGCCGT scrFI
                              mvaI                           scrFI                                              taqI
                              ecoRII mvaI                    bstNI                          mnII drdI           hgaI
                              dsaV   ecoRII                  dsaV                                               tru9I
                       hinPI  bstNI  dsaV                    apyI[dcm+]                                         mseI
              hhaI/cfoI mnII  bsaJI  apyI[dcm+]                                                       hinPI     aseI/asnI/vspI
6801 GGGTCGGAAC AGGAGGAGC TCCAGGGGG AACGCCTGG TATCTTTATA GTCCTGTCGG GTTTCGCCAC CTCTGACTG AGGGTCGATT
     CCCAGCCTTG TCCTCCTCG AGGTCCCCC TTTGCGGACC ATAGAAATAT CAGGACAGCC CAAAGCGGTG GAGACTGAAC TCGAGCTAA nlaIV            aluI
                       acII             pvuII                                                      hinPI
6901 TTTGTGATGC TGGTCAGGGG GGGGAGCCT ATGGAAAAAC GCCAGCTGGC TCCCGACTGG ACGACAGGTT AAAGGGGCA GTGAGGCCAA CGGAATTAAT
     AAACACTACG AGCAGTCCCC CCCCTCGGA TACCTTTTTG CGGTCGACCG AGGGCTGACC TGCTGTCCAA TTTCGCCGT CACTCCGGTT GCCTTAATTA
                                                                  ^deltaI.PVU scrFI
                         mvaI
                         ecoRII                                          mspI           acII
                         dsaV                                            hpaII          bsrBI
              nlaIV      bstNI
              hgiCI apyI[dcm+]
       mnII   banI bsaJI
       maeIII
7001 GTGAGTTACC TCACTCATTA GGCACCCCAG GCTTTACACT TTATGCTTCC GGCTCGTATG TTGTGTGGAA TTGTGAGCGG ATAACAATTT CACACAGGAA
     CACTCAATGG AGTGAGTAAT CCGTGGGGTC CGAAATGTGA AATACGAAGG CCGAGCATAC AACACACCTT AACACTCGCC TATTGTTAAA GTGTGTCCTT tru9I
                    mseI
                    aseI/asnI/vspI
              xmnI
        aluI  asp700
        nlaIII
7101 ACAGGTATGA CCATGATTAC GAATTAA
     TGTCCATACT GGTACTAATG CTTAATT >length: 7127
```

FIG. 16V

SEQ ID NO: 3

```
hWSXR   1  M I C Q K F C V V L L H W E F I Y V I T A F N L S Y P I T P W R F K L S C M P P N S T Y D Y F L P
mWSXR   1  M M C Q K F Y V V L L H W E F L Y V I A A L N L A Y P I S P W K F K L F C G P P N T T D D S F L S P

51  A G L S K N T S N S N G H Y E T A V E P K F N S S G T H F S N L S K T T F H C C F R S E Q D R N C S
       51  A G A P N N A S A L K G A S E A I V E A K F N S S G I Y V P E L S K T V F H C C F G N E Q G Q N C S

101  L C A D N I E G K T F V S T V N S L V F Q Q I D A N W N I Q C W L K G D L K L F I C Y V E S L F K N
      101  A L T D N T E G K T L A S V V K A S V F R Q L G V N W D I E C W M K G D L T L F I C H M E P L P K N

151  L F R N Y N Y K V H L L Y V L P E V L E D S P L V P Q K G S F Q M V H C N C S V H E C C E C L V P V
      151  P F K N Y D S K V H L L Y D L P E V I D D S P L P P L K D S F Q T V Q C N C S L R G - C E C H V P V

201  P T A K L N D T L L M C L K I T S G G V I F Q S P L M S V Q P I N M V K P D P P L G L H M E I T D D
      200  P R A K L N Y A L L M Y L E I T S A G V S F Q S P L M S L Q P M L V V K P D P P L G L H M E V T D D

251  G N L K I S W S S P P L V P F P L Q Y Q V K Y S E N S T T V I R E A D K I V S A T S L L V D S I L P
      250  G N L K I S W D S Q T M A P F P L Q Y Q V K Y L E N S - T I V R E A A E I V S A T S L L V D S V L P

301  G S S Y E V Q V R G K R L D G P G I W S D W S T P R V F T T Q D V I Y F P P K I L T S V G S N V S F
      299  G S S Y E V Q V R S K R L D G S G V W S D W S S P Q V F T T Q D V V Y F P P K I L T S V G S N A S F

351  H C I Y K K E N K I V P S K E I V W W M N L A E K I P Q S Q Y D V V S D H V S K V T F F N L N E T K
      349  H C I Y K N E N Q I I S S K Q I V W W R N L A E K I P E I Q Y S I V S D R V S K V T F S N L K A T R

401  P R G K F T Y D A V Y C C N E H E C H H R Y A E L Y V I D V N I N I S C E T D G Y L T K M T C R W S
      399  P R G K F T Y D A V Y C C N E Q A C H H R Y A E L Y V I D V N I N I S C E T D G Y L T K M T C R W S

451  T S T I Q S L A E S T L Q L R Y H R S S L Y C S D I P S I H P I S E P K D C Y L Q S D G F Y E C I F
      449  P S T I Q S L V G S T V Q L R Y H R R S L Y C P D S P S I H P T S E P K N C V L Q R D G F Y E C V F

501  Q P I F L L S G Y T M W I R I N H S L G S L D S P P T C V L P D S V V K P L P P S S V K A E I T I N
      499  Q P I F L L S G Y T M W I R I N H S L G S L D S P P T C V L P D S V V K P L P P S N V K A E I T V N

551  I G L L K I S W E K P V F P E N N L Q F Q I R Y G L S G K E V Q W K M Y E V Y D A K S K S V S L P V
      549  T G L L K V S W E K P V F P E N N L Q F Q I R Y G L S G K E I Q W K T H E V F D A K S K S A S L L V

601  P D L C A V Y A V Q V R C K R L D G L G Y W S N W S N P A Y T V V M D I K V P M R G P E F W R I I N
      599  S D L C A V Y V V Q V R C R R L D G L G Y W S N W S S P A Y T L V M D V K V P M R G P E F W R K M D

651  G D T M K K E K N V T L L W K P L M K N D S L C S V Q R Y V I N H H T S C N G T W S E D V G N H T K
      649  G D V T K K E R N V T L L W K P L T K N D S L C S V R R Y V V K H R T A H N G T W S E D V G N R T N

701  F T F L W T E Q A H T V T V L A I N S I G A S V A N F N L T F S W P M S K V N I V Q S L S A Y P L N
      699  L T F L W T E P A H T V T V L A V N S L G A S L V N F N L T F S W P M S K V S A V E S L S A Y P L S

751  S S C V I V S W I L S P S D Y K L M Y F I I E W K N L N E D G E I K W L R I S S S V K K Y I H D H
      749  S S C V I L S W T L S P D D Y S L L Y L V I E W K I L N E D D G M K W L R I P S N V K K F Y I H D N

801  F I P I E K Y Q F S L Y P I F M E G V G K P K I I N S F T Q D D I E K H Q S D A G L Y V I V P V I I
      799  F I P I E K Y Q F S L Y P V F M E G V G K P K I I N G F T K D A I D K Q Q N D A G L Y V I V P I I I

851  S S S I L L L G T L L I S H Q R M K K L F W E D V P N P K N C S W A Q G L N F Q K R T D I L
      849  S S C V L L L G T L L I S H Q R M K K L F W D D V P N P K N C S W A Q G L N F Q K R T D T L
```

SEQ ID NO: 51

FIG. 21

| | | |
|---|---|---|
| 17.scfv | 1 | QVRLQQSGGGLVQPGRSLRLSCAASGRFTD*DYAMH*WVRQAPGKGLEWVSG |
| 3.scfv | 1 | EVQLVQSGAEVKKPGASVKVSCKASGYTFT *GYYMY*WVRQAPGQGLEWMGW |
| 4.scfv | 1 | EVQLVQSGAEVKKPGESLKISCQGSGFTFS *SYKMN*WVRQAPGKGLEWMGG |

CDR H1

| | | |
|---|---|---|
| 17.scfv | 51 | MT*WNSGS*IGYADSVKGRFTISRDNAKNSLYLQMNSLRAEDTAVYYCAREP |
| 3.scfv | 51 | IN*PNSGG*TNYAQKFQGRVTMTRDTSIGTAYMELSRLSSDDTAVYYCARDR |
| 4.scfv | 51 | II*PIFG*TANYAQKFQGRVTITADESTSTAYMELSSLRSEDTAVYYCARDR |

CDR H2

| | | |
|---|---|---|
| 17.scfv | 101 | *HNTDA--------FDI*WGRGTLVTVSSGGGGPGGGGSGGGGSDVVMTQSP |
| 3.scfv | 101 | *YYGSSAYHRGSYYMDV*WGRGTLVTVSSGGGGTGGGGSGGGGS-SELTQDP |
| 4.scfv | 101 | *VVVPATSLRGG--MDV*WGQGTTVTVSSGGGGSGGGGSGGGGSQSVLTQPA |

CDR H3

| | | |
|---|---|---|
| 17.scfv | 143 | SFLSAFVGDTITITCRASQ---*GIYNYLA*WYQQKPGKAPKLLIY*AASTLQ* |
| 3.scfv | 150 | A-VSVALGQTVRITCQGDS--*LRSY-YAS*WYQQKPGQAPVLVIY*GKNNRP* |
| 4.scfv | 149 | S-VSGSPGQSITISCTG*TSSDVGGYNYVS*WYQQHPGKAPKLMIY*EGSKRP* |

CDR L1                  CDR L2

| | | |
|---|---|---|
| 17.scfv | 190 | SGVPSRFSGSGSGTEFTLTISSLQPEDFGTYYC *QQLI--SYPLT*FGGGTK |
| 3.scfv | 196 | SGIPDRFSGSSSGNTASLTITGAQAEDEADYYC *NSRDSSGNHVV*FGGGTK |
| 4.scfv | 198 | SGVSNRFSGSKSGSTASLTISGLQAEDEADYYC *SSYTTRSTR-*VFGGGTK |

CDR L3

| | | | |
|---|---|---|---|
| 17.scfv | 238 | VEIK | SEQ ID NO: 50 |
| 3.scfv | 246 | LTVL | SEQ ID NO: 48 |
| 4.scfv | 247 | LTVL | SEQ ID NO: 49 |

FIG. 25

SEQUENCE LISTING

<160> NUMBER OF SEQ ID NOS: 51

<210> SEQ ID NO 1
<211> LENGTH: 4102
<212> TYPE: DNA
<213> ORGANISM: Homo sapiens

<400> SEQUENCE: 1

```
gaattctcga gtcgacggcg ggcgttaaag ctctcgtggc attatccttc agtggggcta      60
ttggactgac ttttcttatg ctgggatgtg ccttagagga ttatgggtgt acttctctga     120
agtaagatga tttgtcaaaa attctgtgtg gttttgttac attgggaatt tatttatgtg     180
ataactgcgt ttaacttgtc atatccaatt actccttgga gatttaagtt gtcttgcatg     240
ccaccaaatt caacctatga ctacttcctt ttgcctgctg gactctcaaa gaatacttca     300
aattcgaatg gacattatga gacagctgtt gaacctaagt ttaattcaag tggtactcac     360
ttttctaact tatccaaaac aactttccac tgttgctttc ggagtgagca agatagaaac     420
tgctccttat gtgcagacaa cattgaagga aagacatttg tttcaacagt aaattcttta     480
gtttttcaac aaatagatgc aaactggaac atacagtgct ggctaaaagg agacttaaaa     540
ttattcatct gttatgtgga gtcattattt aagaatctat tcaggaatta taactataag     600
gtccatcttt tatatgttct gcctgaagtg ttagaagatt cacctctggt tccccaaaaa     660
ggcagttttc agatggttca ctgcaattgc agtgttcatg aatgttgtga atgtcttgtg     720
cctgtgccaa cagccaaact caacgacact ctccttatgt gtttgaaaat cacatctggt     780
ggagtaattt tccagtcacc tctaatgtca gttcagccca taaatggt gaagcctgat     840 ccaccattag gtttgcatat ggaaatcaca gatgatggta atttaaagat ttcttggtcc     900
agcccaccat tggtaccatt tccacttcaa tatcaagtga aatattcaga gaattctaca     960
acagttatca gagaagctga caagattgtc tcagctacat ccctgctagt agacagtata    1020
cttcctgggt cttcgtatga ggttcaggtg aggggcaaga gactggatgg cccaggaatc    1080
tggagtgact ggagtactcc tcgtgtcttt accacacaag atgtcatata ctttccacct    1140
aaaattctga caagtgttgg gtctaatgtt tcttttcact gcatctataa gaaggaaaac    1200
aagattgttc cctcaaaaga gattgtttgg tggatgaatt tagctgagaa aattcctcaa    1260
agccagtatg atgttgtgag tgatcatgtt agcaaagtta ctttttttcaa tctgaatgaa    1320
```

```
accaaacctc gaggaaagtt tacctatgat gcagtgtact gctgcaatga acatgaatgc   1380
catcatcgct atgctgaatt atatgtgatt gatgtcaata tcaatatctc atgtgaaact   1440
gatgggtact taactaaaat gacttgcaga tggtcaacca gtacaatcca gtcacttgcg   1500
gaaagcactt tgcaattgag gtatcatagg agcagccttt actgttctga tattccatct   1560
attcatccca tatctgagcc caaagattgc tatttgcaga gtgatggttt ttatgaatgc   1620 atttttccagc caatcttcct attatctggc tacacaatgt ggattaggat caatcactct   1680
ctaggttcac ttgactctcc accaacatgt gtccttcctg attctgtggt gaagccactg   1740
cctccatcca gtgtgaaagc agaaattact ataaacattg gattattgaa atatcttgg    1800 gaaaagccag tctttccaga gaataacctt caattccaga ttcgctatgg tttaagtgga   1860
aaagaagtac aatggaagat gtatgaggtt tatgatgcaa aatcaaaatc tgtcagtctc   1920
ccagttccag acttgtgtgc agtctatgct gttcaggtgc gctgtaagag gctagatgga   1980
ctgggatatt ggagtaattg gagcaatcca gcctacacag ttgtcatgga tataaaagtt   2040
cctatgagag gacctgaatt ttggagaata attaatggag atactatgaa aaaggagaaa   2100
aatgtcactt tactttggaa gcccctgatg aaaaatgact cattgtgcag tgttcagaga   2160
tatgtgataa accatcatac ttcctgcaat ggaacatggt cagaagatgt gggaaatcac   2220
acgaaattca ctttcctgtg gacagagcaa gcacatactg ttacggttct ggccatcaat   2280
tcaattggtg cttctgttgc aaattttaat ttaacctttt catggcctat gagcaaagta   2340
aatatcgtgc agtcactcag tgcttatcct ttaaacagca gttgtgtgat tgtttcctgg   2400
atactatcac ccagtgatta caagctaatg tattttatta ttgagtggaa aaatcttaat   2460
gaagatggtg aaataaaatg gcttagaatc tcttcatctg ttaagaagta ttatatccat   2520 gatcattta tccccattga gaagtaccag ttcagtcttt acccaatatt tatggaagga   2580
gtgggaaaac caaagataat taatagtttc actcaagatg atattgaaaa acaccagagt   2640
gatgcaggtt tatatgtaat tgtgccagta attatttcct cttccatctt attgcttgga   2700
acattattaa tatcacacca aagaatgaaa aagctatttt gggaagatgt tccgaacccc   2760
aagaattgtt cctgggcaca aggacttaat tttcagaagc cagaaacgtt tgagcatctt   2820
tttatcaagc atacagcatc agtgacatgt ggtcctcttc ttttggagcc tgaaacaatt   2880
tcagaagata tcagtgttga tacatcatgg aaaaataaag atgagatgat gccaacaact   2940
gtggtctctc tactttcaac aacagatctt gaaaagggct ctgtttgtat tagtgaccag   3000
ttcaacagtg ttaacttctc tgaggctgag ggtactgagg taacctatga ggacgaaagc   3060
cagagacaac cctttgttaa atacgccacg ctgatcagca actctaaacc aagtgaaact   3120
ggtgaagaac aagggcttat aaatagttca gtcaccaagt gcttctctag caaaaattct   3180
ccgttgaagg attctttctc taatagctca tgggagatag aggcccaggc attttttata   3240
ttatcagatc agcatcccaa cataatttca ccacacctca cattctcaga aggattggat   3300
gaacttttga aattggaggg aaatttccct gaagaaaata atgataaaaa gtctatctat   3360
tatttagggg tcacctcaat caaaaagaga gagagtggtg tgcttttgac tgacaagtca   3420
agggtatcgt gcccattccc agcccctgt ttattcacgg acatcagagt tctccaggac   3480
agttgctcac actttgtaga aaataatatc aacttaggaa cttctagtaa gaagacttt    3540 gcatcttaca tgcctcaatt ccaaacttgt tctactcaga ctcataagat catggaaaac   3600
aagatgtgtg acctaactgt gtaatttcac tgaagaaacc ttcagatttg tgttataatg   3660
```

-continued

```
ggtaatataa agtgtaatag attatagttg tgggtgggag agagaaaaga aaccagagtc    3720
aaatttgaaa ataattgttc caaatgaatg ttgtctgttt gttctctctt agtaacatag    3780
acaaaaaatt tgagaaagcc ttcataagcc taccaatgta gacacgctct tctattttat    3840
tcccaagctc tagtgggaag gtcccttgtt tccagctaga aataagccca acagacacca    3900
tcttttgtga gatgtaattg ttttttcaga gggcgtgttg ttttacctca agttttgtt     3960 ttgtaccaac acacacacac acacacattc ttaacacatg tccttgtgtg ttttgagagt    4020
atattatgta tttatatttt gtgctatcag actgtaggat ttgaagtagg actttcctaa    4080
atgtttaaga taaacagaat tc                                             4102
```

<210> SEQ ID NO 2
<211> LENGTH: 1165
<212> TYPE: PRT
<213> ORGANISM: Homo sapiens

<400> SEQUENCE: 2

```
Met Ile Cys Gln Lys Phe Cys Val Val Leu Leu His Trp Glu Phe Ile
  1               5                  10                  15

Tyr Val Ile Thr Ala Phe Asn Leu Ser Tyr Pro Ile Thr Pro Trp Arg
                 20                  25                  30

Phe Lys Leu Ser Cys Met Pro Pro Asn Ser Thr Tyr Asp Tyr Phe Leu
             35                  40                  45

Leu Pro Ala Gly Leu Ser Lys Asn Thr Ser Asn Ser Asn Gly His Tyr
         50                  55                  60

Glu Thr Ala Val Glu Pro Lys Phe Asn Ser Ser Gly Thr His Phe Ser
 65                  70                  75                  80

Asn Leu Ser Lys Thr Thr Phe His Cys Cys Phe Arg Ser Glu Gln Asp
                 85                  90                  95

Arg Asn Cys Ser Leu Cys Ala Asp Asn Ile Glu Gly Lys Thr Phe Val
            100                 105                 110

Ser Thr Val Asn Ser Leu Val Phe Gln Gln Ile Asp Ala Asn Trp Asn
        115                 120                 125

Ile Gln Cys Trp Leu Lys Gly Asp Leu Lys Leu Phe Ile Cys Tyr Val
    130                 135                 140

Glu Ser Leu Phe Lys Asn Leu Phe Arg Asn Tyr Asn Tyr Lys Val His
145                 150                 155                 160

Leu Leu Tyr Val Leu Pro Glu Val Leu Glu Asp Ser Pro Leu Val Pro
                165                 170                 175

Gln Lys Gly Ser Phe Gln Met Val His Cys Asn Cys Ser Val His Glu
            180                 185                 190

Cys Cys Glu Cys Leu Val Pro Val Pro Thr Ala Lys Leu Asn Asp Thr
        195                 200                 205

Leu Leu Met Cys Leu Lys Ile Thr Ser Gly Gly Val Ile Phe Gln Ser
    210                 215                 220

Pro Leu Met Ser Val Gln Pro Ile Asn Met Val Lys Pro Asp Pro Pro
225                 230                 235                 240

Leu Gly Leu His Met Glu Ile Thr Asp Asp Gly Asn Leu Lys Ile Ser
                245                 250                 255

Trp Ser Ser Pro Pro Leu Val Pro Phe Pro Leu Gln Tyr Gln Val Lys
            260                 265                 270

Tyr Ser Glu Asn Ser Thr Thr Val Ile Arg Glu Ala Asp Lys Ile Val
        275                 280                 285

Ser Ala Thr Ser Leu Leu Val Asp Ser Ile Leu Pro Gly Ser Ser Tyr
```

-continued

```
            290                 295                 300
Glu Val Gln Val Arg Gly Lys Arg Leu Asp Gly Pro Gly Ile Trp Ser
305                 310                 315                 320

Asp Trp Ser Thr Pro Arg Val Phe Thr Thr Gln Asp Val Ile Tyr Phe
                325                 330                 335

Pro Pro Lys Ile Leu Thr Ser Val Gly Ser Asn Val Ser Phe His Cys
                340                 345                 350

Ile Tyr Lys Lys Glu Asn Lys Ile Val Pro Ser Lys Glu Ile Val Trp
                355                 360                 365

Trp Met Asn Leu Ala Glu Lys Ile Pro Gln Ser Gln Tyr Asp Val Val
370                 375                 380

Ser Asp His Val Ser Lys Val Thr Phe Phe Asn Leu Asn Glu Thr Lys
385                 390                 395                 400

Pro Arg Gly Lys Phe Thr Tyr Asp Ala Val Tyr Cys Cys Asn Glu His
                405                 410                 415

Glu Cys His His Arg Tyr Ala Glu Leu Tyr Val Ile Asp Val Asn Ile
                420                 425                 430

Asn Ile Ser Cys Glu Thr Asp Gly Tyr Leu Thr Lys Met Thr Cys Arg
                435                 440                 445

Trp Ser Thr Ser Thr Ile Gln Ser Leu Ala Glu Ser Thr Leu Gln Leu
        450                 455                 460

Arg Tyr His Arg Ser Ser Leu Tyr Cys Ser Asp Ile Pro Ser Ile His
465                 470                 475                 480

Pro Ile Ser Glu Pro Lys Asp Cys Tyr Leu Gln Ser Asp Gly Phe Tyr
                485                 490                 495

Glu Cys Ile Phe Gln Pro Ile Phe Leu Leu Ser Gly Tyr Thr Met Trp
                500                 505                 510

Ile Arg Ile Asn His Ser Leu Gly Ser Leu Asp Ser Pro Pro Thr Cys
                515                 520                 525

Val Leu Pro Asp Ser Val Val Lys Pro Leu Pro Ser Ser Val Lys
                530                 535                 540

Ala Glu Ile Thr Ile Asn Ile Gly Leu Leu Lys Ile Ser Trp Glu Lys
545                 550                 555                 560

Pro Val Phe Pro Glu Asn Asn Leu Gln Phe Gln Ile Arg Tyr Gly Leu
                565                 570                 575

Ser Gly Lys Glu Val Gln Trp Lys Met Tyr Glu Val Tyr Asp Ala Lys
                580                 585                 590

Ser Lys Ser Val Ser Leu Pro Val Pro Asp Leu Cys Ala Val Tyr Ala
                595                 600                 605

Val Gln Val Arg Cys Lys Arg Leu Asp Gly Leu Gly Tyr Trp Ser Asn
                610                 615                 620

Trp Ser Asn Pro Ala Tyr Thr Val Val Met Asp Ile Lys Val Pro Met
625                 630                 635                 640

Arg Gly Pro Glu Phe Trp Arg Ile Ile Asn Gly Asp Thr Met Lys Lys
                645                 650                 655

Glu Lys Asn Val Thr Leu Leu Trp Lys Pro Leu Met Lys Asn Asp Ser
                660                 665                 670

Leu Cys Ser Val Gln Arg Tyr Val Ile Asn His His Thr Ser Cys Asn
                675                 680                 685

Gly Thr Trp Ser Glu Asp Val Gly Asn His Thr Lys Phe Thr Phe Leu
        690                 695                 700

Trp Thr Glu Gln Ala His Thr Val Thr Val Leu Ala Ile Asn Ser Ile
705                 710                 715                 720
```

```
Gly Ala Ser Val Ala Asn Phe Asn Leu Thr Phe Ser Trp Pro Met Ser
                725                 730                 735

Lys Val Asn Ile Val Gln Ser Leu Ser Ala Tyr Pro Leu Asn Ser Ser
            740                 745                 750

Cys Val Ile Val Ser Trp Ile Leu Ser Pro Ser Asp Tyr Lys Leu Met
        755                 760                 765

Tyr Phe Ile Ile Glu Trp Lys Asn Leu Asn Glu Asp Gly Glu Ile Lys
    770                 775                 780

Trp Leu Arg Ile Ser Ser Val Lys Tyr Tyr Ile His Asp His
785                 790                 795                 800

Phe Ile Pro Ile Glu Lys Tyr Gln Phe Ser Leu Tyr Pro Ile Phe Met
                805                 810                 815

Glu Gly Val Gly Lys Pro Lys Ile Ile Asn Ser Phe Thr Gln Asp Asp
            820                 825                 830

Ile Glu Lys His Gln Ser Asp Ala Gly Leu Tyr Val Ile Val Pro Val
        835                 840                 845

Ile Ile Ser Ser Ser Ile Leu Leu Leu Gly Thr Leu Leu Ile Ser His
    850                 855                 860

Gln Arg Met Lys Lys Leu Phe Trp Glu Asp Val Pro Asn Pro Lys Asn
865                 870                 875                 880

Cys Ser Trp Ala Gln Gly Leu Asn Phe Gln Lys Pro Glu Thr Phe Glu
                885                 890                 895

His Leu Phe Ile Lys His Thr Ala Ser Val Thr Cys Gly Pro Leu Leu
            900                 905                 910

Leu Glu Pro Glu Thr Ile Ser Glu Asp Ile Ser Val Asp Thr Ser Trp
        915                 920                 925

Lys Asn Lys Asp Glu Met Met Pro Thr Thr Val Val Ser Leu Leu Ser
    930                 935                 940

Thr Thr Asp Leu Glu Lys Gly Ser Val Cys Ile Ser Asp Gln Phe Asn
945                 950                 955                 960

Ser Val Asn Phe Ser Glu Ala Glu Gly Thr Glu Val Thr Tyr Glu Asp
                965                 970                 975

Glu Ser Gln Arg Gln Pro Phe Val Lys Tyr Ala Thr Leu Ile Ser Asn
            980                 985                 990

Ser Lys Pro Ser Glu Thr Gly Glu Glu Gln Gly Leu Ile Asn Ser Ser
        995                1000                1005

Val Thr Lys Cys Phe Ser Ser Lys Asn Ser Pro Leu Lys Asp Ser Phe
    1010                1015                1020

Ser Asn Ser Ser Trp Glu Ile Glu Ala Gln Ala Phe Phe Ile Leu Ser
1025                1030                1035                1040

Asp Gln His Pro Asn Ile Ile Ser Pro His Leu Thr Phe Ser Glu Gly
                1045                1050                1055

Leu Asp Glu Leu Leu Lys Leu Glu Gly Asn Phe Pro Glu Glu Asn Asn
            1060                1065                1070

Asp Lys Lys Ser Ile Tyr Tyr Leu Gly Val Thr Ser Ile Lys Lys Arg
        1075                1080                1085

Glu Ser Gly Val Leu Leu Thr Asp Lys Ser Arg Val Ser Cys Pro Phe
    1090                1095                1100

Pro Ala Pro Cys Leu Phe Thr Asp Ile Arg Val Leu Gln Asp Ser Cys
1105                1110                1115                1120

Ser His Phe Val Glu Asn Asn Ile Asn Leu Gly Thr Ser Ser Lys Lys
                1125                1130                1135
```

```
Thr Phe Ala Ser Tyr Met Pro Gln Phe Gln Thr Cys Ser Thr Gln Thr
        1140                1145                1150

His Lys Ile Met Glu Asn Lys Met Cys Asp Leu Thr Val
        1155                1160                1165

<210> SEQ ID NO 3
<211> LENGTH: 896
<212> TYPE: PRT
<213> ORGANISM: Homo sapiens

<400> SEQUENCE: 3

Met Ile Cys Gln Lys Phe Cys Val Val Leu Leu His Trp Glu Phe Ile
1               5                   10                  15

Tyr Val Ile Thr Ala Phe Asn Leu Ser Tyr Pro Ile Thr Pro Trp Arg
            20                  25                  30

Phe Lys Leu Ser Cys Met Pro Pro Asn Ser Thr Tyr Asp Tyr Phe Leu
        35                  40                  45

Leu Pro Ala Gly Leu Ser Lys Asn Thr Ser Asn Ser Asn Gly His Tyr
    50                  55                  60

Glu Thr Ala Val Glu Pro Lys Phe Asn Ser Ser Gly Thr His Phe Ser
65                  70                  75                  80

Asn Leu Ser Lys Thr Thr Phe His Cys Cys Phe Arg Ser Glu Gln Asp
                85                  90                  95

Arg Asn Cys Ser Leu Cys Ala Asp Asn Ile Glu Gly Lys Thr Phe Val
            100                 105                 110

Ser Thr Val Asn Ser Leu Val Phe Gln Gln Ile Asp Ala Asn Trp Asn
        115                 120                 125

Ile Gln Cys Trp Leu Lys Gly Asp Leu Lys Leu Phe Ile Cys Tyr Val
    130                 135                 140

Glu Ser Leu Phe Lys Asn Leu Phe Arg Asn Tyr Asn Tyr Lys Val His
145                 150                 155                 160

Leu Leu Tyr Val Leu Pro Glu Val Leu Glu Asp Ser Pro Leu Val Pro
                165                 170                 175

Gln Lys Gly Ser Phe Gln Met Val His Cys Asn Cys Ser Val His Glu
            180                 185                 190

Cys Cys Glu Cys Leu Val Pro Val Pro Thr Ala Lys Leu Asn Asp Thr
        195                 200                 205

Leu Leu Met Cys Leu Lys Ile Thr Ser Gly Gly Val Ile Phe Gln Ser
    210                 215                 220

Pro Leu Met Ser Val Gln Pro Ile Asn Met Val Lys Pro Asp Pro Pro
225                 230                 235                 240

Leu Gly Leu His Met Glu Ile Thr Asp Asp Gly Asn Leu Lys Ile Ser
                245                 250                 255

Trp Ser Ser Pro Pro Leu Val Pro Phe Pro Leu Gln Tyr Gln Val Lys
            260                 265                 270

Tyr Ser Glu Asn Ser Thr Thr Val Ile Arg Glu Ala Asp Lys Ile Val
        275                 280                 285

Ser Ala Thr Ser Leu Leu Val Asp Ser Ile Leu Pro Gly Ser Ser Tyr
    290                 295                 300

Glu Val Gln Val Arg Gly Lys Arg Leu Asp Gly Pro Gly Ile Trp Ser
305                 310                 315                 320

Asp Trp Ser Thr Pro Arg Val Phe Thr Thr Gln Asp Val Ile Tyr Phe
                325                 330                 335

Pro Pro Lys Ile Leu Thr Ser Val Gly Ser Asn Val Ser Phe His Cys
            340                 345                 350
```

```
Ile Tyr Lys Lys Glu Asn Lys Ile Val Pro Ser Lys Glu Ile Val Trp
            355                 360                 365

Trp Met Asn Leu Ala Glu Lys Ile Pro Gln Ser Gln Tyr Asp Val Val
        370                 375                 380

Ser Asp His Val Ser Lys Val Thr Phe Phe Asn Leu Asn Glu Thr Lys
385                 390                 395                 400

Pro Arg Gly Lys Phe Thr Tyr Asp Ala Val Tyr Cys Cys Asn Glu His
                405                 410                 415

Glu Cys His His Arg Tyr Ala Glu Leu Tyr Val Ile Asp Val Asn Ile
            420                 425                 430

Asn Ile Ser Cys Glu Thr Asp Gly Tyr Leu Thr Lys Met Thr Cys Arg
        435                 440                 445

Trp Ser Thr Ser Thr Ile Gln Ser Leu Ala Glu Ser Thr Leu Gln Leu
    450                 455                 460

Arg Tyr His Arg Ser Ser Leu Tyr Cys Ser Asp Ile Pro Ser Ile His
465                 470                 475                 480

Pro Ile Ser Glu Pro Lys Asp Cys Tyr Leu Gln Ser Asp Gly Phe Tyr
                485                 490                 495

Glu Cys Ile Phe Gln Pro Ile Phe Leu Leu Ser Gly Tyr Thr Met Trp
            500                 505                 510

Ile Arg Ile Asn His Ser Leu Gly Ser Leu Asp Ser Pro Pro Thr Cys
        515                 520                 525

Val Leu Pro Asp Ser Val Val Lys Pro Leu Pro Pro Ser Ser Val Lys
    530                 535                 540

Ala Glu Ile Thr Ile Asn Ile Gly Leu Leu Lys Ile Ser Trp Glu Lys
545                 550                 555                 560

Pro Val Phe Pro Glu Asn Asn Leu Gln Phe Gln Ile Arg Tyr Gly Leu
                565                 570                 575

Ser Gly Lys Glu Val Gln Trp Lys Met Tyr Glu Val Tyr Asp Ala Lys
            580                 585                 590

Ser Lys Ser Val Ser Leu Pro Val Pro Asp Leu Cys Ala Val Tyr Ala
        595                 600                 605

Val Gln Val Arg Cys Lys Arg Leu Asp Gly Leu Gly Tyr Trp Ser Asn
    610                 615                 620

Trp Ser Asn Pro Ala Tyr Thr Val Val Met Asp Ile Lys Val Pro Met
625                 630                 635                 640

Arg Gly Pro Glu Phe Trp Arg Ile Ile Asn Gly Asp Thr Met Lys Lys
                645                 650                 655

Glu Lys Asn Val Thr Leu Leu Trp Lys Pro Leu Met Lys Asn Asp Ser
            660                 665                 670

Leu Cys Ser Val Gln Arg Tyr Val Ile Asn His His Thr Ser Cys Asn
        675                 680                 685

Gly Thr Trp Ser Glu Asp Val Gly Asn His Thr Lys Phe Thr Phe Leu
    690                 695                 700

Trp Thr Glu Gln Ala His Thr Val Thr Val Leu Ala Ile Asn Ser Ile
705                 710                 715                 720

Gly Ala Ser Val Ala Asn Phe Asn Leu Thr Phe Ser Trp Pro Met Ser
                725                 730                 735

Lys Val Asn Ile Val Gln Ser Leu Ser Ala Tyr Pro Leu Asn Ser Ser
            740                 745                 750

Cys Val Ile Val Ser Trp Ile Leu Ser Pro Ser Asp Tyr Lys Leu Met
        755                 760                 765
```

-continued

Tyr Phe Ile Ile Glu Trp Lys Asn Leu Asn Glu Asp Gly Glu Ile Lys
770                 775                 780

Trp Leu Arg Ile Ser Ser Val Lys Lys Tyr Tyr Ile His Asp His
785                 790                 795                 800

Phe Ile Pro Ile Glu Lys Tyr Gln Phe Ser Leu Tyr Pro Ile Phe Met
                805                 810                 815

Glu Gly Val Gly Lys Pro Lys Ile Ile Asn Ser Phe Thr Gln Asp Asp
                820                 825                 830

Ile Glu Lys His Gln Ser Asp Ala Gly Leu Tyr Val Ile Val Pro Val
                835                 840                 845

Ile Ile Ser Ser Ser Ile Leu Leu Leu Gly Thr Leu Leu Ile Ser His
                850                 855                 860

Gln Arg Met Lys Lys Leu Phe Trp Glu Asp Val Pro Asn Pro Lys Asn
865                 870                 875                 880

Cys Ser Trp Ala Gln Gly Leu Asn Phe Gln Lys Arg Thr Asp Ile Leu
                885                 890                 895

<210> SEQ ID NO 4
<211> LENGTH: 923
<212> TYPE: PRT
<213> ORGANISM: Homo sapiens

<400> SEQUENCE: 4

Met Ile Cys Gln Lys Phe Cys Val Val Leu Leu His Trp Glu Phe Ile
1               5                   10                  15

Tyr Val Ile Thr Ala Phe Asn Leu Ser Tyr Pro Ile Thr Pro Trp Arg
                20                  25                  30

Phe Lys Leu Ser Cys Met Pro Pro Asn Ser Thr Tyr Asp Tyr Phe Leu
            35                  40                  45

Leu Pro Ala Gly Leu Ser Lys Asn Thr Ser Asn Ser Asn Gly His Tyr
50                  55                  60

Glu Thr Ala Val Glu Pro Lys Phe Asn Ser Ser Gly Thr His Phe Ser
65                  70                  75                  80

Asn Leu Ser Lys Thr Thr Phe His Cys Cys Phe Arg Ser Glu Gln Asp
                85                  90                  95

Arg Asn Cys Ser Leu Cys Ala Asp Asn Ile Glu Gly Lys Thr Phe Val
            100                 105                 110

Ser Thr Val Asn Ser Leu Val Phe Gln Gln Ile Asp Ala Asn Trp Asn
        115                 120                 125

Ile Gln Cys Trp Leu Lys Gly Asp Leu Lys Leu Phe Ile Cys Tyr Val
130                 135                 140

Glu Ser Leu Phe Lys Asn Leu Phe Arg Asn Tyr Asn Tyr Lys Val His
145                 150                 155                 160

Leu Leu Tyr Val Leu Pro Glu Val Leu Glu Asp Ser Pro Leu Val Pro
                165                 170                 175

Gln Lys Gly Ser Phe Gln Met Val His Cys Asn Cys Ser Val His Glu
            180                 185                 190

Cys Cys Glu Cys Leu Val Pro Val Pro Thr Ala Lys Leu Asn Asp Thr
        195                 200                 205

Leu Leu Met Cys Leu Lys Ile Thr Ser Gly Gly Val Ile Phe Gln Ser
210                 215                 220

Pro Leu Met Ser Val Gln Pro Ile Asn Met Val Lys Pro Asp Pro Pro
225                 230                 235                 240

Leu Gly Leu His Met Glu Ile Thr Asp Asp Gly Asn Leu Lys Ile Ser
                245                 250                 255

```
Trp Ser Ser Pro Pro Leu Val Pro Phe Pro Leu Gln Tyr Gln Val Lys
            260                 265                 270

Tyr Ser Glu Asn Ser Thr Thr Val Ile Arg Glu Ala Asp Lys Ile Val
        275                 280                 285

Ser Ala Thr Ser Leu Leu Val Asp Ser Ile Leu Pro Gly Ser Ser Tyr
    290                 295                 300

Glu Val Gln Val Arg Gly Lys Arg Leu Asp Gly Pro Gly Ile Trp Ser
305                 310                 315                 320

Asp Trp Ser Thr Pro Arg Val Phe Thr Thr Gln Asp Val Ile Tyr Phe
                325                 330                 335

Pro Pro Lys Ile Leu Thr Ser Val Gly Ser Asn Val Ser Phe His Cys
            340                 345                 350

Ile Tyr Lys Lys Glu Asn Lys Ile Val Pro Ser Lys Glu Ile Val Trp
        355                 360                 365

Trp Met Asn Leu Ala Glu Lys Ile Pro Gln Ser Gln Tyr Asp Val Val
    370                 375                 380

Ser Asp His Val Ser Lys Val Thr Phe Phe Asn Leu Asn Glu Thr Lys
385                 390                 395                 400

Pro Arg Gly Lys Phe Thr Tyr Asp Ala Val Tyr Cys Cys Asn Glu His
                405                 410                 415

Glu Cys His His Arg Tyr Ala Glu Leu Tyr Val Ile Asp Val Asn Ile
            420                 425                 430

Asn Ile Ser Cys Glu Thr Asp Gly Tyr Leu Thr Lys Met Thr Cys Arg
        435                 440                 445

Trp Ser Thr Ser Thr Ile Gln Ser Leu Ala Glu Ser Thr Leu Gln Leu
    450                 455                 460

Arg Tyr His Arg Ser Ser Leu Tyr Cys Ser Asp Ile Pro Ser Ile His
465                 470                 475                 480

Pro Ile Ser Glu Pro Lys Asp Cys Tyr Leu Gln Ser Asp Gly Phe Tyr
                485                 490                 495

Glu Cys Ile Phe Gln Pro Ile Phe Leu Leu Ser Gly Tyr Thr Met Trp
            500                 505                 510

Ile Arg Ile Asn His Ser Leu Gly Ser Leu Asp Ser Pro Pro Thr Cys
        515                 520                 525

Val Leu Pro Asp Ser Val Val Lys Pro Leu Pro Pro Ser Ser Val Lys
    530                 535                 540

Ala Glu Ile Thr Ile Asn Ile Gly Leu Leu Lys Ile Ser Trp Glu Lys
545                 550                 555                 560

Pro Val Phe Pro Glu Asn Asn Leu Gln Phe Gln Ile Arg Tyr Gly Leu
                565                 570                 575

Ser Gly Lys Glu Val Gln Trp Lys Met Tyr Glu Val Tyr Asp Ala Lys
            580                 585                 590

Ser Lys Ser Val Ser Leu Pro Val Pro Asp Leu Cys Ala Val Tyr Ala
        595                 600                 605

Val Gln Val Arg Cys Lys Arg Leu Asp Gly Leu Gly Tyr Trp Ser Asn
    610                 615                 620

Trp Ser Asn Pro Ala Tyr Thr Val Val Met Asp Ile Lys Val Pro Met
625                 630                 635                 640

Arg Gly Pro Glu Phe Trp Arg Ile Ile Asn Gly Asp Thr Met Lys Lys
                645                 650                 655

Glu Lys Asn Val Thr Leu Leu Trp Lys Pro Leu Met Lys Asn Asp Ser
            660                 665                 670
```

| | | | | | | | | | | | | | |
|---|---|---|---|---|---|---|---|---|---|---|---|---|---|
| Leu | Cys | Ser | Val | Gln | Arg | Tyr | Val | Ile | Asn | His | His | Thr | Ser | Cys | Asn |
| | | | 675 | | | | 680 | | | | 685 | | |

Gly Thr Trp Ser Glu Asp Val Gly Asn His Thr Lys Phe Thr Phe Leu
    690                    695                    700

Trp Thr Glu Gln Ala His Thr Val Thr Val Leu Ala Ile Asn Ser Ile
705                   710                    715                720

Gly Ala Ser Val Ala Asn Phe Asn Leu Thr Phe Ser Trp Pro Met Ser
           725                  730                735

Lys Val Asn Ile Val Gln Ser Leu Ser Ala Tyr Pro Leu Asn Ser Ser
        740                  745                750

Cys Val Ile Val Ser Trp Ile Leu Ser Pro Ser Asp Tyr Lys Leu Met
       755                  760                765

Tyr Phe Ile Ile Glu Trp Lys Asn Leu Asn Glu Asp Gly Glu Ile Lys
   770                775                780

Trp Leu Arg Ile Ser Ser Val Lys Lys Tyr Tyr Ile His Asp His
785                  790                795              800

Phe Ile Pro Ile Glu Lys Tyr Gln Phe Ser Leu Tyr Pro Ile Phe Met
        805                  810                815

Glu Gly Val Gly Lys Pro Lys Ile Ile Asn Ser Phe Thr Gln Asp Asp
       820                  825                830

Ile Glu Lys His Gln Ser Asp Ala Gly Leu Tyr Val Ile Val Pro Val
       835                  840                845

Ile Ile Ser Ser Ser Ile Leu Leu Leu Gly Thr Leu Leu Ile Ser His
       850                  855                860

Gln Arg Met Lys Lys Leu Phe Trp Glu Asp Val Pro Asn Pro Lys Asn
865                  870                875              880

Cys Ser Trp Ala Gln Gly Leu Asn Phe Gln Lys Met Phe Arg Thr Pro
        885                  890                895

Arg Ile Val Pro Gly His Lys Asp Leu Ile Phe Arg Arg Cys Leu Lys
           900                  905                910

Ala Ala Cys Ser Leu Arg Val Ile Thr Thr Pro
       915                  920

```
<210> SEQ ID NO 5
<211> LENGTH: 3004
<212> TYPE: DNA
<213> ORGANISM: Homo sapiens
<220> FEATURE:
<221> NAME/KEY: misc_feature
<222> LOCATION: 552
<223> OTHER INFORMATION: n = A,T,C or G

<400> SEQUENCE: 5
```

| | |
|---|---:|
| gaattccggg ttaaagctct cgtggcatta tccttcagtg gggctattgg actgactttt | 60 |
| cttatgctgg gatgtgcctt agaggattat ggatttgcca gttcaccctg accatcttga | 120 |
| aaataagtta tctctgatct ctgtctgtat gttacttctc tcccctcacc aatggagaac | 180 |
| aaatgtgggc aaagtgtact tctctgaagt aagatgattt gtcaaaaatt ctgtgtggtt | 240 |
| ttgttacatt gggaatttat ttatgtgata actgcgttta acttgtcata tccaattact | 300 |
| ccttggagat ttaagttgtc ttgcatgcca ccaaattcaa cctatgacta cttccttttg | 360 |
| cctgctggac tctcaaagaa tacttcaaat tcgaatggac attatgagac agctgttgaa | 420 |
| cctaagttta attcaagtgg tactcacttt tctaacttat ccaaaacaac tttccactgt | 480 |
| tgctttcgga gtgagcaaga tagaaactgc tcccttatgtg cagacaacat tgaaggaaag | 540 |
| acatttgttt cnacagtaaa ttctttagtt tttcaacaaa tagatgcaaa ctggaacata | 600 |

```
cagtgctggc taaaaggaga cttaaaatta ttcatctgtt atgtggagtc attatttaag     660
aatctattca ggaattataa ctataaggtc catcttttat atgttctgcc tgaagtgtta     720
gaagattcac ctctggttcc ccaaaaaggc agttttcaga tggttcactg caattgcagt     780
gttcatgaat gttgtgaatg tcttgtgcct gtgccaacag ccaaactcaa cgacactctc     840
cttatgtgtt tgaaaatcac atctggtgga gtaattttcc agtcacctct aatgtcagtt     900
cagcccataa atatggtgaa gcctgatcca ccattaggtt tgcatatgga aatcacagat     960
gatggtaatt taaagatttc ttggtccagc ccaccattgg taccatttcc acttcaatat    1020
caagtgaaat attcagagaa ttctacaaca gttatcagag aagctgacaa gattgtctca    1080
gctcatcccc tgctagtaga cagtatactt cctgggtctt cgtatgaggt tcaggtgagg    1140
ggcaagagac tggatggccc aggaatctgg agtgactgga gtactcctcg tgtctttacc    1200
acacaagatg tcatatactt tccacctaaa attctgacaa gtgttgggtc taatgtttct    1260
tttcactgca tctataagaa ggaaaacaag attgttccct caaagagat tgtttggtgg    1320
atgaatttag ctgagaaaat tcctcaaagc cagtatgatg ttgtgagtga tcatgttagc    1380
aaagttactt ttttcaatct gaatgaaacc aaacctcgag gaaagtttac ctatgatgca    1440
gtgtactgct gcaatgaaca tgaatgccat catcgctatg ctgaattata tgtgattgat    1500
gtcaatatca atatctcatg tgaaactgat gggtacttaa ctaaaatgac ttgcagatgg    1560
tcaaccagta caatccagtc acttgcggaa agcactttgc aattgaggta tcataggagc    1620
agcctttact gttctgatat tccatctatt catcccatat ctgagcccaa agattgctat    1680
ttgcagagtg atggttttta tgaatgcatt ttccagccaa tcttcctatt atctggctac    1740
acaatgtgga ttaggatcaa tcactctcta ggttcacttg actctccacc aacatgtgtc    1800
cttcctgatt ctgtggtgaa gccactgcct ccatccagtg tgaaagcaga aattactata    1860
aacattggat tattgaaaat atcttgggaa aagccagtct ttccagagaa taaccttcaa    1920
ttccagattc gctatggttt aagtggaaaa gaagtacaat ggaagatgta tgaggtttat    1980
gatgcaaaat caaaatctgt cagtctccca gttccagact tgtgtgcagt ctatgctgtt    2040
caggtgcgct gtaagaggct agatggactg ggatattgga gtaattggag caatccagcc    2100
tacacagttg tcatggatat aaaagttcct atgagaggac ctgaattttg gagaataatt    2160
aatggagata ctatgaaaaa ggagaaaaat gtcactttac tttggaagcc cctgatgaaa    2220
aatgactcat tgtgcagtgt tcagagatat gtgataaacc atcatacttc ctgcaatgga    2280
acatggtcag aagatgtggg aaatcacacg aaattcactt tcctgtggac agagcaagca    2340
catactgtta cggttctggc catcaattca attggtgctt ctgttgcaaa ttttaattta    2400
accttttcat ggcctatgag caaagtaaat atcgtgcagt cactcagtgc ttatccttta    2460
aacagcagtt gtgtgattgt ttcctggata ctatcaccca gtgattacaa gctaatgtat    2520
tttattattg agtggaaaaa tcttaatgaa gatggtgaaa taaaatggct tagaatctct    2580
tcatctgtta agaagtatta tatccatgat cattttatcc ccattgagaa gtaccagttc    2640
agtctttacc caatatttat ggaaggagtg ggaaaaccaa agataattaa tagtttcact    2700
caagatgata ttgaaaaaca ccagagtgat gcaggtttat atgtaattgt gccagtaatt    2760
atttcctctt ccatcttatt gcttggaaca ttattaatat cacaccaaag aatgaaaaag    2820
ctattttggg aagatgttcc gaaccccaag aattgttcct gggcacaagg acttaatttt    2880
cagaagagaa cggacattct ttgaagtcta atcatgatca ctacagatga acccaatgtg    2940
```

```
ccaacttccc aacagtctat agagtattag aagatttta cattttgaag aagggccgga    3000
attc                                                                3004

<210> SEQ ID NO 6
<211> LENGTH: 3102
<212> TYPE: DNA
<213> ORGANISM: Homo sapiens

<400> SEQUENCE: 6
gaattctcga gtcgacggcg ggcgttaaag ctctcgtggc attatccttc agtggggcta      60
ttggactgac ttttcttatg ctgggatgtg ccttagagga ttatgggtgt acttctctga     120
agtaagatga tttgtcaaaa attctgtgtg gttttgttac attgggaatt tatttatgtg     180
ataactgcgt ttaacttgtc atatccaatt actccttgga gatttaagtt gtcttgcatg     240
ccaccaaatt caacctatga ctacttcctt ttgcctgctg gactctcaaa gaatacttca     300
aattcgaatg gacattatga gacagctgtt gaacctaagt ttaattcaag tggtactcac     360
ttttctaact tatccaaaac aactttccac tgttgctttc ggagtgagca agatagaaac     420
tgctccttat gtgcagacaa cattgaagga agacatttg tttcaacagt aaattcttta     480 gttttcaac aaatagatgc aaactggaac atacagtgct ggctaaaagg agacttaaaa     540
ttattcatct gttatgtgga gtcattattt aagaatctat tcaggaatta taactataag     600
gtccatcttt tatatgttct gcctgaagtg ttagaagatt caccctctggt tccccaaaaa     660 ggcagttttc agatggttca ctgcaattgc agtgttcatg aatgttgtga atgtcttgtg     720
cctgtgccaa cagccaaact caacgacact ctccttatgt gtttgaaaat cacatctggt     780
ggagtaattt tccagtcacc tctaatgtca gttcagccca taaatatggt gaagcctgat     840
ccaccattag gtttgcatat ggaaatcaca gatgatggta atttaaagat ttcttggtcc     900
agcccaccat tggtaccatt tccacttcaa tatcaagtga atattcaga gaattctaca     960 acagttatca gagaagctga caagattgtc tcagctacat ccctgctagt agacagtata    1020
cttcctgggt cttcgtatga ggttcaggtg aggggcaaga gactggatgg cccaggaatc    1080
tggagtgact ggagtactcc tcgtgtcttt accacacaag atgtcatata ctttccacct    1140
aaaattctga caagtgttgg gtctaatgtt tcttttcact gcatctataa gaaggaaaac    1200
aagattgttc cctcaaaaga gattgtttgg tggatgaatt tagctgagaa aattcctcaa    1260
agccagtatg atgttgtgag tgatcatgtt agcaaagtta ctttttttcaa tctgaatgaa    1320 accaaacctc gaggaaagtt tacctatgat gcagtgtact gctgcaatga acatgaatgc    1380
catcatcgct atgctgaatt atatgtgatt gatgtcaata tcaatatctc atgtgaaact    1440
gatgggtact taactaaaat gacttgcaga tggtcaacca gtacaatcca gtcacttgcg    1500
gaaagcactt tgcaattgag gtatcatagg agcagccttt actgttctga tattccatct    1560
attcatccca tatctgagcc caaagattgc tatttgcaga gtgatggttt ttatgaatgc    1620
attttccagc caatcttcct attatctggc tacacaatgt ggattaggat caatcactct    1680
ctaggttcac ttgactctcc accaacatgt gtccttcctg attctgtggt gaagccactg    1740
cctccatcca gtgtgaaagc agaaattact ataaacattg gattattgaa aatatcttgg    1800
gaaaagccag tctttccaga gaataacctt caattccaga ttcgctatgg tttaagtgga    1860
aaagaagtac aatggaagat gtatgaggtt tatgatgcaa aatcaaaatc tgtcagtctc    1920
ccagttccag acttgtgtgc agtctatgct gttcaggtgc gctgtaagag gctagatgga    1980
ctgggatatt ggagtaattg gagcaatcca gcctacacag ttgtcatgga tataaaagtt    2040
```

-continued

```
cctatgagag gacctgaatt ttggagaata attaatggag atactatgaa aaaggagaaa    2100
aatgtcactt tactttggaa gcccctgatg aaaaatgact cattgtgcag tgttcagaga    2160
tatgtgataa accatcatac ttcctgcaat ggaacatggt cagaagatgt gggaaatcac    2220
acgaaattca ctttcctgtg gacagagcaa gcacatactg ttacggttct ggccatcaat    2280
tcaattggtg cttctgttgc aaattttaat ttaaccttt catggcctat gagcaaagta     2340
aatatcgtgc agtcactcag tgcttatcct ttaaacagca gttgtgtgat tgtttcctgg    2400
atactatcac ccagtgatta caagctaatg tattttatta ttgagtggaa aaatcttaat    2460
gaagatggtg aaataaaatg cttagaatc tcttcatctg ttaagaagta ttatatccat     2520
gatcatttta tccccattga gaagtaccag ttcagtcttt acccaatatt tatggaagga    2580
gtgggaaaac caaagataat taatagtttc actcaagatg atattgaaaa acaccagagt    2640
gatgcaggtt tatatgtaat tgtgccagta attatttcct cttccatctt attgcttgga    2700
acattattaa tatcacacca aagaatgaaa aagctatttt gggaagatgt tccgaacccc    2760
aagaattgtt cctgggcaca aggacttaat tttcagaaga tgttccgaac cccaagaatt    2820
gttcctgggc acaaggactt aattttcaga agatgcttga aggcagcatg ttcgttaaga    2880
gtcatcacca ctccctaatc tcaagtaccc agggacacaa acactgcgga aggccacagg    2940
gtcctctgca taggaaaacc agagacctt gttcacttgt ttatctgctg accctccctc     3000
cactattgtc ctatgaccct gccaaatccc cctctgtgag aaacacccaa gaatgatcaa    3060
taaaaaaaaa aaaaaaaaa aaaaagtcg actcgagaat tc                        3102
```

<210> SEQ ID NO 7
<211> LENGTH: 783
<212> TYPE: PRT
<213> ORGANISM: Mus musculus

<400> SEQUENCE: 7

```
Met Met Cys Gln Lys Phe Tyr Val Val Leu Leu His Trp Glu Phe Leu
  1               5                  10                  15

Tyr Val Ile Ala Ala Leu Asn Leu Ala Tyr Pro Ile Ser Pro Trp Lys
             20                  25                  30

Phe Lys Leu Phe Cys Gly Pro Pro Asn Thr Thr Asp Asp Ser Phe Leu
         35                  40                  45

Ser Pro Ala Gly Ala Pro Asn Asn Ala Ser Ala Leu Lys Gly Ala Ser
     50                  55                  60

Glu Ala Ile Val Glu Ala Lys Phe Asn Ser Ser Gly Ile Tyr Val Pro
 65                  70                  75                  80

Glu Leu Ser Lys Thr Val Phe His Cys Cys Phe Gly Asn Glu Gln Gly
                 85                  90                  95

Gln Asn Cys Ser Ala Leu Thr Asp Asn Thr Glu Gly Lys Thr Leu Ala
            100                 105                 110

Ser Val Val Lys Ala Ser Val Phe Arg Gln Leu Gly Val Asn Trp Asp
        115                 120                 125

Ile Glu Cys Trp Met Lys Gly Asp Leu Thr Leu Phe Ile Cys His Met
    130                 135                 140

Glu Pro Leu Pro Lys Asn Pro Phe Lys Asn Tyr Asp Ser Lys Val His
145                 150                 155                 160

Leu Leu Tyr Asp Leu Pro Glu Val Ile Asp Asp Ser Pro Leu Pro Pro
                165                 170                 175

Leu Lys Asp Ser Phe Gln Thr Val Gln Cys Asn Cys Ser Leu Arg Gly
```

-continued

```
            180                 185                 190
Cys Glu Cys His Val Pro Val Pro Arg Ala Lys Leu Asn Tyr Ala Leu
        195                 200                 205
Leu Met Tyr Leu Glu Ile Thr Ser Ala Gly Val Ser Phe Gln Ser Pro
    210                 215                 220
Leu Met Ser Leu Gln Pro Met Leu Val Val Lys Pro Asp Pro Pro Leu
225                 230                 235                 240
Gly Leu His Met Glu Val Thr Asp Asp Gly Asn Leu Lys Ile Ser Trp
                245                 250                 255
Asp Ser Gln Thr Met Ala Pro Phe Pro Leu Gln Tyr Gln Val Lys Tyr
            260                 265                 270
Leu Glu Asn Ser Thr Ile Val Arg Glu Ala Ala Glu Ile Val Ser Ala
        275                 280                 285
Thr Ser Leu Leu Val Asp Ser Val Leu Pro Gly Ser Ser Tyr Glu Val
    290                 295                 300
Gln Val Arg Ser Lys Arg Leu Asp Gly Ser Gly Val Trp Ser Asp Trp
305                 310                 315                 320
Ser Ser Pro Gln Val Phe Thr Thr Gln Asp Val Val Tyr Phe Pro Pro
                325                 330                 335
Lys Ile Leu Thr Ser Val Gly Ser Asn Ala Ser Phe His Cys Ile Tyr
            340                 345                 350
Lys Asn Glu Asn Gln Ile Val Ser Ser Lys Gln Ile Val Trp Trp Arg
        355                 360                 365
Asn Leu Ala Glu Lys Ile Pro Glu Ile Gln Tyr Ser Ile Val Ser Asp
    370                 375                 380
Arg Val Ser Lys Val Thr Phe Ser Asn Leu Lys Ala Thr Arg Pro Arg
385                 390                 395                 400
Gly Lys Phe Thr Tyr Asp Ala Val Tyr Cys Cys Asn Glu Gln Ala Cys
                405                 410                 415
His His Arg Tyr Ala Glu Leu Tyr Val Ile Asp Val Asn Ile Asn Ile
            420                 425                 430
Ser Cys Glu Thr Asp Gly Tyr Leu Thr Lys Met Thr Cys Arg Trp Ser
        435                 440                 445
Pro Ser Thr Ile Gln Ser Leu Val Gly Ser Thr Val Gln Leu Arg Tyr
    450                 455                 460
His Arg Cys Ser Leu Tyr Cys Pro Asp Ser Pro Ser Ile His Pro Thr
465                 470                 475                 480
Ser Glu Pro Lys Thr Ala Ser Tyr Arg Glu Thr Ala Phe Met Asn Val
                485                 490                 495
Phe Ser Ser Gln Ser Phe Tyr Tyr Leu Ala Ile Gln Cys Gly Phe Arg
            500                 505                 510
Ile Asn His Ser Leu Gly Ser Leu Asp Ser Pro Pro Thr Cys Val Leu
        515                 520                 525
Pro Asp Ser Val Val Lys Pro Leu Pro Pro Ser Asn Val Lys Ala Glu
    530                 535                 540
Ile Thr Val Asn Thr Gly Leu Leu Lys Val Ser Trp Glu Lys Pro Val
545                 550                 555                 560
Phe Pro Glu Asn Asn Leu Gln Phe Gln Ile Arg Tyr Gly Leu Ser Gly
                565                 570                 575
Lys Glu Ile Gln Trp Lys Thr His Glu Val Phe Asp Ala Lys Ser Lys
            580                 585                 590
Ser Ala Ser Leu Leu Val Ser Asp Leu Cys Ala Val Tyr Val Val Gln
        595                 600                 605
```

```
Val Arg Cys Arg Arg Leu Asp Gly Leu Gly Tyr Trp Ser Asn Trp Ser
    610                 615                 620
Ser Pro Ala Tyr Thr Leu Val Met Asp Val Lys Val Pro Met Arg Gly
625                 630                 635                 640
Pro Glu Phe Trp Arg Lys Met Asp Gly Asp Val Thr Lys Lys Glu Arg
                645                 650                 655
Asn Val Thr Leu Leu Trp Lys Pro Leu Thr Lys Asn Asp Ser Leu Cys
                    660                 665                 670
Ser Val Arg Arg Tyr Val Val Lys His Arg Thr Ala His Asn Gly Thr
            675                 680                 685
Trp Ser Glu Asp Val Gly Asn Arg Thr Asn Leu Thr Phe Leu Trp Thr
690                 695                 700
Glu Pro Ala His Thr Val Thr Val Leu Ala Val Asn Ser Leu Gly Ala
705                 710                 715                 720
Ser Leu Val Asn Phe Asn Leu Thr Phe Ser Trp Pro Met Ser Lys Val
                725                 730                 735
Ser Ala Val Glu Ser Leu Ser Ala Tyr Pro Leu Ser Ser Ser Cys Val
            740                 745                 750
Ile Leu Ser Trp Thr Leu Ser Pro Asp Asp Tyr Ser Leu Leu Tyr Leu
        755                 760                 765
Val Ile Glu Trp Lys Ile Leu Asn Glu Asp Asp Gly Met Lys Trp
    770                 775                 780

<210> SEQ ID NO 8
<211> LENGTH: 2868
<212> TYPE: DNA
<213> ORGANISM: Mus musculus

<400> SEQUENCE: 8
gggccccccc tcgaagtcga cggtatcgat aagcttgata tcgaattccg gccgggacac        60
aggtgggaca ctcttttagt cctcaatccc tggcgcgagg ccacccaagg caacgcagga      120
cgcagggcgt ttggggacca ggcagcagac tggggcggta cctgcggaga gccacgcaac      180
ttctccaggc ctctgactac tttggaaact gcccggggct gcgacatcaa ccccttaagt      240
cccggaggcg gaaagagggt gggttggttt gaaagacaca aggaagaaaa atgtgctgtg      300
gggcgggtta agtttcccac cctcttcccc cttcccgagc aaattagaaa caaaacaaat      360
agaaaagcca gccctccggc caaccaaagc cccaagcgga ccccaagcg agccccagc      420
cggagcactc ctttaaaagg atttgcagcg gtgaggaaaa aaccagaccc gaccgaggaa      480
tcgttctgca aatccaggtg tacacctctg aagaaagatg atgtgtcaga aattctatgt      540
ggttttgtta cactgggaat ttcttttatgt gatagctgca cttaacctgg catatccaat      600
ctctcccctgg aaatttaagt tgttttgtgg accaccgaac acaacgatg actcctttct      660
ctcacctgct ggagccccaa acaatgcctc ggctttgaag gggcttctg aagcaattgt      720
tgaagctaaa tttaattcaa gtggtatcta cgttcctgag ttatccaaaa cagtcttcca      780
ctgttgcttt gggaatgagc aaggtcaaaa ctgctctgca ctcacagaca cactgaagg      840
gaagacactg gcttcagtag tgaaggcttc agttttcgc cagctaggtg taaactggga      900
catagagtgc tggatgaaag gggacttgac attattcatc tgtcatatgg agccattacc      960
taagaacccc tcaagaatt atgactctaa ggtccatctt ttatatgatc tgcctgaagt     1020
catagatgat tcgcctctgc ccccactgaa agacagcttt cagactgtcc aatgcaactg     1080
cagtcttcgg ggatgtgaat gtcatgtgcc agtacccaga gccaaactca actacgctct     1140
```

```
tctgatgtat ttggaaatca catctgccgg tgtgagtttt cagtcacctc tgatgtcact    1200
gcagcccatg cttgttgtga aacccgatcc acccttaggt ttgcatatgg aagtcacaga    1260
tgatggtaat ttaaagattt cttgggacag ccaaacaatg gcaccatttc cgcttcaata    1320
tcaggtgaaa tatttagaga attctacaat tgtaagagag gctgctgaaa ttgtctcagc    1380
tacatctctg ctggtagaca gtgtgcttcc tggatcttca tatgaggtcc aggtgaggag    1440
caagagactg gatggttcag gagtctggag tgactggagt tcacctcaag tctttaccac    1500
acaagatgtt gtgtatttc cacccaaaat tctgactagt gttggatcga atgcttcctt    1560
tcattgcatc tacaaaaacg aaaaccagat tgtctcctca aaacagatag tttggtggag    1620
gaatctagct gagaaaatcc ctgagataca gtacagcatt gtgagtgacc gagttagcaa    1680
agttaccttc tccaacctga agccaccag acctcgaggg aagtttacct atgacgcagt    1740
gtactgctgc aatgagcagg cgtgccatca ccgctatgct gaattatacg tgatcgatgt    1800
caatatcaat atatcatgtg aaactgacgg gtacttaact aaaatgactt gcagatggtc    1860
acccagcaca atccaatcac tagtgggaag cactgtgcag ctgaggtatc acaggtgcag    1920
cctgtattgt cctgatagtc catctattca tcctacgtct gagcccaaaa ctgcgtctta    1980
cagagagacg gcttttatga atgtgttttc cagccaatct ttctattatc tggctataca    2040
atgtggattc aggatcaacc attctttagg ttcacttgac tcgccaccaa cgtgtgtcct    2100
tcctgactcc gtagtaaaac cactacctcc atctaacgta aaagcagaga ttactgtaaa    2160
cactggatta ttgaaagtat cttggaaaa gccagtcttt ccggagaata accttcaatt    2220
ccagattcga tatggcttaa gtggaaaaga aatacaatgg aagacacatg aggtattcga    2280
tgcaaagtca aagtctgcca gcctgctggt gtcagacctc tgtgcagtct atgtggtcca    2340
ggttcgctgc cggcggttgg atggactagg atattggagt aattggagca gtccagccta    2400
tacgcttgtc atggatgtaa aagttcctat gagagggcct gaattttgga gaaaaatgga    2460
tggggacgtt actaaaaagg agagaaatgt caccttgctt tggaagcccc tgacgaaaaa    2520
tgactcactg tgtagtgtga ggaggtacg ggtgaagcat cgtactgccc acaatgggac    2580
gtggtcagaa gatgtgggaa atcggaccaa tctcactttc ctgtggacag aaccagcgca    2640
cactgttaca gttctggctg tcaattccct cggcgcttcc cttgtgaatt ttaaccttac    2700
cttctcatgg cccatgagta aagtgagtgc tgtggagtca ctcagtgctt atcccctgag    2760
cagcagctgt gtcatccttt cctggacact gtcacctgat gattatagtc tgttatatct    2820
ggttattgaa tggaagatcc ttaatgaaga tgatggaatg aagtggct             2868
```

<210> SEQ ID NO 9
<211> LENGTH: 18
<212> TYPE: DNA
<213> ORGANISM: Artificial Sequence
<220> FEATURE:
<223> OTHER INFORMATION: Synthetic oligonucleotide sequence

<400> SEQUENCE: 9
gggttaagtt tcccaccc                                                    18

<210> SEQ ID NO 10
<211> LENGTH: 18
<212> TYPE: DNA
<213> ORGANISM: Artificial Sequence
<220> FEATURE:
<223> OTHER INFORMATION: Synthetic oligonucleotide sequence

```
<400> SEQUENCE: 10
gggtgggaaa cttaaccc                                             18

<210> SEQ ID NO 11
<211> LENGTH: 18
<212> TYPE: DNA
<213> ORGANISM: Artificial Sequence
<220> FEATURE:
<223> OTHER INFORMATION: Synthetic oligonucleotide sequence

<400> SEQUENCE: 11
aggatacagt gggatccc                                             18

<210> SEQ ID NO 12
<211> LENGTH: 18
<212> TYPE: DNA
<213> ORGANISM: Artificial Sequence
<220> FEATURE:
<223> OTHER INFORMATION: Synthetic oligonucleotide sequence

<400> SEQUENCE: 12
gcccgagcac tcctttaa                                             18

<210> SEQ ID NO 13
<211> LENGTH: 18
<212> TYPE: DNA
<213> ORGANISM: Artificial Sequence
<220> FEATURE:
<223> OTHER INFORMATION: Synthetic oligonucleotide sequence

<400> SEQUENCE: 13
ttaaaggagt gctcccgc                                             18

<210> SEQ ID NO 14
<211> LENGTH: 18
<212> TYPE: DNA
<213> ORGANISM: Artificial Sequence
<220> FEATURE:
<223> OTHER INFORMATION: Synthetic oligonucleotide sequence

<400> SEQUENCE: 14
gagcggccct gttagata                                             18

<210> SEQ ID NO 15
<211> LENGTH: 18
<212> TYPE: DNA
<213> ORGANISM: Artificial Sequence
<220> FEATURE:
<223> OTHER INFORMATION: Synthetic oligonucleotide sequence

<400> SEQUENCE: 15
gtatacacct ctgaagaa                                             18

<210> SEQ ID NO 16
<211> LENGTH: 18
<212> TYPE: DNA
<213> ORGANISM: Artificial Sequence
<220> FEATURE:
<223> OTHER INFORMATION: Synthetic oligonucleotide sequence

<400> SEQUENCE: 16
ttcttcagag gtgtacac                                             18

<210> SEQ ID NO 17
<211> LENGTH: 18
```

```
<212> TYPE: DNA
<213> ORGANISM: Artificial Sequence
<220> FEATURE:
<223> OTHER INFORMATION: Synthetic oligonucleotide sequence

<400> SEQUENCE: 17
atgcgaggct acttctat                                                     18

<210> SEQ ID NO 18
<211> LENGTH: 18
<212> TYPE: DNA
<213> ORGANISM: Artificial Sequence
<220> FEATURE:
<223> OTHER INFORMATION: Synthetic oligonucleotide sequence

<400> SEQUENCE: 18
ctctccctgg aaatttaa                                                     18

<210> SEQ ID NO 19
<211> LENGTH: 18
<212> TYPE: DNA
<213> ORGANISM: Artificial Sequence
<220> FEATURE:
<223> OTHER INFORMATION: Synthetic oligonucleotide sequence

<400> SEQUENCE: 19
ttaaatttcc agggagag                                                     18

<210> SEQ ID NO 20
<211> LENGTH: 18
<212> TYPE: DNA
<213> ORGANISM: Artificial Sequence
<220> FEATURE:
<223> OTHER INFORMATION: Synthetic oligonucleotide sequence

<400> SEQUENCE: 20
atttgaagga gttaagcc                                                     18

<210> SEQ ID NO 21
<211> LENGTH: 18
<212> TYPE: DNA
<213> ORGANISM: Artificial Sequence
<220> FEATURE:
<223> OTHER INFORMATION: Synthetic oligonucleotide sequence

<400> SEQUENCE: 21
aatttaattc aagtggta                                                     18

<210> SEQ ID NO 22
<211> LENGTH: 18
<212> TYPE: DNA
<213> ORGANISM: Artificial Sequence
<220> FEATURE:
<223> OTHER INFORMATION: Synthetic oligonucleotide sequence

<400> SEQUENCE: 22
taccagttga attaaatt                                                     18

<210> SEQ ID NO 23
<211> LENGTH: 18
<212> TYPE: DNA
<213> ORGANISM: Artificial Sequence
<220> FEATURE:
<223> OTHER INFORMATION: Synthetic oligonucleotide sequence

<400> SEQUENCE: 23
```

-continued gtatcacttc ataatata                                                18

<210> SEQ ID NO 24
<211> LENGTH: 18
<212> TYPE: DNA
<213> ORGANISM: Artificial Sequence
<220> FEATURE:
<223> OTHER INFORMATION: Synthetic oligonucleotide sequence

<400> SEQUENCE: 24
gatggtcagg gtgaactg                                                18

<210> SEQ ID NO 25
<211> LENGTH: 18
<212> TYPE: DNA
<213> ORGANISM: Artificial Sequence
<220> FEATURE:
<223> OTHER INFORMATION: Synthetic oligonucleotide sequence

<400> SEQUENCE: 25
cagttcaccc tgaccatc                                                18

<210> SEQ ID NO 26
<211> LENGTH: 18
<212> TYPE: DNA
<213> ORGANISM: Artificial Sequence
<220> FEATURE:
<223> OTHER INFORMATION: Synthetic oligonucleotide sequence

<400> SEQUENCE: 26
gaggcgaatg tgcggatt                                                18

<210> SEQ ID NO 27
<211> LENGTH: 18
<212> TYPE: DNA
<213> ORGANISM: Artificial Sequence
<220> FEATURE:
<223> OTHER INFORMATION: Synthetic oligonucleotide sequence

<400> SEQUENCE: 27
cttaaatctc caaggagt                                                18

<210> SEQ ID NO 28
<211> LENGTH: 18
<212> TYPE: DNA
<213> ORGANISM: Artificial Sequence
<220> FEATURE:
<223> OTHER INFORMATION: Synthetic oligonucleotide sequence

<400> SEQUENCE: 28
actccttgga gatttaag                                                18

<210> SEQ ID NO 29
<211> LENGTH: 18
<212> TYPE: DNA
<213> ORGANISM: Artificial Sequence
<220> FEATURE:
<223> OTHER INFORMATION: Synthetic oligonucleotide sequence

<400> SEQUENCE: 29
aagtcttaag ccagactt                                                18

<210> SEQ ID NO 30
<211> LENGTH: 18
<212> TYPE: DNA
<213> ORGANISM: Artificial Sequence

```
<220> FEATURE:
<223> OTHER INFORMATION: Synthetic oligonucleotide sequence

<400> SEQUENCE: 30
tctaaggcac atcccagc                                                    18

<210> SEQ ID NO 31
<211> LENGTH: 18
<212> TYPE: DNA
<213> ORGANISM: Artificial Sequence
<220> FEATURE:
<223> OTHER INFORMATION: Synthetic oligonucleotide sequence

<400> SEQUENCE: 31
gctgggatgt gccttaga                                                    18

<210> SEQ ID NO 32
<211> LENGTH: 18
<212> TYPE: DNA
<213> ORGANISM: Artificial Sequence
<220> FEATURE:
<223> OTHER INFORMATION: Synthetic oligonucleotide sequence

<400> SEQUENCE: 32
cgcaatgaat tgacaccc                                                    18

<210> SEQ ID NO 33
<211> LENGTH: 18
<212> TYPE: DNA
<213> ORGANISM: Artificial Sequence
<220> FEATURE:
<223> OTHER INFORMATION: Synthetic oligonucleotide sequence

<400> SEQUENCE: 33
tacttcagag aagtacac                                                    18

<210> SEQ ID NO 34
<211> LENGTH: 18
<212> TYPE: DNA
<213> ORGANISM: Artificial Sequence
<220> FEATURE:
<223> OTHER INFORMATION: Synthetic oligonucleotide sequence

<400> SEQUENCE: 34
gtgtacttct ctgaagta                                                    18

<210> SEQ ID NO 35
<211> LENGTH: 18
<212> TYPE: DNA
<213> ORGANISM: Artificial Sequence
<220> FEATURE:
<223> OTHER INFORMATION: Synthetic oligonucleotide sequence

<400> SEQUENCE: 35
gaatcacggt aactatca                                                    18

<210> SEQ ID NO 36
<211> LENGTH: 18
<212> TYPE: DNA
<213> ORGANISM: Artificial Sequence
<220> FEATURE:
<223> OTHER INFORMATION: Synthetic oligonucleotide sequence

<400> SEQUENCE: 36
cagctgtctc ataatgtc                                                    18
```

```
<210> SEQ ID NO 37
<211> LENGTH: 18
<212> TYPE: DNA
<213> ORGANISM: Artificial Sequence
<220> FEATURE:
<223> OTHER INFORMATION: Synthetic oligonucleotide sequence

<400> SEQUENCE: 37
gacattatga gacagctg                                                18

<210> SEQ ID NO 38
<211> LENGTH: 18
<212> TYPE: DNA
<213> ORGANISM: Artificial Sequence
<220> FEATURE:
<223> OTHER INFORMATION: Synthetic oligonucleotide sequence

<400> SEQUENCE: 38
ttcgtcaagc catctgat                                                18

<210> SEQ ID NO 39
<211> LENGTH: 8
<212> TYPE: PRT
<213> ORGANISM: Artificial Sequence
<220> FEATURE:
<223> OTHER INFORMATION: Exemplary salvage receptor binding epitope
      sequence

<400> SEQUENCE: 39

His Gln Asn Leu Ser Asp Gly Lys
 1               5

<210> SEQ ID NO 40
<211> LENGTH: 8
<212> TYPE: PRT
<213> ORGANISM: Artificial Sequence
<220> FEATURE:
<223> OTHER INFORMATION: Exemplary salvage receptor binding epitope
      sequence

<400> SEQUENCE: 40

His Gln Asn Ile Ser Asp Gly Lys
 1               5

<210> SEQ ID NO 41
<211> LENGTH: 7
<212> TYPE: PRT
<213> ORGANISM: Artificial Sequence
<220> FEATURE:
<223> OTHER INFORMATION: Exemplary salvage receptor binding epitope
      sequence

<400> SEQUENCE: 41

His Gln Ser Leu Gly Thr Gln
 1               5

<210> SEQ ID NO 42
<211> LENGTH: 8
<212> TYPE: PRT
<213> ORGANISM: Artificial Sequence
<220> FEATURE:
<223> OTHER INFORMATION: Exemplary salvage receptor binding epitope
      sequence

<400> SEQUENCE: 42

Val Ile Ser Ser His Leu Gly Gln
 1               5
```

<210> SEQ ID NO 43
<211> LENGTH: 11
<212> TYPE: PRT
<213> ORGANISM: Artificial Sequence
<220> FEATURE:
<223> OTHER INFORMATION: Exemplary salvage receptor binding epitope
      sequence

<400> SEQUENCE: 43

Pro Lys Asn Ser Ser Met Ile Ser Asn Thr Pro
 1               5                  10

<210> SEQ ID NO 44
<211> LENGTH: 10
<212> TYPE: PRT
<213> ORGANISM: Homo sapiens

<400> SEQUENCE: 44

Asp Lys Thr His Thr Cys Pro Pro Cys Pro
 1               5                  10

<210> SEQ ID NO 45
<211> LENGTH: 51
<212> TYPE: DNA
<213> ORGANISM: Artificial Sequence
<220> FEATURE:
<223> OTHER INFORMATION: Synthetic oligonucleotide probe sequence

<400> SEQUENCE: 45
gtcagtctcc cagttccaga cttgtgtgca gtctatgctg ttcaggtgcg c            51

<210> SEQ ID NO 46
<211> LENGTH: 7127
<212> TYPE: DNA
<213> ORGANISM: Homo sapiens

<400> SEQUENCE: 46
ttcgagctcg cccgacattg attattgact agttattaat agtaatcaat tacggggtca     60
ttagttcata gcccatatat ggagttccgc gttacataac ttacggtaaa tggcccgcct    120
ggctgaccgc ccaacgaccc ccgcccattg acgtcaataa tgacgtatgt tcccatagta    180
acgccaatag ggactttcca ttgacgtcaa tgggtggagt atttacggta aactgcccac    240
ttggcagtac atcaagtgta tcatatgcca gtacgccccc tattgacgtc aatgacggt     300 aaatggcccg cctggcatta tgcccagtac atgaccttat gggactttcc tacttggcag    360
tacatctacg tattagtcat cgctattacc atggtgatgc ggttttggca gtacatcaat    420
gggcgtggat agcggtttga ctcacgggga tttccaagtc tccaccccat tgacgtcaat    480
gggagtttgt tttggcacca aaatcaacgg gactttccaa aatgtcgtaa caactccgcc    540
ccattgacgc aaatgggcgg taggcgtgta cggtgggagg tctatataag cagagctcgt    600
ttagtgaacc gtcagatcgc ctggagacgc catccacgct gttttgacct ccatagaaga    660
caccgggacc gatccagcct ccgcggccgg gaacggtgca ttggaacgcg gattccccgt    720
gccaagagtg acgtaagtac cgcctataga gtctataggc ccaccccctt ggcttcgtta    780
gaacgcggct acaattaata cataacctta tgtatcatac acatacgatt taggtgacac    840
tatagaataa catccacttt gcctttctct ccacaggtgt ccactcccag gtccaactgc    900
acctcggttc tatcgatatg cattggggaa cctgtgcgg attcttgtgg ctttggcccct    960 atcttttcta tgtccaagct gtgcccatcc aaaaagtcca agatgacacc aaaaccctca   1020

-continued

```
tcaagacaat tgtcaccagg atcaatgaca tttcacacac gcagtcagtc tcctccaaac   1080
agaaagtcac cggtttggac ttcattcctg ggctccaccc catcctgacc ttatccaaga   1140
tggaccagac actggcagtc taccaacaga tcctcaccag tatgccttcc agaaacgtga   1200
tccaaatatc caacgacctg gagaacctcc gggatcttct tcacgtgctg gccttctcta   1260
agagctgcca cttgccctgg gccagtggcc tggagacctt ggacagcctg ggggtgtcc    1320 tggaagcttc aggctactcc acagaggtgg tggccctgag caggctgcag gggtctctgc   1380
aggacatgct gtggcagctg gacctcagcc ctgggtgcgg ggtcaccgac aaaactcaca   1440
catgcccacc gtgcccagca cctgaactcc tggggggacc gtcagtcttc ctcttccccc   1500
caaaacccaa ggacaccctc atgatctccc ggacccctga ggtcacatgc gtggtggtgg   1560
acgtgagcca cgaagaccct gaggtcaagt tcaactggta cgtggacggc gtggaggtgc   1620
ataatgccaa gacaaagccg cgggaggagc agtacaacag cacgtaccgt gtggtcagcg   1680
tcctcaccgt cctgcaccag gactggctga atggcaagga gtacaagtgc aaggtctcca   1740
acaaagccct cccagccccc atcgagaaaa ccatctccaa agccaaaggg cagccccgag   1800
aaccacaggt gtacaccctg cccccatccc gggaagagat gaccaagaac caggtcagcc   1860
tgacctgcct ggtcaaaggc ttctatccca gcgacatcgc cgtggagtgg gagagcaatg   1920
ggcagccgga gaacaactac aagaccacgc ctcccgtgct ggactccgac ggctccttct   1980
tcctctacag caagctcacc gtggacaaga gcaggtggca gcaggggaac gtcttctcat   2040
gctccgtgat gcatgaggct ctgcacaacc actacacgca gaagagcctc tccctgtctc   2100
cgggtaaatg agtgcgacgg ccctagagtc gacctgcaga agcttctaga gtcgacctgc   2160
agaagcttgg ccgccatggc ccaacttgtt tattgcagct tataatggtt acaaataaag   2220
caatagcatc acaaatttca caaataaagc atttttttca ctgcattcta gttgtggttt   2280
gtccaaactc atcaatgtat cttatcatgt ctggatcgat cgggaattaa ttcggcgcag   2340
caccatggcc tgaaataacc tctgaaagag gaacttggtt aggtaccttc tgaggcggaa   2400
agaaccagct gtggaatgtg tgtcagttag ggtgtggaaa gtccccaggc tccccagcag   2460
gcagaagtat gcaaagcatg catctcaatt agtcagcaac caggtgtgga aagtccccag   2520 gctcccagc aggcagaagt atgcaaagca tgcatctcaa ttagtcagca accatagtcc   2580
cgcccctaac tccgcccatc ccgcccctaa ctccgcccag ttccgcccat tctccgcccc   2640
atggctgact aatttttttt atttatgcag aggccgaggc cgcctcggcc tctgagctat   2700
tccagaagta gtgaggaggc ttttttggag gcctaggctt ttgcaaaaag ctgttaattc   2760
gaacacgcag atgcagtcgg ggcggcgcgg tcccaggtcc acttcgcata ttaaggtgac   2820
gcgtgtggcc tcgaacaccg agcgaccctg cagcgacccg cttaacagcg tcaacagcgt   2880
gccgcagatc tgatcaagag acaggatgag gatcgtttcg catgattgaa caagatggat   2940
tgcacgcagg ttctccggcc gcttgggtgg agaggctatt cggctatgac tgggcacaac   3000
agacaatcgg ctgctctgat gccgccgtgt tccggctgtc agcgcagggg cgcccggttc   3060
tttttgtcaa gaccgacctg tccggtgccc tgaatgaact gcaggacgag gcagcgcggc   3120
tatcgtggct ggccacgacg ggcgttcctt gcgcagctgt gctcgacgtt gtcactgaag   3180
cgggaaggga ctggctgcta ttgggcgaag tgccggggca ggatctcctg tcatctcacc   3240
ttgctcctgc cgagaaagta tccatcatgg ctgatgcaat gcggcggctg catacgcttg   3300
atccggctac ctgcccattc gaccaccaag cgaaacatcg catcgagcga gcacgtactc   3360
```

```
ggatggaagc cggtcttgtc gatcaggatg atctggacga agagcatcag gggctcgcgc    3420
cagccgaact gttcgccagg ctcaaggcgc gcatgcccga cggcgaggat ctcgtcgtga    3480
cccatggcga tgcctgcttg ccgaatatca tggtggaaaa tggccgcttt tctggattca    3540
tcgactgtgg ccggctgggt gtggcggacc gctatcagga catagcgttg gctacccgtg    3600
atattgctga agagcttggc ggcgaatggg ctgaccgctt cctcgtgctt tacggtatcg    3660
ccgctcccga ttcgcagcgc atcgccttct atcgccttct tgacgagttc ttctgagcgg    3720
gactctgggg ttcgaaatga ccgaccaagc gacgcccaac ctgccatcac gagatttcga    3780
ttccaccgcc gccttctatg aaaggttggg cttcggaatc gttttccggg acgccggctg    3840
gatgatcctc cagcgcgggg atctcatgct ggagttcttc gcccacccca ggagatgggg    3900
gaggctaact gaaacacgga aggagacaat accggaagga acccgcgcta tgacggcaat    3960
aaaaagacag aataaaacgc acgggtgttg ggtcgtttgt tcataaacgc ggggttcggt    4020
cccagggctg gcactctgtc gatacccccac cgagacccca ttggggccaa tacgcccgcg    4080
tttcttcctt ttccccaccc caaccccccaa gttcgggtga aggcccaggg ctcgcagcca    4140
acgtcggggc ggcaagcccg ccatagccac ggggccccgtg ggttagggac ggggtccccc    4200
atggggaatg gtttatggtt cgtgggggtt attcttttgg gcgttgcgtg gggtcaggtc    4260
cacgactgga ctgagcagac agacccatgg ttttggatg gcctgggcat ggaccgcatg    4320
tactggcgcg acacgaacac cgggcgtctg tggctgccaa acaccccga cccccaaaaa    4380 ccaccgcgcg gatttctggc gccgccggac gaactaaacc tgactacggc atctctgccc    4440
cttcttcgct ggtacgagga gcgcttttgt tttgtattgg tcaccacggc cgagtttccg    4500
cgggaccccg gccagggcac ctgtcctacg agttgcatga taaagaagac agtcataagt    4560
gcggcgacga tagtcatgcc ccgcgcccac cggaaggagc tgactgggtt gaaggctctc    4620
aagggcatcg gtcgagcggc cgcatcaaag caaccatagt acgcgccctg tagcggcgca    4680
ttaagcgcgg cgggtgtggt ggttacgcgc agcgtgaccg ctacacttgc cagcgcccta    4740
gcgcccgctc ctttcgcttt cttcccttcc tttctcgcca cgttcgccgg ctttccccgt    4800
caagctctaa atcgggggct cccctttaggg ttccgattta gtgctttacg gcacctcgac    4860
cccaaaaaac ttgatttggg tgatggttca cgtagtgggc catcgccctg atagacggtt    4920
tttcgccctt tgacgttgga gtccacgttc tttaatagtg gactcttgtt ccaaactgga    4980
acaacactca accctatctc gggctattct tttgatttat aagggatttt gccgatttcg    5040
gcctattggt taaaaatga gctgatttaa caaaaattta acgcgaattt taacaaaata    5100
ttaacgttta caatttttatg gtgcaggcct cgtgatacgc ctatttttat aggttaatgt    5160
catgataata atggtttctt agacgtcagg tggcactttt cggggaaatg tgcgcggaac    5220
ccctatttgt ttatttttct aaatacattc aaatatgtat ccgctcatga caataaacc    5280 ctgataaatg cttcaataat attgaaaaag gaagagtatg agtattcaac atttccgtgt    5340
cgcccttatt ccctttttg cggcattttg ccttcctgtt tttgctcacc cagaaacgct    5400
ggtgaaagta aaagatgctg aagatcagtt gggtgcacga gtgggttaca tcgaactgga    5460
tctcaacagc ggtaagatcc ttgagagttt tcgccccgaa gaacgttttc caatgatgag    5520
cacttttaaa gttctgctat gtggcgcggt attatcccgt gatgacgccg gcaagagca    5580 actcggtcgc cgcatacact attctcagaa tgacttggtt gagtactcac cagtcacaga    5640
aaagcatctt acgatggca tgacagtaag agaattatgc agtgctgcca taaccatgag    5700
tgataacact gcggccaact tacttctgac aacgatcgga ggaccgaagg agctaaccgc    5760
```

```
ttttttgcac aacatggggg atcatgtaac tcgccttgat cgttgggaac cggagctgaa    5820
tgaagccata ccaaacgacg agcgtgacac cacgatgcca gcagcaatgg caacaacgtt    5880
gcgcaaacta ttaactggcg aactacttac tctagcttcc cggcaacaat taatagactg    5940
gatggaggcg ataaagttg caggaccact tctgcgctcg gcccttccgg ctggctggtt    6000
tattgctgat aaatctggag ccggtgagcg tgggtctcgc ggtatcattg cagcactggg    6060
gccagatggt aagccctccc gtatcgtagt tatctacacg acggggagtc aggcaactat    6120
ggatgaacga atagacaga tcgctgagat aggtgcctca ctgattaagc attggtaact    6180
gtcagaccaa gtttactcat atatacttta gattgattta aaacttcatt tttaatttaa    6240
aaggatctag gtgaagatcc ttttgataa tctcatgacc aaaatccctt aacgtgagtt    6300
ttcgttccac tgagcgtcag accccgtaga aagatcaaa ggatcttctt gagatccttt    6360
ttttctgcgc gtaatctgct gcttgcaaac aaaaaaacca ccgctaccag cggtggtttg    6420
tttgccggat caagagctac caactctttt tccgaaggta actggcttca gcagagcgca    6480
gataccaaat actgtccttc tagtgtagcc gtagttaggc caccacttca gaactctgt    6540 agcaccgcct acatacctcg ctctgctaat cctgttacca gtggctgctg ccagtggcga    6600
taagtcgtgt cttaccgggt tggactcaag acgatagtta ccggataagg cgcagcggtc    6660
gggctgaacg gggggttcgt gcacacagcc cagcttggag cgaacgacct acaccgaact    6720
gagataccta cagcgtgagc attgagaaag cgccacgctt cccgaaggga aaaggcgga    6780 caggtatccg gtaagcggca gggtcggaac aggagagcgc acgagggagc ttccaggggg    6840
aaacgcctgg tatctttata gtcctgtcgg gtttcgccac ctctgacttg agcgtcgatt    6900
tttgtgatgc tcgtcagggg gcggagcct atggaaaaac gccagctggc acgacaggtt    6960
tcccgactgg aaagcgggca gtgagcgcaa cgcaattaat gtgagttacc tcactcatta    7020
ggcaccccag gctttacact ttatgcttcc ggctcgtatg ttgtgtggaa ttgtgagcgg    7080
ataacaattt cacacaggaa acagctatga ccatgattac gaattaa                 7127
```

<210> SEQ ID NO 47
<211> LENGTH: 397
<212> TYPE: PRT
<213> ORGANISM: Homo sapiens

<400> SEQUENCE: 47

Met His Trp Gly Thr Leu Cys Gly Phe Leu Trp Leu Trp Pro Tyr Leu
 1               5                  10                  15

Phe Tyr Val Gln Ala Val Pro Ile Gln Lys Val Gln Asp Asp Thr Lys
              20                  25                  30

Thr Leu Ile Lys Thr Ile Val Thr Arg Ile Asn Asp Ile Ser His Thr
         35                  40                  45

Gln Ser Val Ser Ser Lys Gln Lys Val Thr Gly Leu Asp Phe Ile Pro
     50                  55                  60

Gly Leu His Pro Ile Leu Thr Leu Ser Lys Met Asp Gln Thr Leu Ala
 65                  70                  75                  80

Val Tyr Gln Gln Ile Leu Thr Ser Met Pro Ser Arg Asn Val Ile Gln
                 85                  90                  95

Ile Ser Asn Asp Leu Glu Asn Leu Arg Asp Leu Leu His Val Leu Ala
            100                 105                 110

Phe Ser Lys Ser Cys His Leu Pro Trp Ala Ser Gly Leu Glu Thr Leu
        115                 120                 125

Asp Ser Leu Gly Gly Val Leu Glu Ala Ser Gly Tyr Ser Thr Glu Val
    130                 135                 140

Val Ala Leu Ser Arg Leu Gln Gly Ser Leu Gln Asp Met Leu Trp Gln
145                 150                 155                 160

Leu Asp Leu Ser Pro Gly Cys Gly Val Thr Asp Lys Thr His Thr Cys
                165                 170                 175

Pro Pro Cys Pro Ala Pro Glu Leu Leu Gly Gly Pro Ser Val Phe Leu
            180                 185                 190

Phe Pro Pro Lys Pro Lys Asp Thr Leu Met Ile Ser Arg Thr Pro Glu
        195                 200                 205

Val Thr Cys Val Val Val Asp Val Ser His Glu Asp Pro Glu Val Lys
    210                 215                 220

Phe Asn Trp Tyr Val Asp Gly Val Glu Val His Asn Ala Lys Thr Lys
225                 230                 235                 240

Pro Arg Glu Glu Gln Tyr Asn Ser Thr Tyr Arg Val Val Ser Val Leu
                245                 250                 255

Thr Val Leu His Gln Asp Trp Leu Asn Gly Lys Glu Tyr Lys Cys Lys
            260                 265                 270

Val Ser Asn Lys Ala Leu Pro Ala Pro Ile Glu Lys Thr Ile Ser Lys
        275                 280                 285

Ala Lys Gly Gln Pro Arg Glu Pro Gln Val Tyr Thr Leu Pro Pro Ser
    290                 295                 300

Arg Glu Glu Met Thr Lys Asn Gln Val Ser Leu Thr Cys Leu Val Lys
305                 310                 315                 320

Gly Phe Tyr Pro Ser Asp Ile Ala Val Glu Trp Glu Ser Asn Gly Gln
                325                 330                 335

Pro Glu Asn Asn Tyr Lys Thr Thr Pro Pro Val Leu Asp Ser Asp Gly
            340                 345                 350

Ser Phe Phe Leu Tyr Ser Lys Leu Thr Val Asp Lys Ser Arg Trp Gln
        355                 360                 365

Gln Gly Asn Val Phe Ser Cys Ser Val Met His Glu Ala Leu His Asn
    370                 375                 380

His Tyr Thr Gln Lys Ser Leu Ser Leu Ser Pro Gly Lys
385                 390                 395

<210> SEQ ID NO 48
<211> LENGTH: 249
<212> TYPE: PRT
<213> ORGANISM: Homo sapiens

<400> SEQUENCE: 48

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met Tyr Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Gly Thr Ala Tyr
65                  70                  75                  80

Met Glu Leu Ser Arg Leu Ser Ser Asp Thr Ala Val Tyr Tyr Cys
                85                  90                  95

Ala Arg Asp Arg Tyr Tyr Gly Ser Ser Ala Tyr His Arg Gly Ser Tyr
            100                 105                 110

```
Tyr Met Asp Val Trp Gly Arg Gly Thr Leu Val Thr Val Ser Ser Gly
        115                 120                 125

Gly Gly Gly Thr Gly Gly Gly Ser Gly Gly Gly Ser Ser Glu
        130                 135                 140

Leu Thr Gln Asp Pro Ala Val Ser Val Ala Leu Gly Gln Thr Val Arg
145                 150                 155                 160

Ile Thr Cys Gln Gly Asp Ser Leu Arg Ser Tyr Tyr Ala Ser Trp Tyr
                165                 170                 175

Gln Gln Lys Pro Gly Gln Ala Pro Val Leu Val Ile Tyr Gly Lys Asn
                180                 185                 190

Asn Arg Pro Ser Gly Ile Pro Asp Arg Phe Ser Gly Ser Ser Ser Gly
                195                 200                 205

Asn Thr Ala Ser Leu Thr Ile Thr Gly Ala Gln Ala Glu Asp Glu Ala
            210                 215                 220

Asp Tyr Tyr Cys Asn Ser Arg Asp Ser Ser Gly Asn His Val Val Phe
225                 230                 235                 240

Gly Gly Gly Thr Lys Leu Thr Val Leu
                245
```

<210> SEQ ID NO 49
<211> LENGTH: 250
<212> TYPE: PRT
<213> ORGANISM: Homo sapiens

<400> SEQUENCE: 49

```
Glu Val Gln Leu Val Gln Ser Gly Ala Glu Val Lys Lys Pro Gly Glu
1               5                   10                  15

Ser Leu Lys Ile Ser Cys Gln Gly Ser Gly Phe Thr Phe Ser Ser Tyr
            20                  25                  30

Lys Met Asn Trp Val Arg Gln Ala Pro Gly Lys Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Arg Val Val Val Pro Ala Thr Ser Leu Arg Gly Gly Met
                100                 105                 110

Asp Val Trp Gly Gln Gly Thr Thr Val Thr Val Ser Ser Gly Gly Gly
            115                 120                 125

Gly Ser Gly Gly Gly Gly Ser Gly Gly Gly Ser Gln Ser Val Leu
        130                 135                 140

Thr Gln Pro Ala Ser Val Ser Gly Ser Pro Gly Gln Ser Ile Thr Ile
145                 150                 155                 160

Ser Cys Thr Gly Thr Ser Ser Asp Val Gly Gly Tyr Asn Tyr Val Ser
                165                 170                 175

Trp Tyr Gln Gln His Pro Gly Lys Ala Pro Lys Leu Met Ile Tyr Glu
                180                 185                 190

Gly Ser Lys Arg Pro Ser Gly Val Ser Asn Arg Phe Ser Gly Ser Lys
                195                 200                 205

Ser Gly Ser Thr Ala Ser Leu Thr Ile Ser Gly Leu Gln Ala Glu Asp
            210                 215                 220

Glu Ala Asp Tyr Tyr Cys Ser Ser Tyr Thr Thr Arg Ser Thr Arg Val
```

```
                225                 230                 235                 240

Phe Gly Gly Gly Thr Lys Leu Thr Val Leu
                        245                 250

<210> SEQ ID NO 50
<211> LENGTH: 241
<212> TYPE: PRT
<213> ORGANISM: Homo sapiens

<400> SEQUENCE: 50

Gln Val Arg Leu Gln Gln Ser Gly Gly Leu Val Gln Pro Gly Arg
        1               5                   10                  15

Ser Leu Arg Leu Ser Cys Ala Ala Ser Gly Phe Thr Phe Asp Asp Tyr
                        20                  25                  30

Ala Met His Trp Val Arg Gln Ala Pro Gly Lys Gly Leu Glu Trp Val
                        35                  40                  45

Ser Gly Met Thr Trp Asn Ser Gly Ser Ile Gly Tyr Ala Asp Ser Val
                        50                  55                  60

Lys Gly Arg Phe Thr Ile Ser Arg Asp Asn Ala Lys Asn Ser Leu Tyr
        65                  70                  75                  80

Leu Gln Met Asn Ser Leu Arg Ala Glu Asp Thr Ala Val Tyr Tyr Cys
                        85                  90                  95

Ala Arg Glu Pro His Asn Thr Asp Ala Phe Asp Ile Trp Gly Arg Gly
                        100                 105                 110

Thr Leu Val Thr Val Ser Ser Gly Gly Gly Pro Gly Gly Gly Gly
                        115                 120                 125

Ser Gly Gly Gly Gly Ser Asp Val Val Met Thr Gln Ser Pro Ser Phe
                        130                 135                 140

Leu Ser Ala Phe Val Gly Asp Thr Ile Thr Ile Thr Cys Arg Ala Ser
        145                 150                 155                 160

Gln Gly Ile Tyr Asn Tyr Leu Ala Trp Tyr Gln Gln Lys Pro Gly Lys
                        165                 170                 175

Ala Pro Lys Leu Leu Ile Tyr Ala Ala Ser Thr Leu Gln Ser Gly Val
                        180                 185                 190

Pro Ser Arg Phe Ser Gly Ser Gly Ser Gly Thr Glu Phe Thr Leu Thr
                        195                 200                 205

Ile Ser Ser Leu Gln Pro Glu Asp Phe Gly Thr Tyr Tyr Cys Gln Gln
                        210                 215                 220

Leu Ile Ser Tyr Pro Leu Thr Phe Gly Gly Gly Thr Lys Val Glu Ile
        225                 230                 235                 240

Lys

<210> SEQ ID NO 51
<211> LENGTH: 894
<212> TYPE: PRT
<213> ORGANISM: Mus musculus

<400> SEQUENCE: 51

Met Met Cys Gln Lys Phe Tyr Val Val Leu Leu His Trp Glu Phe Leu
        1               5                   10                  15

Tyr Val Ile Ala Ala Leu Asn Leu Ala Tyr Pro Ile Ser Pro Trp Lys
                        20                  25                  30

Phe Lys Leu Phe Cys Gly Pro Pro Asn Thr Thr Asp Asp Ser Phe Leu
                        35                  40                  45

Ser Pro Ala Gly Ala Pro Asn Asn Ala Ser Ala Leu Lys Gly Ala Ser
                        50                  55                  60
```

-continued

```
Glu Ala Ile Val Glu Ala Lys Phe Asn Ser Ser Gly Ile Tyr Val Pro
 65                  70                  75                  80

Glu Leu Ser Lys Thr Val Phe His Cys Cys Phe Gly Asn Glu Gln Gly
                 85                  90                  95

Gln Asn Cys Ser Ala Leu Thr Asp Asn Thr Glu Gly Lys Thr Leu Ala
            100                 105                 110

Ser Val Val Lys Ala Ser Val Phe Arg Gln Leu Gly Val Asn Trp Asp
        115                 120                 125

Ile Glu Cys Trp Met Lys Gly Asp Leu Thr Leu Phe Ile Cys His Met
130                 135                 140

Glu Pro Leu Pro Lys Asn Pro Phe Lys Asn Tyr Asp Ser Lys Val His
145                 150                 155                 160

Leu Leu Tyr Asp Leu Pro Glu Val Ile Asp Asp Ser Pro Leu Pro Pro
                165                 170                 175

Leu Lys Asp Ser Phe Gln Thr Val Gln Cys Asn Cys Ser Leu Arg Gly
            180                 185                 190

Cys Glu Cys His Val Pro Val Pro Arg Ala Lys Leu Asn Tyr Ala Leu
        195                 200                 205

Leu Met Tyr Leu Glu Ile Thr Ser Ala Gly Val Ser Phe Gln Ser Pro
210                 215                 220

Leu Met Ser Leu Gln Pro Met Leu Val Val Lys Pro Asp Pro Pro Leu
225                 230                 235                 240

Gly Leu His Met Glu Val Thr Asp Asp Gly Asn Leu Lys Ile Ser Trp
                245                 250                 255

Asp Ser Gln Thr Met Ala Pro Phe Pro Leu Gln Tyr Gln Val Lys Tyr
            260                 265                 270

Leu Glu Asn Ser Thr Ile Val Arg Glu Ala Ala Glu Ile Val Ser Ala
        275                 280                 285

Thr Ser Leu Leu Val Asp Ser Val Leu Pro Gly Ser Ser Tyr Glu Val
290                 295                 300

Gln Val Arg Ser Lys Arg Leu Asp Gly Ser Gly Val Trp Ser Asp Trp
305                 310                 315                 320

Ser Ser Pro Gln Val Phe Thr Thr Gln Asp Val Val Tyr Phe Pro Pro
                325                 330                 335

Lys Ile Leu Thr Ser Val Gly Ser Asn Ala Ser Phe His Cys Ile Tyr
            340                 345                 350

Lys Asn Glu Asn Gln Ile Ile Ser Ser Lys Gln Ile Val Trp Trp Arg
        355                 360                 365

Asn Leu Ala Glu Lys Ile Pro Glu Ile Gln Tyr Ser Ile Val Ser Asp
370                 375                 380

Arg Val Ser Lys Val Thr Phe Ser Asn Leu Lys Ala Thr Arg Pro Arg
385                 390                 395                 400

Gly Lys Phe Thr Tyr Asp Ala Val Tyr Cys Cys Asn Glu Gln Ala Cys
                405                 410                 415

His His Arg Tyr Ala Glu Leu Tyr Val Ile Asp Val Asn Ile Asn Ile
            420                 425                 430

Ser Cys Glu Thr Asp Gly Tyr Leu Thr Lys Met Thr Cys Arg Trp Ser
        435                 440                 445

Pro Ser Thr Ile Gln Ser Leu Val Gly Ser Thr Val Gln Leu Arg Tyr
450                 455                 460

His Arg Arg Ser Leu Tyr Cys Pro Asp Ser Pro Ser Ile His Pro Thr
465                 470                 475                 480
```

```
Ser Glu Pro Lys Asn Cys Val Leu Gln Arg Asp Gly Phe Tyr Glu Cys
            485                 490                 495

Val Phe Gln Pro Ile Phe Leu Leu Ser Gly Tyr Thr Met Trp Ile Arg
                500                 505                 510

Ile Asn His Ser Leu Gly Ser Leu Asp Ser Pro Pro Thr Cys Val Leu
            515                 520                 525

Pro Asp Ser Val Val Lys Pro Leu Pro Pro Ser Asn Val Lys Ala Glu
        530                 535                 540

Ile Thr Val Asn Thr Gly Leu Leu Lys Val Ser Trp Glu Lys Pro Val
545                 550                 555                 560

Phe Pro Glu Asn Asn Leu Gln Phe Gln Ile Arg Tyr Gly Leu Ser Gly
                565                 570                 575

Lys Glu Ile Gln Trp Lys Thr His Glu Val Phe Asp Ala Lys Ser Lys
            580                 585                 590

Ser Ala Ser Leu Leu Val Ser Asp Leu Cys Ala Val Tyr Val Val Gln
            595                 600                 605

Val Arg Cys Arg Arg Leu Asp Gly Leu Gly Tyr Trp Ser Asn Trp Ser
        610                 615                 620

Ser Pro Ala Tyr Thr Leu Val Met Asp Val Lys Val Pro Met Arg Gly
625                 630                 635                 640

Pro Glu Phe Trp Arg Lys Met Asp Gly Asp Val Thr Lys Lys Glu Arg
                645                 650                 655

Asn Val Thr Leu Leu Trp Lys Pro Leu Thr Lys Asn Asp Ser Leu Cys
            660                 665                 670

Ser Val Arg Arg Tyr Val Val Lys His Arg Thr Ala His Asn Gly Thr
            675                 680                 685

Trp Ser Glu Asp Val Gly Asn Arg Thr Asn Leu Thr Phe Leu Trp Thr
        690                 695                 700

Glu Pro Ala His Thr Val Thr Val Leu Ala Val Asn Ser Leu Gly Ala
705                 710                 715                 720

Ser Leu Val Asn Phe Asn Leu Thr Phe Ser Trp Pro Met Ser Lys Val
                725                 730                 735

Ser Ala Val Glu Ser Leu Ser Ala Tyr Pro Leu Ser Ser Ser Cys Val
            740                 745                 750

Ile Leu Ser Trp Thr Leu Ser Pro Asp Asp Tyr Ser Leu Leu Tyr Leu
            755                 760                 765

Val Ile Glu Trp Lys Ile Leu Asn Glu Asp Asp Gly Met Lys Trp Leu
        770                 775                 780

Arg Ile Pro Ser Asn Val Lys Lys Phe Tyr Ile His Asp Asn Phe Ile
785                 790                 795                 800

Pro Ile Glu Lys Tyr Gln Phe Ser Leu Tyr Pro Val Phe Met Glu Gly
                805                 810                 815

Val Gly Lys Pro Lys Ile Ile Asn Gly Phe Thr Lys Asp Ala Ile Asp
            820                 825                 830

Lys Gln Gln Asn Asp Ala Gly Leu Tyr Val Ile Val Pro Ile Ile Ile
        835                 840                 845

Ser Ser Cys Val Leu Leu Leu Gly Thr Leu Leu Ile Ser His Gln Arg
850                 855                 860

Met Lys Lys Leu Phe Trp Asp Asp Val Pro Asn Pro Lys Asn Cys Ser
865                 870                 875                 880

Trp Ala Gln Gly Leu Asn Phe Gln Lys Arg Thr Asp Thr Leu
                885                 890
```

WSX RECEPTOR AGONIST ANTIBODIES

CROSS REFERENCES

This non-provisional application is a continuation of U.S. application Ser. No. 10/921,710, filed Aug. 18, 2004, now abandoned. U.S. application Ser. No. 10/921,710 is a continuation of U.S. application Ser. No. 08/779,457 filed Jan. 7, 1997. U.S. application Ser. No. 08/779,457 (now abandoned) is a non-provisional application filed under 35 U.S.C. § 1.53 (b) claiming priority under 35 U.S.C. § 119(e) to provisional application 60/064,855 filed Jan. 8, 1996 which was originally filed as non-provisional Ser. No. 08/585,005 and later converted to the provisional. U.S. application Ser. No. 08/779,457, and the present application, also claim priority and are continuations-in-part of non-provisional application Ser. No. 08/667,197 filed Jun. 20, 1996, issued as U.S. Pat. No. 7,074,397, Jul. 11, 2006. All of the previous applications are incorporated by reference in their entireties.

BACKGROUND OF THE INVENTION

1. Field of the Invention

The present invention pertains generally to the WSX receptor and ligands and uses for these molecules. In particular, the invention relates to agonist antibodies which bind to and activate the WSX receptor.

2. Description of Related Art

Hematopoiesis

The process of blood cell formation whereby red and white blood cells are replaced through the division of cells located in the bone marrow is called hematopoiesis. For a review of hematopoiesis see Dexter and Spooncer (*Ann. Rev. Cell Biol.* 3:423-441 (1987)).

There are many different types of blood cells which belong to distinct cell lineages. Along each lineage, there are cells at different stages of maturation. Mature blood cells are specialized for different functions. For example, erythrocytes are involved in $O_2$ and $CO_2$ transport; T and B lymphocytes are involved in cell and antibody mediated immune responses, respectively; platelets are required for blood clotting; and the granulocytes and macrophages act as general scavengers and accessory cells. Granulocytes can be further divided into basophils, eosinophils, neutrophils and mast cells.

Each of the various blood cell types arises from pluripotent or totipotent stem cells which are able to undergo self-renewal or give rise to progenitor cells or Colony Forming Units (CFU) that yield a more limited array of cell types. As stem cells progressively lose their ability to self-renew, they become increasingly lineage restricted. It has been shown that stem cells can develop into multipotent cells (called "CFC-Mix" by Dexter and Spooncer, supra). Some of the CFC-Mix cells can undergo renewal whereas others lead to lineage-restricted progenitors which eventually develop into mature myeloid cells (e.g., neutrophils, megakaryocytes, macrophages and basophils). Similarly, pluripotent stem cells are able to give rise to PreB and PreT lymphoid cell lineages which differentiate into mature B and T lymphocytes, respectively. Progenitors are defined by their progeny, e.g., granulocyte/macrophage colony-forming progenitor cells (GM-CFU) differentiate into neutrophils or macrophages; primitive erythroid burst-forming units (BFU-E) differentiate into erythroid colony-forming units (CFU-E) which give rise to mature erythrocytes. Similarly, the Meg-CFU, Eos-CFU and Bas-CFU progenitors are able to differentiate into megakaryocytes, eosinophils and basophils, respectively.

Hematopoietic growth factors (reviewed in D'Andrea, NEJM 330(12):839-846 (1994)) have been shown to enhance growth and/or differentiation of blood cells via activation of receptors present on the surface of blood progenitor cells of the bone marrow. While some of these growth factors stimulate proliferation of restricted lineages of blood cells, others enhance proliferation of multiple lineages of blood cells. For example, erythropoietin (EPO) supports the proliferation of erythroid cells, whereas interleukin-3 (IL-3) induces proliferation of erythroid and myeloid lineages and is therefore considered a multi-lineage factor.

In recent years, several hematopoietic growth factor receptors have been isolated. Due to their low abundance and their existence in both high-affinity and low-affinity forms, biochemical characterization of these receptors has been hampered.

Cytokine receptors frequently assemble into multi-subunit complexes. Sometimes, the a subunit of this complex is involved in binding the cognate growth factor and the P-subunit may contain an ability to transduce a signal to the cell. These receptors 1 have been assigned to three subfamilies depending on the complexes formed. Subfamily 1 includes the receptors for erythropoietin (EPO), granulocyte colony-stimulating factor (G-CSF), interleukin-4 (IL-4), interleukin-7 (IL-7), growth hormone (GH) and prolactin (PRL). Ligand binding to receptors belonging to this subfamily is thought to result in homodimerization of the receptor. Subfamily 2 includes receptors for IL-3, granulocyte-macrophage colony-stimulating factor (GM-CSF), interleukin-5 (IL-5), interleukin-6 (IL-6), leukemia inhibitory factor (LIF), oncostatin M (OSM) and ciliary neurotrophic factor (CNTF). Subfamily 2 receptors are heterodimers having an α-subunit for ligand binding and β-subunit (either the shared β-subunit of the IL-3, GM-CSF and IL-5 receptors or the gp130 subunit of the IL-6, LIF, OSM and CNTF receptors) for signal transduction. Subfamily 3 contains only the interleukin-2 (IL-2) receptor. The β and γ subunits of the IL-2 receptor complex are cytokine-receptor polypeptides which associate with the α-subunit of the unrelated Tac antigen.

Obesity

Obesity is the most common nutritional disorder which, according to recent epidemiologic studies, affects about one third of all Americans 20 years of age or older. Kuczmarski et al., *J. Am. Med. Assoc.* 272:205-11 (1994). Obesity is responsible for a variety of serious health problems, including cardiovascular disorders, type II diabetes, insulin-resistance, hypertension, hypertriglyceridemia, dyslipoproteinemia, and some forms of cancer. Pi-Sunyer, F., *Anns. Int. Med.* 119: 655-60 (1993); Colfitz, G., *Am. J. Clin. Nutr.* 55:503S-507S (1992). A single-gene mutation (the obesity or "ob" mutation) has been shown to result in obesity and type II diabetes in mice. Friedman, *Genomics* 11:1054-1062 (1991).

Zhang et al., *Nature* 372:425-431 (1994) have recently reported the cloning and sequencing of the mouse ob gene and its human homologue, and suggested that the ob gene product, leptin or OB protein, may function as part of a signalling pathway from adipose tissue that acts to regulate the size of the body fat depot. Parabiosis experiments performed more than 20 years ago predicted that the genetically obese mouse containing two mutant copies of the ob gene (ob/ob mouse) does not produce a satiety factor which regulates its food intake, while the diabetic (db/db) mouse produces but does not respond to a satiety factor. Coleman and Hummal, *Am. J. Physiol.* 217:1298-1304 (1969); Coleman, *Diabetol* 9:294-98 (1973). Recent reports by three independent research teams have demonstrated that daily injections of recombinant OB protein inhibit food intake and reduce body weight and fat in grossly obese ob/ob mice but not in db/db mice (Pelleymounter et al., *Science* 269:540-43 (1995); Halaas et al., *Science* 269:543-46 (1995); Campfield et al., *Science* 269: 546-49 (1995)), suggesting that the OB protein is such a satiety factor as proposed in early cross-circulation studies.

Researchers suggest that at least one OB receptor is localized in the brain. The identification and expression cloning of a leptin receptor (OB-R) was reported by Tartaglia et al. *Cell* 83:1263-71 (1995). Various isoforms of a OB receptor are described by Cioffi et al. *Nature* 2:585-89 (1996). See, also, WO 96/08510.

The mouse db gene has recently been cloned (Lee et al. *Nature* 379:632 (1996) and Chen et al. *Cell* 84:491-495 (1996)). Previous data had suggested that the db gene encoded the receptor for the obese (ob) gene product, leptin (Coleman et al., *Diebetologia* 9:294-8 (1973) and Coleman et al., *Diebetologia* 14:141-8 (1978)). It has been very recently confirmed that the db/db mouse results from a truncated splice variant of the OB receptor which likely renders the receptor defective in signal transduction (Lee et al., *Nature* 379:632 (1996) and Chen et al., *Cell* 84: 491-495 (1996)).

SUMMARY OF THE INVENTION

This application relates to agonist antibodies which specifically bind to the WSX receptor and mimic one or more biological activities of naturally occurring WSX ligand, OB protein. Preferred antibodies are those with a strong binding affinity for human WSX receptor (e.g. having a Kd of no more than about $1 \times 10^8$M; and preferably no more than about $1 \times 10^9$M). In preferred embodiments, the agonist antibody binds to both human and murine WSX receptor.

Antibodies with defined agonistic activity in a bioassay, the KIRA ELISA, are disclosed herein. Preferred antibodies have an IC50 in the KIRA ELISA of about 0.5 micrograms/ml or less, preferably about 0.2 micrograms/ml or less, and most preferably about 0.1 micrograms/ml or less.

The agonist antibodies of interest herein may have one or more of the biological characteristics of antibody 2D7, 1G4, 1E11 or 1C11 (see Example 13) or clones 3, 4, or 17 (see Example 14). For example, the antibody may bind to the epitope bound by any one of these antibodies, and/or may have some or all of the hypervariable region residues of these antibodies.

The agonist antibody may be one which decreases body weight and/or fat-depot weight and/or food intake in an obese mammal (e.g. in an ob/ob mouse). The preferred agonist antibody is one which exerts an adipose-reducing effect in an obese mammal (e.g. an ob/ob mouse) which is in excess of that induced by a reduction in food intake (Levin et al. Proc. Natl. Acad. Sci. USA 93:1726-1730 (1996)).

The agonist antibody may also have the property of inducing differentiation and/or proliferation and/or survival of hematopoietic progenitor cells. For example, the agonist antibody may induce lymphopoiesis, erythropoiesis and/or myelopoiesis.

The invention further provides a composition comprising the agonist antibody and a physiologically acceptable carrier. The composition for therapeutic use is sterile and may be lyophilized. For use in hematopoiesis, for example, the composition may further comprise a cytokine.

In another aspect, the invention provides a method for activating the WSX receptor which comprises exposing the WSX receptor to an amount of an agonist anti-WSX receptor antibody which is effective for activating the WSX receptor. The invention further provides a method for enhancing proliferation and/or differentiation of a cell which expresses the WSX receptor at its cell surface comprising exposing the cell to an amount of exogenous agonist anti-WSX receptor antibody which is effective for enhancing proliferation and/or differentiation of the cell. In another embodiment, the invention provides a method for decreasing body weight and/or fat-depot weight and/or food intake in an obese mammal (e.g. a human) comprising administering an effective amount of the agonist antibody to the mammal. Also, the invention provides a method for treating the medical sequelae of obesity in a mammal, such as, e.g., arteriosclerosis, Type II diabetes, polycystic ovarian disease, cardiovascular diseases, osteoarthritis, dermatological disorders, hypertension, insulin resistance, hypercholesterolemia, hypertriglyceridemia, cancer and cholelithiasis, comprising administering an effective amount of an agonist anti-WSX receptor antibody to the mammal. The mammal to be treated may be one diagnosed with any one or more of these diseases, or may be predisposed to these diseases.

In another aspect, the present invention pertains to the discovery herein that WSX ligands, such as obesity (OB) protein, play a role in hematopoiesis via signalling through the WSX receptor. The role of the WSX receptor-ligand signalling pathway appears to be at the level of the early hematopoietic precursor as is evident by the ability of OB protein to simulate myelopoiesis, erythropoiesis (e.g. splenic erythropoiesis) and most dramatically, lymphopoiesis. Accordingly, WSX ligands can be used to stimulate proliferation and/or differentiation and/or survival of hematopoietic progenitor cells either in vitro or in vivo (e.g. for treating hematopoietic diseases or disorders).

Thus, the invention provides a method for stimulating proliferation and/or differentiation of a cell which expresses the WSX receptor (especially the WSX receptor variant 13.2, which is demonstrated herein to have the capacity to transmit a proliferative signal) at its cell surface comprising the step of contacting the WSX receptor with an amount of WSX ligand which is effective for stimulating proliferation and/or OB protein differentiation of the cell. In prefered embodiments, the cell which is exposed to the WSX ligand is a hematopoeitic precursor, e.g. a CD34+ cell. The WSX ligand may be OB protein or an agonist antibody which binds to the WSX receptor. For in vivo use, the WSX ligand of choice may be a long half-life derivative of an OB protein, such as OB-immunoglobulin chimera and/or OB protein modified with a nonproteinaceous polymer, such as polyethylene glycol (PEG). The method contemplated herein may lead to an increase in the proliferation and/or differentiation of lymphoid, myeloid and/or erythroid blood cell lineages and encompasses both in vitro and in vivo methods. For in vitro uses, the cell possessing the WSX receptor may be present in cell culture. As to in vivo methods, the cell may be present in a mammal, especially a human (e.g. one who is suffering from decreased blood levels and who could benefit from an increase in various blood cells). Potential patients include those who have undergone chemo- or radiation therapy, or bone marrow transplantation therapy. Thus, the invention provides a method for repopulating blood cells (e.g. erythroid, myeloid and/or lymphoid blood cells) in a mammal comprising administering to the mammal a therapeutically effective amount of a WSX ligand.

Mammals which may benefit from an enhancement of lymphopoiesis include those predisposed to, or suffering from, any ony or more of the following exemplary conditions: lymphocytopenia; lymphorrhea; lymphostasis; immunodeficiency (e.g. HIV and AIDS); infections (including, for example, opportunistic infections and tuberculosis (TB)); lupus; and other disorders characterized by lymphocyte deficiency. An effective amount of the WSX ligand can be used in a method of immunopotentiation or to improve immune function in a mammal.

On the other hand, WSX receptor or WSX ligand antagonists (such as WSX receptor ECD or immunoadhesin, and WSX receptor or OB protein neutralizing antibodies) may be used in the treatment of those disorders wherein unacceptable lymphocyte levels are present in the mammal, particularly where this is caused by excessive activation of the WSX receptor. Examples of conditions in which administration of such an antagonist may be beneficial include: neoplastic disorders (such as Hodkin's disease; lymphosarcoma; lymphoblastoma; lymphocytic leukemia; and lymphoma) and lymphocytosis.

Diseases or disorders in which an increase in erythropoiesis may be beneficial include, but are not limited to: erythrocytopenia; erthrodegenerative disorders; erythroblastopenia; leukoerythroblastosis; erythroclasis; thalassemia; and anemia (e.g. hemolytic anemia, such as acquired, autoimmune, or microangiopathic hemolytic anemia; aplastic anemia; congenital anemia, e.g., congenital dyserythropoietic anemia, congenital hemolytic anemia or congenital hypoplastic anemia; dyshemopoietic anemia; Faconi's anemia; genetic anemia; hemorrhagic anemia; hyperchromic or hypochromic anemia; nutritional, hypoferric, or iron deficiency anemia; hypoplastic anemia; infectious anemia; lead anemia; local anemia; macrocytic or microcytic anemia; malignant or pernicious anemia; megaloblastic anemia; molecular anemia; normocytic anemia; physiologic anemia; traumatic or posthemorrhagic anemia; refractory anemia; radiation anemia; sickle cell anemia; splenic anemia; and toxic anemia).

Conversely, WSX receptor or WSX ligand antagonists may be used to treat those conditions in which excessive erythrocyte levels are present in a mammal, e.g. in neoplastic disorders such as erythroleukemia; erythroblastosis; and erythrocythemia or polycythemia.

An increase in myelopoiesis may be beneficial in any of the above-mentioned diseases or disorders as well as the following exemplary conditions: myelofibrosis; thrombocytopenia; hypoplasia; disseminated intravascular coagulation (DIC); immune (autoimmune) thrombocytopenic purpura (ITP); HIV induced ITP; myelodysplasia; thrombocytotic diseases and thrombocytosis.

Antagonists of the WSX receptor-WSX ligand interaction may also be used to treat myeloid cell-related conditions such as malignancies (e.g. myelosarcoma, myeloblastoma, myeloma, myeloleukemia and myelocytomatosis); myeloblastosis; myelocytosis; and myelosis.

The method may further involve the step of exposing hematopoeitic cells (whether they be in cell culture or in a mammal) to one or more other cytokines (e.g. lineage-4 specific cytokines) and this may lead to a synergistic enhancement of the proliferation and/or differentiation of the cells. Exemplary cytokines include thrombopoietin (TPO); erythropoietin (EPO); macrophage-colony stimulating factor (M-CSF); granulocyte-macrophage-CSF (GM-CSF); granulocyte-CSF (G-CSF); interleukin-1 (IL-1); IL-1alpha; IL-2; IL-3; IL-4; IL-5; IL-6; IL-7; IL-8; IL-9; IL-11; IL10; IL-12; leukemia inhibitory factor (LIEF) or kit ligand (KL). In this embodiment, exposure to the cytokine may proceed, occur simultaneously with, or follow, exposure to the WSX ligand. Preferably, the WSX ligand and one or more further cytokines are administered simultaneously to the patient (where the method is an in vivo one) and, optionally, are combined to form a pharmaceutical composition.

For use in the above methods, the invention also provides an article of manufacture, comprising: a container; a label on the container; and a composition comprising an active agent within the container; wherein the composition is effective for enhancing proliferation and/or differentiation of cells comprising the WSX receptor in a mammal, the label on the container indicates that the composition can be used for enhancing proliferation and/or differentiation of those cells and the active agent in the composition is a WSX ligand. Optionally, the article of manufacture includes one or more futher containers which hold further cytokine(s) in a packaged combination with the container holding the WSX ligand.

In another embodiment, an effective amount of the WSX ligand may be used to improve engraftment in bone marrow transplantation or to stimulate mobilization of hematopoietic stem cells in a mammal prior to harvesting hematopoietic progenitors from the peripheral blood thereof.

According to a further aspect, the invention is concerned with the WSX cytokine receptor and a soluble form of the receptor which is the WSX receptor extracellular domain (ECD). The WSX receptor polypeptides are optionally conjugated with, or fused to, molecules which increase the serum half-lives thereof and can be formulated as pharmaceutical compositions comprising the polypeptide and a physiologically acceptable carrier.

In certain embodiments, the WSX receptor ECD may be used as an antagonist insofar as it may bind to WSX ligand and thereby reduce activation of endogenous WSX receptor. This may be useful in conditions characterized by excess levels of WSX ligand and/or excess WSX receptor activation in a mammal. WSX receptor ECD may, for example, be used to treat metabolic disorders (e.g., anorexia or steroid-induced truncalobesity), stem cell tumors and other tumors which express WSX receptor.

Pharmaceutical compositions of the WSX receptor ECD may further include a WSX ligand. Such dual compositions may be beneficial where it is therapeutically useful to prolong the half-life of WSX ligand and/or activate endogenous WSX receptor directly as a heterotrimeric complex.

The invention also relates to chimeric WSX receptor molecules, such as WSX receptor immunoadhesins (having long half-lives in the serum of a patient treated therewith) and epitope tagged WSX receptor. Immunoadhesins may be employed as WSX receptor antagonists in conditions or disorders in which neutralization of WSX receptor biological activity may be beneficial. Bispecific immunoadhesins (combining a WSX receptor ECD with a domain of another cytokine receptor) may form high affinity binding complexes for WSX ligand.

The invention further provides methods for identifying a molecule which binds to and/or activates the WSX receptor. This is useful for discovering molecules (such as peptides, antibodies, and small molecules) which are agonists or antagonists of the WSX receptor. Such methods generally involve exposing an immobilized WSX receptor to a molecule suspected of binding thereto and determining binding of the molecule to the immobilized WSX receptor and/or evaluating whether or not the molecule activates (or blocks activation of) the WSX receptor. In order to identify such WSX ligands, the WSX receptor may be expressed on the surface of a cell and used to screen libraries of synthetic compounds and naturally occurring compounds (e.g., endogenous sources of such naturally occurring compounds, such as serum). The WSX receptor can also be used as a diagnostic tool for measuring serum levels of endogenous WSX ligand.

In a further embodiment, a method for purifying a molecule which binds to the WSX receptor is provided. This can be used in the commercial production and purification of therapeutically active molecules which bind to this receptor. In the method, the molecule of interest (generally a composition comprising one or more contaminants) is adsorbed to immobilized WSX receptor (e.g., WSX receptor immunoadhesin immobilized on a protein A column). The contaminants, by virtue of their inability to bind to the WSX receptor, will generally flow through the column. Accordingly, it is then possible to recover the molecule of interest from the column by changing the elution conditions, such that the molecule no longer binds to the immobilized receptor.

In further embodiments, the invention provides antibodies that specifically bind to the WSX receptor. Preferred antibodies are monoclonal antibodies which are non-immunogenic in a human and bind to an epitope in the extracellular domain of the receptor. Preferred antibodies bind the WSX receptor with an affinity of at least about $10^6$ L/mole, more preferably $10^7$ L/mole.

Antibodies which bind to the WSX receptor may optionally be fused to a heterologous polypeptide and the antibody or fusion thereof may be used to isolate and purify WSX receptor from a source of the receptor.

In a further aspect, the invention provides a method for detecting the WSX receptor in vitro or in vivo comprising contacting the antibody with a sample suspected of containing the receptor and detecting if binding has occurred. Based on the observation herein that CD34+ cells possess WSX receptor, use of WSX antibodies for identification and/or enrichment of stem cell populations (in a similar manner to that in which CD34 antibodies are presently used) is envisaged.

For certain applications, it is desirable to have an agonist antibody which can be screened for as described herein. Such agonist antibodies are useful for activating the WSX receptor for in vitro uses whereby enhancement of proliferation and/or differentiation of a cell comprising the receptor is desired. Furthermore, these antibodies may be used to treat conditions in which an effective amount of WSX receptor activation leads to a therapeutic benefit in the mammal treated therewith. For example, the agonist antibody can be used to enhance survival, proliferation and/or differentiation of a cell comprising the WSX receptor. In particular, agonist antibodies and other WSX ligands may be used to stimulate proliferation of stem cells/progenitor cells either in vitro or in vivo. Other potential therapeutic applications include the use of agonist antibodies to treat metabolic disorders (such as obesity and diabetes) and to promote kidney, liver or lung growth and/or repair (e.g., in renal failure).

For therapeutic applications it is desirable to prepare a composition comprising the agonist antibody and a physiologically acceptable carrier. Optionally, such a composition may further comprise one or more cytokines.

In other embodiments, the antibody is a neutralizing antibody. Such molecules can be used to treat conditions characterized by unwanted or excessive activation of the WSX receptor.

In addition to the above, the invention provides isolated nucleic acid molecules, expression vectors and host cells encoding the WSX receptor which can be used in the recombinant production of WSX receptor as described herein. The isolated nucleic acid molecules and vectors are also useful for gene therapy applications to treat patients with WSX receptor defects and/or to increase responsiveness of cells to WSX ligand.

BRIEF DESCRIPTION OF THE DRAWINGS

Figure 1A:
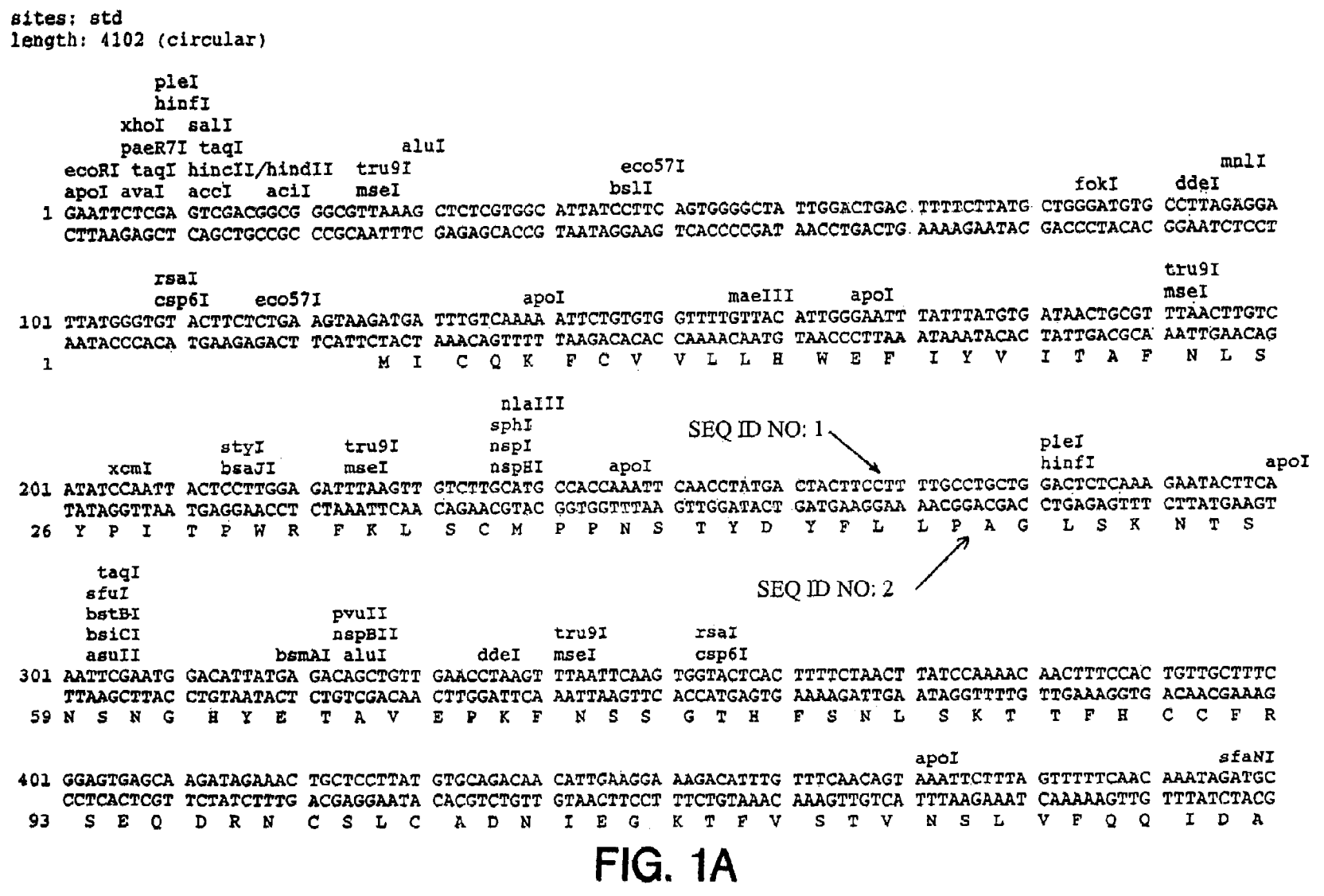
Figure 1C:
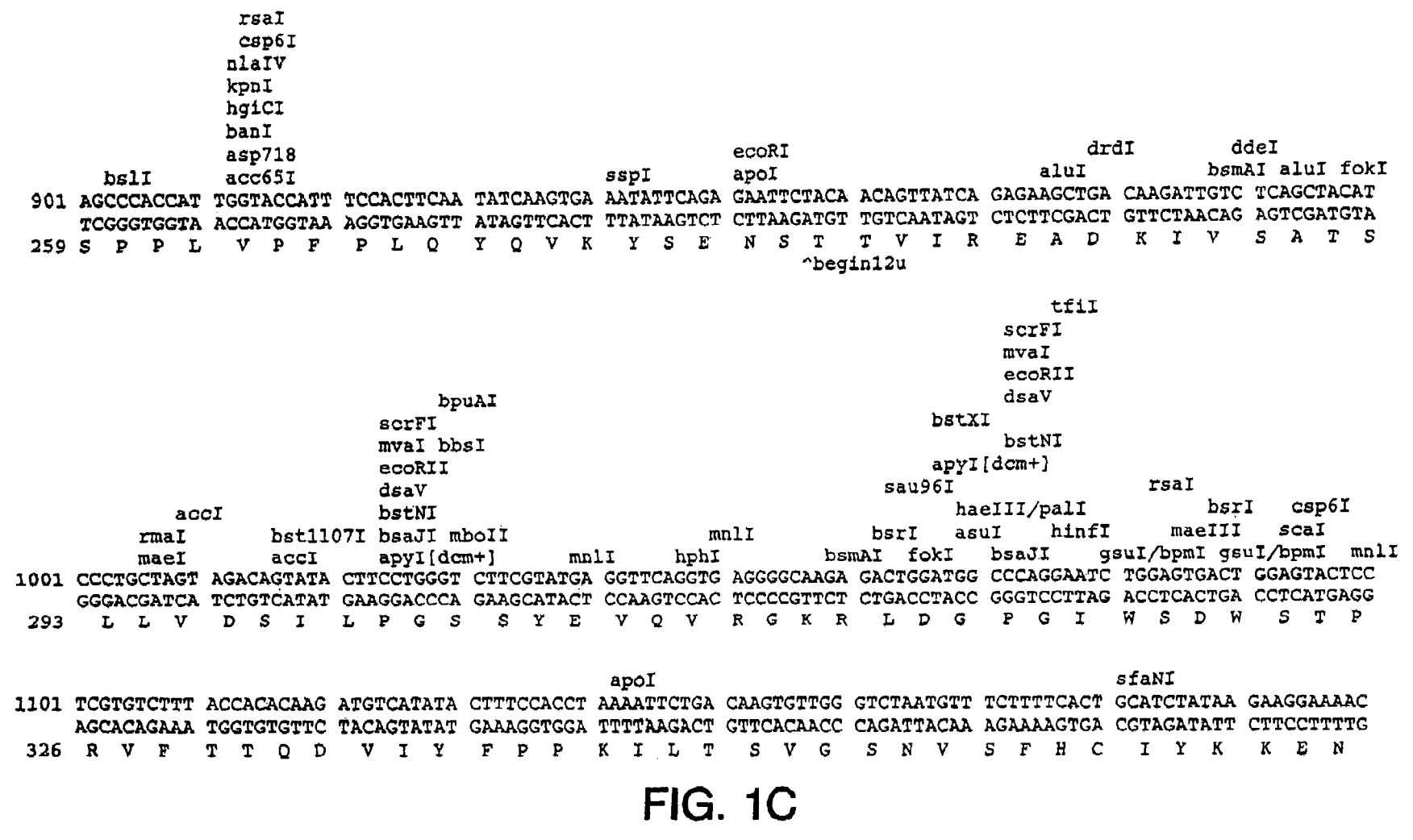
Figure 1D:
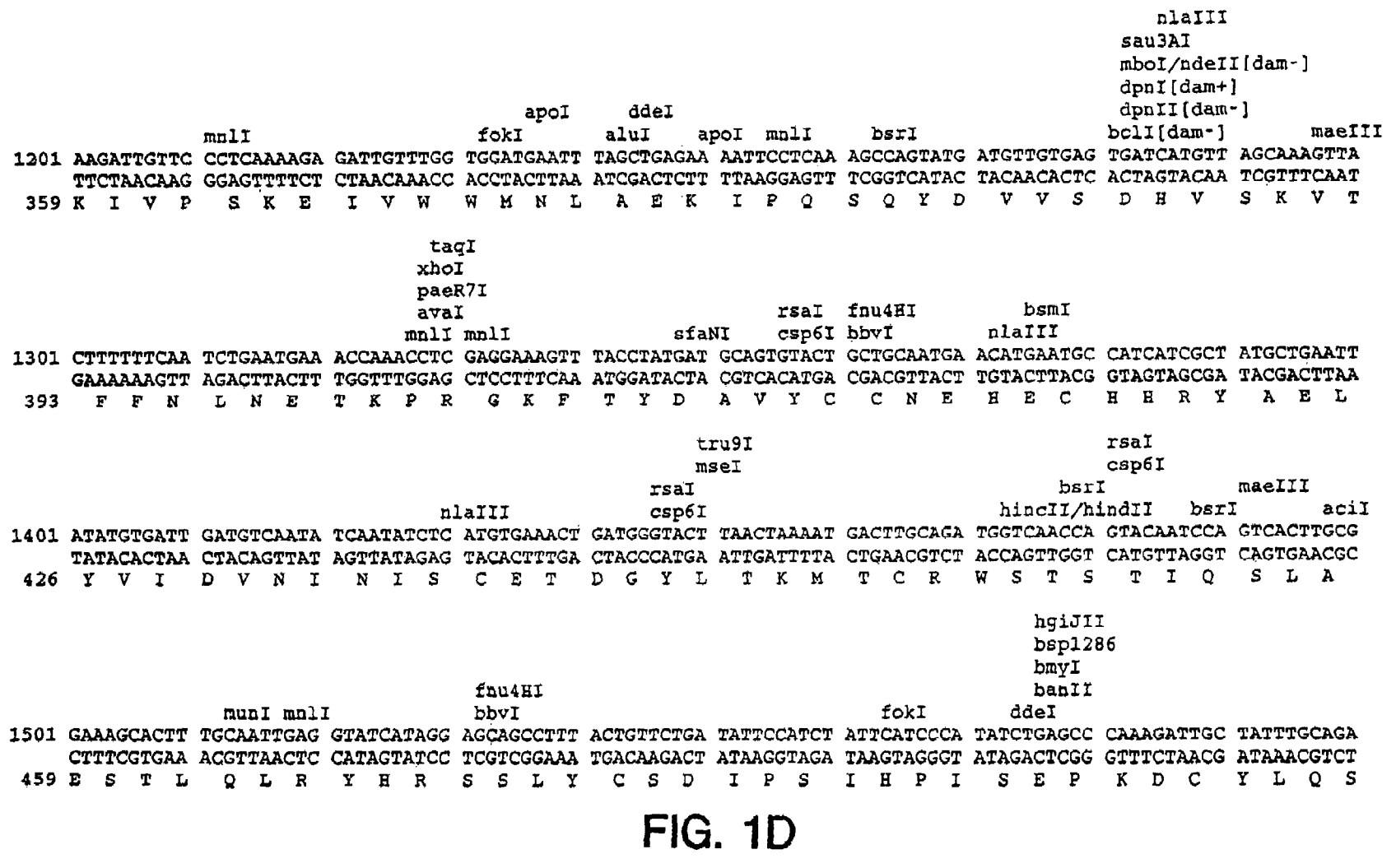

FIGS. 1A-J together depict the double stranded nucleotide (SEQ ID NO: 1) and deduced amino acid sequence (SEQ ID NO:2) encoding full length human WSX receptor variant 13.2. Nucleotides are numbered at the beginning of the sense strand. Amino acid residues are numbered at the beginning of the amino acid sequence. Restriction enzyme sites are depicted above the nucleotide sequence.

Figure 2D:
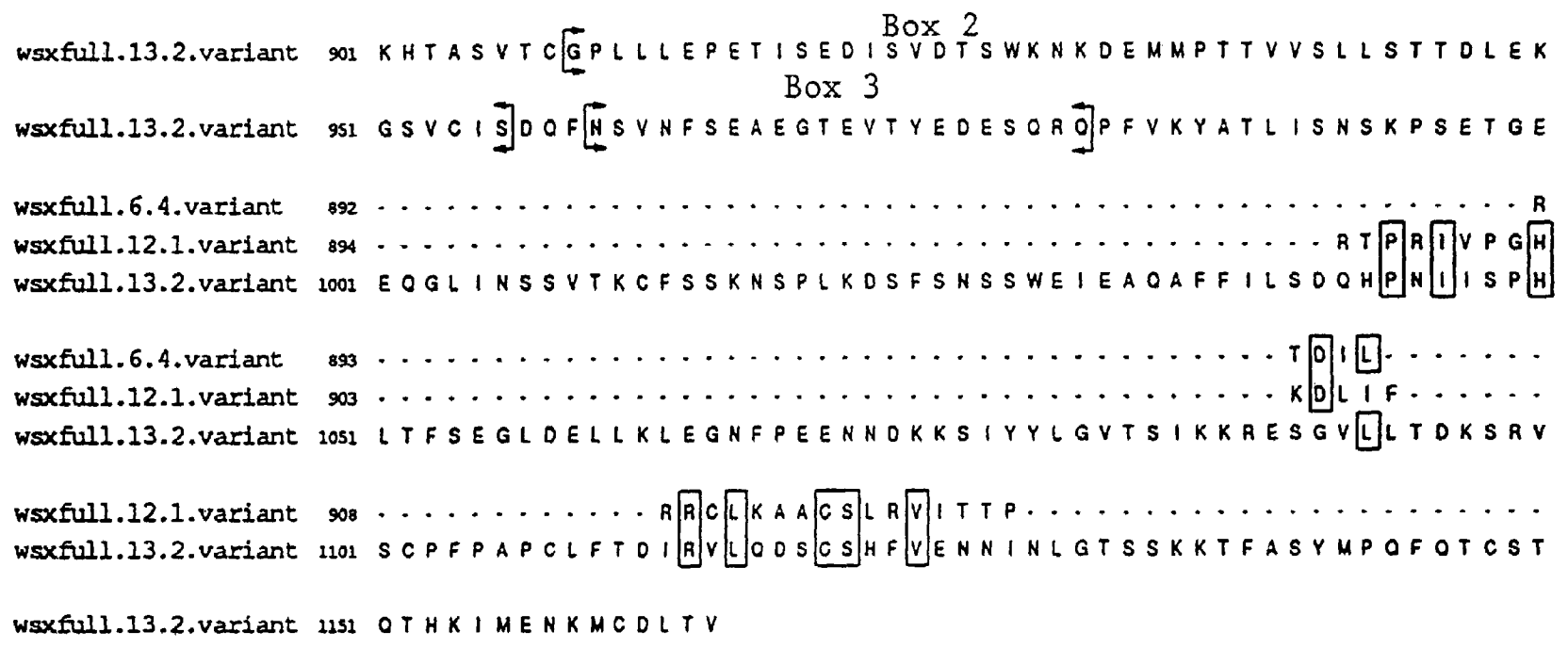

FIGS. 2A-D together depict an amino acid sequence alignment of full length human WSX receptor variants 6.4 (SEQ ID NO:3), 12.1 (SEQ ID NO:4) and 13.2, respectively. Homologous residues are boxed. WSX receptor variants 6.4, 12.1 and 13.2 are native sequence human WSX receptor variants which, without being bound to any one theory, appear to be generated by alternate splicing of WSX receptor mRNA. The putative signal peptide, transmembrane, Box 1, Box 2, and Box 3 domains are indicated. The extracellular and cytoplasmic domains are amino- and carboxy-terminal, respectively, to the transmembrane domain. The Box 1-3 domains shown correspond to the box 1-3 motifs described in Baumann et al., *Mol. Cell. Biol.* 14(1):138-146 (1994).

Figure 3A:
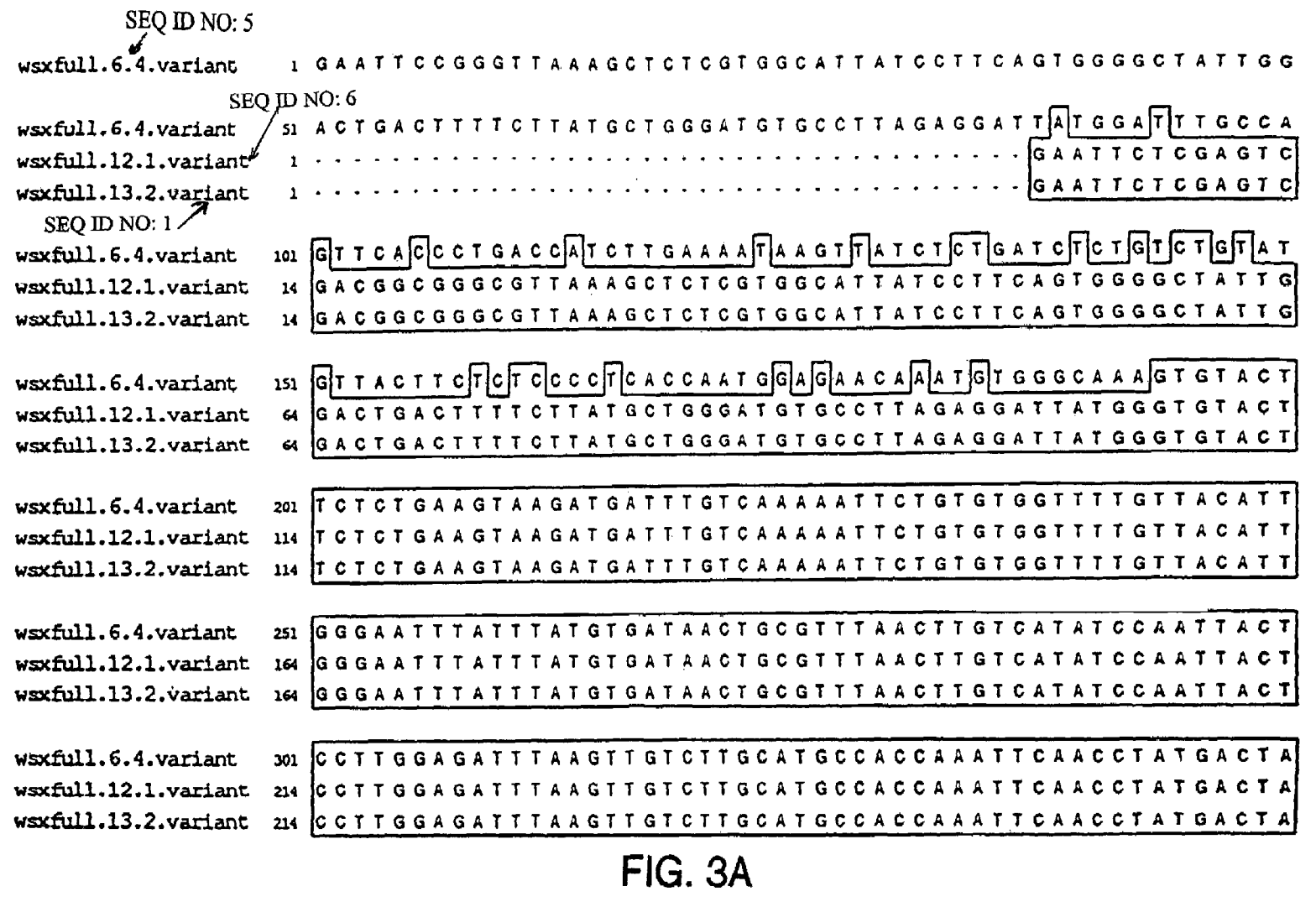
Figure 3E:
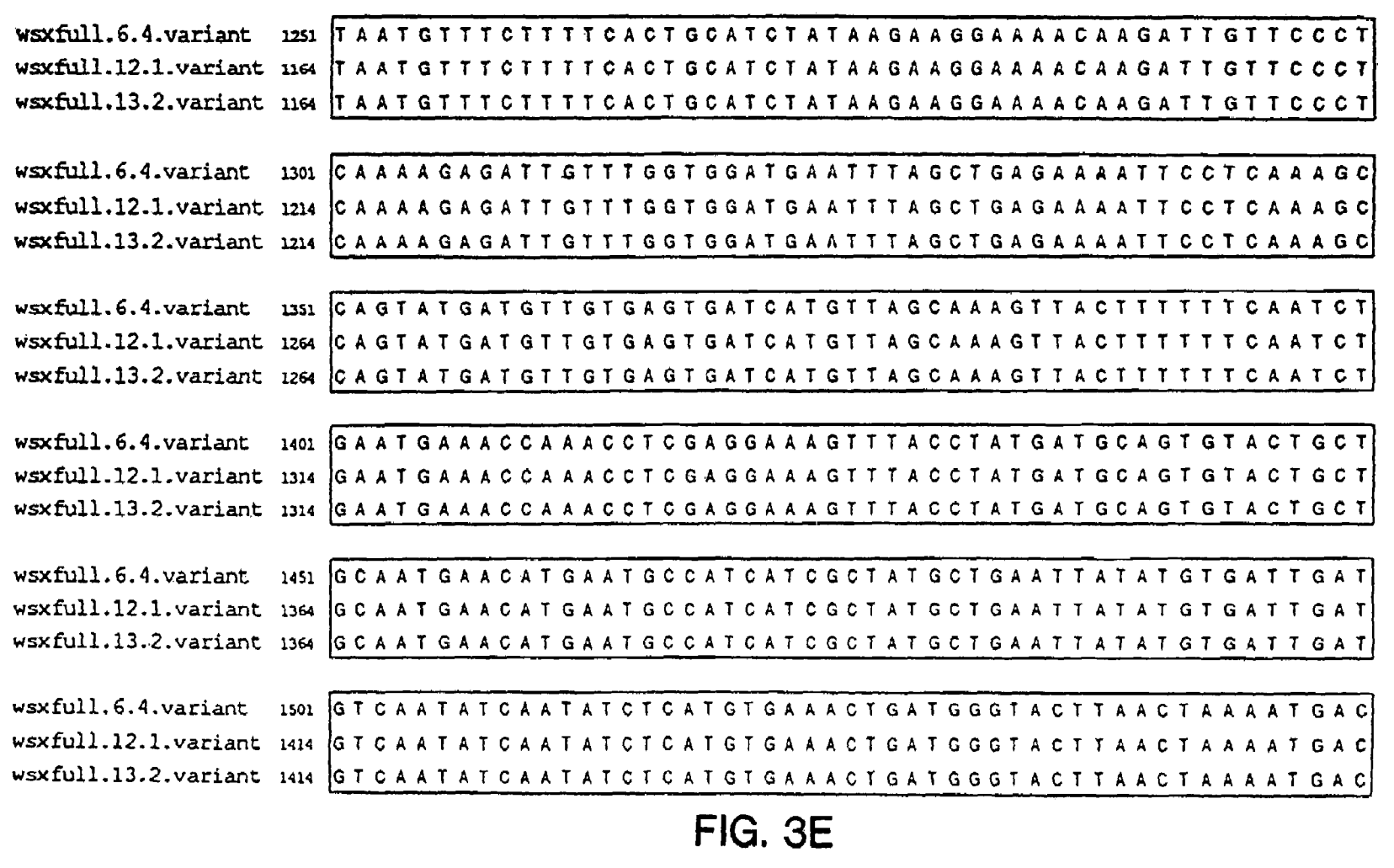
Figure 3H:
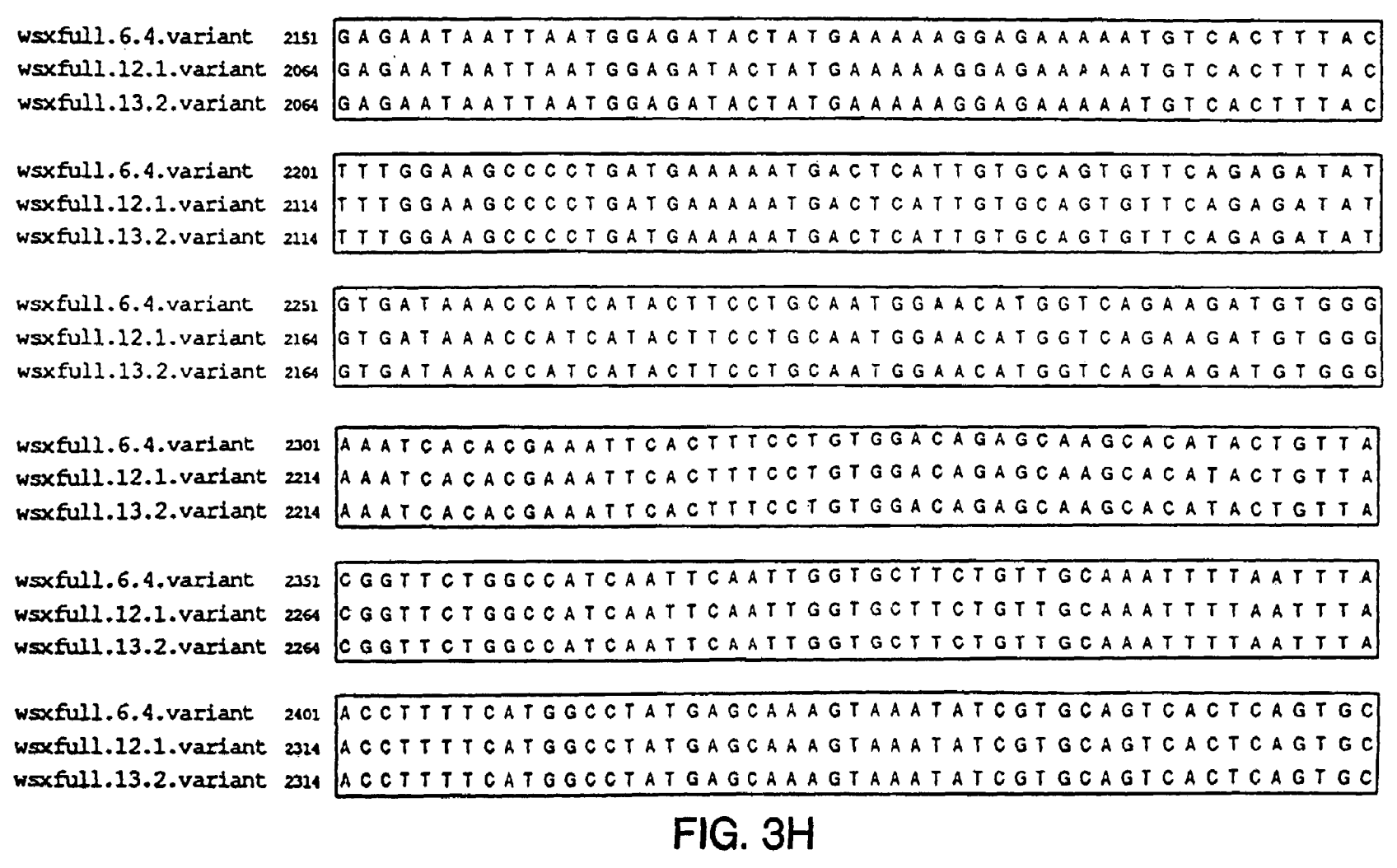
Figure 3I:
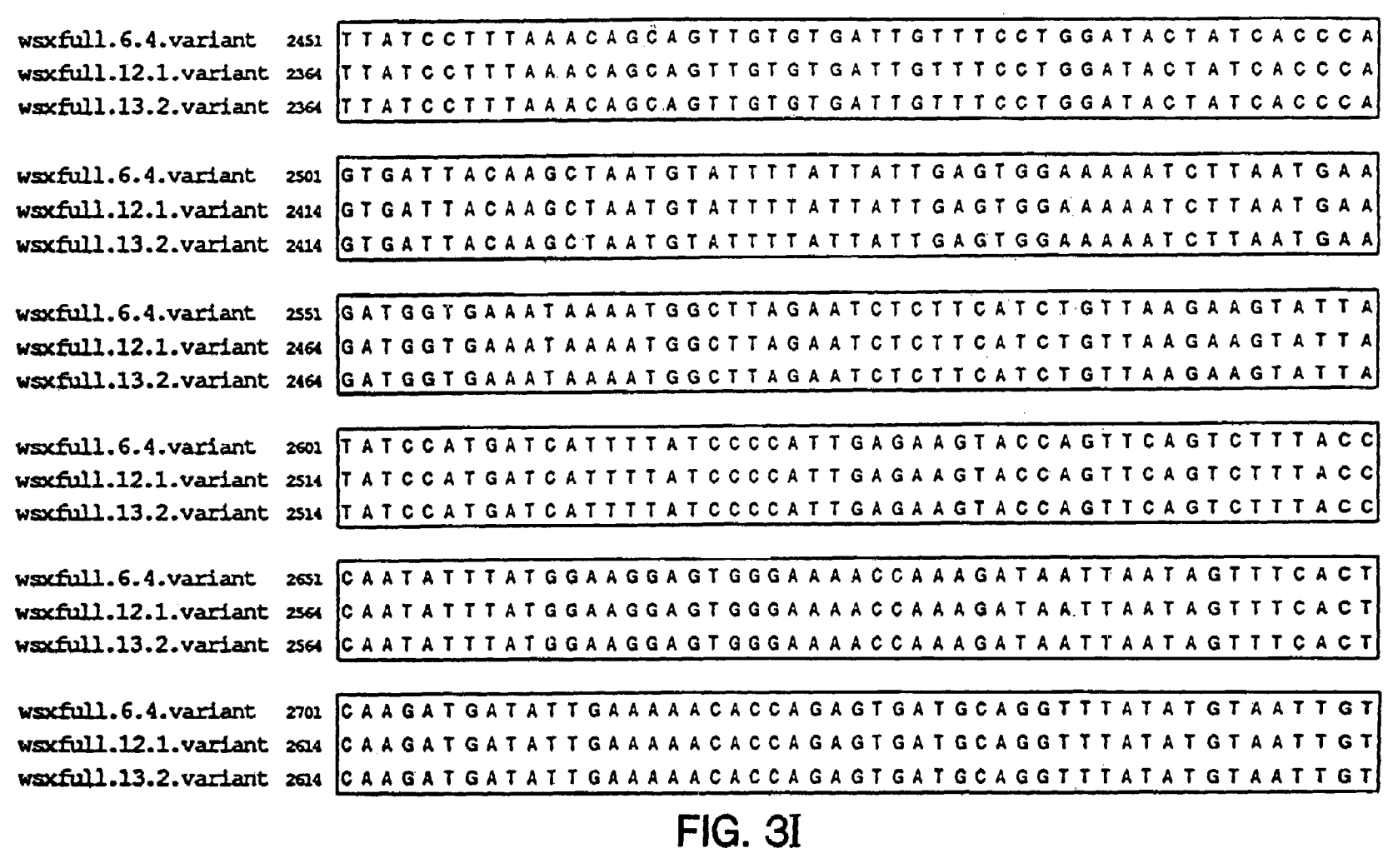
Figure 3J:
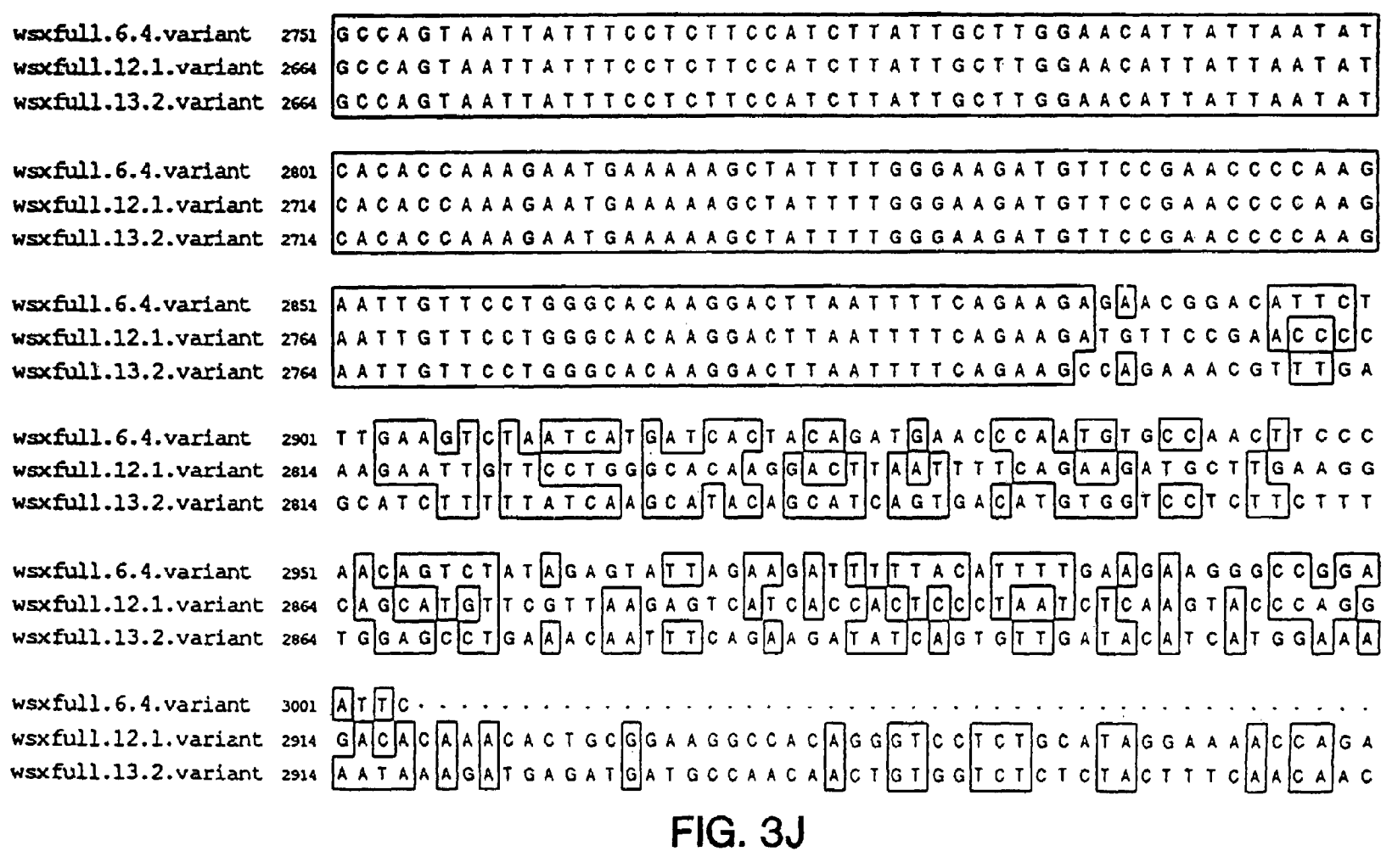
Figure 3K:
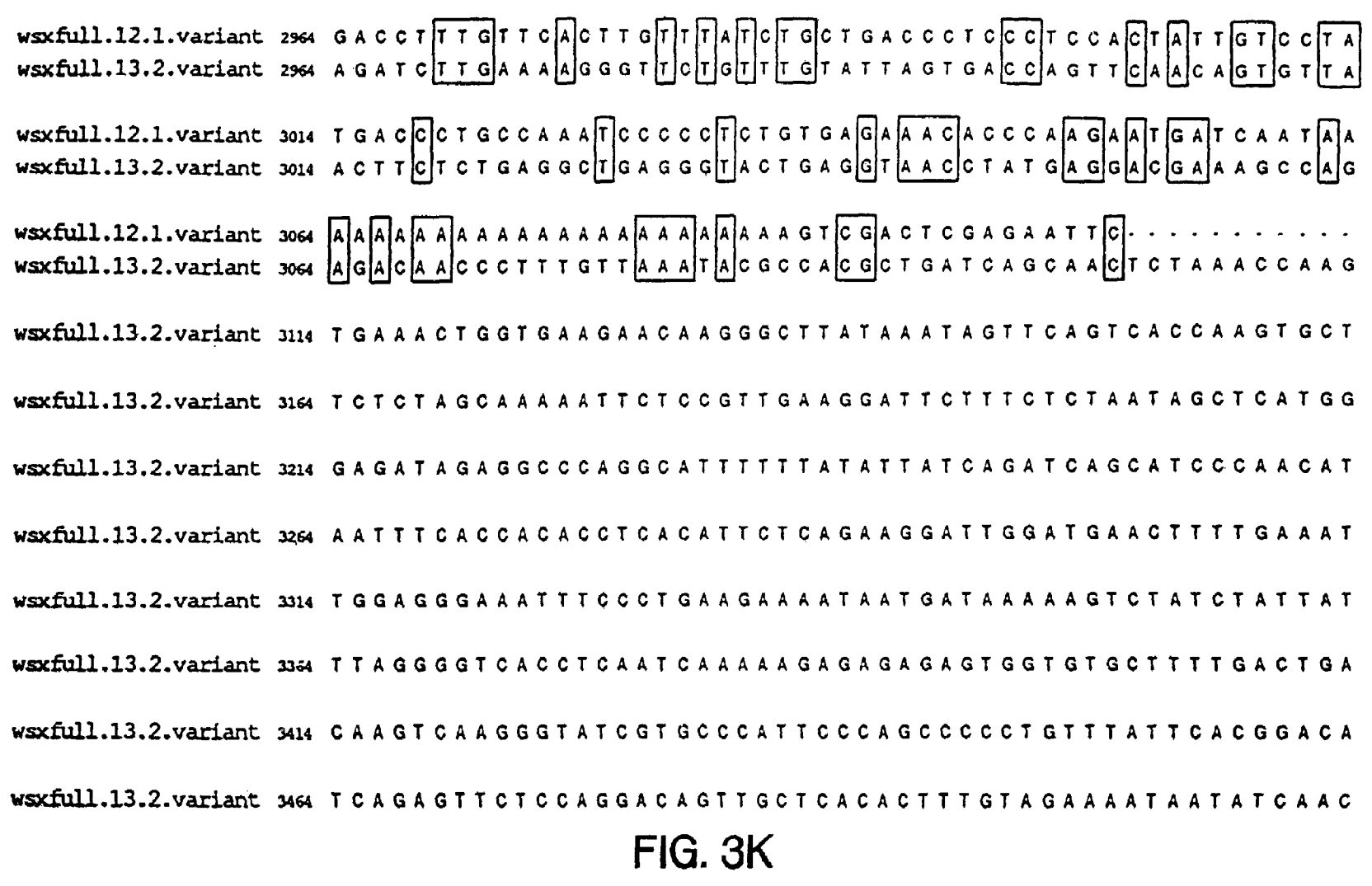

FIGS. 3A-L together depict an alignment of the nucleotide sequences encoding human WSX receptor variants 6.4 (SEQ ID NO:5), 12.1 (SEQ ID NO:6) and 13.2, respectively.

Figure 4A:
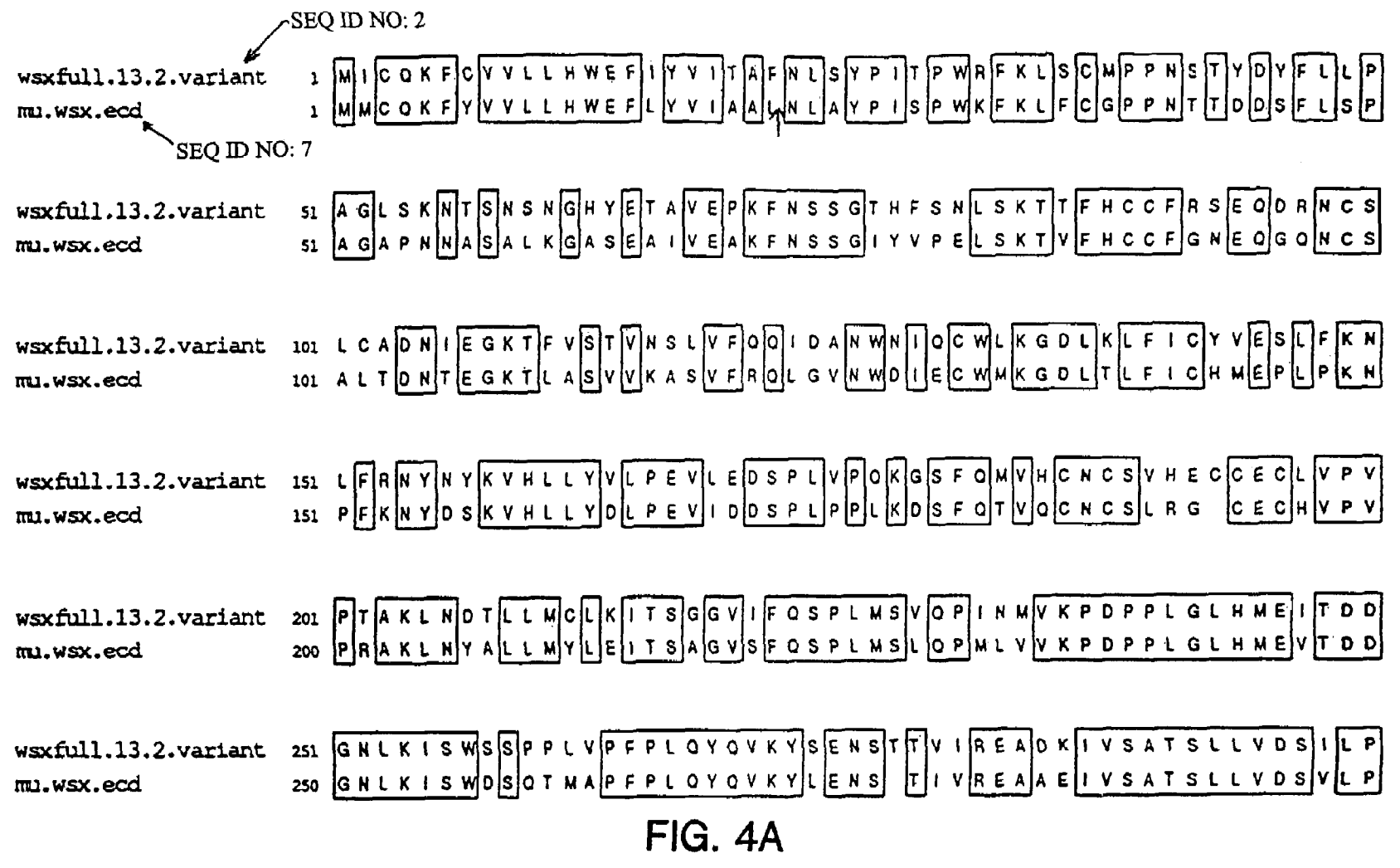
Figure 4B:
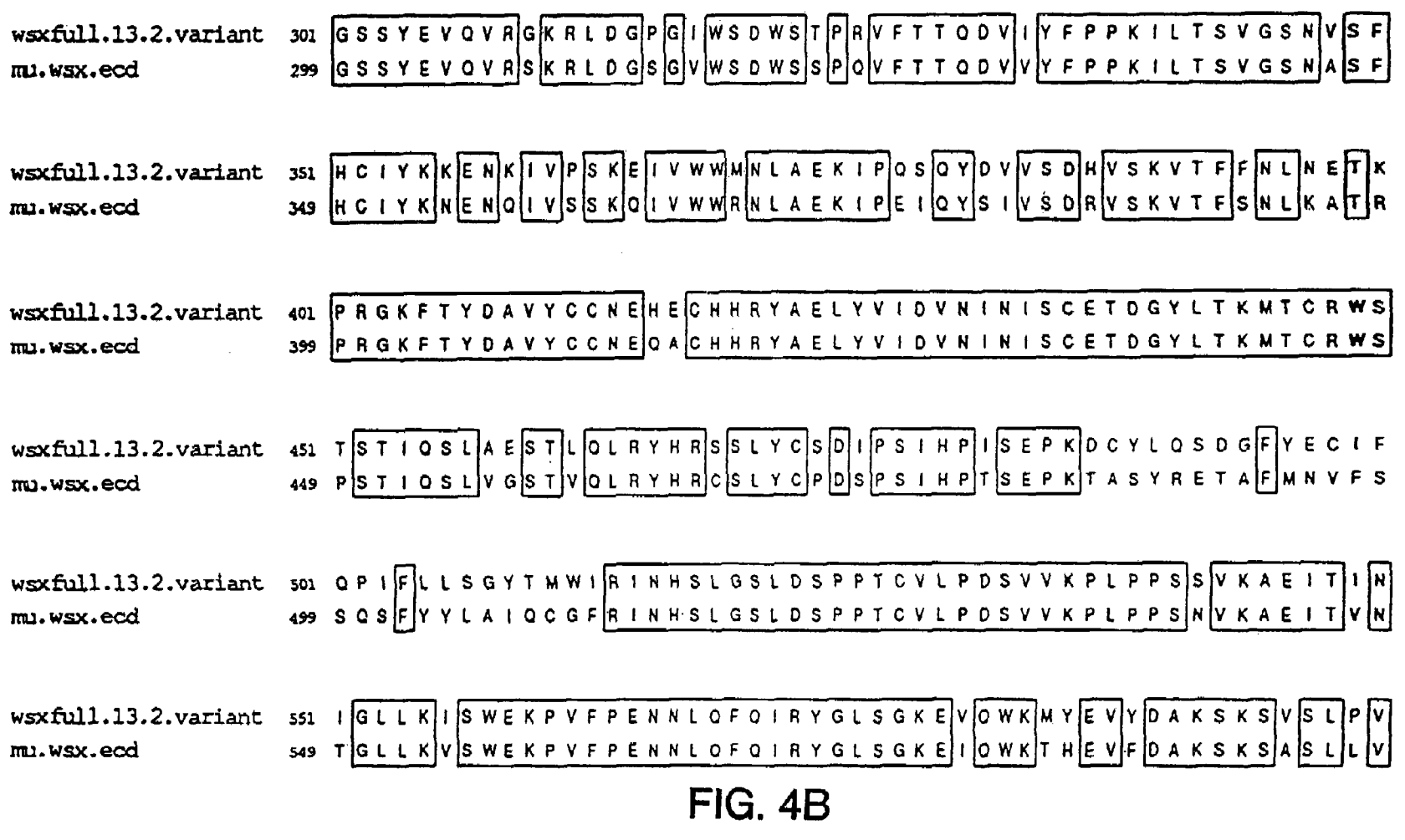

FIGS. 4A-D depict an alignment of the full length human WSX receptor variant 13.2 amino acid sequence (top) with that of partial murine WSX receptor extracellular domain sequence (bottom) (SEQ ID NO:7) obtained as described in Example 7. The putative murine signal peptide is marked with an arrow.

Figure 5B:
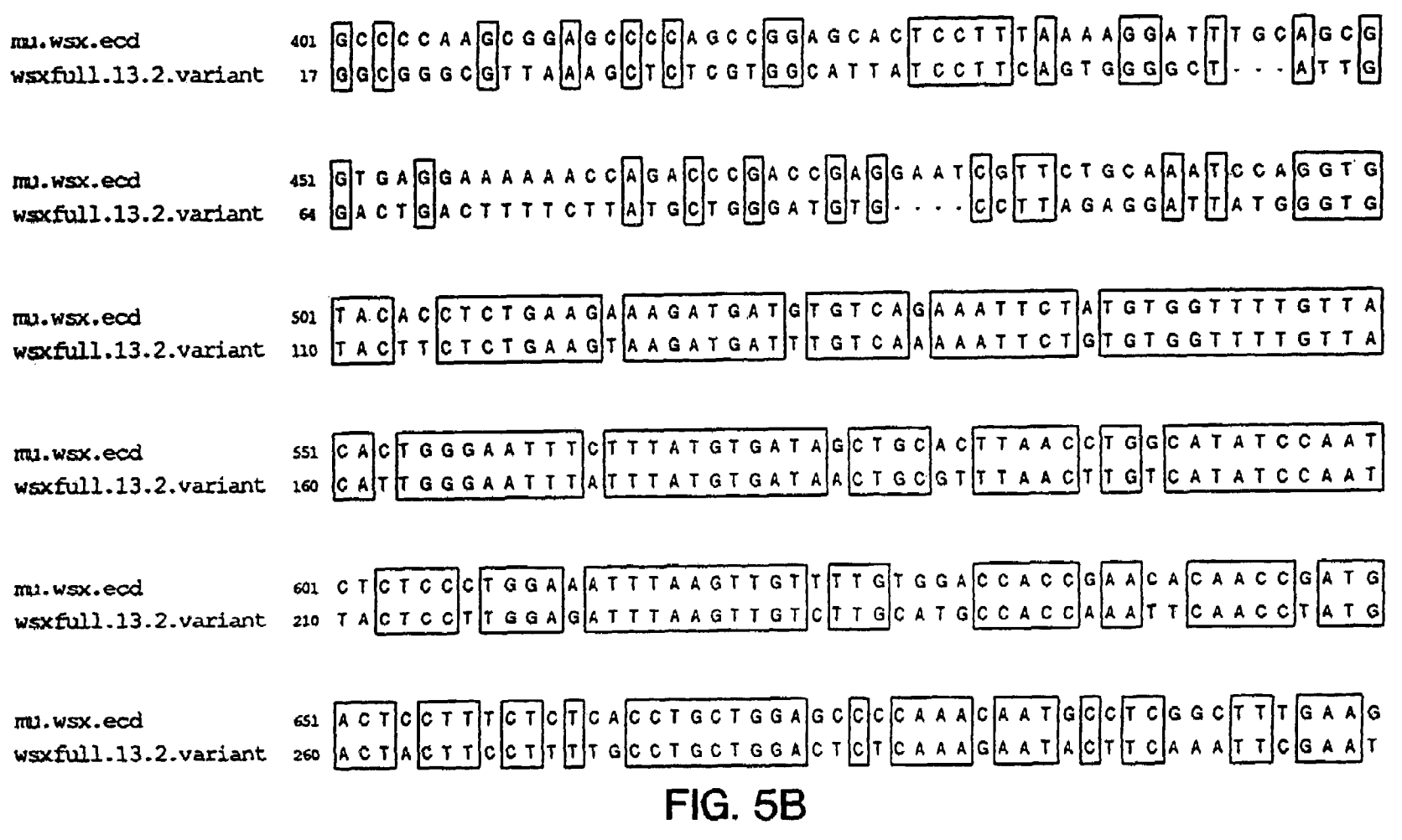
Figure 5C:
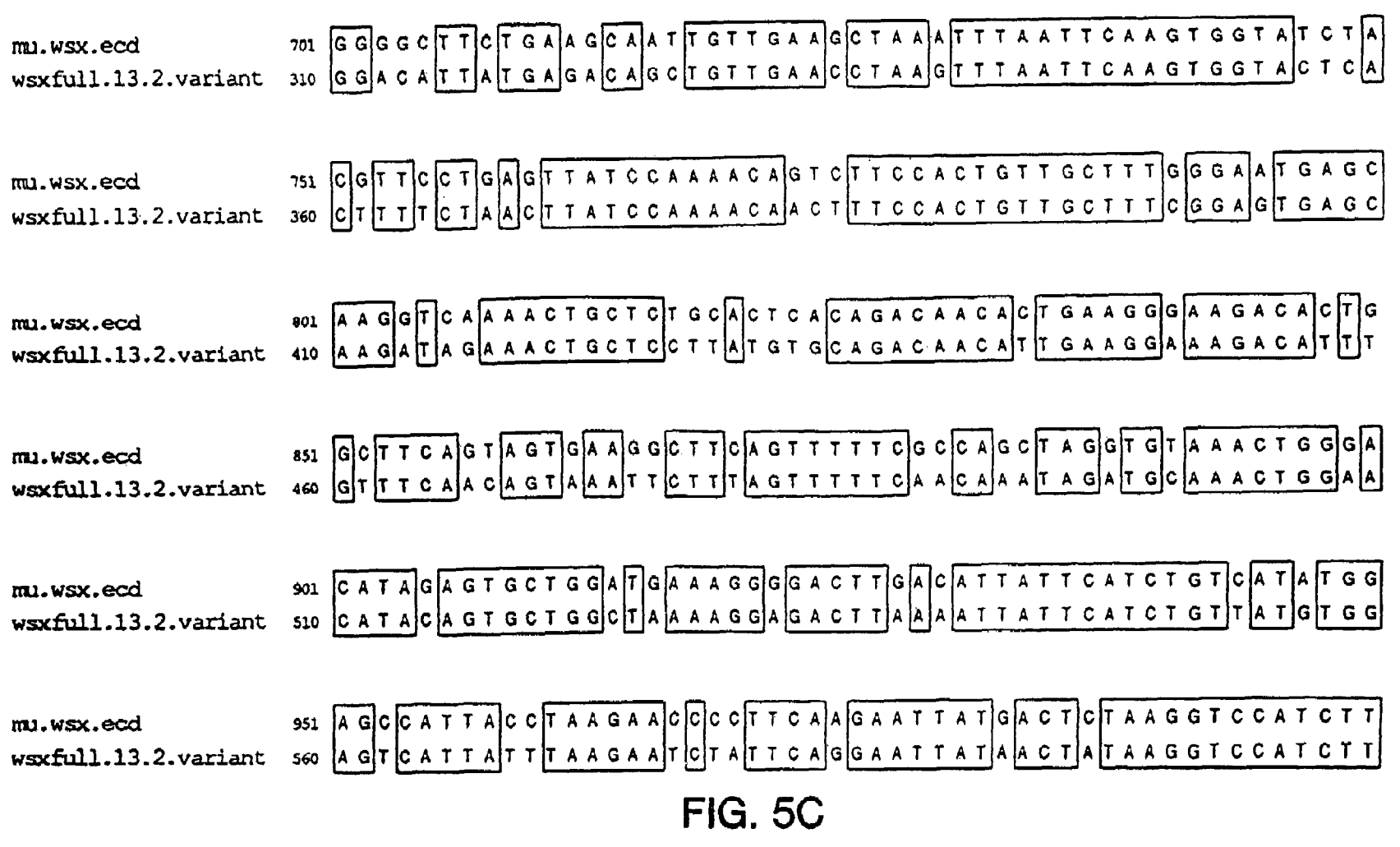
Figure 5D:
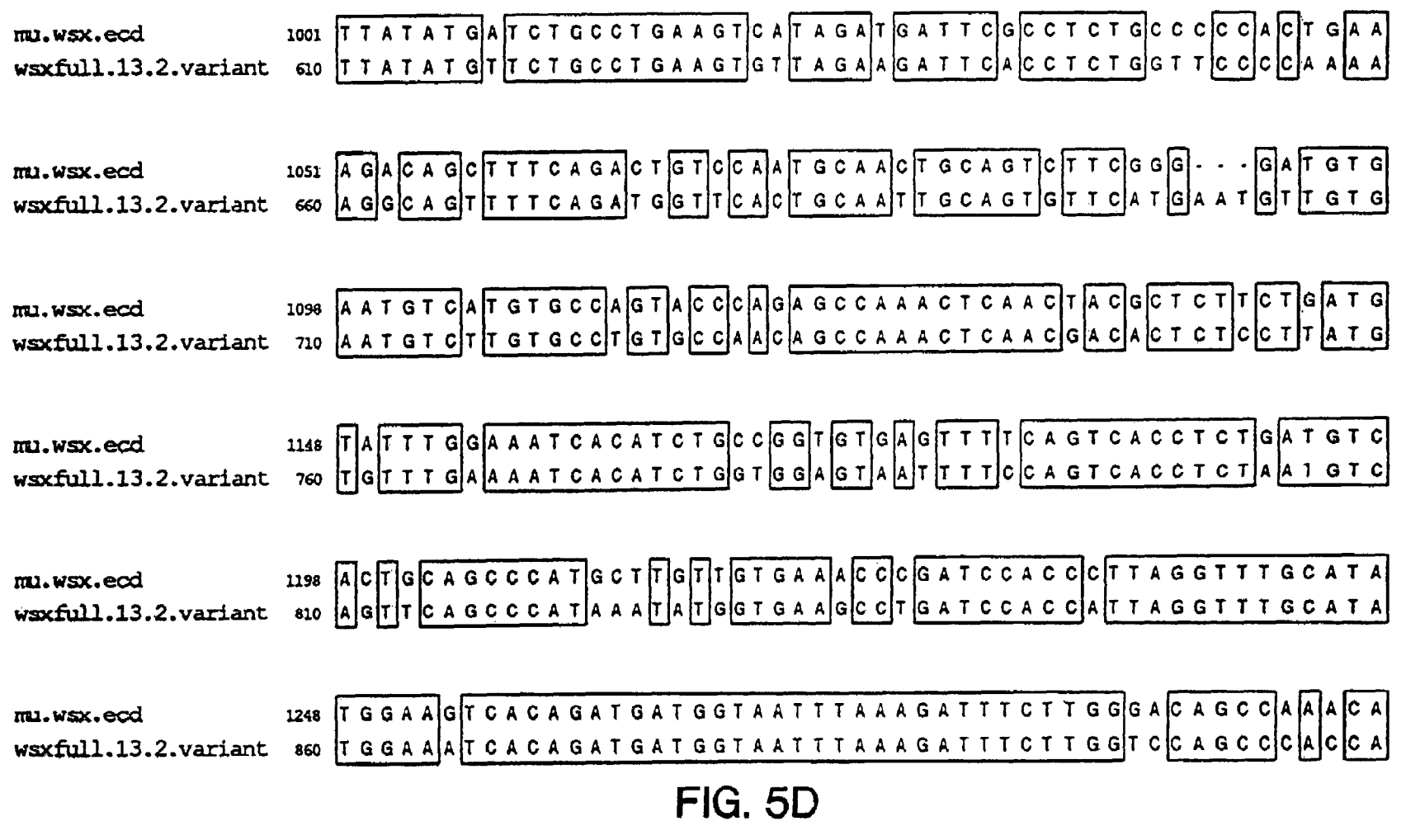
Figure 5E:
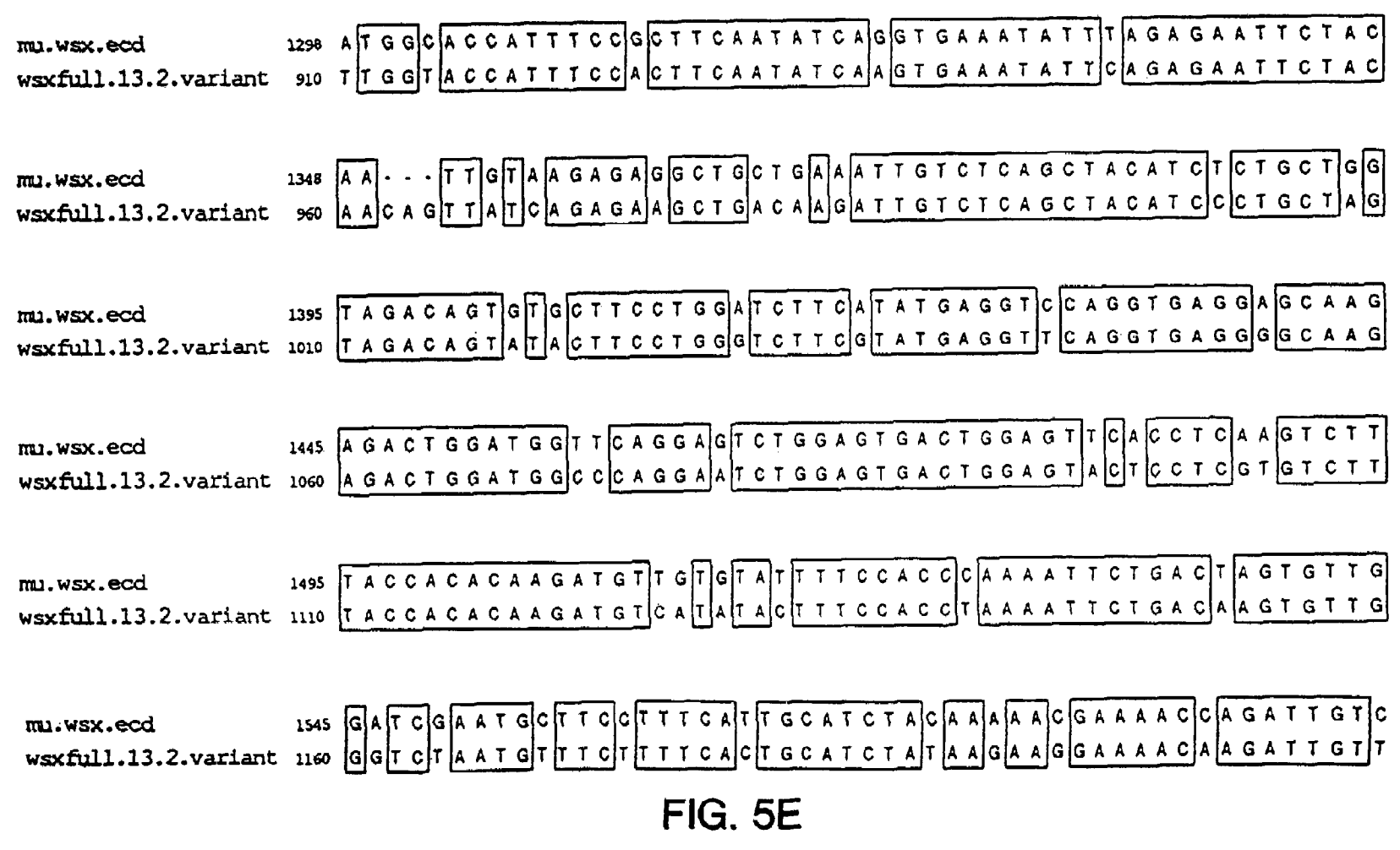
Figure 5F:
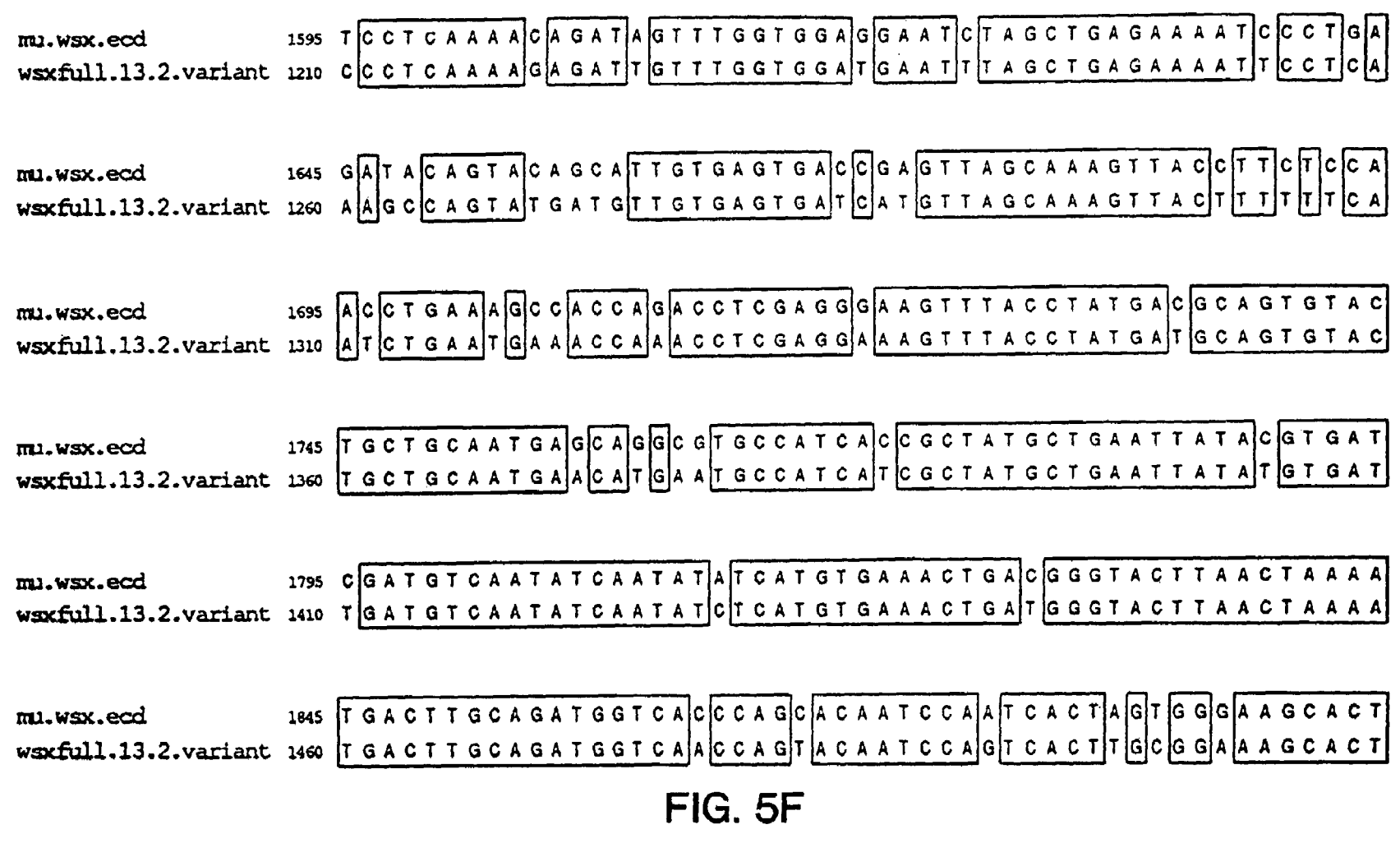
Figure 5G:
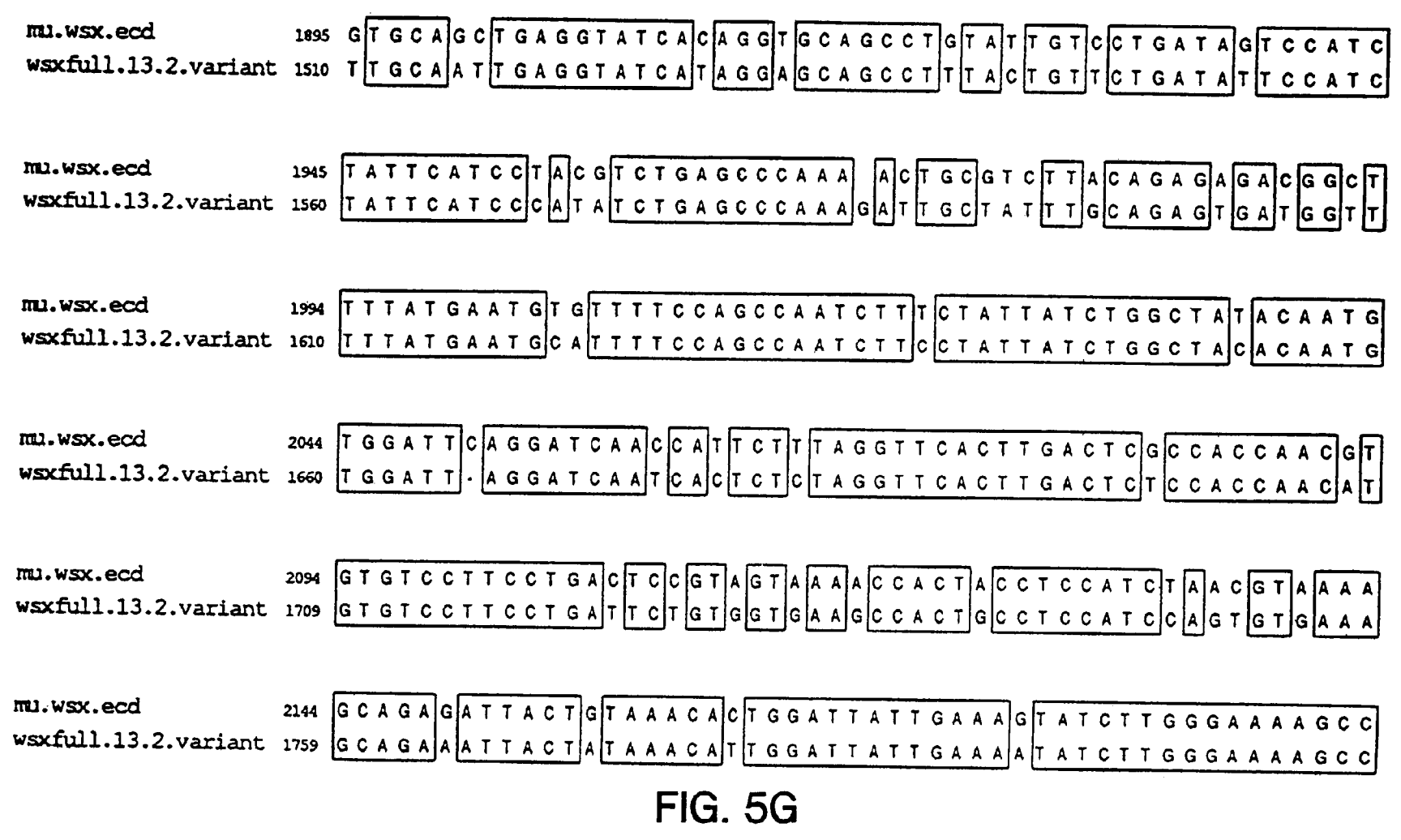
Figure 5H:
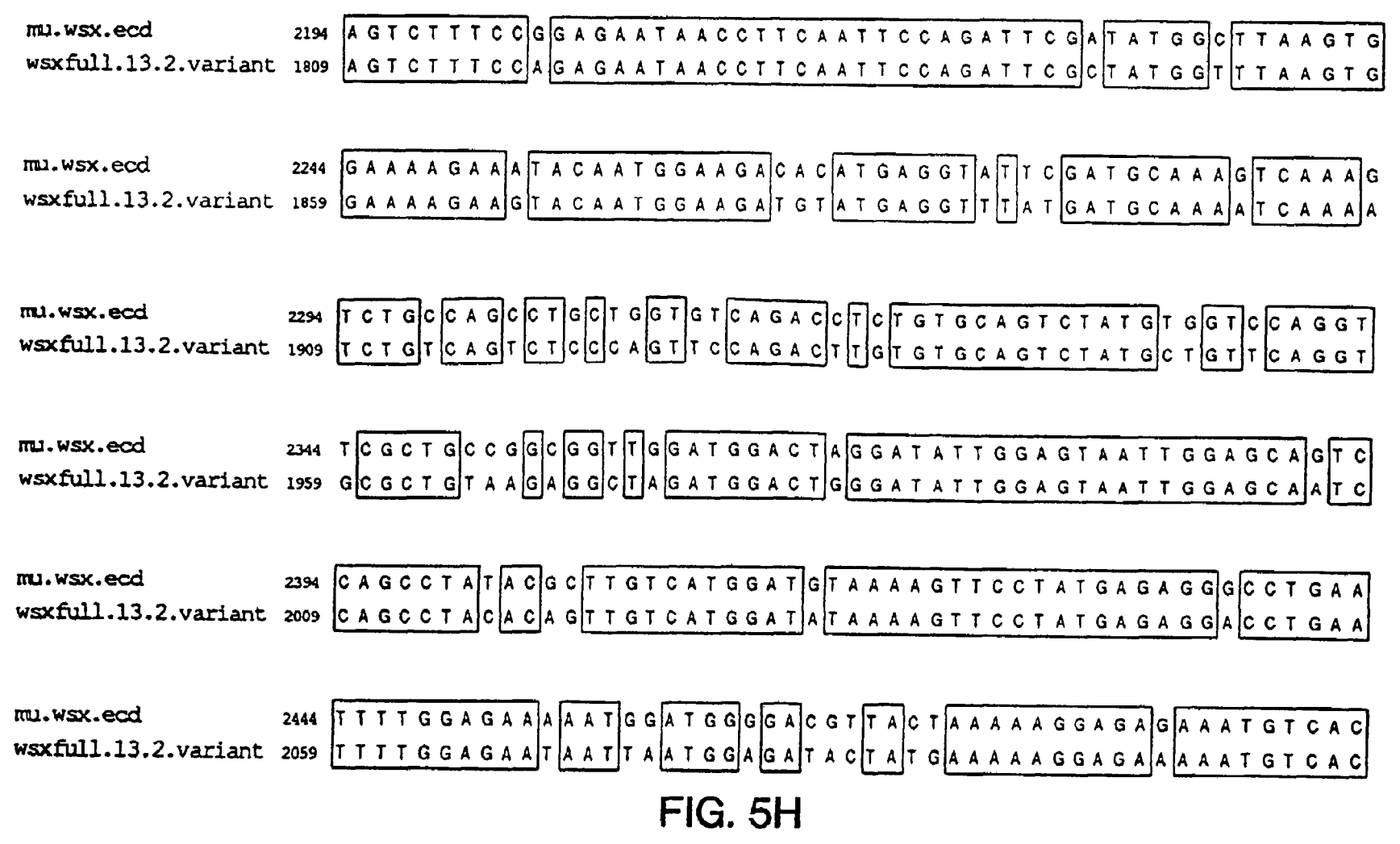
Figure 5I:
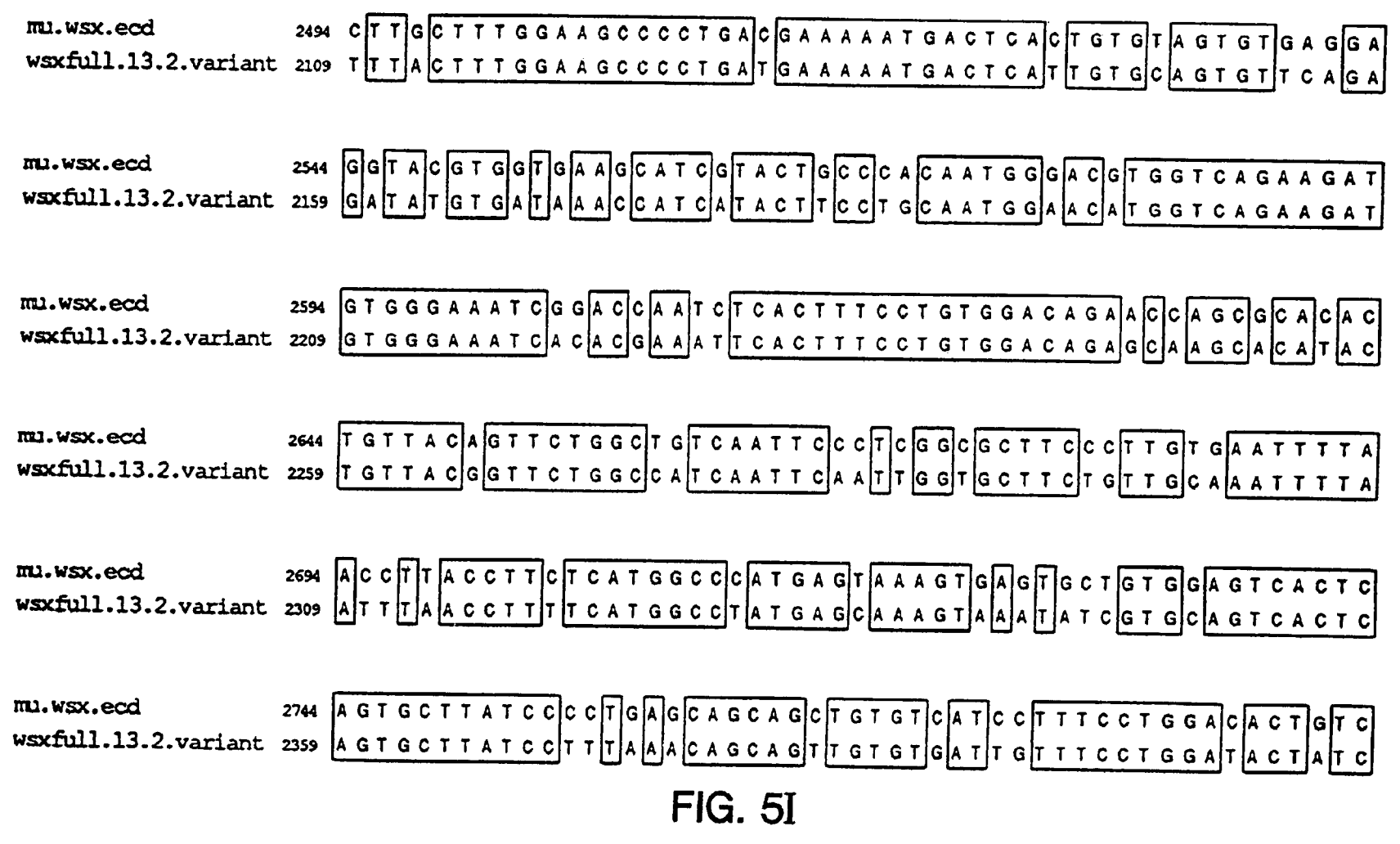

FIGS. 5A-M represent an alignment of the nucleotide sequences encoding human WSX receptor variant 13.2 (bottom) and partial murine WSX receptor extracellular domain (top) (SEQ ID NO:8), respectively.

FIG. 7 shows the human and murine oligonucleotides (SEQ ID NOS:9-38, respectively) used for the antisense experiment described in Example 8.

In FIG. 8, GH receptor-WSX receptor variant 12.1 or 13.2 chimeric proteins were expressed in Baf-3 cells as described in Example 5. These transfected cells and the parental Baf-3 line were stimulated with hGH and the incorporation of titrated thymidine determined.

In FIG. 9, Baf-3 cells were stably transfected with WSX receptor variant 13.2. Thymidine incorporation was then determined in these cell lines following stimulation with human OB protein.

In FIG. 10A, flASK cells were cultured in suspension culture containing serum with kit ligand (KL) or kit ligand and OB protein. Cell counts and cytospin analyses were performed 7 days later. In FIG. 10B, flASK cells were seeded into methylcellulose under either myeloid or lymphoid conditions as described in Example 10. Colony counts were performed 14 days later. For colonies produced under lymphoid conditions, FACS analysis demonstrated the vast majority of cells to be B220 positive. In FIG. 10C, flASK cells were seeded into methylcellulose containing kit ligand. To this base media, erythropoietin (EPO) or erythropoietin and OB protein were then added. The resultant colonies were counted 14 days later. FACS analysis demonstrated approximately 95% of these colonies to be TER 119 positive. All assays were performed in triplicate and confirmed in at least three independent experiments.

FIG. 12A shows cellular profiles determined using anti-B220, anti-CD43, and anti-TERI 19 antibodies. FIG. 12B shows cellular profiles of the spleens from the above groups.

FIGS. 16A-V together show the nucleotide sequence (SEQ ID NO:46) and the amino acid sequence (SEQ ID NO: 47) of the human OB-immunoglobulin chimera in the plasmid described in of Example 11.

FIG. 20A shows blocking ability of anti-WSX receptor antibodies on Epitope A using biotinylated 2D7. FIG. 20B shows blocking ability of anti-WSX receptor antibodies on Epitope B using biotinylated 1C11. Based on the competitive binding ELISA, 2D7 bound a different epitope from 1E11, 1C11 and 1G4.

FIG. 21 depicts an alignment of the amino acid sequences of full length human WSX receptor variant 6.4 (hWSXR) (SEQ ID NO:3) and murine WSX receptor (mWSXR) (SEQ ID NO:51).

FIG. 25 aligns the amino acid sequences of agonist antibody clone #3 (3.scFv) (SEQ ID NO:48), clone #4 (4.scFv) (SEQ ID NO:49) and clone #17 (17.scFv) (SEQ ID NO:50) obtained as described in Example 14. Complementarity determining region (CDR) residues according to Kabat et al., *Sequences of Proteins of Immunological Interest.* 5th Ed. Public Health Service, National Institutes of Health, Bethesda, Md. (1991) are underlined and hypervariable loop residues (Chothia et al., *Nature* 342:8767 (1989)) are in italics.

DETAILED DESCRIPTION OF THE PREFERRED EMBODIMENTS

Definitions

Figure 6:
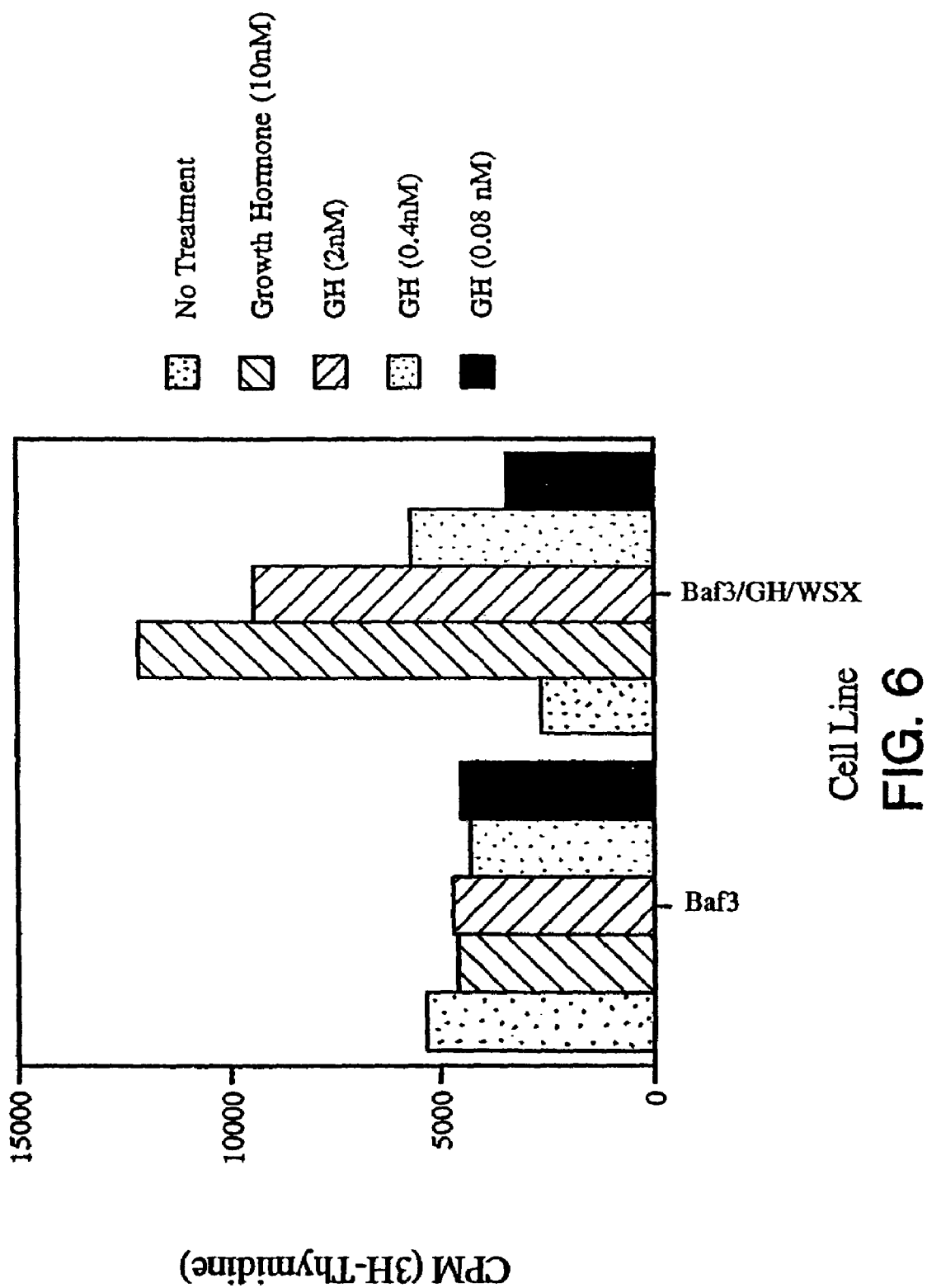
FIG. 6 is a bar graph depicting results of the thymidine incorporation assay described in Example 5. $^3$H-thymidine incorporation (counts per minute, CPM) in parental Baf3 cells or Baf3 cells electroporated with GH/WSX variant 13.2 chimera in the presence of varying concentrations of human growth hormone (GH) is shown.

In describing the present invention, the following terms will be employed, and are intended to be defined as indicated below.

The terms "WSX receptor" or "WSX receptor polypeptide" when used herein encompass native sequence WSX receptor; WSX receptor variants; WSX extracellular domain; and chimeric WSX receptor (each of which is defined herein). Optionally, the WSX receptor is not associated with native glycosylation. "Native glycosylation" refers to the carbohydrate moieties which are covalently attached to WSX receptor when it is produced in the mammalian cell from which it is derived in nature. Accordingly, human WSX receptor produced in a non-human cell is an example of a WSX receptor which is "not associated with native glycosylation". Sometimes, the WSX receptor is unglycosylated (e.g.,as a result of being produced recombinantly in a prokaryote).

"WSX ligand" is a molecule which binds to and activates native sequence WSX receptor (especially WSX receptor variant 13.2). The ability of a molecule to bind to WSX receptor can be determined by the ability of a putative WSk ligand to bind to WSX receptor immunoadhesin (see Example 2) coated on an assay plate, for example. The thymidine incorporation assay provides a means for screening for WSX ligands which activate the WSX receptor. Exemplary WSX ligands include anti-WSX receptor agonist antibodies and OB protein (e.g., described in Zhang et al. *Nature* 372:425-431 (1994)).

The terms "OB protein" and "OB" are used interchangeably herein and refer to native sequence OB proteins (also known as "leptins") and their functional derivatives.

A "native sequence" polypeptide is one which has the same amino acid sequence as a polypeptide (e.g., WSX receptor or OB protein) derived from nature. Such native sequence polypeptides can be isolated from nature or can be produced by recombinant or synthetic means. Thus, a native sequence polypeptide can have the amino acid sequence of naturally occurring human polypeptide, murine polypeptide, or polypeptide from any other mammalian species.

The term "native sequence WSX receptor" specifically encompasses naturally-occurring truncated forms of the WSX receptor, naturally-occurring variant forms (e.g.,alternatively spliced forms such as human WSX receptor variants 6.4, 12.1 and 13.2 described herein) and naturally-occurring allelic variants of the WSX receptor. The preferred native sequence WSX receptor is a mature native sequence human WSX receptor, such as human WSX receptor variant 6.4, human WSX receptor variant 12.1 or human WSX receptor variant 13.2 (each shown in FIGS. 2A-D). Most preferred is mature human WSX receptor variant 13.2.

The term "native sequence OB protein" includes those OB proteins from any animal species (e.g. human, murine, rabbit, cat, cow, sheep, chicken, porcine, equine, etc.) as occurring in nature. The definition specifically includes variants with or without a glutamine at amino acid position 49, using the amino acid numbering of Zhang et al., supra. The term "native sequence OB protein" includes the native proteins with or without the initiating N-terminal methionine (Met), and with or without the native signal sequence, either in monomeric or in dimeric form. The native sequence human and murine OB proteins known in the art are 167 amino acids long, contain two conserved cysteines, and have the features of a secreted protein. The protein is largely hydrophilic, and the predicted signal sequence cleavage site is at position 21, using the amino acid numbering of Zhang et al., supra. The overall sequence homology of the human and murine sequences is about 84%. The two proteins show a more extensive identity in the N-terminal region of the mature protein, with only four conservative and three non-conservative substitutions among the residues between the signal sequence cleavage site and the conserved Cys at position 117. The molecular weight of OB protein is about 16 kD in a monomeric form.

The "WSX receptor extracellular domain" (ECD) is a form of the WSX receptor which is essentially free of the transmembrane and cytoplasmic domains of WSX receptor, i.e., has less than 1% of such domains, preferably 0.5 to 0% of such domains, and more preferably 0.1 to 0% of such domains. Ordinarily, the WSX receptor ECD will have an amino acid sequence having at least about 95% amino acid sequence identity with the amino acid sequence of the ECD of WSX receptor indicated in FIGS. 2A-D for human WSX receptor variants 6.4, 12.1 and 13.2, preferably at least about 98%, more preferably at least about 99% amino acid sequence identity, and thus includes WSX receptor variants as defined below.

A "variant" polypeptide means a biologically active polypeptide as defined below having less than 100% sequence identity with a native sequence polypeptide (e.g., WSX receptor having the deduced amino acid sequence shown in FIGS. 1A-H for human WSX receptor variant 13.2). Such variants include polypeptides wherein one or more amino acid residues are added at the N- or C-terminus of, or within, the native sequence; from about one to thirty amino acid residues are deleted, and optionally substituted by one or more amino acid residues; and derivatives of the above polypeptides, wherein an amino acid residue has been covalently modified so that the resulting product has a non-naturally occurring amino acid. Ordinarily, a biologically active WSX receptor variant will have an amino acid sequence having at least about 90% amino acid sequence identity with human WSX receptor variant 13.2 shown in FIGS. 1A-J, preferably at least about 95%, more preferably at least about 99%. Ordinarily, a biologically active OB protein variant will have an amino acid sequence having at least about 90% amino acid sequence identity with a native sequence OB protein, preferably at least about 95%, more preferably at least about 99%.

A "chimeric" OB protein or WSX receptor is a polypeptide comprising OB protein or full-length WSX receptor or one or more domains thereof (e.g.,the extracellular domain of the WSX receptor) fused or bonded to heterologous polypeptide. The chimeric WSX receptor will generally share at least one biological property in common with human WSX receptor variant 13.2. The chimeric OB protein will generally share at least one biological property in common with a native sequence OB protein. Examples of chimeric polypeptides include immunoadhesins and epitope tagged polypeptides.

The term "WSX immunoadhesin" is used interchangeably with the expression "WSX receptor-immunoglobulin chimera" and refers to a chimeric molecule that combines a portion of the WSX receptor (generally the extracellular domain thereof) with an immunoglobulin sequence. Likewise, an "OB protein immunoadhesin" or "OB-immunoglobulin chimera" refers to a chimeric molecule which combines OB protein (or a portion thereof) with an immunoglobulin sequence. The immunoglobulin sequence preferably, but not necessarily, is an immunoglobulin constant domain. The immunoglobulin moiety in the chimeras of the present invention may be obtained from IgG1, IgG2, IgG3 or IgG4 subtypes, IgA, IgE, IgD or IgM, but preferably IgG1 or IgG3.

The term "epitope tagged" when used herein refers to a chimeric polypeptide comprising WSX receptor or OB protein fused to a "tag polypeptide". The tag polypeptide has enough residues to provide an epitope against which an antibody thereagainst can be made, yet is short enough such that it does not interfere with biological activity of the WSX receptor or OB protein. The tag polypeptide preferably also is fairly unique so that the antibody thereagainst does not substantially cross-react with other epitopes. Suitable tag polypeptides generally have at least six amino acid residues and usually between about 8-50 amino acid residues (preferably between about 9-30 residues).

"Isolated" WSX receptor (or OB protein) means WSX receptor (or OB protein) that has been purified from a WSX receptor (or OB protein) source or has been prepared by recombinant or synthetic methods and is sufficiently free of other peptides or proteins (1) to obtain at least 15 and preferably 20 amino acid residues of the N-terminal or of an internal amino acid sequence by using a spinning cup sequenator or the best commercially available amino acid sequenator marketed or as modified by published methods as of the filing date of this application, or (2) to homogeneity by SDS-PAGE under non-reducing or reducing conditions using Coomassie blue or, preferably, silver stain. Homogeneity here means less than about 5% contamination with other source proteins.

"Essentially pure" protein means a composition comprising at least about 90% by weight of the protein, based on total weight of the composition, preferably at least about 95% by weight. "Essentially homogeneous" protein means a composition comprising at least about 99% by weight of protein, based on total weight of the composition.

"Biological property" when used in conjunction with either "WSX receptor" or "isolated WSX receptor" means having an effector or antigenic function or activity that is directly or indirectly caused or performed by native sequence WSX receptor (whether in its native or denatured conformation). Effector functions include ligand binding; and enhancement of survival, differentiation and/or proliferation of cells (especially proliferation of cells). However, effector functions do not include possession of an epitope or antigenic site that is capable of cross-reacting with antibodies raised against native sequence WSX receptor.

"Biological property" when used in conjunction with either "OB protein" or "isolated OB protein" means having an effector function that is directly or indirectly caused or performed by native sequence OB protein. Effector functions of native sequence OB protein include WSX receptor binding and activation; and enhancement of differentiation and/or proliferation of cells expressing this receptor (as determined in the thymidine incorporation assay, for example). A "biologically active" OB protein is one which possesses a biological property of native sequence OB protein.

A "functional derivative" of a native sequence OB protein is a compound having a qualitative biological property in common with a native sequence OB protein. "Functional derivatives" include, but are not limited to, fragments of native sequence OB proteins and derivatives of native sequence OB proteins and their fragments, provided that they have a biological activity in common with a corresponding native sequence OB protein. The term "derivative" encompasses both amino acid sequence variants of OB protein and covalent modifications thereof.

The phrase "long half-life" as used in connection with OB derivatives, concerns OB derivatives having a longer plasma half-life and/or slower clearance than a corresponding native sequence OB protein. The long half-life derivatives preferably will have a half-life at least about 1.5-times longer than a native OB protein; more preferably at least about 2-times longer than a native OB protein, more preferably at least about 3-time longer than a native OB protein. The native OB protein preferably is that of the individual to be treated.

An "antigenic function" means possession of an epitope or antigenic site that is capable of cross-reacting with antibodies raised against native sequence WSX receptor. The principal antigenic function of a WSX receptor is that it binds with an affinity of at least about $10^6$ L/mole to an antibody raised against native sequence WSX receptor. Ordinarily, the polypeptide binds with an affinity of at least about $10^7$ L/mole. The antibodies used to define "antigenic function" are rabbit polyclonal antibodies raised by formulating the WSX receptor in Freund's complete adjuvant, subcutaneously injecting the formulation, and boosting the immune response by intraperitoneal injection of the formulation until the titer of the anti-WSX receptor or antibody plateaus.

"Biologically active" when used in conjunction with either "WSX receptor" or "isolated WSX receptor" means a WSX receptor polypeptide that exhibits or shares an effector function of native sequence WSX receptor and that may (but need not) in addition possess an antigenic function. A principal effector function of the WSX receptor is its ability to induce proliferation of CD34+ human umbilical cord blood cells in the colony assay described in Example 8.

"Antigenically active" WSX receptor is defined as a polypeptide that possesses an antigenic function of WSX receptor and that may (but need not) in addition possess an effector function.

"Percent amino acid sequence identity" is defined herein as the percentage of amino acid residues in the candidate sequence that are identical with the residues in the native sequence, after aligning the sequences and introducing gaps, if necessary, to achieve the maximum percent sequence identity, and not considering any conservative substitutions as part of the sequence identity. None of N-terminal, C-terminal, or internal extensions, deletions, or insertions into the candidate sequence shall be construed as affecting sequence identity or homology.

A "thymidine incorporation assay" can be used to screen for molecules which activate the WSX receptor. In order to perform this assay, IL-3 dependent Baf3 cells (Palacios et al., Cell, 41:727-734 (1985)) are stably transfected with full length native sequence WSX receptor as described in Example 4. The WSX receptor/Baf3 cells so generated are starved of IL-3 for, e.g., 24 hours in a humidified incubator at 37° C. in 5% $CO_2$ and air. Following IL-3 starvation, the cells are plated out in 96 well culture dishes with, or without, a test sample containing a potential agonist (such test samples are optionally diluted) and cultured for 24 hours in a cell culture incubator. 20 µl of serum free RPMI media containing 1 µCi of $^3H$ thymidine is added to each well for the last 6-8 hours. The cells are then harvested in 96 well filter plates and washed with water. The filters are then counted using a Packard Top Count Microplate Scintillation Counter, for example. Agonists are expected to induce a statistically significant increase (to a P value of 0.05) in $^3H$ uptake, relative to control. Preferred agonists leads to an increase in $^3H$ uptake which is at least two fold of that of the control.

An "isolated" WSX receptor nucleic acid molecule is a nucleic acid molecule that is identified and separated from at least one contaminant nucleic acid molecule with which it is ordinarily associated in the natural source of the WSX receptor nucleic acid. An isolated WSX receptor nucleic acid molecule is other than in the form or setting in which it is found in nature. Isolated WSX receptor nucleic acid molecules therefore are distinguished from the WSX receptor nucleic acid molecule as it exists in natural cells. However, an isolated WSX receptor nucleic acid molecule includes WSX receptor nucleic acid molecules contained in cells that ordinarily express WSX receptor where, for example, the nucleic acid molecule is in a chromosomal location different from that of natural cells.

The expression "control sequences" refers to DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

The term "antibody" is used in the broadest sense and specifically covers monoclonal antibodies, antibody compositions with polyepitopic specificity, bispecific antibodies, diabodies, and single-chain molecules, as well as antibody fragments (e.g., Fab, F(ab')$_2$, and Fv), so long as they exhibit the desired biological activity.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature* 256:495 (1975), or may be made by recombinant DNA methods (see, e.g., U.S. Pat. No. 4,816,567 (Cabilly et al.)). The "monoclonal antibodies" may also be isolated from phage antibody libraries using the techniques described in Clackson et al., *Nature* 352:624-628 (1991) and Marks et al., *J. Mol. Biol.* 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (Cabilly et al., supra; Morrison et al., *Proc. Natl. Acad. Sci. USA*, 81:6851-6855 (1984)).

"Humanized" forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., *Nature* 321:522-525 (1986); Reichmann et al., *Nature* 332:323-329 (1988); and Presta, *Curr. Op. Struct. Biol.* 2:593-596 (1992). The humanized antibody includes a Primatized™ antibody wherein the antigen-binding region of the antibody is derived from an antibody produced by immunizing macaque monkeys with the antigen of interest.

The term "hypervariable region" when used herein refers to the amino acid residues of an antibody which are responsible for antigen-binding. The hypervariable region comprises amino acid residues from a "complementarity determining region" or "CDR" (i.e. residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest*, 5th Ed. Public Health Service, National Institutes of Health, Bethesda, Md. (1991)) and/or those residues from a "hypervariable loop" (i.e. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196: 901-917 (1987)). "Framework" or "FR" residues are those variable domain residues other than the hypervariable region residues as herein defined.

"Non-immunogenic in a human" means that upon contacting the polypeptide of interest in a physiologically acceptable carrier and in a therapeutically effective amount with the appropriate tissue of a human, no state of sensitivity or resistance to the polypeptide of interest is demonstrable upon the second administration of the polypeptide of interest after an appropriate latent period (e.g., 8 to 14 days).

By "agonist antibody" is meant an antibody which is able to activate native sequence WSX receptor. The agonist antibody of particular interest herein is one which mimics one or more (e.g. all) of the biological properties of naturally occurring WSX ligand, OB protein. In preferred embodiments, the agonist antibody has a quantitative biological property of OB protein which is within about two orders of magnitude, and preferably within about one order of magnitude, that of OB protein. The agonist antibody may bind to and activate WSX receptor and thereby stimulate proliferation and/or differentiation and/or maturation and/or survival of a cell which expresses the WSX receptor (e.g. WSX receptor variant 13.2). In this embodiment of the invention, the agonist antibody may be one which enhances proliferation and/or differentiation of a hematopoietic progenitor cell which expresses the WSX receptor at its cell surface; enhances proliferation and/or differentiation of lymphoid blood cell lineages; enhances proliferation and/or differentiation of myeloid blood cell lineages; and/or enhances proliferation and/or differentiation of erythroid blood cell lineages. The agonist antibody may display agonist activity upon binding to a chimeric receptor comprising the WSX receptor extracellular domain in the KIRA ELISA. The agonist antibody may stimulate $^3$H uptake in the thymidine incorporation assay using a signaling WSX receptor (see above); decrease body weight and/or fat-depot weight and/or food intake in an obese mammal (e.g. in the ob/ob mouse); effect $Ca^{2+}$ influx in adipocytes; and/or activate downstream signaling molecules of OB protein.

A "neutralizing antibody" is one which is able to block or significantly reduce an effector function of native sequence WSX receptor or OB protein. For example, a neutralizing antibody may inhibit or reduce WSX receptor activation by a WSX ligand as determined in the thymidine incorporation assay or in a KIRA ELISA. The term "cytotoxic agent" as used herein refers to a substance that inhibits or prevents the function of cells and/or causes destruction of cells. The term is intended to include radioactive isotopes (e.g., $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "chemotherapeutic agent" is a chemical compound useful in the treatment of cancer. Examples of chemotherapeutic agents include Adriamycin, Doxorubicin, 5-Fluorouracil, Cytosine arabinoside ("Ara-C"), Cyclophosphamide, Thiotepa, Taxotere (docetaxel), Busulfan, Cytoxin, Taxol, Methotrexate, Cisplatin, Melphalan, Vinblastine, Bleomycin, Etoposide, Ifosfamide, Mitomycin C, Mitoxantrone, Vincreistine, Vinorelbine, Carboplatin, Teniposide, Daunomycin, Carminomycin, Aminopterin, Dactinomycin, Mitomycins, Esperamicins (see U.S. Pat. No. 4,675,187), Melphalan and other related nitrogen mustards.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" *Biochemical Society Transactions,* 14, pp.375-382, 615th Meeting Belfast (1986) and Stella et al., "Prodrugs: A Chemical Approach to Targeted Drug Delivery," *Directed Drug Delivery*, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

An "antagonist" of the WSX receptor and/or OB protein is a molecule which prevents, or interferes with, binding and/or activation of the WSX receptor or OB protein. Such molecules can be screened for their ability to competitively inhibit WSX receptor activation by OB protein in the thymidine incorporation assay disclosed herein, for example. Examples of such molecules include: WSX receptor ECD; WSX receptor immunoadhesin; neutralizing antibodies against WSX receptor or OB protein; small molecule and peptide antagonists; and antisense nucleotides against the WSX receptor or ob gene.

The phrase "enhancing proliferation of a cell" encompasses the step of increasing the extent of growth and/or reproduction of the cell relative to an untreated cell either in vitro or in vivo. An increase in cell proliferation in cell culture can be detected by counting the number of cells before and after exposure to a molecule of interest. The extent of proliferation can be quantified via microscopic examination of the degree of confluency. Cell proliferation can also be quantified using the thymidine incorporation assay described herein.

By "enhancing differentiation of a cell" is meant the act of increasing the extent of the acquisition or possession of one or more characteristics or functions which differ from that of the original cell (i.e. cell specialization). This can be detected by screening for a change in the phenotype of the cell (e.g., identifying morphological changes in the cell).

A "hematopoietic progenitor cell" or "primitive hematopoietic cell" is one which is able to differentiate to form a more committed or mature blood cell type.

"Lymphoid blood cell lineages" are those hematopoietic precursor cells which are able to differentiate to form lymphocytes (B-cells or T-cells). Likewise, "lymphopoeisis" is the formation of lymphocytes.

"Erythroid blood cell lineages" are those hematopoietic precursor cells which are able to differentiate to form erythrocytes (red blood cells) and "erythropoeisis" is the formation of erythrocytes.

The phrase "myeloid blood cell lineages", for the purposes herein, encompasses all hematopoietic precursor cells, other than lymphoid and erythroid blood cell lineages as defined above, and "myelopoiesis" involves the formation of blood cells (other than lymphocytes and erythrocytes).

A "CD34+ cell population" is enriched for hematopoietic stem cells. A CD34+ cell population can be obtained from umbilical cord blood or bone marrow, for example. Human umbilical cord blood CD34+ cells can be selected for using immunomagnetic beads sold by Miltenyi (California), following the manufacturer's directions.

"Physiologically acceptable" carriers, excipients, or stabilizers are ones which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

As used herein, the term "salvage receptor binding epitope" refers to an epitope of the Fc region of an IgG molecule (e.g., IgG1, IgG2, IgG3, and IgG4) that is responsible for increasing the in vivo serum half-life of the IgG molecule. Exemplary salvage receptor binding epitope sequences include HQNLSDGK (SEQ ID NO:39); HQNISDGK (SEQ ID NO:40); HQSLGTQ (SEQ ID NO:41); VISSHLGQ (SEQ ID NO:42); and PKNSSMISNTP (SEQ ID NO:43).

The term "cytokine" is a generic term for proteins released by one cell population which act on another cell as intercellular mediators. Examples of such cytokines are lymphokines, monokines, and traditional polypeptide hormones. Included among the cytokines are OB protein; growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-11, IL-12; and other polypeptide factors including leukemia inhibitory factor (LIF) and kit ligand (KL). As used herein, the term cytokine includes proteins from natural sources or from recombinant cell culture and biologically active equivalents of the native sequence cytokines.

A "lineage-specific cytokine" is one which acts on relatively committed cells in the hematopoietic cascade and gives rise to an expansion in blood cells of a single lineage. Examples of such cytokines include EPO, TPO, and G-CSF.

"Treatment" refers to both therapeutic treatment and prophylactic or preventative measures. Those in need of treatment include those already with the disorder as well as those in which the disorder is to be prevented.

The term "obesity" is used to designate a condition of being overweight associated with excessive bodily fat. The desirable weight for a certain individual depends on a number of factors including sex, height, age, overall built, etc. The same factors will determine when an individual is considered obese. The determination of an optimum body weight for a given individual is well within the skill of an ordinary physician.

"Mammal" for purposes of treatment refers to any animal classified as a mammal, including humans, domestic and farm animals, and zoo, sports, or pet animals, such as dogs, horses, cats, cows, etc. Preferably, the mammal is human.

By "solid phase" is meant a non-aqueous matrix to which a reagent of interest (e.g., the WSX receptor or an antibody thereto) can adhere. Examples of solid phases encompassed herein include those formed partially or entirely of glass (e.g.,controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g, an affinity chromatography column). This term also includes a discontinuous solid phase of discrete particles, such as those described in U.S. Pat. No. 4,275,149.

A. Modes for Carrying Out the Invention

The present invention is based on the discovery of the WSX receptor. The experiments described herein demonstrate that this molecule is a cytokine receptor which appears to play a role in enhancing proliferation and/or differentiation of hematopoietic cells. In particular, this receptor has been found to be present in enriched human stem cell populations, thus indicating that WSX ligands, such as agonist antibodies, may be used to stimulate proliferation of hematopoietic stem cells/progenitor cells. Other uses for this receptor will be apparent from the following discussion. A description follows as to how WSX receptor or OB proteins may be prepared.

B. Preparation of WSX Receptor or OB Protein

Techniques suitable for the production of WSX receptor or OB protein are well known in the art and include isolating WSX receptor or OB protein from an endogenous source of the polypeptide, peptide synthesis (using a peptide synthesizer) and recombinant techniques (or any combination of these techniques). The preferred technique for production of WSX receptor or OB protein is a recombinant technique to be described below.

Most of the discussion below pertains to recombinant production of WSX receptor or OB protein by culturing cells transformed with a vector containing WSX receptor or OB protein nucleic acid and recovering the polypeptide from the cell culture. It is further envisioned that the WSX receptor or OB protein of this invention may be produced by homologous recombination, as provided for in WO 91/06667, published 16 May 1991.

Briefly, this method involves transforming primary human cells containing a WSX receptor or OB protein-encoding gene with a construct (i.e., vector) comprising an amplifiable gene (such as dihydrofolate reductase (DHFR) or others discussed below) and at least one flanking region of a length of at least about 150 bp that is homologous with a DNA sequence at the locus of the coding region of the WSX receptor or OB protein gene to provide amplification of the WSX receptor or OB protein gene. The amplifiable gene must be at a site that does not interfere with expression of the WSX receptor or OB protein gene. The transformation is conducted such that the construct becomes homologously integrated into the genome of the primary cells to define an amplifiable region.

Primary cells comprising the construct are then selected for by means of the amplifiable gene or other marker present in the construct. The presence of the marker gene establishes the presence and integration of the construct into the host genome. No further selection of the primary cells need be made, since selection will be made in the second host. If desired, the occurrence of the homologous recombination event can be determined by employing PCR and either sequencing the resulting amplified DNA sequences or determining the appropriate length of the PCR fragment when DNA from correct homologous integrants is present and expanding only those cells containing such fragments. Also if desired, the selected cells may be amplified at this point by stressing the cells with the appropriate amplifying agent (such as methotrexate if the amplifiable gene is DHFR), so that multiple copies of the target gene are obtained. Preferably, however, the amplification step is not conducted until after the second transformation described below.

After the selection step, DNA portions of the genome, sufficiently large to include the entire amplifiable region, are isolated from the selected primary cells. Secondary mammalian expression host cells are then transformed with these genomic DNA portions and cloned, and clones are selected that contain the amplifiable region. The amplifiable region is then amplified by means of an amplifying agent if not already amplified in the primary cells. Finally, the secondary expression host cells now comprising multiple copies of the amplifiable region containing WSX receptor or OB protein are grown so as to express the gene and produce the protein.

1. Isolation of DNA Encoding WSX Receptor or OB Protein

The DNA encoding WSX receptor or OB protein may be obtained from any cDNA library prepared from tissue believed to possess the WSX receptor or OB protein mRNA and to express it at a detectable level. Accordingly, WSX receptor or OB protein DNA can be conveniently obtained from a cDNA library prepared from mammalian fetal liver. The WSX receptor or OB protein-encoding gene may also be obtained from a genomic library or by oligonucleotide synthesis.

Libraries are screened with probes (such as antibodies to the WSX receptor or OB protein, or oligonucleotides of about 20-80 bases) designed to identify the gene of interest or the protein encoded by it. Screening the cDNA or genomic library with the selected probe may be conducted using standard procedures as described in chapters 10-12 of Sambrook et al., *Molecular Cloning: A Laboratory Manual* (New York: Cold Spring Harbor Laboratory Press, 1989). An alternative means to isolate the gene encoding WSX receptor or OB protein is to use PCR methodology as described in section 14 of Sambrook et al., supra.

A preferred method of practicing this invention is to use carefully selected oligonucleotide sequences to screen cDNA libraries from various human tissues, preferably human fetal liver. The oligonucleotide sequences selected as probes should be of sufficient length and sufficiently unambiguous that false positives are minimized.

The oligonucleotide must be labeled such that it can be detected upon hybridization to DNA in the library being screened. The preferred method of labeling is to use $^{32}$P-labeled ATP with polynucleotide kinase, as is well known in the art, to radiolabel the oligonucleotide. However, other methods may be used to label the oligonucleotide, including, but not limited to, biotinylation or enzyme labeling.

Amino acid sequence variants of WSX receptor or OB protein are prepared by introducing appropriate nucleotide changes into the WSX receptor or OB protein DNA, or by synthesis of the desired WSX receptor or OB protein. Such variants represent insertions, substitutions, and/or specified deletions of, residues within or at one or both of the ends of the amino acid sequence of a naturally occurring human WSX receptor or OB protein, such as the WSX receptor variants shown in FIGS. 2A-D or the human OB protein of Zhang et al., supra. Preferably, these variants represent insertions and/or substitutions within or at one or both ends of the mature sequence, and/or insertions, substitutions and/or specificed deletions within or at one or both of the ends of the signal sequence of the WSX receptor or OB protein. Any combination of insertion, substitution, and/or specified deletion is made to arrive at the final construct, provided that the final construct possesses the desired biological activity as defined herein. The amino acid changes also may alter post-translational processes of the WSX receptor or OB protein, such as changing the number or position of glycosylation sites, altering the membrane anchoring characteristics, and/or altering the intracellular location of the WSX receptor or OB protein by inserting, deleting, or otherwise affecting the leader sequence of the WSX receptor or OB protein.

Variations in the native sequence as described above can be made using any of the techniques and guidelines for conservative and non-conservative mutations set forth in U.S. Pat. No. 5,364,934. These include oligonucleotide-mediated (site-directed) mutagenesis, alanine scanning, and PCR mutagenesis. See also, for example, Table I therein and the discussion surrounding this table for guidance on selecting amino acids to change, add, or delete.

2. Insertion of Nucleic Acid into Replicable Vector

The nucleic acid (e.g., cDNA or genomic DNA) encoding the WSX receptor or OB protein is inserted into a replicable vector for further cloning (amplification of the DNA) or for expression. Many vectors are available. The vector components generally include, but are not limited to, one or more of the following: a signal sequence, an origin of replication, one or more marker genes, an enhancer element, a promoter, and a transcription termination sequence.

a. Signal Sequence Component

The WSX receptor or OB proteins of this invention may be produced recombinantly not only directly, but also as a fusion polypeptide with a heterologous polypeptide, which is preferably a signal sequence or other polypeptide having a specific cleavage site at the N-terminus of the mature protein or polypeptide. In general, the signal sequence may be a component of the vector, or it may be a part of the WSX receptor or OB protein DNA that is inserted into the vector. The heterologous signal sequence selected preferably is one that is recognized and processed (i.e., cleaved by a signal peptidase) by the host cell. For prokaryotic host cells that do not recognize and process the native WSX receptor or OB protein signal sequence, the signal sequence is substituted by a prokaryotic signal sequence selected, for example, from the group of the alkaline phosphatase, penicillinase, lpp, or heat-stable enterotoxin II leaders. For yeast secretion the native signal sequence may be substituted by, e.g., the yeast invertase leader, α factor leader (including *Saccharomyces* and *Kluyveromyces* α-factor leaders, the latter described in U.S. Pat. No. 5,010,182 issued 23 Apr. 1991), or acid phosphatase leader, the *C. albicans* glucoamylase leader (EP 362,179 published 4 Apr. 1990), or the signal described in WO 90/13646 published 15 Nov. 1990. In mammalian cell expression the native signal sequence (e.g., the WSX receptor or OB protein presequence that normally directs secretion of WSX receptor or OB protein from human cells in vivo) is satisfactory, although other mammalian signal sequences may be suitable, such as signal sequences from other animal WSX receptors or OB proteins, and signal sequences from secreted polypeptides of the same or related species, as well as viral secretory leaders, for example, the herpes simplex gD signal.

The DNA for such precursor region is ligated in reading frame to DNA encoding the mature WSX receptor or OB protein.

b. Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Most expression vectors are "shuttle" vectors, i.e., they are capable of replication in at least one class of organisms but can be transfected into another organism for expression. For example, a vector is cloned in *E. coli* and then the same vector is transfected into yeast or mammalian cells for expression even though it is not capable of replicating independently of the host cell chromosome.

DNA may also be amplified by insertion into the host genome. This is readily accomplished using *Bacillus* species as hosts, for example, by including in the vector a DNA sequence that is complementary to a sequence found in *Bacillus* genomic DNA. Transfection of *Bacillus* with this vector results in homologous recombination with the genome and insertion of WSX receptor or OB protein DNA. However, the recovery of genomic DNA encoding WSX receptor or OB protein is more complex than that of an exogenously replicated vector because restriction enzyme digestion is required to excise the WSX receptor or OB protein DNA.

C. Selection Gene Component

Expression and cloning vectors should contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., 4 ampicillin, neomycin, methotrexate, or tetracycline, (b) complement auxotrophic deficiencies, or (c) supply critical nutrients not available from complex media, e.g., the gene encoding D-alanine racemase for *Bacilli*.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the WSX receptor or OB protein nucleic acid, such as DHFR or thymidine kinase. The mammalian cell transformants are placed under selection pressure that only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes WSX receptor or OB protein. Amplification is the process by which genes in greater demand for the production of a protein critical for growth are reiterated in tandem within the chromosomes of successive generations of recombinant cells. Increased quantities of WSX receptor or OB protein are synthesized from the amplified DNA. Other examples of amplifiable genes include metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub et al., *Proc. Natl. Acad. Sci. USA* 77:4216 (1980). The transformed cells are then exposed to increased levels of methotrexate. This leads to the synthesis of multiple copies of the DHFR gene, and, concomitantly, multiple copies of other DNA comprising the expression vectors, such as the DNA encoding WSX receptor or OB protein. This amplification technique can be used with any otherwise suitable host, e.g., ATCC No. CCL61 CHO-K1, notwithstanding the presence of endogenous DHFR if, for example, a mutant DHFR gene that is highly resistant to Mtx is employed (EP 117,060).

Alternatively, host cells (particularly wild-type hosts that contain endogenous DHFR) transformed or co-transformed with DNA sequences encoding WSX receptor or OB protein, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., *Nature* 282:39 (1979)). The trp1 gene provides a selection marker for a mutant strain of yeast lacking the ability to grow in tryptophan, for example, ATCC No.44076 or PEP4-1. Jones, *Genetics* 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 μm circular plasmid pKD1 can be used for transformation of *Kluyveromyces* yeasts. Bianchietal., *Curr. Genet.* 12:185 (1987). More recently, an expression system for large-scale production of recombinant calf chymosin was reported for *K. lactis*. Van den Berg, *Bio/Technology* 8:135 (1990). Stable multi-copy expression vectors for secretion of mature recombinant human serum albumin by industrial strains of *Kluyveromyces* have also been disclosed. Fleer et al., *Bio/Technology* 9:968-975 (1991).

d. Promoter Component

Expression and cloning vectors usually contain a promoter that is recognized by the host organism and is operably linked to the WSX receptor or OB protein nucleic acid. Promoters are untranslated sequences located upstream (5') to the start codon of a structural gene (generally within about 100 to 1000 bp) that control the transcription and translation of particular nucleic acid sequence, such as the WSX receptor or OB protein nucleic acid sequence, to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. At this time a large number of promoters recognized by a variety of potential host cells are well known. These promoters are operably linked to WSX receptor or OB protein-encoding DNA by removing the promoter from the source DNA by restriction enzyme digestion and inserting the isolated promoter sequence into the vector. Both the native WSX receptor or OB protein promoter sequence and many heterologous promoters may be used to direct amplification and/or expression of the WSX receptor or OB protein DNA. However, heterologous promoters are preferred, as they generally permit greater transcription and higher yields of WSX receptor or OB protein as compared to the native WSX receptor or OB protein promoter.

Promoters suitable for use with prokaryotic hosts include the β-lactamase and lactose promoter systems (Chang et al., *Nature* 275:615 (1978); Goeddel et al., *Nature* 281:544 (1979)), alkaline phosphatase, a tryptophan (trp) promoter system (Goeddel, *Nucleic Acids Res.* 8:4057 (1980); EP 36,776), and hybrid promoters such as the tac promoter. deBoer et al., *Proc. Natl. Acad. Sci. USA* 80:21-25 (1983). However, other known bacterial promoters are suitable. Their nucleotide sequences have been published, thereby enabling a skilled worker operably to ligate them to DNA encoding WSX receptor or OB protein (Siebenlist et al., *Cell* 20:269 (1980)) using linkers or adaptors to supply any required restriction sites. Promoters for use in bacterial systems also will contain a Shine-Dalgarno (S.D.) sequence operably linked to the DNA encoding WSX receptor or OB protein.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase (Hitzeman et al., *J. Biol. Chem.* 255:2073 (1980)) or other glycolytic enzymes (Hess et al., *J. Adv. Enzyme Reg.* 7:149 (1968); Holland, *Biochemistry* 17:4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

WSX receptor or OB protein transcription from vectors in mammalian host cells is controlled, for example, by promoters obtained from the genomes of viruses such as polyoma virus, fowipox virus (UK 2,211,504 published 5 Jul. 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, and from the promoter normally associated with the WSX receptor or OB protein sequence, provided such promoters are compatible with the host cell systems.

The early and late promoters of the SV40 virus are conveniently obtained as an SV40 restriction fragment that also contains the SV40 viral origin of replication. Fiers et al., *Nature* 273:113 (1978); Mulligan et al., *Science* 209:1422-1427 (1980); Pavlakis et al., *Proc. Natl. Acad. Sci. USA* 78:7398-7402 (1981). The immediate early promoter of the human cytomegalovirus is conveniently obtained as a HindIII E restriction fragment. Greenaway et al., *Gene* 18:355-360 (1982). A system for expressing DNA in mammalian hosts using the bovine papilloma virus as a vector is disclosed in U.S. Pat. No. 4,419,446. A modification of this system is described in U.S. Pat. No. 4,601,978. See also Gray et al., *Nature* 295:503-508 (1982) on expressing cDNA encoding immune interferon in monkey cells; Reyes et al., *Nature* 297:598-601 (1982) on expression of human β-interferon cDNA in mouse cells under the control of a thymidine kinase promoter from herpes simplex virus; Canaani et al., *Proc. Natl. Acad. Sci. USA* 79:5166-5170 (1982) on expression of the human interferon β1 gene in cultured mouse and rabbit cells; and Gorman et al., *Proc. Natl. Acad. Sci. USA* 79:6777-6781 (1982) on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter.

e. Enhancer Element Component

Transcription of a DNA encoding the WSX receptor or OB protein of this invention by higher eukaryotes is often increased by inserting an enhancer sequence into the vector. Enhancers are cis-acting elements of DNA, usually about from 10 to 300 bp, that act on a promoter to increase its transcription. Enhancers are relatively orientation and position independent, having been found 5' (Laimins et al., *Proc. Natl. Acad. Sci. USA* 78:993 (1981)) and 3' (Lusky et al., *Mol. Cell Bio.* 3:1108 (1983)) to the transcription unit, within an intron (Banerdji et al., *Cell* 33:729 (1983)), as well as within the coding sequence itself. Osborne et al., *Mol. Cell Bio.* 4:1293 (1984). Many enhancer sequences are now known from mammalian genes (globin, elastase, albumin, a-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, *Nature* 29-7:17-18 (1982) on enhancing elements for activation of eukaryotic promoters. The enhancer may be spliced into the vector at a position 5' or 3' to the WSX receptor or OB protein-encoding sequence, but is preferably located at a site 5' from the promoter.

f. Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding WSX receptor or OB protein.

g. Construction and Analysis of Vectors

Construction of suitable vectors containing one or more of the above-listed components employs standard ligation techniques. Isolated plasmids or DNA fragments are cleaved, tailored, and re-ligated in the form desired to generate the plasmids required.

For analysis to confirm correct sequences in plasmids constructed, the ligation mixtures are used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., *Nucleic Acids Res.* 9:309 (1981) or by the method of Maxam et al., *Methods in Enzymology* 65:499 (1980).

3. Transient Expression Vectors

Particularly useful in the practice of this invention are expression vectors that provide for the transient expression in mammalian cells of DNA encoding WSX receptor or OB protein. In general, transient expression involves the use of an expression vector that is able to replicate efficiently in a host cell, such that the host cell accumulates many copies of the expression vector and, in turn, synthesizes high levels of a desired polypeptide encoded by the expression vector. Sambrook et al., supra, pp. 16.17-16.22. Transient expression systems, comprising a suitable expression vector and a host cell, allow for the convenient positive identification of polypeptides encoded by cloned DNAs, as well as for the rapid screening of such polypeptides for desired biological or physiological properties. Thus, transient expression systems are particularly useful in the invention for purposes of identifying analogs and variants of WSX receptor or OB protein that are biologically active WSX receptor or OB protein.

a. Suitable Exemplary Vertebrate Cell Vectors

Other methods, vectors, and host cells suitable for adaptation to the synthesis of WSX receptor or OB protein in recombinant vertebrate cell culture are described in Gething et al., *Nature* 293:620-625 (1981); Mantei et al., *Nature* 281:40-46 (1979); EP 117,060; and EP 117,058. A particularly useful plasmid for mammalian cell culture expression of WSX receptor or OB protein is pRK5 (EP 307,247) orpSVI6B. WO 91/08291 published 13 Jun. 1991.

4. Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia inarcescans*, and *Shigella*, as well as *Bacilli* such as *B. subtilis* and *B. licheniformis* (e.g., *B. licheniformis* 41 P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting. Strain W3110 is a particularly preferred host or parent host because it is a common host strain for recombinant DNA product fermentations. Preferably, the host cell should secrete minimal amounts of proteolytic enzymes. For example, strain W3110 may be modified to effect a genetic mutation in the genes encoding proteins, with examples of such hosts including *E. coli* W3110 strain 27C7. The complete genotype of 27C7 is tonAΔ ptr3 phoAΔE15 A(argF-lac)169 ompTΔ degP41kan$^r$. Strain 27C7 was deposited on 30 Oct. 1991 in the American Type Culture Collection as ATCC No. 55,244. Alternatively, the strain of *E. coli* having mutant periplasmic protease disclosed in U.S. Pat. No.4,946,783 issued 7 Aug. 1990 may be employed. Alternatively still, methods of cloning, e.g., PCR or other nucleic acid polymerase reactions, are suitable.

In addition to prokaryotes, eukaryotic microbes such as filamentous fungi or yeast are suitable cloning or expression hosts for WSX receptor or OB protein-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe* (Beach et al., *Nature*, 290:140 (1981); EP 139,383 published 2 May 1985); *Kluyveromyces* hosts (U.S. Pat. No. 4,943,529; Fleer et al., supra) such as, e.g., *K. lactis* (MW98-8C, CBS683, CBS4574), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., supra), *K. thermotolerans*, and *K. marxianus*, yarrowia (EP 402,226); *Pichia pastoris* (EP 183,070; Sreekrishna et al., *J. Basic Microbiol.* 28:265-278 (1988)); *Candida, Trichoderma reesia* (EP 244, 234); *Neurospora crassa* (Case et al., *Proc. Natl. Acad. Sci. USA* 76:5259-5263 (1979)); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., *Biochem. Biophys. Res. Commun.* 112:284-289 (1983); Tilburn et al., *Gene* 26:205-221 (1983); Yelton et al., *Proc. Natl. Acad. Sci. USA* 81:1470-1474 (1984)) and *A. niger*. Kelly et al., *EMBO J.* 4:475-479 (1985).

Suitable host cells for the expression of glycosylated WSX receptor or OB protein are derived from multicellular organisms. Such host cells are capable of complex processing and glycosylation activities. In principle, any higher eukaryotic cell culture is workable, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. See, e.g., Luckow et al., *Bio/Technology* 6:47-55 (1988); Miller et al., in *Genetic Engineering*, Setlow et al., eds., Vol. 8 (Plenum Publishing, 1986), pp. 277-279; and Maeda et al., *Nature* 315:592-594 (1985). A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can be utilized as hosts. Typically, plant cells are transfected by incubation with certain strains of the bacterium *Agrobacterium tumefaciens*, which has been previously manipulated to contain the WSX receptor or OB protein-encoding DNA. During incubation of the plant cell culture with *A. tumefaciens*, the DNA encoding the WSX receptor or OB protein is transferred to the plant cell host such that it is transfected, and will, under appropriate conditions, express the WSX receptor or OB protein-encoding DNA. In addition, regulatory and signal sequences compatible with plant cells are available, such as the nopaline synthase promoter and polyadenylation signal sequences. Depicker et al., *J. Mol. Appl. Gen.* 1:561 (1982). In addition, DNA segments isolated from the upstream region of the T-DNA 780 gene are capable of activating or increasing transcription levels of plant-expressible genes in recombinant DNA-containing plant tissue. EP 321,196 published 21 Jun. 1989.

However, interest has been greatest in vertebrate cells, and propagation of vertebrate cells in culture (tissue culture) has become a routine procedure. See, e.g., *Tissue Culture*, Academic Press, Kruse and Patterson, editors (1973). Examples of useful mammalian host cell lines are monkey kidney CVI line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/-DHFR (CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkeykidneycells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2).

Host cells are transfected and preferably transformed with the above-described expression or cloning vectors for WSX receptor or OB protein production and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., supra, or electroporation is generally used for prokaryotes or other cells that contain substantial cell-wall barriers. Infection with *Agrobacterium tumefaciens* is used for transformation of certain plant cells, as described by Shaw et al., *Gene* 23:315 (1983) and WO 89/05859 published 29 Jun. 1989. In addition, plants may be transfected using ultrasound treatment as described in WO 91/00358 published 10 Jan. 1991.

For mammalian cells without such cell walls, the calcium phosphate precipitation method of Graham et al., *Virology* 52:456-457 (1978) is preferred. General aspects of mammalian cell host system transformations have been described in U.S. Pat. No. 4,399,216 issued 16 Aug. 1983. Transformations into yeast are typically carried out according to the method of Van Solingen et al., *J. Bact.* 130:946 (1977) and Hsiao et al., *Proc. Natl. Acad. Sci. USA* 76:3829 (1979). However, other methods for introducing DNA into cells, such as by nuclear microinjection, electroporation, bacterial protoplast fusion with intact cells, or polycations, e.g., polybrene, polyornithine, etc., may also be used. For various techniques for transforming mammalian cells, see Keown et al., *Methods in Enzymology* 185:527-537 (1990) and Mansour et al., *Nature* 336:348-352 (1988).

5. Culturing the Host Cells

Prokaryotic cells used to produce the WSX receptor or OB protein of this invention are cultured in suitable media as described generally in Sambrook et al., supra.

The mammalian host cells used to produce the WSX receptor or OB protein of this invention may be cultured in a variety of media. Commercially available media such as Ham's F10 (Sigma), Minimal Essential Medium ((MEM), Sigma), RPMI-1640 (Sigma), and Dulbecco's Modified Eagle's Medium ((DMEM), Sigma) are suitable for culturing the host cells. In addition, any of the media described in Ham et al. *Meth. Enz.* 58:44. (1979), Barnes et al., *Anal. Biochem.* 102: 255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

In general, principles, protocols, and practical techniques for maximizing the productivity of mammalian cell cultures can be found in *Mammalian Cell Biotechnology: a Practical Approach*, M. Butler, ed. (IRL Press, 1991).

The host cells referred to in this disclosure encompass cells in culture as well as cells that are within a host animal.

6. Detecting Gene Amplification/Expression

Gene amplification and/or expression may be measured in a sample directly, for example, by conventional Southern blotting, Northern blotting to quantitate the transcription of mRNA (Thomas, *Proc. Natl. Acad. Sci. USA* 77:5201-5205 (1980)), dot blotting (DNA analysis), or in situ hybridization, using an appropriately labeled probe, based on the sequences provided herein. Various labels may be employed, most commonly radioisotopes, particularly $^{32}P$. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like. A particularly sensitive staining technique suitable for use in the present invention is described by Hsu et al., *Am. J. Clin. Path.* 75:734-738 (1980).

Antibodies useful for immunohistochemical staining and/or assay of sample fluids may be either monoclonal or polyclonal, and may be prepared as described herein.

7. Purification of WSX Receptor or OB Protein

WSX receptor (e.g., WSX receptor ECD) or OB protein preferably is recovered from the culture medium as a secreted polypeptide, although it also may be recovered from host cell lysates. If the WSX receptor is membrane-bound, it can be released from the membrane using a suitable detergent solution (e.g. Triton-X 100) When WSX receptor or OB protein is produced in a recombinant cell other than one of human origin, the WSX receptor or OB protein is completely free of proteins or polypeptides of human origin. However, it is necessary to purify WSX receptor or OB protein from recombinant cell proteins or polypeptides to obtain preparations that are substantially homogeneous as to WSX receptor or OB protein. As a first step, the culture medium or lysate is centrifuged to remove particulate cell debris. WSX receptor or OB protein thereafter is purified from contaminant soluble proteins and polypeptides, with the following procedures being exemplary of suitable purification procedures: by fractionation on an ion-exchange column; ethanol precipitation; reverse phase HPLC; chromatography on silica or on a cation-exchange resin such as DTAE; chromatofocusing; SDS-PAGE; ammonium sulfate precipitation; gel filtration using, for example, Sephadex G-75™; and protein A Sepharose™ columns to remove contaminants such as IgG.

WSX receptor or OB protein variants in which residues have been deleted, inserted, or substituted are recovered in the same fashion as native sequence WSX receptor or OB protein, taking account of any substantial changes in properties occasioned by the variation. Immunoaffinity columns such as a rabbit polyclonal anti-WSX receptor or OB protein column can be employed to absorb the WSX receptor or OB protein variant by binding it to at least one remaining immune epitope.

A protease inhibitor such as phenyl methyl sulfonyl fluoride (PMSF) also may be useful to inhibit proteolytic degradation during purification, and antibiotics may be included to prevent the growth of adventitious contaminants.

8. Covalent Modifications

Covalent modifications of WSX receptor or OB protein are included within the scope of this invention. Both native sequence WSX receptor or OB protein and amino acid sequence variants of the WSX receptor or OB protein may be covalently modified. One type of covalent modification of the WSX receptor or OB protein is introduced into the molecule by reacting targeted amino acid residues of the WSX receptor or OB protein with an organic derivatizing agent that is capable of reacting with selected side chains or the N- or C-terminal residues of the WSX receptor or OB protein.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing a-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed under alkaline conditions because of the high $pK_a$ of the guanidine functional group. Furthermore, these reagents may react with the groups of lysine as well as with the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$, or $^{131}I$ to prepare labeled proteins for use in radioimmunoassay, the chloramine T method being suitable.

Carboxyl side groups (aspartyl or glutamyl) are selectively modified by reaction with carbodiimides (R—N=C=N—R'), where R and R' are different alkyl groups, such as 1-cyclohexyl-3-(2-morpholinyl-4-ethyl) carbodiimide or 1-ethyl-3-(4-azonia-4,4-dimethylpentyl)carbodiimide. Furthermore, aspartyl and glutamyl residues are converted to asparaginyl and glutaminyl residues by reaction with ammonium ions.

Derivatization with bifunctional agents is useful for crosslinking WSX receptor or OB protein to a water-insoluble support matrix or surface for use in the method for purifying anti-WSX receptor or OB protein antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-((p-azidophenyl)dithio)propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, *Proteins: Structure and Molecular Properties*, W.H. Freeman & Co., San Francisco, pp. 79-86 (1983)), acetylation of the N-terminal amine, and amidation of any C-terminal carboxyl group.

Another type of covalent modification of the WSX receptor or OB protein included within the scope of this invention comprises altering the native glycosylation pattern of the polypeptide. By altering is meant deleting one or more carbohydrate moieties found in native WSX receptor or OB protein, and/or adding one or more glycosylation sites that are not present in the native WSX receptor or OB protein.

Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. 0-linked glycosylation refers to the attachment of one of the sugars N-acetylgalactosamine, galactose, or xylose to a hydroxylamino acid, most commonly serine or threonine, although 5-hydroxyproline or 5-hydroxylysine may also be used.

Addition of glycosylation sites to the WSX receptor or OB protein is conveniently accomplished by altering the amino acid sequence such that it contains one or more of the above-described tripeptide sequences (for N-linked glycosylation sites). The alteration may also be made by the addition of, or substitution by, one or more serine or threonine residues to the native WSX receptor or OB protein sequence (for O-linked glycosylation sites). For ease, the WSX receptor or OB protein amino acid sequence is preferably altered through changes at the DNA level, particularly by mutating the DNA encoding the WSX receptor or OB protein at preselected bases such that codons are generated that will translate into the desired amino acids. The DNA mutation(s) may be made using methods described above and in U.S. Pat. No. 5,364, 934, supra.

Another means of increasing the number of carbohydrate moieties on the WSX receptor or OB protein is by chemical or enzymatic coupling of glycosides to the polypeptide. These procedures are advantageous in that they do not require production of the polypeptide in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published 11 Sept. 1987, and in Aplin et al., *CRC Crit. Rev. Biochem.* 259-306 (1981).

Removal of carbohydrate moieties present on the WSX receptor or OB protein may be accomplished chemically or enzymatically. Chemical deglycosylation requires exposure of the polypeptide to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin, et al., *Arch. Biochem. Biophys.* 259:52 (1987) and by Edge et al., *Anal. Biochem.* 118:131 (1981). Enzymatic cleavage of carbohydrate moieties on polypeptides can be achieved by the use of a variety of endo- and exo-glycosidases as described by Thotakura et al., *Meth. Enzymol.* 138:350 (1987).

Glycosylation at potential glycosylation sites may be prevented by the use of the compound tunicamycin as described by Duskin et al., *J. Biol. Chem.* 257:3105 (1982). Tunicamycin blocks the formation of protein-N-glycoside linkages.

Another type of covalent modification of WSX receptor or OB protein comprises linking the WSX receptor or OB protein to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

Since it is often difficult to predict in advance the characteristics of a variant WSX receptor or OB protein, it will be appreciated that some screening of the recovered variant will be needed to select the optimal variant. A change in the immunological character of the WSX receptor or OB protein molecule, such as affinity for a given antibody, is also able to be measured by a competitive-type immunoassay. The WSX receptor variant is assayed for changes in the ability of the protein to induce cell proliferation in the colony assay of Example 8. Other potential modifications of protein or polypeptide properties such as redox or thermal stability, hydrophobicity, susceptibility to proteolytic degradation, or the tendency to aggregate with carriers or into multimers are assayed by methods well known in the art.

9. Epitope-Tagged WSX Receptor or OB Protein

This invention encompasses chimeric polypeptides comprising WSX receptor or OB protein fused to a heterologous polypeptide. A chimeric WSX receptor or OB protein is one type of WSX receptor or OB protein variant as defined herein. In one preferred embodiment, the chimeric polypeptide comprises a fusion of the WSX receptor or OB protein with a tag polypeptide which provides an epitope to which an anti-tag antibody can selectively bind. The epitope tag is generally provided at the amino- or carboxyl-terminus of the WSX receptor or OB protein. Such epitope-tagged forms of the WSX receptor or OB protein are desirable as the presence thereof can be detected using a labeled antibody against the tag polypeptide. Also, provision of the epitope tag enables the WSX receptor or OB protein to be readily purified by affinity purification using the anti-tag antibody. Affinity purification techniques and diagnostic assays involving antibodies are described later herein.

Tag polypeptides and their respective antibodies are well known in the art. Examples include the flu HA tag polypeptide and its antibody 12CA5 (Field et al., *Mol. Cell. Biol.* 8:2159-2165 (1988)); the c-myc tag and the 8F9, 3C7, 6E10, G4, B7 and 9E10 antibodies thereto (Evan et al., *Molecular and Cellular Biology* 5:3610-3616 (1985)); and the Herpes Simplex virus glycoprotein D (gD) tag and its antibody. Paborsky et al., *Protein Engineering* 3(6):547-553 (1990). Other tag polypeptides have been disclosed. Examples include the Flag-peptide (Hopp et al., *BioTechnology* 6: 1204-1210 (1988)); the KT3 epitope peptide (Martin et al., *Science* 255:192-194 (1992)); an α-tubulin epitopepeptide (Skinner et al., *J. Biol. Chem.* 266:15163-15166 (1991)); and the T7 gene 10 protein peptide tag. Lutz-Freyermuth et al., *Proc. Natl. Acad. Sci. USA* 87:6393-6397 (1990). Once the tag polypeptide has been selected, an antibody thereto can be generated using the techniques disclosed herein.

The general methods suitable for the construction and production of epitope-tagged WSX receptor or OB protein are the same as those disclosed hereinabove. WSX receptor or OB protein-tag polypeptide fusions are most conveniently constructed by fusing the cDNA sequence encoding the WSX receptor or OB protein portion in-frame to the tag polypeptide DNA sequence and expressing the resultant DNA fusion construct in appropriate host cells. Ordinarily, when preparing the WSX receptor or OB protein-tag polypeptide chimeras of the present invention, nucleic acid encoding the WSX receptor or OB protein will be fused at its 3' end to nucleic acid encoding the N-terminus of the tag polypeptide, however 5' fusions are also possible.

Epitope-tagged WSX receptor or OB protein can be conveniently purified by affinity chromatography using the anti-tag antibody. The matrix to which the affinity antibody is attached is most often agarose, but other matrices are available (e.g. controlled pore glass or poly(styrenedivinyl)benzene). The epitope-tagged WSX receptor or OB protein can be eluted from the affinity column by varying the buffer pH or ionic strength or adding chaotropic agents, for example.

10. WSX Receptor or OB Protein Immunoadhesins

Chimeras constructed from a receptor sequence linked to an appropriate immunoglobulin constant domain sequence (immunoadhesins) are known in the art. Immunoadhesins reported in the literature include fusions of the T cell receptor* (Gascoigne et al., *Proc. Natl. Acad. Sci. USA* 84: 2936-2940 (1987)); CD4* (Capon et al., *Nature* 337: 525-531 (1989); Traunecker et al., *Nature* 339: 68-70 (1989); Zettmeissl et al., *DNA Cell Biol. USA* 9: 347-353 (1990); Byrn et al., *Nature* 344: 667-670 (1990)); L-selectin (homing receptor) ((Watson et al., *J. Cell. Biol.* 110:2221-2229 (1990); Watson et al., *Nature* 349: 164-167(1991)); CD44* (Aruffo et al., *Cell* 61:1303-1313(1990)); CD28 and B7* (Linsley et al., *J. Exp. Med.* 173: 721-730 (199 1)); CTLA-4* (Lisley et al., *J. Exp. Med.* 174: 561-569 (1991)); CD22* (Stamenkovic et al., *Cell* 66:1133-1144 (1991)); TNF receptor (Ashkenazi et al., *Proc. Natl. Acad. Sci. USA* 88: 10535-10539 (1991);

Lesslauer et al., *Eur. J Immunol.* 27: 2883-2886 (1991); Peppel et al., *J. Exp. Med.* 174:1483-1489 (1991)); NP receptors (Bennett et al., *J. Biol. Chem.* 266:23060-23067 (1991)); and IgE receptor α* (Ridgway et al., *J. Cell. Biol.* 115:abstr. 1448 (1991)), where the asterisk (*) indicates that the receptor is a member of the immunoglobulin superfamily.

The simplest and most straightforward immunoadhesin design combines the binding region(s) of the "adhesin" protein with the hinge and Fc regions of an immunoglobulin heavy chain. Ordinarily, when preparing the WSX receptor or OB-immunoglobulin chimeras of the present invention, nucleic acid encoding OB protein or the extracellular domain of the WSX receptor will be fused C-terminally to nucleic acid encoding the N-terminus of an immunoglobulin constant domain sequence, however N-terminal fusions are also possible. For OB-immunoglobulin chimeras, an OB protein fragment which retains the ability to bind to the WSX receptor may be employed.

Typically, in such fusions the encoded chimeric polypeptide will retain at least functionally active hinge, CH2 and CH3 domains of the constant region of an immunoglobulin heavy chain. Fusions are also made to the C-terminus of the Fc portion of a constant domain, or immediately N-terminal to the CH1 of the heavy chain or the corresponding region of the light chain.

The precise site at which the fusion is made is not critical; particular sites are well known and may be selected in order to optimize the biological activity, secretion or binding characteristics of the WSX receptor or OB-immunoglobulin chimeras.

In some embodiments, the WSX receptor or OB-immunoglobulin chimeras are assembled as monomers, or hetero- or homo-multimers, and particularly as dimers or tetramers, essentially as illustrated in WO 91/08298.

In a preferred embodiment, the OB protein sequence or WSX receptor extracellular domain sequence is fused to the N-terminus of the C-terminal portion of an antibody (in particular the Fc domain), containing the effector functions of an immunoglobulin, e.g. immunoglobulin G1 (IgG1). It is possible to fuse the entire heavy chain constant region to the OB protein or WSX receptor extracellular domain sequence. However, more preferably, a sequence beginning in the hinge region just upstream of the papain cleavage site (which defines IgG Fc chemically; residue 216, taking the first residue of heavy chain constant region to be 114, or analogous sites of other immunoglobulins) is used in the fusion. In a particularly preferred embodiment, the OB protein or WSX receptor amino acid sequence is fused to the hinge region, CH2 and CH3, or the CH1, hinge, CH2 and CH3 domains of an IgG1, IgG2, or IgG3 heavy chain. The precise site at which the fusion is made is not critical, and the optimal site can be determined by routine experimentation.

In some embodiments, the WSX receptor or OB-immunoglobulin chimeras are assembled as multimers, and particularly as homo-dimers or -tetramers. Generally, these assembled immunoglobulins will have known unit structures. A basic four chain structural unit is the form in which IgG, IgD, and IgE exist. A four unit is repeated in the higher molecular weight immunoglobulins; IgM generally exists as a pentamer of basic four units held together by disulfide bonds. IgA globulin, and occasionally IgG globulin, may also exist in multimeric form in serum. In the case of multimer, each four unit may be the same or different.

Various exemplary assembled WSX receptor or OB-immunoglobulin chimeras within the scope herein are schematically diagrammed below:

(a) $AC_L$-$AC_L$;
(b) $AC_H$-($AC_H$, $AC_L$-$AC_H$, $AC_L$-$V_HC_H$, or $V_LC_L$-$AC_H$);
(c) $AC_L$-$AC_H$-($AC_L$-$AC_H$, $AC_L$-$V_HC_H$, $V_LC_L$-$AC_H$, or $V_LC_L$—$V_HC_H$);
(d) $AC_L$-$V_HC_H$-($AC_H$, or $AC_L$-$V_HC_H$, or $V_LC_L$-$AC_H$);
(e) $V_LC_L$-$AC_H$-($AC_L$—$V_HC_H$, or $V_LC_L$-$AC_H$); and
(f) $(A-Y)_n$—$(V_LC_L$—$V_HC_H)_2$, wherein
each A represents identical or different OB protein or WSX receptor amino acid sequences;
$V_L$ is an immunoglobulin light chain variable domain;
$V_H$ is an immunoglobulin heavy chain variable domain;
$C_L$ is an immunoglobulin light chain constant domain;
$C_H$ is an immunoglobulin heavy chain constant domain;
n is an integer greater than 1;
Y designates the residue of a covalent cross-linking agent.

In the interests of brevity, the foregoing structures only show key features; they do not indicate joining (J) or other domains of the immunoglobulins, nor are disulfide bonds shown. However, where such domains are required for binding activity, they shall be constructed as being present in the ordinary locations which they occupy in the immunoglobulin molecules.

Alternatively, the OB protein or WSX receptor extracellular domain sequence can be inserted between immunoglobulin heavy chain and light chain sequences such that an immunoglobulin comprising a chimeric heavy chain is obtained. In this embodiment, the OB protein or WSX receptor sequence is fused to the 3' end of an immunoglobulin heavy chain in each arm of an immunoglobulin, either between the hinge and the CH2 domain, or between the CH2 and CH3 domains. Similar constructs have been reported by Hoogenboom et al., *Mol. Immunol.*, 28:1027-1037 (1991).

Although the presence of an immunoglobulin light chain is not required in the immunoadhesins of the present invention, an immunoglobulin light chain might be present either covalently associated to an OB protein or WSX receptor-immunoglobulin heavy chain fusion polypeptide, or directly fused to the WSX receptor extracellular domain or OB protein. In the former case, DNA encoding an immunoglobulin light chain is typically coexpressed with the DNA encoding the OB protein or WSX receptor-immunoglobulin heavy chain fusion protein. Upon secretion, the hybrid heavy chain and the light chain will be covalently associated to provide an immunoglobulin-like structure comprising two disulfide-linked immunoglobulin heavy chain-light chain pairs. Methods suitable for the preparation of such structures are, for example, disclosed in U.S. Pat. No.4,816,567 issued 28 Mar. 1989.

In a preferred embodiment, the immunoglobulin sequences used in the construction of the immunoadhesins of the present invention are from an IgG immunoglobulin heavy chain constant domain. For human immunoadhesins, the use of human IgG1 and IgG3 immunoglobulin sequences is preferred. A major advantage of using IgG1 is that IgG1 immunoadhesins can be purified efficiently on immobilized protein A. In contrast, purification of IgG3 requires protein G, a significantly less versatile medium. However, other structural and functional properties of immunoglobulins should be considered when choosing the Ig fusion partner for a particular immunoadhesin construction. For example, the IgG3 hinge is longer and more flexible, so it can accommodate larger adhesin domains that may not fold or function properly when fused to IgG1. Another consideration may be valency; IgG immunoadhesins are bivalent homodimers, whereas Ig subtypes like IgA and IgM may give rise to dimeric or pentameric structures, respectively, of the basic Ig homodimer unit. For immunoadhesins designed for in vivo application, the pharmacokinetic properties and the effector functions specified by the Fc region are important as well. Although IgG1, IgG2 and IgG4 all have in vivo half-lives of 21 days, their relative potencies at activating the complement system are different. IgG4 does not activate complement, and IgG2 is significantly weaker at complement activation than IgG1. Moreover, unlike IgG1, IgG2 does not bind to Fc receptors on mononuclear cells or neutrophils. While IgG3 is optimal for complement activation, its in vivo half-life is approximately one third of the other IgG isotypes. Another important consideration for immunoadhesins designed to be used as human therapeutics is the number of allotypic variants of the particular isotype. In general, IgG isotypes with fewer serologically-defined allotypes are preferred. For example, IgG1 has only four serologically-defined allotypic sites, two of which (G1m and 2) are located in the Fc region; and one of these sites G1m1, is non-immunogenic. In contrast, there are 12 serologically-defined allotypes in IgG3, all of which are in the Fc region; only three of these sites (G3m5, 11 and 21) have one allotype which is nonimmunogenic. Thus, the potential immunogenicity of a γ3 immunoadhesin is greater than that of a γ1 immunoadhesin.

With respect to the parental immunoglobulin, a useful joining point is just upstream of the cysteines of the hinge that form the disulfide bonds between the two heavy chains. In a frequently used design, the codon for the C-terminal residue of the WSX receptor or OB protein part of the molecule is placed directly upstream of the codons for the sequence DKTHTCPPCP (SEQ ID NO:44) of the IgG1 hinge region.

The general methods suitable for the construction and expression of immunoadhesins are the same as those disclosed hereinabove with regard to WSX receptor and OB protein. Immunoadhesins are most conveniently constructed by fusing the cDNA sequence encoding the WSX receptor or OB protein portion in-frame to an Ig cDNA sequence. However, fusion to genomic Ig fragments can also be used (see, e.g., Gascoigne et al., *Proc. Natl. Acad. Sci. USA*, 84:2936-2940 (1987); Aruffo et al., *Cell* 61:1303-1313 (1990); Stamenkovic et al., *Cell* 66:1133-1144 (1991)). The latter type of fusion requires the presence of Ig regulatory sequences for expression. cDNAs encoding IgG heavy-chain constant regions can be isolated based on published sequence from cDNA libraries derived from spleen or peripheral blood lymphocytes, by hybridization or by polymerase chain reaction (PCR) techniques. The cDNAs encoding the WSX receptor or OB protein and Ig parts of the immunoadhesin are inserted in tandem into a plasmid vector that directs efficient expression in the chosen host cells. For expression in mammalian cells, pRK5-based vectors (Schall et al., *Cell* 61:361-370 (1990)) and CDM8-based vectors (Seed, *Nature* 329:840 (1989)) can be used. The exact junction can be created by removing the extra sequences between the designed junction codons using oligonucleotide-directed deletional mutagenesis (Zoller et al., *Nucleic Acids Res.* 10:6487 (1982); Capon et al., *Nature* 337:525-531 (1989)). Synthetic oligonucleotides can be used, in which each half is complementary to the sequence on either side of the desired junction; ideally, these are 36 to 48-mers. Alternatively, PCR techniques can be used to join the two parts of the molecule in-frame with an appropriate vector.

The choice of host cell line for the expression of the immunoadhesin depends mainly on the expression vector. Another consideration is the amount of protein that is required. Milligram quantities often can be produced by transient transfections. For example, the adenovirus EIA-transformed 293 human embryonic kidney cell line can be transfected transiently with pRK5-based vectors by a modification of the calcium phosphate method to allow efficient immunoadhesin expression. CDM8-based vectors can be used to transfect COS cells by the DEAE-dextran method (Aruffo et al., *Cell* 61:1303-1313 (1990); Zettmeissl et al., *DNA Cell Biol. US* 9:347-353 (1990)). If larger amounts of protein are desired, the immunoadhesin can be expressed after stable transfection of a host cell line. For example, a pRK5-based vector can be introduced into Chinese hamster ovary (CHO) cells in the presence of an additional plasmid encoding dihydrofolate reductase (DHFR) and conferring resistance to G418. Clones resistant to G418 can be selected in culture; these clones are grown in the presence of increasing levels of DHFR inhibitor methotrexate; clones are selected, in which the number of gene copies encoding the DHFR and immunoadhesin sequences is co-amplified. If the immunoadhesin contains a hydrophobic leader sequence at its N-terminus, it is likely to be processed and secreted by the transfected cells. The expression of immunoadhesins with more complex structures may require uniquely suited host cells; for example, components su ch as light chain or J chain may be provided by certain myeloma or hybridoma cell hosts (Gascoigne et al., 1987, supra, Martin et al., *J. Virol.* 67:3561-3568 (1993)).

Immunoadhesins can be conveniently purified by affinity chromatography. The suitability of protein A as an affinity ligand depends on the species and isotype of the immunoglobulin Fc domain that is used in the chimera. Protein A can be used to purify immunoadhesins that are based on human γ1, γ2, or γ4 heavy chains (Lindmark et al., *J. Immunol. Meth.* 62:1-13 (1983)). Protein G is recommended for all mouse isotypes and for human γ3 (Guss et al., *EMBO J.* 5:1567-1575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. The conditions for binding an immunoadhesin to the protein A or G affinity column are dictated entirely by the characteristics of the Fc domain; that is, its species and isotype. Generally, when the proper ligand is chosen, efficient binding occurs directly from unconditioned culture fluid. One distinguishing feature of immunoadhesins is that, for human γ1 molecules, the binding capacity for protein A is somewhat diminished relative to an antibody of the same Fc type. Bound immunoadhesin can be efficiently eluted either at acidic pH (at or above 3.0), or in a neutral pH buffer containing a mildly chaotropic salt. This affinity chromatography step can result in an immunoadhesin preparation that is >95% pure.

Other methods known in the art can be used in place of, or in addition to, affinity chromatography on protein A or G to purify immunoadhesins. Immunoadhesins behave similarly to antibodies in thiophilic gel chromatography (Hutchens et al., *Anal. Biochem.* 159:217-226 (1986)) and immobilized metal chelate chromatography (Al-Mashikhi et al., *J. Dairy Sci.* 71:1756-1763 (1988)). In contrast to antibodies, however, their behavior on ion exchange columns is dictated not only by their isoelectric points, but also by a charge dipole that may exist in the molecules due to their chimeric nature.

If desired, the immunoadhesins can be made bispecific. Thus, the immunoadhesins of the present invention may combine a WSX receptor extracellular domain and a domain, such as the extracellular domain, of another cytokine receptor subunit. Exemplary cytokine receptors from which such bispecific immunoadhesin molecules can be made include TPO (or mpl ligand), EPO, G-CSF, IL-4, IL-7, GH, PRL, IL-3, GM-CSF, IL-5, IL-6, LIEF, OSM,CNTF and IL-2 receptors. Alternatively, an OB protein domain may be combined with another cytokine, such as those exemplified herein, in the generation of a bispecific immunoadhesin. For bispecific molecules, trimeric molecules, composed of a chimeric antibody heavy chain in one arm and a chimeric antibody heavy chain-light chain pair in the other arm of their antibody-like structure are advantageous, due to ease of purification. In contrast to antibody-producing quadromas traditionally used for the production of bispecific immunoadhesins, which produce a mixture of ten tetramers, cells transfected with nucleic acid encoding the three chains of a trimeric immunoadhesin structure produce a mixture of only three molecules, and purification of the desired product from this mixture is correspondingly easier.

a. Long Half-Life Derivatives of OB Protein

Prefered OB protein functional derivatives for use in the methods of the present invention include OB-immunoglobulin chimeras (immunoadhesins) and other longer half-life molecules. Techniques for generating OB protein immunoadhesins have been described above. The prefered OB immunoadhesin is made according to the techniques described in Example 11 below.

Other derivatives of the OB proteins, which possess a longer half-life than the native molecules comprise the OB protein or an OB-immunoglobulin chimera covalently bonded to a nonproteinaceous polymer. The nonproteinaceous polymer ordinarily is a hydrophilic synthetic polymer, i.e., a polymer not otherwise found in nature. However, polymers which exist in nature and are produced by recombinant or in vitro methods are useful, as are polymers which are isolated from native sources. Hydrophilic polyvinyl polymers fall within the scope of this invention, e.g. polyvinylalcohol and polyvinylpyrrolidone. Particularly useful are polyalkylene ethers such as polyethylene glycol (PEG); polyelkylenes such as polyoxyethylene, polyoxypropylene, and block copolymers of polyoxyethylene and polyoxypropylene (Pluronics™); polymethacrylates; carbomers; branched or unbranched polysaccharides which comprise the saccharide monomers D-mannose, D- and L-galactose, fucose, fructose, D-xylose, L-arabinose, D-glucuronic acid, sialic acid, D-galacturonic acid, D-mannuronic acid (e.g. polymannuronic acid, or alginic acid), D-glucosamine, D-galactosamine, D-glucose and neuraminic acid including homopolysaccharides and heteropolysaccharides such as lactose, amylopectin, starch, hydroxyethyl starch, amylose, dextrane sulfate, dextran, dextrins, glycogen, or the polysaccharide subunit of acid mucopolysaccharides, e.g. hyaluronic acid; polymers of sugar alcohols such as polysorbitol and polymannitol; heparin or heparon. The polymer prior to cross-linking need not be, but preferably is, water soluble, but the final conjugate must be water soluble. In addition, the polymer should not be highly immunogenic in the conjugate form, nor should it possess viscosity that is incompatible with intravenous infusion or injection if it is intended to be administered by such routes.

Preferably the polymer contains only a single group which is reactive. This helps to avoid cross-linking of protein molecules. However, it is within the scope herein to optimize reaction conditions to reduce cross-linking, or to purify the reaction products through gel filtration or chromatographic sieves to recover substantially homogenous derivatives.

The molecular weight of the polymer may desirably range from about 100 to 500,000, and preferably is from about 1,000 to 20,000. The molecular weight chosen will depend upon the nature of the polymer and the degree of substitution. In general, the greater the hydrophilicity of the polymer and the greater the degree of substitution, the lower the molecular weight that can be employed. Optimal molecular weights will be determined by routine experimentation.

The polymer generally is covalently linked to the OB protein or to the OB-immunoglobulin chimera though a multifunctional crosslinking agent which reacts with the polymer and one or more amino acid or sugar residues of the OB protein or OB-immunoglobulin chimera to be linked. However, it is within the scope of the invention to directly crosslink the polymer by reacting a derivatized polymer with the hybrid, or via versa.

The covalent crosslinking site on the OB protein or OB-immunoglobulin chimera includes the N-terminal amino group and epsilon amino groups found on lysine residues, as well as other amino, imino, carboxyl, sulfhydryl, hydroxyl or other hydrophilic groups. The polymer may be covalently bonded directly to the hybrid without the use of a multifunctional (ordinarily bifunctional) crosslinking agent. Covalent binding to amino groups is accomplished by known chemistries based upon cyanuric chloride, carbonyl diimidazole, aldehyde reactive groups (PEG alkoxide plus diethyl acetal of bromoacetaldehyde; PEG plus DMSO and acetic anhydride, or PEG chloride plus the phenoxide of 4-hydroxybenzaldehyde, succinimidyl active esters, activated dithiocarbonate PEG, 2,4,5-trichlorophenylcloroformate or P-nitrophenylcloroformate activated PEG). Carboxyl groups are derivatized by coupling PEG-amine using carbodiimide.

Polymers are conjugated to oligosaccharide groups by oxidation using chemicals, e.g. metaperiodate, or enzymes, e.g. glucose or galactose oxidase (either of which produces the aldehyde derivative of the carbohydrate), followed by reaction with hydrazide or amino derivatized polymers, in the same fashion as is described by Heitzmann et al., P.N.A.S. 71:3537-41 (1974) or Bayer et al., Methods in Enzymology 62:310 (1979), for the labeling of oligosaccharides with biotin or avidin. Further, other chemical or enzymatic methods which have been used heretofore to link oligosaccharides are particularly advantageous because, in general, there are fewer substitutions than amino acid sites for derivatization, and the oligosaccharide products thus will be more homogenous. The oligosaccharide substituents also are optionally modified by enzyme digestion to remove sugars, e.g. by neuraminidase digestion, prior to polymer derivatization.

The polymer will bear a group which is directly reactive with an amino acid side chain, or the N- or C-terminus of the polypeptide linked, or which is reactive with the multifunctional cross-linking agent. In general, polymers bearing such reactive groups are known for the preparation of immobilized proteins. In order to use such chemistries here, one should employ a water soluble polymer otherwise derivatized in the same fashion as insoluble polymers heretofore employed for protein immobilization. Cyanogen bromide activation is a particularly useful procedure to employ in crosslinking polysaccharides.

"Water soluble" in reference to the starting polymer means that the polymer or its reactive intermediate used for conjugation is sufficiently water soluble to participate in a derivatization reaction.

"Water soluble" in reference to the polymer conjugate means that the conjugate is soluble in physiological fluids such as blood.

The degree of substitution with such a polymer will vary depending upon the number of reactive sites on the protein, whether all or a fragment of the protein is used, whether the protein is a fusion with a heterologous protein (e.g. an OB-immunoglobulin chimera), the molecular weight, hydrophilicity and other characteristics of the polymer, and the particular protein derivatization sites chosen. In general, the conjugate contains about from 1 to 10 polymer molecules, while any heterologous sequence may be substituted with an essentially unlimited number of polymer molecules so long as the desired activity is not significantly adversely affected.

The optimal degree of cross-linking is easily determined by an experimental matrix in which the time, temperature and other reaction conditions are varied to change the degree of substitution, after which the ability of the conjugates to function in the desired fashion is determined.

The polymer, e.g. PEG, is cross-linked by a wide variety of methods known per se for the covalent modification of proteins with nonproteinaceous polymers such as PEG. Certain of these methods, however, are not preferred for the purposes herein. Cyanuronic chloride chemistry leads to many side reactions, including protein cross-linking. In addition, it may be particularly likely to lead to inactivation of proteins containing sulfhydryl groups. Carbonyl diimidazole chemistry (Beauchamp et al., *Anal Biochem.* 131:25-33 (1983)) requires high pH (>8.5), which can inactivate proteins. Moreover, since the "activated PEG" intermediate can react with water, a very large molar excess of "activated PEG" over protein is required. The high concentrations of PEG required for the carbonyl diimidazole chemistry also led to problems in purification, as both gel filtration chromatography and hydrophilic interaction chromatography are adversely affected. In addition, the high concentrations of "activated PEG" may precipitate protein, a problem that per se has been noted previously (Davis, U.S. Pat. No. 4,179,337). On the other hand, aldehyde chemistry (Royer, U.S. Pat. No.4,002,531) is more efficient since it requires only a 40-fold molar excess of PEG and a 1-2 hr incubation. However, the manganese dioxide suggested by Royer for preparation of the PEG aldehyde is problematic "because of the pronounced tendency of PEG to form complexes with metal-based oxidizing agents" (Harris et al., *J. Polym. Sci. Polym. Chem. Ed.* 22:341-52 (1984)). The use of a Moffatt oxidation, utilizing DMSO and acetic anhydride, obviates this problem. In addition, the sodium borohydride suggested by Royer must be used at high pH and has a significant tendency to reduce disulfide bonds. In contrast, sodium cyanoborohydride, which is effective at neutral pH and has very little tendency to reduce disulfide bonds is preferred.

Functionalized PEG polymers to modify the OB protein or OB-immunoglobulin chimeras of the present invention are available from Shearwater Polymers, Inc. (Huntsville, Ala.). Such, commercially available PEG derivatives include, but are not limited to, amino-PEG, PEG amino acid esters, PEG-hydrazide, PEG-thiol, PEG-succinate, carboxymethylated PEG, PEG-propionic acid, PEG amino acids, PEG succinimidyl succinate, PEG succinimidyl propionate, succinimidyl ester of carboxymethylated PEG, succinimidyl carbonate of PEG, succinimidyl esters of amino acid PEGs, PEG-oxycarbonylimidazole, PEG-nitrophenyl carbonate, PEG tresylate, PEG-glycidyl ether, PEG-aldehyde, PEG vinylsulfone, PEG-maleimide, PEG-orthopyridyl-disulfide, heterofunctional PEGs, PEG vinyl derivatives, PEG silanes, and PEG phospholides. The reaction conditions for coupling these PEG derivatives will vary depending on the protein, the desired degree of PEGylation, and the PEG derivative utilized. Some factors involved in the choice of PEG derivatives include: the desired point of attachment (lysine or cysteine), hydrolytic stability and reactivity of the derivatives, stability, toxicity and antigenicity of the linkage, suitability for analysis, etc. Specific instructions for the use of any particular derivative are available from the manufacturer.

The long half-life conjugates of this invention are separated from the unreacted starting materials by gel filtration. Heterologous species of the conjugates are purified from one another in the same fashion. The polymer also may be water-insoluble, as a hydrophilic gel.

The conjugates may also be purified by ion-exchange chromatography. The chemistry of many of the electrophilically activated PEG's results in a reduction of amino group charge of the PEGylated product. Thus, high resolution ion exchange chromatography can be used to separate the free and conjugated proteins, and to resolve species with different levels of PEGylation. In fact, the resolution of different species (e.g. containing one or two PEG residues) is also possible due to the difference in the ionic properties of the unreacted amino acids.

C. Therapeutic Uses for the WSX Receptor

The WSX receptor and WSX receptor gene are believed to find therapeutic use for administration to a mammal in the treatment of diseases characterized by a decrease in hematopoietic cells. Examples of these diseases include: anemia (including macrocytic and aplastic anemia); thrombocytopenia; hypoplasia; disseminated intravascular coagulation (DIC); myelodysplasia; immune (autoimmune) thrombocytopenic purpura (ITP); and HIV induced ITP. Additionally, these WSX receptor molecules may be useful in treating myeloproliferative thrombocytotic diseases as well as thrombocytosis from inflammatory conditions and in iron deficiency. WSX receptor polypeptide and WSX receptor gene which lead to an increase in hematopoietic cell proliferation may also be used to enhance repopulation of mature blood cell lineages in cells having undergone chemo- or radiation therapy or bone marrow transplantation therapy. Generally, the WSX receptor molecules are expected to lead to an enhancement of the proliferation and/or differentiation (but especially proliferation) of primitive hematopoietic cells. Other potential therapeutic applications for WSX receptor and WSX receptor gene include the treatment of obesity and diabetes and for promoting kidney, liver and lung growth and/or repair (e.g. in renal failure). WSX receptor can also be used to treat obesity-related conditions, such as type II adult onset diabetes, infertility, hypercholesterolemia, hyperlipidemia, cardiovascular disease and hypertension.

The WSX receptor may be administered alone or in combination with cytokines (such as OB protein), growth factors or antibodies in the above-identified clinical situations. This may facilitate an effective lowering of the dose of WSX receptor. Suitable dosages for such additional molecules will be discussed below.

Administration of WSX receptor to a mammal having depressed levels of endogenous WSX receptor or a defective WSX receptor gene is contemplated, preferably in the situation where such depressed levels lead to a pathological disorder, or where there is lack of activation of the WSX receptor. In these embodiments where the full length WSX receptor is to be administered to the patient, it is contemplated that the gene encoding the receptor may be administered to the patient via gene therapy technology.

In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., *Proc. Natl. Acad. Sci. USA*, 83:4143-4146 (1986)). The oligonucleotides can be modified to enhance their uptake, e.g., by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnology* 11:205-210 (1993)). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, and proteins that target intracellular localization and enhance intracellular half-life. The technique of receptor-mediated endocytosis is described, for example, by Wu.et al., *J. Biol. Chem.* 262: 4429-4432 (1987); and Wagner et al., *Proc. Natl. Acad. Sci. USA* 87:3410-3414 (1990). For review of the currently known gene marking and gene therapy protocols see Anderson et al., *Science* 256:808-813 (1992).

The invention also provides antagonists of WSX receptor activation (e.g. WSX receptor ECD, WSX receptor immunoadhesins and WSX receptor antisense nucleic acid; neutralizing antibodies and uses thereof are discussed in section E below). Administration of WSX receptor antagonist to a mammal having increased or excessive levels of endogenous WSX receptor activation is contemplated, preferably in the situation where such levels of WSX receptor activation lead to a pathological disorder.

In one embodiment, WSX receptor antagonist molecules may be used to bind endogenous ligand in the body, thereby causing desensitized WSX receptors to become responsive to WSX ligand, especially when the levels of WSX ligand in the serum exceed normal physiological levels. Also, it may be beneficial to bind endogenous WSX ligand which is activating undesired cellular responses (such as proliferation of tumor cells). Potential therapeutic applications for WSX antagonists include for example, treatment of metabolic disorders (e.g., anorexia, cachexia, steroid-induced truncalobesity and other wasting diseases characterized by loss of appetite, diminished food intake or body weight loss), stem cell tumors and other tumors which express WSX receptor.

Pharmaceutical compositions of the WSX receptor ECD may further include a WSX ligand. Such dual compositions may be beneficial where it is therapeutically useful to prolong half-life of WSX ligand, and/or activate endogenous WSX receptor directly as a heterotrimeric complex.

Therapeutic formulations of WSX receptor are prepared for storage by mixing WSX receptor having the desired degree of purity with optional physiologically acceptable carriers, excipients, or stabilizers (*Remington's Pharmaceutical Sciences*, 16th edition, Osol, A., Ed., (1980)), in the form of lyophilized cake or aqueous solutions. Acceptable carriers, excipients, or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or non-ionic surfactants such as Tween, Pluronics™ or polyethylene glycol (PEG).

The WSX receptor also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles, and nanocapsules), or in macroemulsions. Such techniques are disclosed in *Remington's Pharmaceutical Sciences*, supra.

WSX receptor to be used for in vivo administration must be sterile. This is readily accomplished by filtration through sterile filtration membranes, prior to or following lyophilization and reconstitution. WSX receptor ordinarily will be stored in lyophilized form or in solution.

Therapeutic WSX receptor compositions generally are placed into a container having a sterile access port, for example, an intravenous solution bag or vial having a stopper pierceable by a hypodermic injection needle.

The route of WSX receptor administration is in accord with known methods, e.g., those routes set forth above for specific indications, as well as the general routes of injection or infusion by intravenous, intraperitoneal, intracerebral, intramuscular, intraocular, intraarterial, or intralesional means, or sustained release systems as noted below. WSX receptor is administered continuously by infusion or by bolus injection. Generally, where the disorder permits, one should formulate and dose the WSX receptor for site-specific delivery.

Suitable examples of sustained-release preparations include semipermeable matrices of solid hydrophobic polymers containing the protein, which matrices are in the form of shaped articles, e.g., films, or microcapsules. Examples of sustained-release matrices include polyesters, hydrogels (e.g., poly(2-hydroxyethyl-methacrylate) as described by Langer et al., *J. Biomed. Mater. Res.* 15:167-277 (1981) and Langer, *Chem. Tech.* 12:98-105 (1982) or poly(vinylalcohol)), polylactides (U.S. Pat. No. 3,773,919, EP 58,481), copolymers of L-glutamic acid and γ ethyl-L-glutamate (Sidman et al., *Biopolymers* 22:547-556 (1983)), non-degradable ethylene-vinyl acetate (Langer et al., supra), degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid (EP 133,988).

While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S-S bond formation through thio-disulfide interchange, stabilization may be achieved by modifying sulfhydryl residues, lyophilizing from acidic solutions, controlling moisture content, using appropriate additives, and developing specific polymer matrix compositions.

Sustained-release WSX receptor compositions also include liposomally entrapped WSX receptor. Liposomes containing WSX receptor are prepared by methods known per se: DE 3,218,121; Epstein et al., *Proc. Natl. Acad. Sci. USA* 82:3688-3692 (1985); Hwang et al., *Proc. Natl. Acad. Sci. USA* 77:4030-4034 (1980); EP 52,322; EP 36,676; EP 88,046; EP 143,949; EP 142,641; Japanese patent application 83-118008; U.S. Pat, Nos. 4,485,045 and 4,544,545; and EP 102,324. Ordinarily the liposomes are of the small (about 200-800 Angstroms) unilamellar type in which the lipid content is greater than about 30 mol. % cholesterol, the selected proportion being adjusted for the optimal WSX receptor therapy.

When applied topically, the WSX receptor is suitably combined with other ingredients, such as carriers and/or adjuvants. There are no limitations on the nature of such other ingredients, except that they must be physiologically acceptable and efficacious for their intended administration, and cannot degrade the activity of the active ingredients of the composition. Examples of suitable vehicles include ointments, creams, gels, or suspensions, with or without purified collagen. The compositions also may be impregnated into transdermal patches, plasters, and bandages, preferably in liquid or semi-liquid form.

For obtaining a gel formulation, the WSX receptor formulated in a liquid composition may be mixed with an effective amount of a water-soluble polysaccharide or synthetic polymer such as PEG to form a gel of the proper viscosity to be applied topically. The polysaccharide that may be used includes, for example, cellulose derivatives such as etherified cellulose derivatives, including alkyl celluloses, hydroxyalkyl celluloses, and alkylhydroxyalkyl celluloses, for example, methylcellulose, hydroxyethyl cellulose, carboxymethyl cellulose, hydroxypropyl methylcellulose, and hydroxypropyl cellulose; starch and fractionated starch; agar; alginic acid and alginates; gum arabic; pullullan; agarose; carrageenan; dextrans; dextrins; fructans; inulin; mannans; xylans; arabinans; chitosans; glycogens; glucans; and synthetic biopolymers; as well as gums such as xanthan gum; guar gum; locust bean gum; gum arabic; tragacanth gum; and karaya gum; and derivatives and mixtures thereof. The preferred gelling agent herein is one that is inert to biological systems, nontoxic, simple to prepare, and not too runny or viscous, and will not destabilize the WSX receptor held within it.

Preferably the polysaccharide is an etherified cellulose derivative, more preferably one that is well defined, purified, and listed in USP, e.g., methylcellulose and the hydroxyalkyl cellulose derivatives, such as hydroxypropyl cellulose, hydroxyethyl cellulose, and hydroxypropyl methylcellulose. Most preferred herein is methylcellulose.

The polyethylene glycol useful for gelling is typically a mixture of low and high molecular weight PEGs to obtain the proper viscosity. For example, a mixture of a PEG of molecular weight 400-600 with one of molecular weight 1500 would be effective for this purpose when mixed in the proper ratio to obtain a paste.

The term "water soluble" as applied to the polysaccharides and PEGs is meant to include colloidal solutions and dispersions. In general, the solubility of the cellulose derivatives is determined by the degree of substitution of ether groups, and the stabilizing derivatives useful herein should have a sufficient quantity of such ether groups per anhydroglucose unit in the cellulose chain to render the derivatives water soluble. A degree of ether substitution of at least 0.35 ether groups per anhydroglucose unit is generally sufficient. Additionally, the cellulose derivatives may be in the form of alkali metal salts, for example, the Li, Na, K, or Cs salts.

If methylcellulose is employed in the gel, preferably it comprises about 2-5%, more preferably about 3%, of the gel and the WSX receptor is present in an amount of about 300-1000 mg per ml of gel.

An effective amount of WSX receptor to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. Typically, the clinician will administer the WSX receptor until a dosage is reached that achieves the desired effect. A typical daily dosage for systemic treatment might range from about 1 μg/kg to up to 10 mg/kg or more, depending on the factors mentioned above. As an alternative general proposition, the WSX receptor is formulated and delivered to the target site or tissue at a dosage capable of establishing in the tissue a WSX receptor level greater than about 0.1 ng/cc up to a maximum dose that is efficacious but not unduly toxic. This intra-tissue concentration should be maintained if possible by continuous infusion, sustained release, topical application, or injection at empirically determined frequencies. The progress of this therapy is easily monitored by conventional assays.

D. Non-Therapeutic Uses for the WSX Receptor

WSX receptor nucleic acid is useful for the preparation of WSX receptor polypeptide by recombinant techniques exemplified herein which can then be used for production of anti-WSX receptor antibodies having various utilities described below.

The WSX receptor (polypeptide or nucleic acid) can be used to induce proliferation and/or differentiation of cells in vitro. In particular, it is contemplated that this molecule may be used to induce proliferation of stem cell/progenitor cell populations (e.g. CD34+ cell populations obtained as described in Example 8 below). These cells which are to be grown ex vivo may simultaneously be exposed to other known growth factors or cytokines, such as those described herein. This results in proliferation and/or differentiation of the cells having the WSX receptor.

In yet another aspect of the invention, the WSX receptor may be used for affinity purification of WSX ligand. Briefly, this technique involves: (a) contacting a source of WSX ligand with an immobilized WSX receptor under conditions whereby the WSX ligand to be purified is selectively adsorbed onto the immobilized receptor; (b) washing the immobilized WSX receptor and its support to remove non-adsorbed material; and (c) eluting the WSX ligand molecules from the immobilized WSX receptor to which they are adsorbed with an elution buffer. In a particularly preferred embodiment of affinity purification, WSX receptor is covalently attaching to an inert and porous matrix (e.g., agarose reacted with cyanogen bromide). Especially preferred is a WSX receptor immunoadhesin immobilized on a protein A column. A solution containing WSX ligand is then passed through the chromatographic material. The WSX ligand adsorbs to the column and is subsequently released by changing the elution conditions (e.g. by changing pH or ionic strength).

The WSX receptor may be used for competitive screening of potential agonists or antagonists for binding to the WSX receptor. Such agonists or antagonists may constitute potential therapeutics for treating conditions characterized by insufficient or excessive WSX receptor activation, respectively.

The preferred technique for identifying molecules which bind to the WSX receptor utilizes a chimeric receptor (e.g., epitope tagged WSX receptor or WSX receptor immunoadhesin) attached to a solid phase, such as the well of an assay plate. Binding of molecules which are optionally labelled (e.g., radiolabelled) to the immobilized receptor can be evaluated.

To identify WSX receptor agonists or antagonists, the thymidine incorporation assay can be used. For screening for antagonists, the WSX receptor can be exposed to a WSX ligand followed by the putative antagonist, or the WSX ligand and antagonist can be added to the WSX receptor simultaneously, and the ability of the antagonist to block receptor activation can be evaluated.

The WSX receptor polypeptides are also useful as molecular weight markers. To use a WSX receptor polypeptide as a molecular weight marker, gel filtration chromatography or SDS-PAGE, for example, will be used to separate protein(s) for which it is desired to determine their molecular weight(s) in substantially the normal way. The WSX receptor and other molecular weight markers will be used as standards to provide a range of molecular weights. For example, phosphorylase b (mw=97,400), bovine serum albumin (mw=68,000), ovalbumin (mw=46,000), WSX receptor (mw=44,800), trypsin inhibitor (mw=20,100), and lysozyme (mw=14,400) can be used as mw markers. The other molecular weight markers mentioned here can be purchased commercially from Amersham Corporation, Arlington Heights, Ill. The molecular weight markers are generally labeled to facilitate detection thereof. For example, the markers may be biotinylated and following separation can be incubated with streptavidin-horseradish peroxidase so that the various markers can be detected by light detection.

The purified WSX receptor, and the nucleic acid encoding it, may also be sold as reagents for mechanism studies of WSX receptor and its ligands, to study the role of the WSX receptor and WSX ligand in normal growth and development, as well as abnormal growth and development, e.g., in malignancies.

WSX receptor variants are useful as standards or controls in assays for the WSX receptor for example ELISA, RIA, or RRA, provided that they are recognized by the analytical system employed, e.g., an anti-WSX receptor antibody.

E. WSX Receptor Antibody Preparation

1. Polyclonal antibodies

Polyclonal antibodies are generally raised in animals by multiple subcutaneous (sc) or intraperitoneal (ip) injections of the relevant antigen and an adjuvant. In that the preferred epitope is in the ECD of the WSX receptor, it is desirable to use WSX receptor ECD or a molecule comprising the ECD (e.g., WSX receptor immunoadhesin) as the antigen for generation of polyclonal and monoclonal antibodies. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining 1 mg or 1 µg of the peptide or conjugate (for rabbits or mice, respectively) with 3 volumes of Freund's complete adjuvant and injecting the solution intradermally at multiple sites. One month later the animals are boosted with 1/5 to 1/10 the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

2. Monoclonal Antibodies

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

For example, the monoclonal antibodies may be made using the hybridoma method first described by Kohler et al., *Nature* 256:495 (1975), or may be made by recombinant DNA methods (Cabilly et al., supra).

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 cells available from the American Type Culture Collection, Rockville, Md. USA. Human myeloma ad mouse-human heteromyeloma cell lines also have been described for the production of human monoclonal antibodies (Kozbor, *J. Immunol.* 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., *Anal. Biochem.* 107:220 (1980).

After hybridoma cells are identified that produce antibodies of the desired specificity, affinity, and/or activity, the clones may be subcloned by limiting dilution procedures and grown by standard methods (Goding, supra). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. Review articles on recombinant expression in bacteria of DNA encoding the antibody include Skerra et al., *Curr. Opinion in Immunol.* 5:256-262 (1993) and Pluckthun, *Immunol. Revs.* 130: 151-188 (1992).

In a further embodiment, antibodies or antibody fragments can be isolated from antibody phage libraries generated using the techniques described in McCafferty et al., *Nature* 348: 552-554(1990). Clackson et al., *Nature* 352:624-628 (1991) and Marks et al., *J. Mol. Biol.* 222:581-597 (1991) describe the isolation of murine and human antibodies, respectively, using phage libraries. Subsequent publications describe the production of high affinity (nM range) human antibodies by chain shuffling (Mark et al., *Bio/Technology* 10:779-783 (1992)), as well as combinatorial infection and in vivo recombination as a strategy for constructing very large phage libraries (Waterhouse et al., *Nuc. Acids. Res.* 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (Cabilly et al., supra; Morrison, et al., *Proc. Nat. Acad. Sci. USA* 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate.

3. Humanized and Human Antibodies

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature* 321:522-525 (1986); Riechmann et al., *Nature* 332:323-327 (1988); Verhoeyen et al., *Science* 239:1534-1536 (1988)), by substituting rodent CDRs or CDR sequences for the corresponding sequences of a human antibody. Accordingly, such "humanized" antibodies are chimeric antibodies (Cabilly et al., supra), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., *J. Immunol.* 151:2296 (1993); Chothia et al., *J. Mol. Biol.* 196:901 (1987)). Another method uses a particular framework derived from the consensus sequence of all human antibodies of a particular subgroup of light or heavy chains. The same framework may be used for several different humanized antibodies (Carter et al., *Proc. Natl. Acad. Sci. USA* 89:4285 (1992); Presta et al., *J. Immnol.* 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding.

Alternatively, it is now possible to produce transgenic animals (e.g. mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA* 90:2551 (1993); Jakobovits et al., *Nature* 362:255-258 (1993); Bruggermann et al., *Year in Immuno.* 7:33 (1993). Human antibodies can also be produced in phage-display libraries (Hoogenboom et al., *J. Mol. Biol.* 227:381 (1991); Marks et al., *J. Mol. Biol.* 222:581 (1991)).

4. Bispecific Antibodies

Bispecific antibodies (BsAbs) are antibodies that have binding specificities for at least two different antigens. BsAbs can be used as tumor targeting or imaging agents and can be used to target enzymes or toxins to a cell possessing the WSX receptor. Such antibodies can be derived from full length antibodies or antibody fragments (e.g. F(ab')$_2$ bispecific antibodies). In accordance with the present invention, the BsAb may possess one arm which binds the WSX receptor and another arm which binds to a cytokine or another cytokine receptor (or a subunit thereof) such as the receptors for TPO, EPO, G-CSF, IL4, IL-7, GH, PRL; the α or β subunits of the IL-3, GM-CSF, IL-5, IL-6, LIF, OSM and CNTF receptors; or the α, β or γ subunits of the IL-2 receptor complex. For example, the BsAb may bind both WSX receptor and gp130.

Methods for making bispecific antibodies are known in the art. Traditional production of full length bispecific antibodies is based on the coexpression of two immunoglobulin heavy chain-light chain pairs, where the two chains have different specificities (Millstein et al., *Nature* 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, published 13 May 1993, and in Traunecker et al., *EMBO J.* 10:3655-3659 (1991).

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690 published Mar. 3, 1994. For further details of generating bispecific antibodies see, for example, Suresh et al., *Methods in Enzymology* 121:210 (1986).

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies maybe made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. The following techniques can also be used for the production of bivalent antibody fragments which are not necessarily bispecific. According to these techniques, Fab'-SH fragments can be recovered from *E. coli*, which can be chemically coupled to form bivalent antibodies. Shalaby et al., *J. Exp. Med.* 175: 217-225 (1992) describe the production of a fully humanized BsAb F(ab')$_2$ molecule. Each Fab' fragment was separately secreted from *E. coli* and subjected to directed chemical coupling in vitro to form the BsAb. The BsAb thus formed was able to bind to cells overexpressing the HER2 receptor and normal human T cells, as well as trigger the lytic activity of human cytotoxic lymphocytes against human breast tumor targets. See also Rodrigues et al., *Int. J Cancers* (Suppl.) 7:45-50 (1992).

Various techniques for making and isolating bivalent antibody fragments directly from recombinant cell culture have also been described. For example, bivalent heterodimers have been produced using leucine zippers. Kostelny et al., *J. Immunol.* 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. The "diabody" technology described by Hollinger et al., *Proc. Natl. Acad. Sci. USA* 90:6444-6448 (1993) has provided an alternative mechanism for making BsAb fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making BsAb fragments by the use of single-chain Fv (sFv) dimers has also been reported. See Gruber et al., *J. Immunol.* 152:5368 (1994).

5. Antibody Screening

It may be desirable to select antibodies with a strong binding affinity for the WSX receptor. Antibody affinities may be determined by saturation binding; enzyme-linked immunoabsorbent assay (ELISA); and competition assays (e.g. RIA's), for example. The antibody with a strong binding affinity may bind the WSX receptor with a binding affinity ($K_d$) value of no more than about $1 \times 10^{-7}$M, preferably no more than about $1 \times 10^{-8}$ M and most preferably no more than about $1 \times 10^{-9}$ M (e.g. to about $1 \times 10^{-12}$M).

In another embodiment, one may screen for an antibody which binds a WSX receptor epitope of interest. For example, an antibody which binds to the epitope bound by antibody 2D7, 1G4, 1E11 or IC11 (see Example 13) or antibody clone

3, #4 or #17 (see Example 14) can be identified. To screen for antibodies which bind to the epitope on WSX receptor bound by an antibody of interest (e.g., those which block binding of any one of the above antibodies to WSX receptor), a routine cross-blocking assay such as that described in *Antibodies, A Laboratory Manual*, Cold Spring Harbor Laboratory, Ed Harlow and David Lane (1988), can be performed. Alternatively, epitope mapping, e.g. as described in Champe et al., *J. Biol. Chem.* 270:1388-1394 (1995), can be performed to determine whether the antibody binds an epitope of interest.

In one particularly preferred embodiment of the invention, agonist antibodies are selected. Various methods for selecting agonist antibodies are available. In one embodiment, one evaluates the agonistic properties of the antibody upon binding to a chimeric receptor comprising the WSX receptor extracellular domain in an assay called the kinase receptor activation enzyme linked immunoadsorbent assay (KIRA ELISA) described in WO95/14930 (expressly incorporated herein by reference).

To perform the KIRA ELISA, a chimeric receptor comprising the extracellular domain of the WSX receptor and the transmembrane and intracellular domain of Rse receptor (Mark et al., *Journal of Biological Chemistry* 269(14):10720-10728 (1994)) with a carboxyl-terminal herpes simplex virus glycoprotein D (gD) tag is produced and dp12.CHO cells are transformed therewith as described in Example 4 of WO95/14930.

The WSX/Rse.gD transformed dp12.CHO cells are seeded ($3 \times 10^4$ per well) in the wells of a flat-bottom-96 well culture plate in 100 µl media and cultured overnight at 37° C. in 5% $CO_2$. The following morning the well supernatants are removed and various concentrations of the antibody are added to separate wells. The cells are stimulated at 37° C. for 30 min., the well supernatants are decanted. To lyse the cells and solubilize the chimeric receptors, 100 µl of lysis buffer is added to each well. The plate is then agitated gently on a plate shaker (Bellco Instruments, Vineland, N.J.) for 60 min. at room temperature.

While the cells are being solubilized, an ELISA microtiter plate (Nunc Maxisorp, Inter Med, Denmark) coated overnight at 4° C. with the 5B6 monoclonal anti-gD antibody (5.0 µg/ml in 50 mM carbonate buffer, pH 9.6, 100 µl/well) is decanted and blocked with 150 µl/well of Block Buffer for 60 min. at room temperature. After 60 minutes, the anti-gD 5B6 coated plate is washed 6 times with wash buffer (PBS containing 0.05% TWEEN 20™ and 0.01 % thimerosal).

The lysate containing solubilized WSX/Rse.gD from the cell-culture microtiter well is transferred (85 µl/well) to anti-gD 5B6 coated and blocked ELISA well and is incubated for 2 h at room temperature. The unbound WSX/Rse.gD is removed by washing with wash buffer and 100µl of biotinylated 4G10 (anti-phosphotyrosine) diluted 1:18000 in dilution buffer (PBS containing 0.5% BSA, 0.05% Tween-20, 5 mM EDTA, and 0.01% thimerosal), i.e. 56 ng/ml is added to each well. After incubation for 2 h at room temperature the plate is washed and HRPO-conjugated streptavidin (Zymed Laboratories, S. San Francisco, Calif.) is added to each well. The plate is incubated for 30 minutes at room temperature with gentle agitation. The free avidin-conjugate is washed away and 100 µl freshly prepared substrate solution (tetramethyl benzidine (TMB); 2-component substrate kit; Kirkegaard and Perry, Gaithersburg, Md.) is added to each well. The reaction is allowed to proceed for 10 minutes, after which the color development is stopped by the addition of 100 µl/well 1.0 M $H_3PO_4$. The absorbance at 450 nm is read with a reference wavelength of 650 nm ($ABS_{450/650}$), using a vmax plate reader (Molecular Devices, Palo Alto, Calif.) controlled with a Macintosh Centris 650 (Apple Computers, Cupertino, Calif.) and DeltaSoft software (BioMetallics, Inc, Princeton, N.J.).

Those antibodies which have an IC50 in the KIRA ELISA of about 0.5 µg/ml or less (e.g. from about 0.5 µg/ml to about 0.001 µg/ml), preferably about 0.2 µg/ml or less and most preferably about 0.1 µg/ml or less are preferred agonists.

In another embodiment, one screens for antibodies which activate downstream signaling molecules for OB protein. For example, the ability of the antibody to activate Signal Transducers and Activators of Transcription (STATs) can be assessed. The agonist antibody of interest may stimulate formation of STAT-1 and STAT-3 complexes, for example. To screen for such antibodies, the assay described in Rosenblum et al. *Endocrinology* 137(11):5178-5181 (1996) may be performed.

Alternatively, an antibody which stimulates proliferation and/or differentiation of hematopoietic cells can be selected. For example, the hematopoiesis assays of Example 10 below can be performed. For example, murine fetal liver flASK stem cells may be isolated from the midgestational fetal liver as described in Zeigler et al., *Blood* 84:2422-2430 (1994) and studied in stem cell suspension culture or methylcellulose assays. For the stem cell suspension cultures, twenty thousand of the FLASK cells are seeded in individual wells in a 12 well format in DMEM 4.5/F12 media supplemented with 10% heat inactivated fetal calf serum (Hyclone, Logan, Utah) and L-glutamine. Growth factors are added at the following concentrations: kit ligand (KL) at 25 ng/mL, interleukin-3 (IL-3) at 25 ng/mL, interleukin-6 (IL-6) at 50 ng/mL, G-CSF at 100 ng/mL, GM-CSF at 100 ng/mL, EPO at 2U/mL, interleukin-7 (IL-7) at 100 ng/mL (all growth factors from R and D Systems, Minneapolis, Minn.). The agonist antibody is then added and the ability of the antibody to expand the flASK cells grown in suspension culture is assessed. Methylcellulose assays are performed as previously described (Zeiger et al., supra). Briefly, methylcellulose colony assays are performed using "complete" methylcellulose or pre-B methylcellulose medium (Stem Cell Technologies, Vancouver, British Columbia, Canada) with the addition of 25 ng/mL KL (R and D Systems, Minneapolis, Minn.). Cytospin analyses of the resultant colonies are performed as previously described in Zeigler et al. The ability of the agonist antibody to augment myeloid, lymphoid and erythroid colony formation is assessed. Also, the effect of the agonist antibody on the murine bone marrow stem cell population; $Lin^{lo}Sca^+$ may be evaluated.

One may select an agonist antibody which induces a statistically significant decrease in body weight and/or fat-depot weight and/or food intake in an obese mammal (e.g. in an ob/ob mouse). Methods for screening for such molecules are described in Levin et al. *Proc. Natl. Acad. Sci. USA* 93:1726-1730 (1996), for example. Preferred agonist antibodies are those which exert adipose-reducing effects in an obese mammal, such as the ob/ob mouse, which are in excess of those induced by reductions in food intake. For ad libitum feeding studies, 7-week-old genetically obese C57BL/6J-ob/ob (ob/ob) and C57BL/KsJ-db/db (db/db) mice and lean littermates (heterozygous C57BL/6J-+/ob for ob/ob and wild-type C57BL/KsJ-+/m for db/db) were purchased from The Jackson Laboratory. Mice were housed in groups of four or five with ad libitum access to water and standard mouse chow (Purina 5010) in a temperature-, humidity-, and light-controlled (lights on at 06:00 hr, off at 18:00 hr) colony room. Miniosmotic pumps (Alzet model 2002; Alza) were filled with purified recombinant ob protein (100 µg/kg per day) in sterile phosphate-buffered saline (PBS) or PBS alone under sterile conditions following manufacturer's instructions and incubated overnight in sterile saline at room temperature before implantation into mice. Mice were anesthetized with ketamine/xylazine, and miniosmotic pumps were implanted s.c. in the midscapular region. The body weight of each mouse (to the nearest 0.1 g) and the weight of the food contained in the food bin in each case (to the nearest 0.1 g) were recorded between 17:00 hr and 18:00 hr every 1 to 2 days. Mice were killed by barbiturate overdose followed by exsanguination via cardiac puncture. Fat pads and organs were immediately dissected, blotted, and weighed to the nearest 0.001 g. Hepatic glycogen content was assessed on paraffin-embedded liver sections that were fixed in 10% neutral-buffered formalin and stained by the periodic acid Schiff reaction with or without previous diastase digestion. Hepatic lipid content was assessed on fresh frozen liver sections that were stained by Oil Red O. Fat pads were histologically examined after fixation in 10% neutral-buffered formalin, sectioning, and hematoxylin/eosin staining. Blood samples (≈0.2 ml) were obtained from the retroorbital sinus of conscious mice on day 13 of treatment at 14:00 hr, after a 5-hr fast. Blood was stored on ice until centrifugation, and then serum was stored at −20° C. until use. Serum insulin concentrations were determined by radioimmunoassay (Linco Research, St. Louis). Serum concentrations of glucose, cholesterol, and triglycerides were determined on a Technicon Chem 1+ System chemistry analyzer (Bayer, Tarrytown, N.Y.). For pair-feeding studies, 8-week-old obese (C57BL/6J-ob/ob; The Jackson Laboratory) or lean (C57BL/6; Charles River Breeding Laboratories) female mice were housed as described above. The three treatment groups for each genotype were ad libitum-fed PBS-treated, ad libitum-fed ob protein-treated, or pair-fed PBS-treated. The ob protein was delivered via miniosmotic pumps as described above at a dose of 270 μg/kg per day. Pair feeding was accomplished by measuring the food intake of the ad libitum-fed ob protein-treated mice every 24 hr and presenting this amount of food to the pair-fed PBS-treated mice. For each of the three treatment groups there were two to three cages of mice, containing two to five mice per cage. Blood samples were obtained, the mice were killed, and tissues were harvested as described above. All data are presented as the mean±SEM and were analyzed by ANOVA with post hoc differences determined by Fisher's protected least significant different test if ANOVA was significant at the level of P<0.05.

The antibody of interest herein may have the hypervariable region residues of one of the antibodies in Examples 13 and 14. Also, the invention encompasses "affinity matured" forms of these antibodies in which hypervariable region residues of these antibodies have been modified. Such affinity matured antibodies will preferably have a biological activity which is the same as or better than that of the original antibody. The affinity matured antibody may have from about 1-10, e.g. 5-10 deletions, insertions or substitutions (but preferably substitutions) in the hypervariable regions thereof. One useful procedure for generating affinity matured antibodies is called "alanine scanning mutagenesis" (Cunningham and Wells *Science* 244:1081-1085 (1989)). Here, one or more of the hypervariable region residue(s) are replaced by alanine or polyalanine residue(s) to affect the interaction of the amino acids with the WSX receptor. Those hypervariable region residue(s) demonstrating functional sensitivity to substitution are then refined by introducing further or other mutations at or for the sites of substitution. The ala-mutants produced this way are screened for their biological activity as described herein. Another procedure is affinity maturation using phage display (Hawkins et al. *J. Mol. Biol.* 254:889-896 (1992) and Lowman et al. *Biochemistry* 30(45):10832-10837 (1991)). Briefly, several hypervariable region sites (e.g. 6-7 sites) are mutated to generate all possible amino substitutions at each site. The antibody mutants thus generated are displayed in a monovalent fashion from filamentous phage particles as fusions to the gene III product of M13 packaged within each particle. The phage-displayed mutants are then screened for their biological activity (e.g. binding affinity).

6. Antibody Modifications

It may be desirable to tailor the antibody for various applications. Exemplary antibody modifications are described here.

In certain embodiments of the invention, it may be desirable to use an antibody fragment, rather than an intact antibody. In this case, it may be desirable to modify the antibody fragment in order to increase its serum half-life. This may be achieved, for example, by incorporation of a salvage receptor binding epitope into the antibody fragment. See WO96/32478 published Oct. 17, 1996. Alternatively, the antibody may be conjugated to a nonproteinaceous polymer, such as those described above for the production of long half-life derivatives of OB protein.

Where the antibody is to be used to treat cancer for example, various modifications of the antibody (e.g. of a neutralizing antibody) which enhance the effectiveness of the antibody for treating cancer are contemplated herein. For example, it may be desirable to modify the antibody of the invention with respect to effector function. For example cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies with enhanced anti-tumor activity may also be prepared using heterobifunctional cross-linkers as described in Wolff et al. *Cancer Research* 53:2560-2565 (1993). Alternatively, an antibody can be engineered which has dual Fc regions and may thereby have enhanced complement lysis and ADCC capabilities. See Stevenson et al. *Anti-Cancer Drug Design* 3:219-230 (1989). The invention also pertains to immunoconjugates comprising the antibody described herein conjugated to a cytotoxic agent such as a chemotherapeutic agent, toxin (e.g. an enzymatically active toxin of bacterial, fungal, plant or animal origin, or fragments thereof), or a radioactive isotope (i.e., a radioconjugate).

Chemotherapeutic agents useful in the generation of such immunoconjugates have been described above. Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. A variety of radionuclides are available for the production of radioconjugate antibodies. Examples include $^{212}$Bi, $^{131}$I, $^{131}$In, $^{90}$Y and $^{186}$Re.

Conjugates of the antibody and cytotoxic agent are made using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al. *Science* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody may be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide).

The antibody may also be formulated as an immunoliposome. Liposomes containing the antibody are prepared by methods known in the art, such as described in Epstein et al., *Proc. Natl. Acad. Sci. USA*, 82:3688 (1985); Hwang et al., *Proc. Natl Acad. Sci. USA*, 77:4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al. *J. Biol. Chem.* 257: 286-288 (1982) via a disulfide interchange reaction. A chemotherapeutic agent (such as Doxorubicin) is optionally contained within the liposome. See Gabizon et al. *J. National Cancer Inst.*81(19)1484 (1989).

The antibody of the present invention may also be used in ADEPT by conjugating the antibody to a prodrug-activating enzyme which converts a prodrug (e.g. a peptidyl chemotherapeutic agent, see WO81/01145) to an active anti-cancer drug. See, for example, WO 88/07378 and U.S. Pat. No. 4,975,278.

The enzyme component of the immunoconjugate useful for ADEPT includes any enzyme capable of acting on a prodrug in such a way so as to covert it into its more active, cytotoxic form.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, *Nature* 328: 457-458 (1987)). Antibody-abzyme conjugates can be prepared as described herein for delivery of the abzyme to a tumor cell population.

The enzymes of this invention can be covalently bound to the antibody mutant by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., *Nature,* 312: 604-608 (1984)).

In other embodiments, the antibody can be covalently modified, with exemplary such modifications described above.

F. Therapeutic Uses for WSX Receptor Ligands and Antibodies

The WSX ligands (e.g. OB protein and anti-WSX receptor agonist antibodies) of the present invention are useful, in one embodiment, for weight reduction, and specifically, in the treatment of obesity, bulimia and other disorders associated with the abnormal expression or function of the OB and/or WSX receptor genes, other metabolic disorders such as diabetes, for reducing excessive levels of insulin in human patients (e.g. to restore or improve the insulin-sensitivity of such patients). Thus, these molecules can be used to treat a patient suffering from excessive food consumption and related pathological conditions such as type II adult onset diabetes, infertility (Chehab et al. *Nature Genentics* 12:318-320 (1996)), hypercholesterolemia, hyperlipidemia, cardiovascular diseases, arteriosclerosis, polycystic ovarian disease, osteoarthritis, dermatological disorders, insulin resistance, hypertriglyceridemia, cancer, cholelithiasis and hypertension.

In addition, the WSX ligands can be used for the treatment of kidney ailments, hypertension, and lung dysfunctions, such as emphysema.

In a further embodiment, the WSX ligands (such as agonist WSX receptor antibodies) of the present invention can be used to enhance repopulation of mature blood cell lineages in mammals having undergone chemo- or radiation therapy or bone marrow transplantation therapy. Generally, the ligands will act via an enhancement of the proliferation and/or differentiation (but especially proliferation) of primitive hematopoietic cells. The ligands may similarly be useful for treating diseases characterized by a decrease in blood cells. Examples of these diseases include: anemia (including macrocytic and aplastic anemia); thrombocytopenia; hypoplasia; immune (autoimmune) thrombocytopenic purpura (ITP); and HIV induced ITP. Also, the ligands may be used to treat a patient having suffered a hemorrhage. WSX ligands may also be used to treat metabolic disorders such as obesity and diabetes mellitus, or to promote kidney, liver or lung growth and/or repair (e.g., in renal failure).

The WSX receptor ligands and antibodies may be administered alone or in concert with one or more cytokines. Furthermore, as an alternative to adminstration of the WSX ligand protein, gene therapy techniques (discussed in the section above entitled "Therapeutic Uses for the WSX Receptor") are also contemplated herein.

Potential therapeutic applications for WSX receptor neutralizing antibodies include the treatment of metabolic disorders (such as cachexia, anorexia and other wasting diseases characterized by loss of appetite, diminished food intake or body weight loss), stem cell tumors and other tumors at sites of WSX receptor expression, especially those tumors characterized by overexpression of WSX receptor.

For therapeutic applications, the WSX receptor ligands and antibodies of the invention are administered to a mammal, preferably a human, in a physiologically acceptable dosage form, including those that may be administered to a human intravenously as a bolus or by continuous infusion over a period of time, by intramuscular, intraperitoneal, intra-cerobrospinal, subcutaneous, intra-articular, intrasynovial, intrathecal, oral, topical, or inhalation routes. The WSX receptor ligands and antibodies also are suitably administered by intratumoral, peritumoral, intralesional, or perilesional routes or to the lymph, to exert local as well as systemic therapeutic effects.

Such dosage forms encompass physiologically acceptable carriers that are inherently non-toxic and non-therapeutic. Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and PEG. Carriers for topical or gel-based forms of WSX receptor antibodies include polysaccharides such as sodium carboxymethylcellulose or methylcellulose, polyvinylpyrrolidone, polyacrylates, polyoxyethylene-polyoxypropylene-block polymers, PEG, and wood wax alcohols. For all administrations, conventional depot forms are suitably used. Such forms include, for example, microcapsules, nano-capsules, liposomes, plasters, inhalation forms, nose sprays, sublingual tablets, and sustained-release preparations. The WSX receptor ligand or antibody will typically be formulated in such vehicles at a concentration of about 0.1 mg/ml to 100 mg/ml.

Suitable examples of sustained-release preparations include semipermeable matrices of solid hydrophobic polymers containing the WSX receptor ligand or antibody, which matrices are in the form of shaped articles, e.g. films, or microcapsules. Examples of sustained-release matrices include polyesters, hydrogels (for example, poly(2-hydroxyethyl-methacrylate) as described by Langer et al., supra and Langer, supra, or poly(vinylalcohol), polylactides (U.S. Pat. No. 3,773,919), copolymers of L-glutamic acid and γ ethyl-L-glutamate (Sidman et al., supra), non-degradable ethylene-vinyl acetate (Langer et al., supra), degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated WSX receptor antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions. 103271 Sustained-release WSX receptor ligand or antibody compositions also include liposomally entrapped antibodies. Liposomes containing the WSX receptor ligand or antibody are prepared by methods known in the art, such as described in Epstein et al., *Proc. Natl. Acad. Sci. USA* 82:3688 (1985); Hwang et al., *Proc. Natl. Acad. Sci. USA* 77:4030 (1980); and U.S. Pat. Nos. 4,485,045 and 4,544,545. Ordinarily, the liposomes are the small (about 200-800 Angstroms) unilamellar type in which the lipid content is greater than about 30 mol. % cholesterol, the selected proportion being adjusted for the optimal WSX receptor ligand or antibody therapy. Liposomes with enhanced circulation time are disclosed in U.S. Pat. No. 5,013,556.

For the prevention or treatment of disease, the appropriate dosage of WSX receptor ligand or antibody will depend on the type of disease to be treated, as defined above, the severity and course of the disease, whether the antibodies are administered for preventive or therapeutic purposes, previous therapy, the patient's clinical history and response to the WSX receptor ligand or antibody, and the discretion of the attending physician. The WSX receptor ligand or antibody is suitably administered to the patient at one time or over a series of treatments.

Depending on the type and severity of the disease, about 1 μg/kg to 15 mg/kg of WSX receptor ligand or antibody is an initial candidate dosage for administration to the patient, whether, for example, by one or more separate administrations, or by continuous infusion. A typical daily dosage might range from about 1 μg/kg to 100 μg/kg (e.g. 1-50 μg/kg) or more, depending on the factors mentioned above. For example, the dose may be the same as that for other cytokines such as G-CSF, GM-CSF and EPO. For repeated administrations over several days or longer, depending on the condition, the treatment is sustained until a desired suppression of disease symptoms occurs. However, other dosage regimens may be useful. The progress of this therapy is easily monitored by conventional techniques and assays.

When one or more cytokines are co-administered with the WSX receptor ligand, lesser doses of the WSX ligand may be employed. Suitable doses of a cytokine are from about 1 μg/kg to about 15 mg/kg of cytokine. A typical daily dosage of the cytokine might range from about 1 μg/kg to 100 μg/kg (e.g. 1-50 μg/kg) or more. For example, the dose may be the same as that for other cytokines such as G-CSF, GM-CSF and EPO. The cytokine(s) may be administered prior to, simultaneously with, or following administration of the WSX ligand. The cytokine(s) and WSX ligand may be combined to form a pharmaceutically composition for simultaneous administration to the mammal. In certain embodiments, the amounts of WSX ligand and cytokine are such that a synergistic repopulation of blood cells (or synergistic increase in proliferation and/or differentiation of hematopoietic cells) occurs in the mammal upon administration of the WSX ligand and cytokine thereto. In other words, the coordinated action of the two or more agents (i.e. the WSX ligand and cytokine(s)) with respect to repopulation of blood cells (or proliferation/differentiation of hematopoietic cells) is greater than the sum of the individual effects of these molecules.

For treating obesity and associated pathological conditions, the WSX ligand may be administered in combination with other treatments for combatting or preventing obesity. Substances useful for this purpose include, e.g., hormones (catecholamines, glucagon, ACTH); clofibrate; halogenate; cinchocaine; chlorpromazine; appetite-suppressing drugs acting on noradrenergic neurotransmitters such as mazindol and derivatives of phenethylamine, e.g., phenylpropanolamine, diethylpropion, phentermine, phendimetrazine, benzphetamine, amphetamine, methamphetamine, and phenmetrazine; drugs acting on serotonin neurotransmitters such as fenfluramine, tryptophan, 5-hydroxytryptophan, fluoxetine, and sertraline; centrally active drugs such as naloxone, neuropeptide-Y, galanin, corticotropin-releasing hormone, and cholecystokinin; a cholinergic agonist such as pyridostigmine; a sphingolipid such as a lysosphingolipid or derivative thereof (EP 321,287 published Jun. 21, 1989); thermogenic drugs such as thyroid hormone, ephedrine, beta-adrenergic agonists; drugs affecting the gastrointestinal tract such as enzyme inhibitors, e.g., tetrahydrolipostatin, indigestible food such as sucrose polyester, and inhibitors of gastric emptying such as threo-chlorocitric acid or its derivatives; β-adrenergic agonist such as isoproterenol and yohimbine; aminophylline to increase the β-adrenergic-like effects of yohimbine, an $\alpha_2$-adrenergic blocking drug such as clonidine alone or in combination with a growth hormone releasing peptide (U.S. Pat: No.5,120,713 issued Jun. 9, 1992); drugs that interfere with intestinal absorption such as biguanides such as metformin and phenformin; bulk fillers such as methylcellulose; metabolic blocking drugs such as hydroxycitrate; progesterone; cholecystokinin agonists; small molecules that mimic ketoacids; agonists to corticotropin-releasing hormone; an ergot-related prolactin-inhibiting compound for reducing body fat stores (U.S. Pat. No.4,783,469 issued Nov. 8, 1988); beta-3-agonists; bromocriptine; antagonists to opioid pepfides; antagonists to neuropeptide Y; glucocorticoid receptor antagonists; growth hormone agonists; combinations thereof; etc. This includes all drugs described by Bray and Greenway, *Clinics in Endocrinol. and Metabol.*, 5:455 (1976).

These adjunctive agents may be administered at the same time as, before, or after the administration of WSX ligand and can be administered by the same or a different administration route than the WSX ligand.

The WSX ligand treatment may occur without, or may be imposed with a dietary restriction such as a limit in daily food or calorie intake, as is desired for the individual patient.

G. Articles of Manufacture

In another embodiment of the invention, an article of manufacture containing materials useful for the treatment of the conditions described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is the WSX ligand. The label on, or associated with, the container indicates that the composition is used for treating the condition of choice. The article of manufacture may further comprise a second container holding a cytokine for co-administration with the WSX ligand. Further container(s) may be provided with the article of manufacture which may hold, for example, a pharmaceutically-acceptable buffer, such as phosphate-buffered saline, Ringer's solution or dextrose solution. The article of manufacture may further include other materials desirable from a commercial and user standpoint, including other buffers, diluents, filters, needles, syringes, and package inserts with instructions for use.

H. Non-Therapeutic Uses for WSX Receptor Ligands and Antibodies

WSX receptor ligands and antibodies may be used for detection of and/or enrichment of hematopoietic stem cell/ progenitor cell populations in a similar manner to that in which CD34 antibodies are presently used. For stem cell enrichment, the WSX receptor antibodies may be utilized in the techniques known in the art such as immune panning, flow cytometry or immunomagnetic beads.

In accordance with one in vitro application of the WSX ligands, cells comprising the WSX receptor are provided and placed in a cell culture medium. Examples of such WSX-receptor-containing cells include hematopoietic progenitor cells, such as CD34+ cells.

Suitable tissue culture media are well known to persons skilled in the art and include, but are not limited to, Minimal Essential Medium (MEM), RPMI-1640, and Dulbecco's Modified Eagle's Medium (DMEM). These tissue culture medias are commercially available from Sigma Chemical Company (St. Louis, Mo.) and GIBCO (Grand Island, N.Y.). The cells are then cultured in the cell culture medium under conditions sufficient for the cells to remain viable and grow in the presence of an effective amount of WSX ligand and, optionally, further cytokines and growth factors. The cells can be cultured in a variety of ways, including culturing in a clot, agar, or liquid culture.

The cells are cultured at a physiologically acceptable temperature such as 37° C., for example, in the presence of an effective amount of WSX ligand. The amount of WSX ligand may vary, but preferably is in the range of about 10 ng/ml to about 1 mg/ml. The WSX ligand can of course be added to the culture at a dose determined empirically by those in the art without undue experimentation. The concentration of WSX ligand in the culture will depend on various factors, such as the conditions under which the cells and WSX ligand are cultured. The specific temperature and duration of incubation, as well as other culture conditions, can be varied depending on such factors as, e.g., the concentration of the WSX ligand, and the type of cells and medium.

It is contemplated that using WSX ligand to enhance cell proliferation and/or differentiation in vitro will be useful in a variety of ways. For instance, hematopoietic cells cultured in vitro in the presence of WSX ligand can be infused into a mammal suffering from reduced levels of the cells. Also, the cultured hematopoietic cells may be used for gene transfer for gene therapy applications. Stable in vitro cultures can be also used for isolating cell-specific factors and for expression of endogenous or recombinantly introduced proteins in the cell. WSX ligand may also be used to enhance cell survival, proliferation and/or differentiation of cells which support the growth and/or differentiation of other cells in cell culture.

The WSX receptor antibodies of the invention are also useful as affinity purification agents. In this process, the antibodies against WSX receptor are immobilized on a suitable support, such a Sephadex resin or filter paper, using methods well known in the art. The immobilized antibody then is contacted with a sample containing the WSX receptor to be purified, and thereafter the support is washed with a suitable solvent that will remove substantially all the material in the sample except the WSX receptor, which is bound to the immobilized antibody. Finally, the support is washed with another suitable solvent, such as glycine buffer, pH 5.0, that will release the WSX receptor from the antibody.

WSX receptor antibodies may also be useful in diagnostic assays for WSX receptor, e.g., detecting its expression in specific cells, tissues, or serum. For diagnostic applications, antibodies typically will be labeled with a detectable moiety. The detectable moiety can be any one which is capable of producing, either directly or indirectly, a detectable signal. For example, the detectable moiety may be a radioisotope, such as $^3H$, $^{14}C$, $^{32}P$, 35S, or 125I; a fluorescent or chemiluminescent compound, such as fluorescein isothiocyanate, rhodamine, or luciferin; radioactive isotopic labels, such as, e.g., $^{125}$I, $^{32}$P, $^{14}$C, or $^{3}$H; or an enzyme, such as alkaline phosphatase, beta-galactosidase, or horseradish peroxidase.

Any method known in the art for separately conjugating the polypeptide variant to the detectable moiety may be employed, including those methods described by Hunter et al., *Nature* 144:945 (1962); David et al., *Biochemistry* 13:1014 (1974); Pain et al., *J. Immunol. Meth* 40:219 (1981); and Nygren, *J. Histochem. and Cytochem.* 30:407 (1982).

The antibodies of the present invention may be employed in any known assay method, such as competitive binding assays, direct and indirect sandwich assays, and immunoprecipitation assays. Zola, *Monoclonal Antibodies: A Manual of Techniques*, pp. 147-158 (CRC Press, Inc., 1987).

Competitive binding assays rely on the ability of a labeled standard to compete with the test sample analyte for binding with a limited amount of antibody. The amount of WSX receptor in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three-part complex. See, e.g., U.S. Pat No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

I. Deposit of Materials

The following biological materials have been deposited with the American Type Culture Collection, 10801 University Blvd., Menassas, Va. 20110-2209 (ATCC):

| Deposit Designation | ATCC No. | Deposit Date |
|---|---|---|
| Baf3/WSX E63x7 sort (Baf3 cells expressing human WSX receptor variant 13.2) | ATCC CRL 12015 | Jan. 10, 1996 |
| 2D7 hybridoma cell line | HB-12249 | Dec. 19, 1996 |
| 1G4 hybridoma cell line | ATCC HB-12243 | Dec. 11, 1996 |
| 1E11 hybridoma cell line | HB-12248 | Dec. 19, 1996 |
| 1C11 hybridoma cell line | HB-12250 | Dec. 19, 1996 |

These deposits were made under the provisions of the Budapest Treaty on the International Recognition of the Deposit of Microorganisms for the Purpose of Patent Procedure and the Regulations thereunder (Budapest Treaty). This assures maintenance of a viable culture for 30 years from the date of deposit. Each of the deposited cultures will be made available by ATCC under the terms of the Budapest Treaty, and subject to an agreement between Genentech, Inc. and ATCC, which assures (a) that access to the culture will be available during pendency of the patent application to one determined by the Commissioner to be entitled thereto under 37 CFR §1.14 and 35 USC §122, and (b) that all restrictions on the availability to the public of the culture so deposited will be irrevocably removed upon the granting of the patent.

The assignee of the present application has agreed that if any of the cultures on deposit should die or be lost or destroyed when cultivated under suitable conditions, it will be promptly replaced on notification with a viable specimen of the same culture. Availability of the deposited cell lines is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by any culture deposited, since the deposited embodiment is intended as an illustration of one aspect of the invention and any culture that is functionally equivalent is within the scope of this invention. The deposit of material herein does not constitute an admission that the written description herein contained is inadequate to enable the practice of any aspect of the invention, including the best mode thereof, nor is it to be construed as limiting the scope of the claims to the specific illustration that it represents. Indeed, various modifications of the invention in addition to those shown and described herein will become apparent to those skilled in the art from the foregoing description and fall within the scope of the appended claims.

J. Experimental

Below are examples of specific embodiments for carrying out the present invention. The examples are offered for illustrative purposes only, and are not intended to limit the scope of the present invention in any way.

The disclosures of all publications, patents and patent applications cited herein, whether supra or infra, are hereby incorporated by reference in their entirety.

EXAMPLE 1

Cloning of Human WSX Receptor

An oligonucleotide probe designated WSX.6 #1 was synthesized based upon the T73849 EST sequence. The WSX.6 #1 probe was a 51mer having the following sequence:

(SEQ ID NO:45)
5'GTCAGTCTCCCAGTTCCAGACTTGTGTGCAGTCTATGCTGTTCA
GGTGCGC-3'.

The radiolabeled WSX.6 #1 probe was used to probe 1.2× $10^6$ clones from a random and oligo dT primed λgt10 fetal liver library (Clontech, Palo Alto, Calif.). Following hybridization at 42° C. overnight, the filters were washed at 50° C. in 0.5×SSC and 0.1% NaDodSO$_4$ (SDS). From the initial screen, 10 clones were selected and upon subsequent screening 5 individual plaque pure clones were isolated. Of these 5 individual clones, four clones designated 1, 5, 6 and 9 were subcloned into pBSSK$^-$ (Stratagene) following EcoRI digestion. Sequence analysis revealed clone 5 and clone 9 contained the putative initiation methionine and signal peptide. Clone 6 (designated 6.4) contained the most 3' end sequence and subsequently was used for further screening.

To obtain the full length gene, clone 6.4 (fragment Nsi-Hind III) was radiolabeled and used to screen 1.2×$10^6$ clones from a λgt 10 library constructed from a hepatoma Hep3B cell line. This screen resulted in 24 positive clones. Following PCR analysis of the clones using λgt10 primers (F and R), the four longest clones 12.1, 13.2,22.3, and 24.3 were isolated. These clones were subcloned into pBSSK$^-$ using the EcoRI site, and following examination by restriction enzyme digest, clones 12.1 and 13.2 were submitted for sequencing. DNA sequencing was performed with the Taq dye deoxynucleotide terminator cycle sequencing kit on an automated Applied Biosystems DNA sequencer.

The assembled contiguous sequence from all the isolated clones encoded a consensus amino terminus for the newly identified polypeptide designated the WSX receptor. However, sequence analysis revealed that at least three naturally occurring variants of the WSX receptor exist which have different cytoplasmic regions. These variants appear to be differentially spliced at the lysine residue at position 891. Clone 6.4 stops 5 amino acids after Lys 891. Clone 12.1 is different from 13.2 and 6.4 following Lys 891 and encodes a putative box 2 region which is distinct from that encoded by clone 13.2. Clone 13.2 contains a potential box 1 region and following Lys 891 encodes putative box 2 and box 3 motifs. See, Baumann et al., *Mol. Cell. Biol.* 14(1):138-146 (1994).

The full length WSX gene based on the clone 13.2 cytoplasmic region putatively encodes an 1165 amino acid transmembrane protein. The 841 amino acid extracellular domain (ECD) contains two WSXWS domains. The ECD is followed by a 24 amino acid transmembrane domain and a 300 amino acid cytoplasmic region.

EXAMPLE 2

WSX Receptor Immunoadhesin

Using polymerase chain amplification, a WSX receptor immunoadhesin was created by engineering an in-frame fusion of the WSX receptor gene extracellular domain (WSX-.ECD) with human CH2CH3(Fc)IgG (Bennett et al., *J. Biol. Chem.* 266(34):23060-23067 (1991)) at the C terminus of the ECD and cloned into pBSSK⁻ (Stratagene). For expression, the WSX-Fc was excised with ClaI and BstEII and ligated into the pRK5.HuIF.grbhIgG Genenase I vector (Beck et al., *Molecular Immunology* 31(17): 1335-1344 (1994)), to create the plasmid pRK5.WSX-IgG Genenase I. This plasmid was transiently transfected into 293 cells using standard calcium phosphate transfection techniques. The transfected cells were cultured at 37° C. in 5% $CO_2$ in DMEM F12 50:50 supplemented with 10% FBS, 100 mM HEPES (pH 7.2) and 1 mM glutamine. The WSX receptor immunoadhesin was purified using a ProSepA™ protein A column.

EXAMPLE 3

Antibody Production

In order to raise antibodies against the WSX receptor, the WSX receptor immunoadhesin of Example 2 was used to inoculate rabbits to raise polyclonal antibodies and mice to raise monoclonal antibodies using conventional technology.

EXAMPLE 4

Generation of a Cell Line Expressing WSX Receptor

The nucleic acid encoding full length WSX receptor variant 13.2 was inserted in the pRKtkNeo plasmid (Holmes et al., *Science* 253:1278-1280 (1991)). 100 μgs of the pRKtk-Neo.WSX plasmid thus generated was linearized, ethanol precipitated and resuspended in, 100 μL of RPMI 1640. $7\times10^6$ Baf3 cells ($5\times10^5$/ml) were suspended in 900 μL of RPMI and added to the linearized plasmid. Following electroporation at 325V, 1180 μF using a BRL electroporation apparatus, the cells were plated into 15 mls of RPMI 1640 containing 5% WEHI3B conditioned media and 15% serum. 48 hours later cells were selected in 2 mg/ml G418.

To obtain the Baf3/WSX cell line expressing WSX receptor variant 13.2, the G418 selected clones were analyzed by FACS using the rabbit polyclonal antisera raised against the WSX-Fc chimeric protein as described above. The highest expressing clone (designated E6) was sorted by FACS to maintain a population with a high level of WSX receptor expression.

EXAMPLE 5

Role of WSX Receptor in Cellular Proliferation

Figure 8:
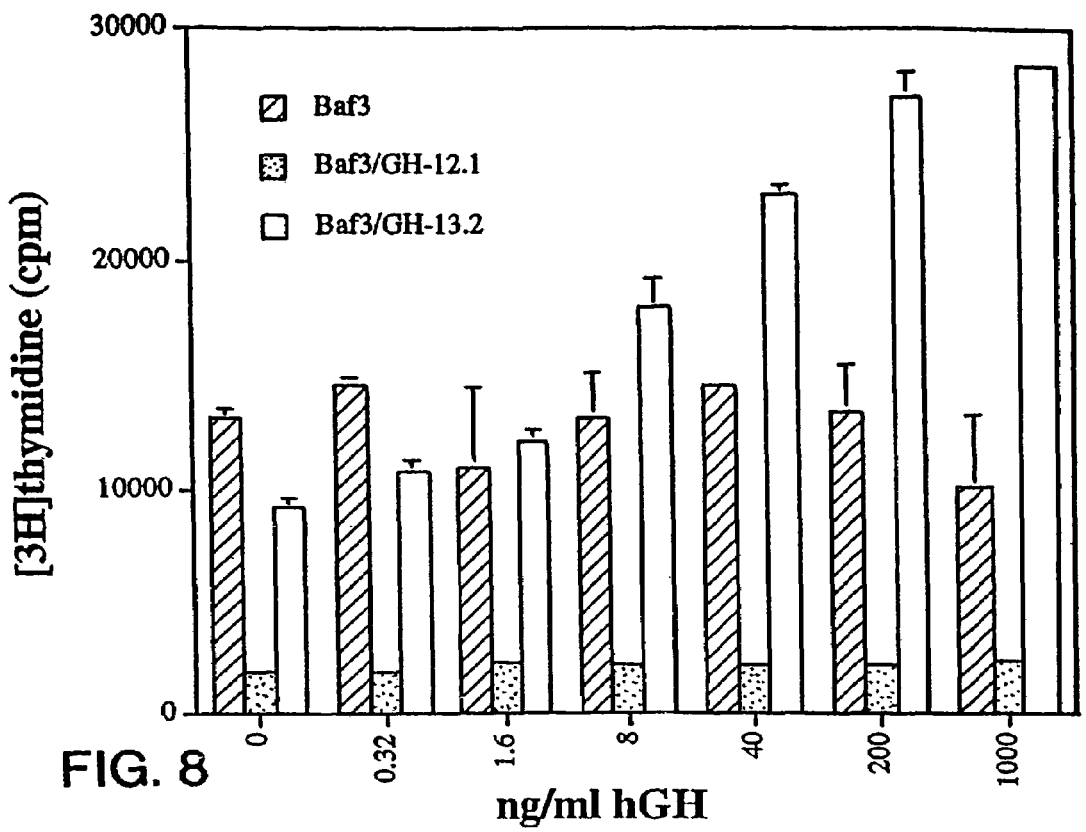
FIGS. 8 and 9 show thymidine incorporation assays in Baf-3 cells. For these assays, cells were deprived of IL-3 for 16-18 hours (in RPMI 1640 supplemented with 10% fetal calf serum (FCS)). Cells were washed in serum free RPMI 1640 and plated at 50,000 cells per well in 0.2 mls of serum free RPMI 1640 supplemented with the indicated concentration of human GH or human OB protein. Cells were stimulated for 24 hours and thymidine incorporation was determined as described (Zeigler et al. *Blood* 84:2422-2430 (1994)). Assays were performed in triplicate and the results were confirmed in three independent experiments.

The proliferative potentials of WSX receptor variants 13.2 and 12.1 were tested by constructing human growth hormone receptor-WSX receptor (GH-WSX) fusions encoding chimeric proteins consisting of the GH receptor extracellular and transmembrane domains and the WSX receptor variant 13.2 or 12.1 intracellular domains. These chimeric gene fusions were transfected into the IL-3 dependent cell line Baf3. The ability of the GH-WSX transfected Baf3 cells to respond to exogenous growth hormone (GH) was tested in a thymidine incorporation assay. As can be seen in FIGS. 6 and 8, the GH-WSX receptor variant 13.2 chimera was capable of increasing thymidine uptake in the transfected Baf3 cells, thus indicating the proliferative potential of the WSX receptor variant 13.2. However, WSX receptor variant 12.1 was unable to transmit a proliferative signal in this experiment (FIG. 8).

Materials and Methods

Recombinant PCR was used to generate the chimeric receptors containing the extracellular and transmembrane domains of the hGH receptor and the cytoplasmic domain of either WSX receptor variant 12.1 or variant 13.2. In short, the cytoplasmic domain of either variant 12.1 or 13.2 beginning with Arg at amino acid 866 and extending down to amino acid 958 or amino acid 1165 respectively, was fused in frame, by sequential PCR, to the hGH receptor extracellular and transmembrane domain beginning with Met at amino acid 18 and extending down to Arg at amino acid 274. The GH-WSX chimera was constructed by first using PCR to generate the extracellular and transmembrane domain of the human GH receptor. The 3' end primer used for this PCR contained 20 nucleotides at the 5' end of the primer corresponding to the first 20 nucleotides of the WSX cytoplasmic domain. The 3' end of the chimera was generated using PCR where the 5' end primer contained the last 19 nucleotides of the human GH receptor transmembrane domain. To generate the full length chimera, the 5' end of the human GH receptor product was combined with the 3' end WSX receptor cytoplasmic PCR product and subsequently amplified to create a fusion of the two products.

This chimeric fusion was digested with ClaI and XbaI and ligated to pRKtkNeo (Holmes et al., *Science* 253:1278-1280 (1991)) to create the chimeric expression vector. The IL-3 dependent cell line Baf3 was then electroporated with this hGH/WSX chimeric expression vector.

Briefly, 100 μg of the pRKtkNeo/GH.WSX plasmid was linearized, ethanol precipitated and resuspended in 100 μL of RPMI 1640. $7\times10^6$ Baf3 cells ($5\times10^5$/ml) were suspended in 900 μL of RPMI and added to the linearized plasmid. Following electroporation at 325V, 1180 μF using a BRL electroporation apparatus, the cells were plated into 15 mls of RPMI 1640 containing 5% wehi conditioned media and 15% serum. 48 hours later, cells were selected in 2 mg/ml G418.

To obtain the Baf3/GH.WSX cell lines, the G418 selected cells were FACS sorted using an anti-human GH mAb (3B7) at 1 μg/ml. The top 10% expressing cells were selected and expanded.

EXAMPLE 6

Expression Analysis of the WSX Receptor

The expression profile of the WSX receptor was initially examined by Northern analysis. Northern blots of human fetal or adult tissue mRNA were obtained from Clontech (Palo Alto, Calif.). A transcript of approximately 6 kb was detected in human fetal lung, liver and kidney. In the adult, low level expression was detected in a variety of tissues including liver, placenta, lung skeletal muscle, kidney, ovary, prostate and small intestine.

PCR analysis of human cord blood identified transcripts in $CD34^+$ subfraction. By PCR analysis, all three variants of the WSX receptor were present in $CD34^+$ cells. The $CD34^-$ subfraction appeared negative by this same PCR analysis.

By PCR analysis, both the 6.4 variant and 13.2 variant were evident in the $AA4^+Sca^+Kit^+$ (flASK) cell population isolated from the mid-gestation fetal liver as described in Zeigler et al., *Blood* 84:2422-2430 (1994). No clones containing the 12.1 variant cytoplasmic tail have been isolated from murine tissues.

Human B cells isolated from peripheral blood using anti-CD19/20 antibodies were also positive for short form (6.4 variant) and long from (13.2 variant) receptor mRNA expression.

The WSX receptor appears to be expressed on both progenitor and more mature hematopoietic cells.

EXAMPLE 7

Cloning of Murine WSX Receptor

The human WSX receptor was used as a probe to isolate murine WSX receptor. The pRKtkNeo.WSX plasmid of Example 4 was digested using Ssp1. This Ssp1 fragment (1624 bps) was isolated, and radiolabelled, and used to screen a murine liver λgt10 library (Clontech). This resulted in 4 positive clones which were isolated and sequenced after subcloning into $pBSSK^-$ via EcoRI digestion. The resultant clones, designated 1, 2, 3, 4 showed homology to the extracellular domain of the human WSX receptor; the contiguous sequences resulting from these clones extended from the initiation methionine to tryptophan at position 783. The overall similarity of human WSX receptor and murine WSX receptor is 73% over this region of the respective extracellular domains (see FIGS. 4A-D).

EXAMPLE 8

The Role of WSX Receptor in Hematopoietic Cell Proliferation

The presence of the WSX receptor in the enriched human stem cell population $CD34^+$ from cord blood is indicative of a potential role for this receptor in stem cell/progenitor cell proliferation. The proliferation of $CD34^+$ human blood cells in methylcellulose media (Stem Cell Technologies) was determined in the presence or absence of WSX receptor antisense oligonucleotides. These experiments were also repeated in the murine hematopoietic system using $AA4^+Sca^+Kit^+$ stem cells from the murine fetal liver. In both instances, the antisense oligonucleotides statistically significantly inhibited colony formation from the hematopoietic progenitor cells. See Table 1 below. The anti-proliferative effects were most pronounced using the −20 antisense and the +85 antisense oligonucleotide constructs. This inhibition was not lineage specific to any particular myeloid lineage that resulted from the progenitor expansion. The principal effect of the antisense oligonucleotides was a reduction of overall colony numbers. The size of the individual colonies was also reduced.

Antisense oligonucleotide experiments using both human and murine stem cells demonstrated an inhibition of myeloid colony formation. Although, the reduction in myelopoiesis observed in these assays could be prevented by the additional inclusion of G-CSF and GM-CSF in the culture medium. These data serve to illustrate the redundancy of cytokine action in the myelopoietic compartment.

TABLE 1

| EXPERIMENT | OLIGO | AVG. COLONY # | % INHIBITION |
|---|---|---|---|
| Human Cord Blood (KL) | (−20)AS | 32 | |
| | (−20)S | 100 | 70 |
| | (−20)SCR | 114 | |
| | (+85)AS | 80 | |
| | (+85)S | 123 | 38 |
| | (+85)SCR | 138 | |
| | Control | 158 | |
| Human Cord Blood (IL-3, IL-6, KL) | (−20)AS | 78 | |
| | (−20)S | 188 | 54 |
| | (−20)SCR | 151 | |
| | (+85)AS | 167 | |
| | (+85)S | 195 | 18 |
| | (+85)SCR | 213 | |
| | Control | 266 | |
| Human Cord Blood (KL) | (−20)AS | 42 | |
| | (−20)S | 146 | 69 |
| | (−20)SCR | 121 | |
| | (+85)AS | 123 | |
| | (+85)S | 162 | 23 |
| | (+85)SCR | 156 | |
| | Control | 145 | |
| Murine Fetal Liver (KL) | (+84)AS | 33 | |
| | (+84)S | 86 | 54 |
| | (+84)SCR | 57 | |
| | (−20)AS | 27 | |
| | (−20)S | 126 | 71 |
| | (−20)SCR | 60 | |
| | (−99)AS | 109 | |
| | (−99)S | 93 | 0 |
| | (−99)SCR | 109 | |
| | Control | 121 | |
| Murine Fetal Liver (KL) | (−213)AS | 51 | |
| | (−213)S | 60 | 10 |
| | (−213)SCR | 53 | |
| | (+211)AS | 58 | |
| | (+211)S | 54 | 3 |
| | (+211)SCR | 66 | |
| | Control | 59 | |

Materials and Methods

Human stem cells: Human umbilical cord blood was collected in PBS/Heparin (1000 μ/ml). The mononuclear fraction was separated using a dextran gradient and any remaining red blood cells lysed in 20 mM $NH_4$ Cl. $CD34^+$ cells were isolated using $CD34^+$ immunomagnetic beads (Miltenyi, Calif.). These isolated $CD34^+$ cells were found to be 90-97% $CD34^+$ by FACS analysis.

Murine stem cells: Midgestation fetal liver were harvested and positively selected for the $AA4^-$ antigen by immune panning. The AA4⁻ positive fraction was then further enriched for stem cell content by FACS isolation of the AA4⁺Sca⁺Kit⁺ fraction.

Antisense experiments: Oligodeoxynucleotides were synthesized against regions of the human or murine WSX receptors. For each oligonucleotide chosen, antisense (AS), sense (S) and scrambled (SCR) versions were synthesized (see FIG. 7). + or − indicates position relative the initiation methionine of the WSX receptor. CD34⁺ or AA4⁺Sca⁺Kit⁺ cells were incubated at a concentration of $10^3$/ml in 50:50 DMEM/F12 media supplemented with 10% FBS, L-glutamine, and GIBCO™ lipid concentrate containing either sense, antisense or scrambled oligonucleotides at a concentration of 70 µg/ml. After 16 hours, a second aliquot of the respective oligonucleotide was added (35 µg/ml) and the cells incubated for a further 6 hours.

Colony assays: 5000 cells from each of the above conditions were aliquoted into 5 ml of methylcellulose (Stem Cell Technologies) containing kit ligand (KL) (25 ng/ml), interleukin-3 (IL-3) (25 ng/ml) and interleukin-6 (IL-6) (50 ng/ml). The methylcellulose cultures were then incubated at 37° C. for 14 days and the resultant colonies counted and phenotyped. All assays were performed in triplicate.

EXAMPLE 9

WSX Receptor Variant 13.2 is a Receptor for OB Protein

Figure 9:
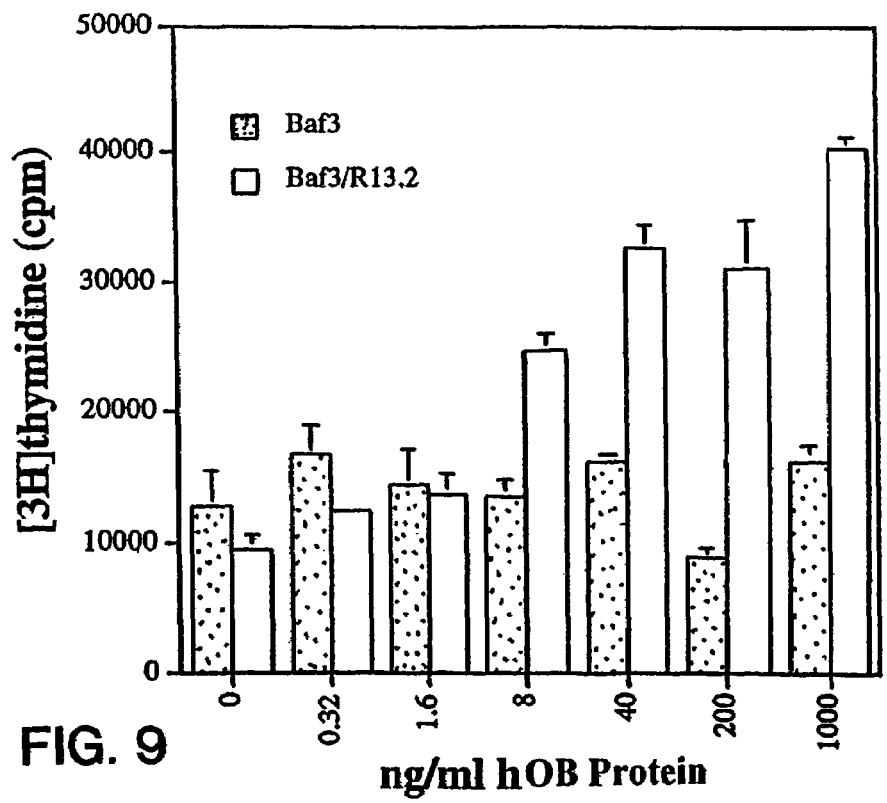

The WSX receptor variant 13.2 has essentially the same amino acid sequence as the recently cloned leptin (OB) receptor. See Tartaglia et al., *Cell* 83:1263-1271 (1995). OB protein was able to stimulate thymidine incorporation in Baf3 cells transfected with WSX receptor variant 13.2 as described in Example 4 (See FIG. 9).

OB protein expression in hematopoietic cells was studied. Oligonucleotide primers designed specifically against the OB protein illustrated the presence of this ligand in fetal liver and fetal brain as well as in two fetal liver stromal cell lines, designated 10-6 and 7-4. Both of these immortalized stromal cell lines have been demonstrated to support both myeloid and lymphoid proliferation of stem cell populations (Zeigler et al., *Blood* 84:2422-2430 (1994)).

EXAMPLE 10

Role of OB Protein in Hematopoiesis

To examine the hematopoietic activity of OB protein, a variety of in vitro assays were performed.

Murine fetal liver fLASK stem cells were isolated from the midgestational fetal liver as described in Zeigler et al., *Blood* 84:2422-2430 (1994) and studied in stem cell suspension culture or methylcellulose assays. For the stem cell suspension cultures, twenty thousand of the fLASK cells were seeded in individual wells in a 12 well format in DMEM 4.5/F12 media supplemented with 10% heat inactivated fetal calf serum (Hyclone, Logan, Utah) and L-glutamine. Growth factors were added at the following concentrations: kit ligand (KL) at 25 ng/mL, interleukin-3 (IL-3) at 25 ng/mL, interleukin-6 (IL-6) at 50 ng/mL, G-CSF at 100 ng/mL, GM-CSF at 100 ng/mL, EPO at 2U/mL, interleukin-7 (IL-7) at 100 ng/mL (all growth factors from R and D Systems, Minneapolis, Minn.). OB protein was added at 100 ng/mL unless indicated otherwise. Recombinant OB protein was produced as described in Levin et al., *Proc. Natl. Acad. Sci.* (*USA*) 93:1726-1730 (1996).

Figure 10A:
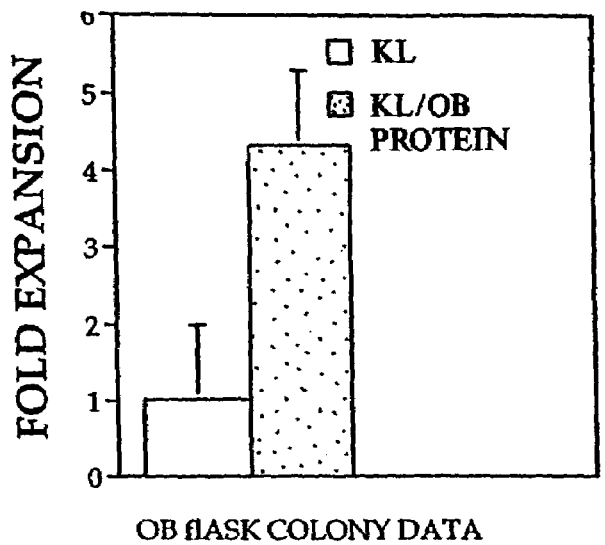
In FIGS. 10A-C, murine fetal liver AA4$^+$Sca$^+$Kit$^+$ (flASK) stem cells were cultured in suspension culture or methylcellulose.

In keeping with its ability to transduce a proliferative signal in Baf3 cells (see previous Example), OB protein dramatically stimulated the expansion of fLASK cells grown in suspension culture in the presence of kit ligand (FIG. 10A). The addition of OB protein alone to these suspension cultures was unable to effect survival of the hematopoietic stem cells (HSCs). When a variety of hematopoietic growth factors in suspension culture assays were tested, the main synergy of OB protein appeared to be with KL, GM-CSF and IL-3 (Table 2). No preferential expansion of any particular lineage was observed from cytospin analysis of the resultant cultures.

TABLE 2

| Factor | KL | KL + OB protein | OB protein |
|---|---|---|---|
| N/A | 128 +/− 9 | 192 +/− 13 | |
| G-CSF | 131 +/− 3 | 177 +/− 8 | 30 +/− 5 |
| GM-CSF | 148 +/− 4 | 165 +/− 6 | 134 +/− 10 |
| IL-3 | 189 +/− 7 | 187 +/− 4 | 144 +/− |
| IL-6 | 112 +/− 4 | 198 +/− 5 | 32 +/− 3 |
| EPO | 121 +/− 3 | 177 +/− 8 | 30 +/− 6 |
| IL-3 &IL-6 | 112 +/− 12 | 198 +/− 7 | 32 +/− 7 | fLASK stem cells were isolated. Twenty thousand cells were plated in suspension culture with the relevant growth factor combination. Cells were harvested and counted after 7 days. Cell numbers are presented $\times 10^3$. Assays were performed in triplicate and repeated in two independent experiments.

Methylcellulose assays were performed as previously described (Zeiger et al., supra). Briefly, methylcellulose colony assays were performed using "complete" methylcellulose or pre-B methylcellulose medium (Stem Cell Technologies, Vancouver, British Columbia, Canada) with the addition of 25 ng/mL KL (R and D Systems, Minneapolis, Minn.). Cytospin analyses of the resultant colonies were performed as previously described in Zeigler et al.

Figure 10B:
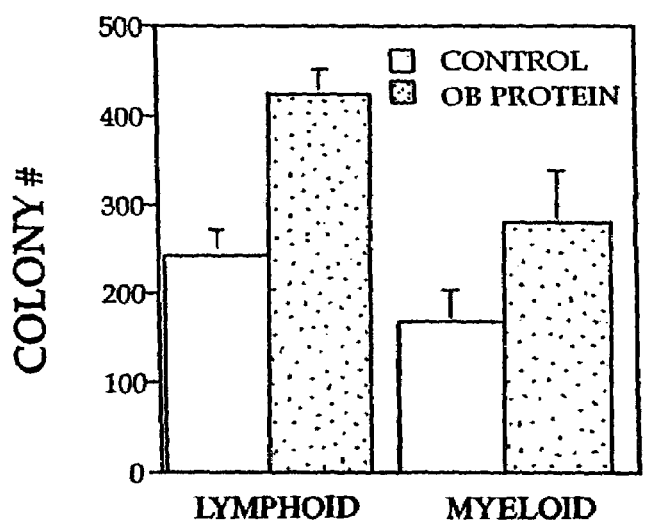
Figure 10C:
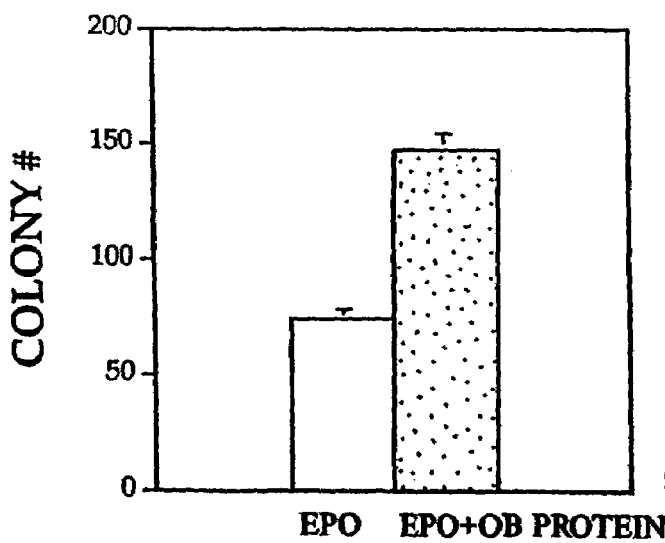

When these methylcellulose assays were employed, OB protein augmented myeloid colony formation and dramatically increased lymphoid and erythroid colony formation (FIGS. 10B and 10C) which demonstrates that OB protein can act on very early cells of the hematopoietic lineage. Importantly, the hematopoietic activity of OB protein was not confined to fetal liver stem cells, the murine bone marrow stem cell population; Lin$^{lo}$Sca⁺ also proliferated in response to OB protein (KL: 5 fold expansion, KL and OB protein: 10 fold expansion).

Further hematopoietic analysis of the role of the WSX receptor was carried out by examining hematopoietic defects in the db/db mouse.

Figure 11:
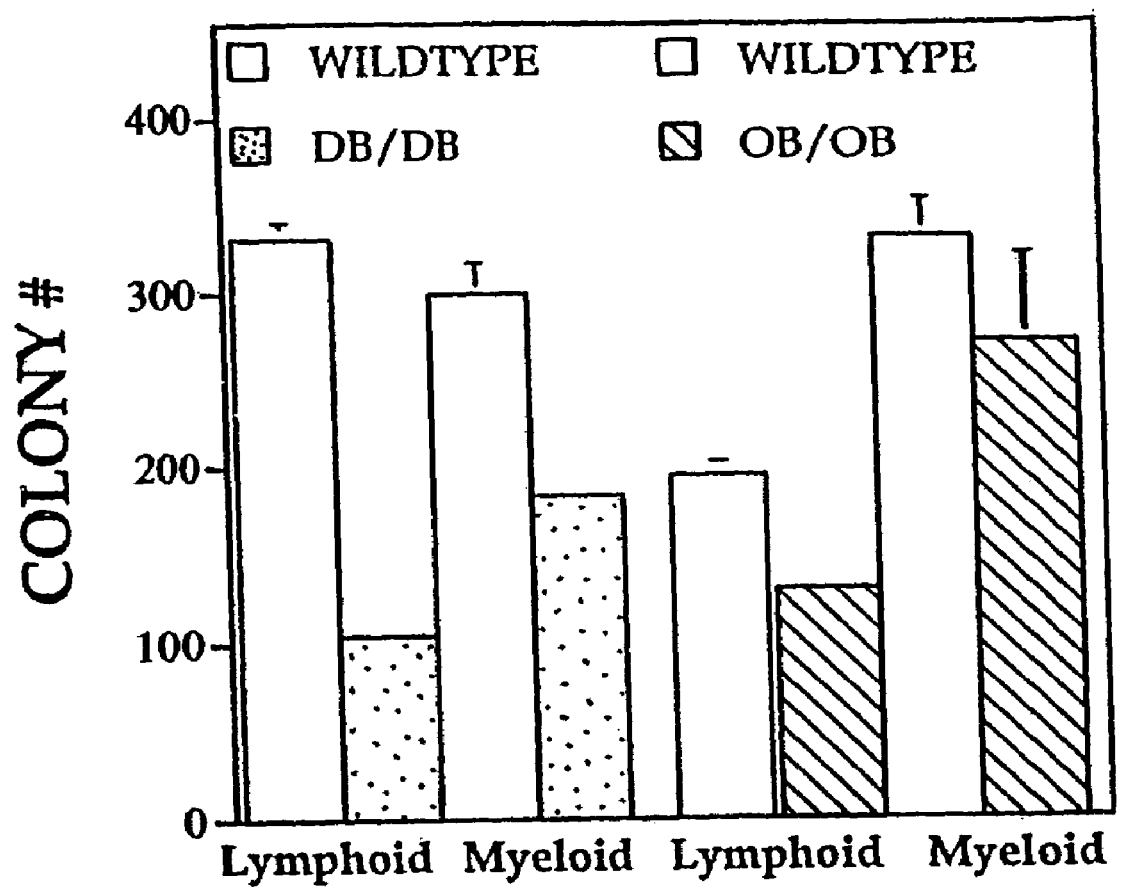
FIG. 11 illustrates methylcellulose assays to determine the colony forming potential of db/db, ob/ob and the corresponding wild-type marrow. 100,000 bone marrow cells were seeded into methylcellulose and the resultant colonies counted after 14 days. Assays were performed using both myeloid and lymphoid conditions. Assays were performed in triplicate and the experiments were repeated a minimum of 3 times.

These defects were assessed by measuring the proliferative potential of db/db homozygous mutant marrow. Under conditions favoring either myeloid (Humphries et al., *Proc. Natl. Acad. Sci.* (*USA*) 78:3629-3633 (1981)) or lymphoid (McNiece et al., *J. Immunol.* 146:3785-90(1991)) expansion, the colony forming potential of the db/db marrow was significantly reduced when compared to the wild-type control marrow (FIG. 11). This was particularly evident when the comparison was made under pre-B methylcellulose conditions where KL and IL-7 are used to drive lymphopoiesis (McNiece et al., supra). Corresponding analysis of the complementary mouse mutation ob/ob, which is deficient in the production of OB protein (Zhang et al., *Nature* 372:425-431 (1994)), also indicated that the lymphoproliferative capacity is compromised in the absence of a functional OB protein signalling pathway (FIG. 11). However, this reduction was less than the reduction observed using db/db marrow.

Figure 12A:
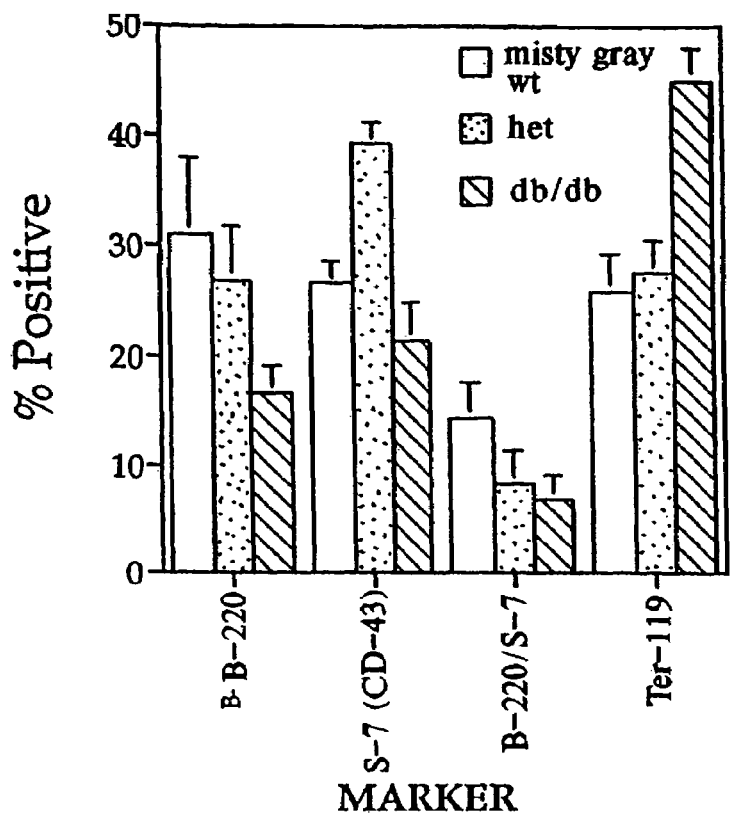
FIGS. 12A-B show bone marrow cellular profiles in wild-type misty gray homozygotes, misty gray/db heterozygotes, and homozygote db/db mice. Overall cellularity in the db/db marrow was unchanged compared to controls.

Analysis of the cellular profile of the db/db and wild-type marrow revealed significant differences between the two. Overall cellularity of the db/db marrow was unchanged. However, when various B cell populations in the db/db marrow were examined, both decreased levels of $B220^+$ and $B220^+/CD43^+$ cells were found. $B220^+$ cells represent all B cell lineages while CD43 is considered to be expressed preferentially on the earliest cells of the B cell hierarchy (Hardy et al., *J. Exp. Med.* 173:1213-25 (1991)). No differences were observed between the CD4/CD8 staining profiles of the two groups. The TER119 (a red cell lineage marker) population was increased in the db/db marrow (FIG. 12A).

Figure 12B:
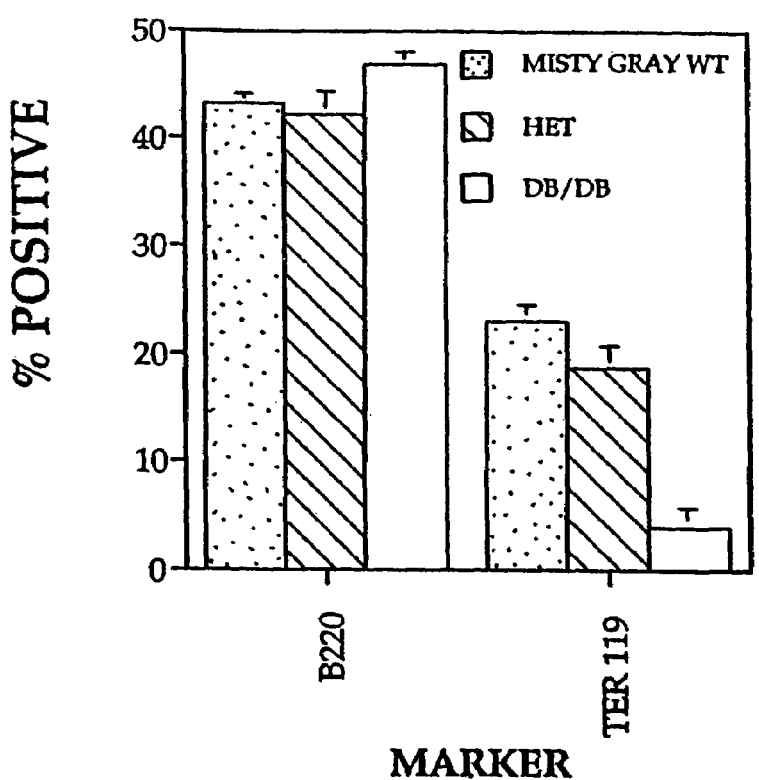

Comparison of the spleens from the two groups revealed a significant decrease in both tissue weight and cellularity of the db/db mice compared to the homozygote misty gray controls ($0.063 \pm 0.009$ g vs. $0.037 \pm 0.006$ g and $1.10 \times 10^7 \pm 1 \times 10^4$ vs. $4.3 \times 10^6 \pm 10^3$ cells >p0.05). This decreased cellularity in the db spleen was reflected in a marked reduction in TER119 staining (FIG. 12B). This result appears to confirm the synergy demonstrated between OB protein and EPO and points to a role for OB protein in the regulation of erythropoiesis.

Examination of the hematopoietic compartment of the db/db mouse in vivo demonstrated a significant reduction in peripheral blood lymphocytes when compared to heterozygote or wild-type controls. Db/db mice fail to regulate blood glucose levels and become diabetic at approximately 6-8 weeks of age; therefore, peripheral blood counts as the animals matured were followed.

Figure 13A:
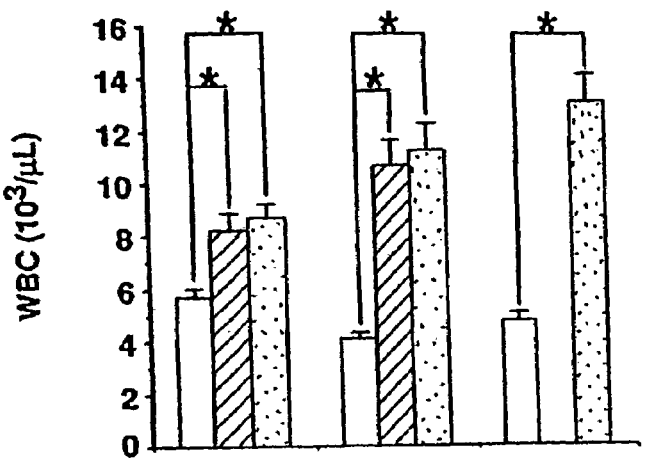
FIGS. 13A-C are an analysis of peripheral blood in db/db homozygotes, db/db misty gray heterozygotes and misty gray homozygotes. 40 microliters of peripheral blood was taken via orbital bleed and analyzed on a Serrono Baker system 9018. All areas described by the boxes represent the mean± one standard deviation of the two parameters.
Figure 13B:
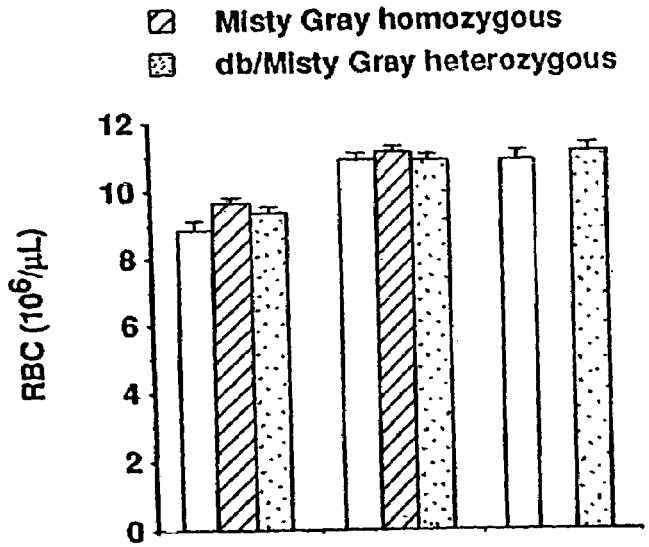
Figure 13C:
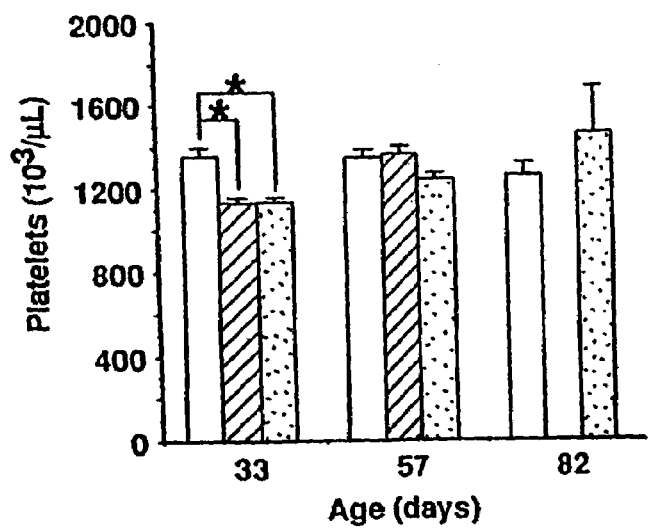

For procurement of blood samples, prior to the experiment and at time points throughout the study, 40 μL of blood was taken from the orbital sinus and immediately diluted into 10 mL of diluent to prevent clotting. The complete blood count from each blood sample was measured on a Serrono Baker system 9018 blood analyzer within 60 min. of collection. Only half the animals in each dose group were bled on any given day, thus, each animal was bled on alternate time points. Blood glucose levels were measured in orbital sinus blood samples using One Touch glucose meters and test strips (Johnson and Johnson). The results of this experiment are shown in FIGS. 13A-C.

This analysis demonstrated that peripheral blood lymphocytes are significantly reduced at all time points compared to control animals and that the peripheral lymphocyte population of the db/db mouse does not change significantly with age. FACS analysis revealed that the decreased lymphocyte population represented a decrease in both $B220^+$ cells and CD4/CD8 cells. Both erythrocyte and platelets are at wild-type levels throughout all time periods examined. The peripheral blood lymphocyte levels in ob/ob homozygous mutant mice were unchanged from wild-type controls.

Figure 14:
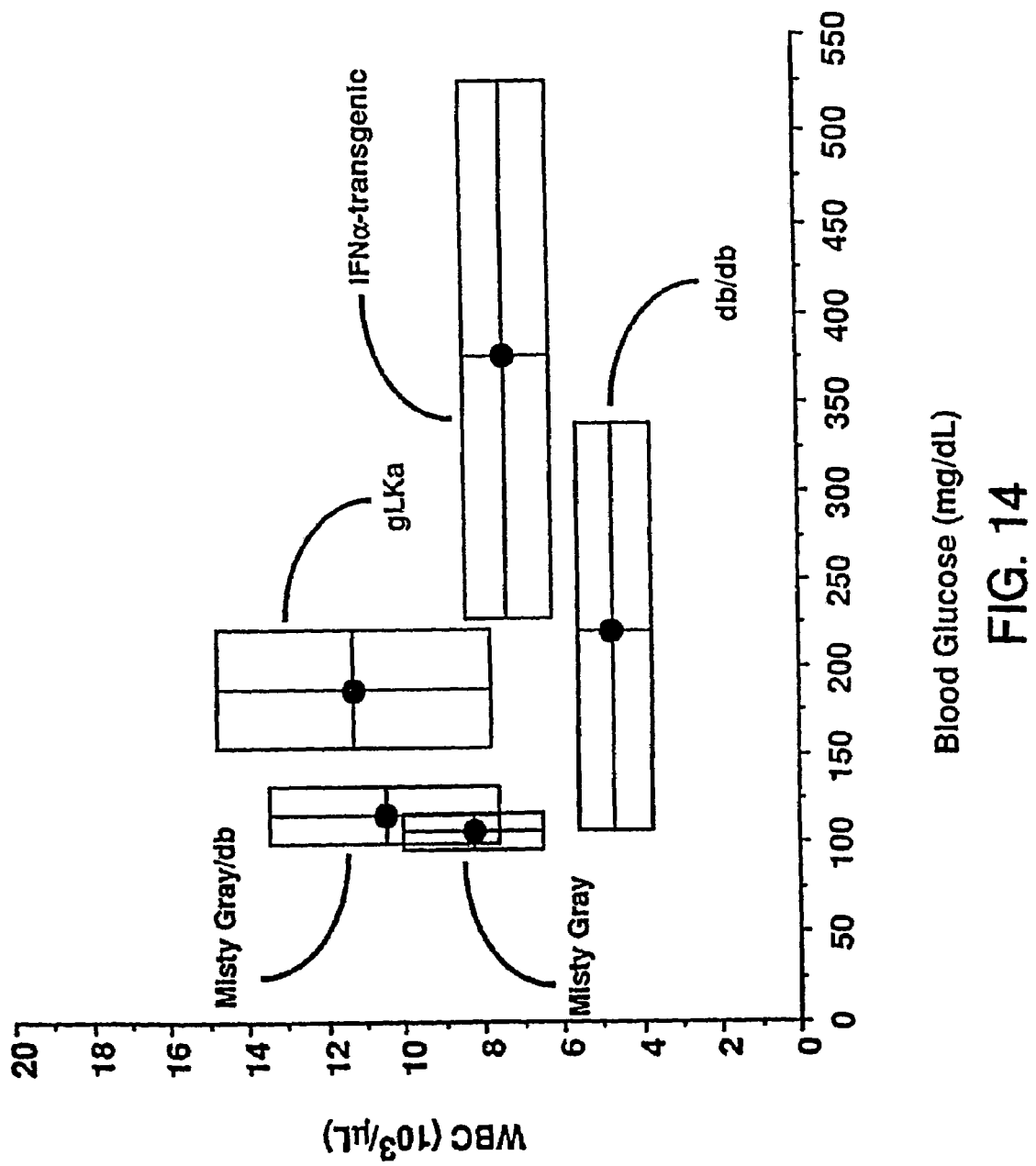
FIG. 14 is a comparison of peripheral lymphocyte counts and blood glucose level. Five groups of animals, misty-gray, misty-gray/db, db/db, interferon α-transgenic, and glucokinase transgenic heterozygote mice (gLKa) were sampled via retro-orbital bleed. Blood glucose levels in these mice were determined. All areas described by the boxes represent the mean±standard deviation of the two parameters.
Figure 15A:
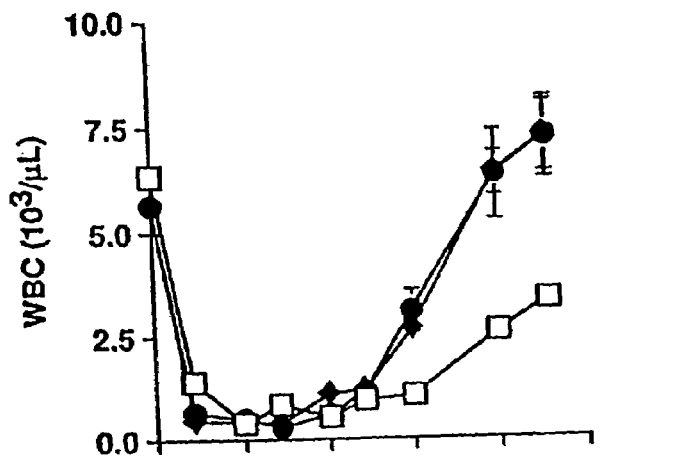
In FIGS. 15A-C, misty gray homozygotes, db/misty gray heterozygotes, and homozygous db/db mice were subjected to sub-lethal irradiation and the recovery kinetics of the peripheral blood was determined via retro-orbital bleeds.
Figure 15B:
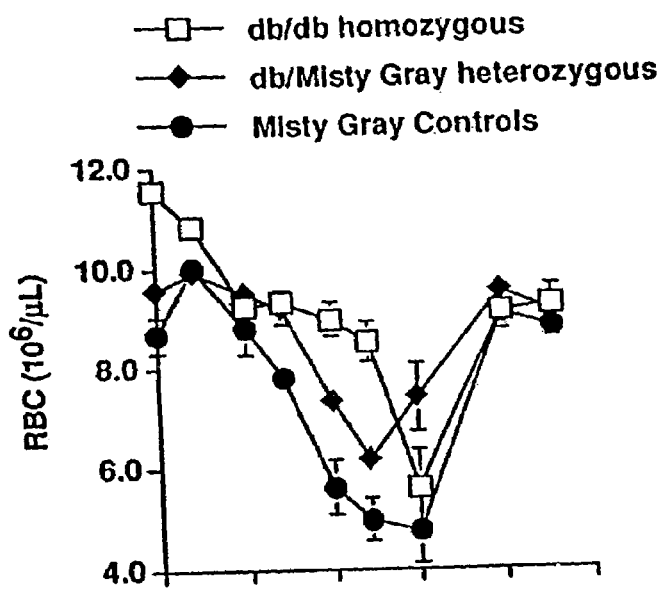
Figure 15C:
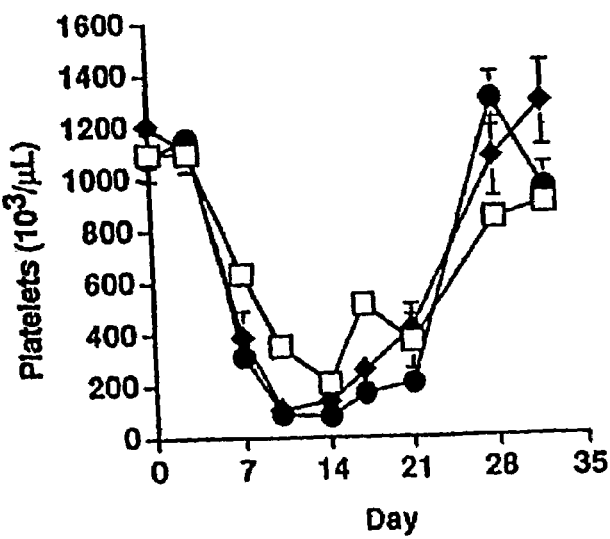
Figure 17:
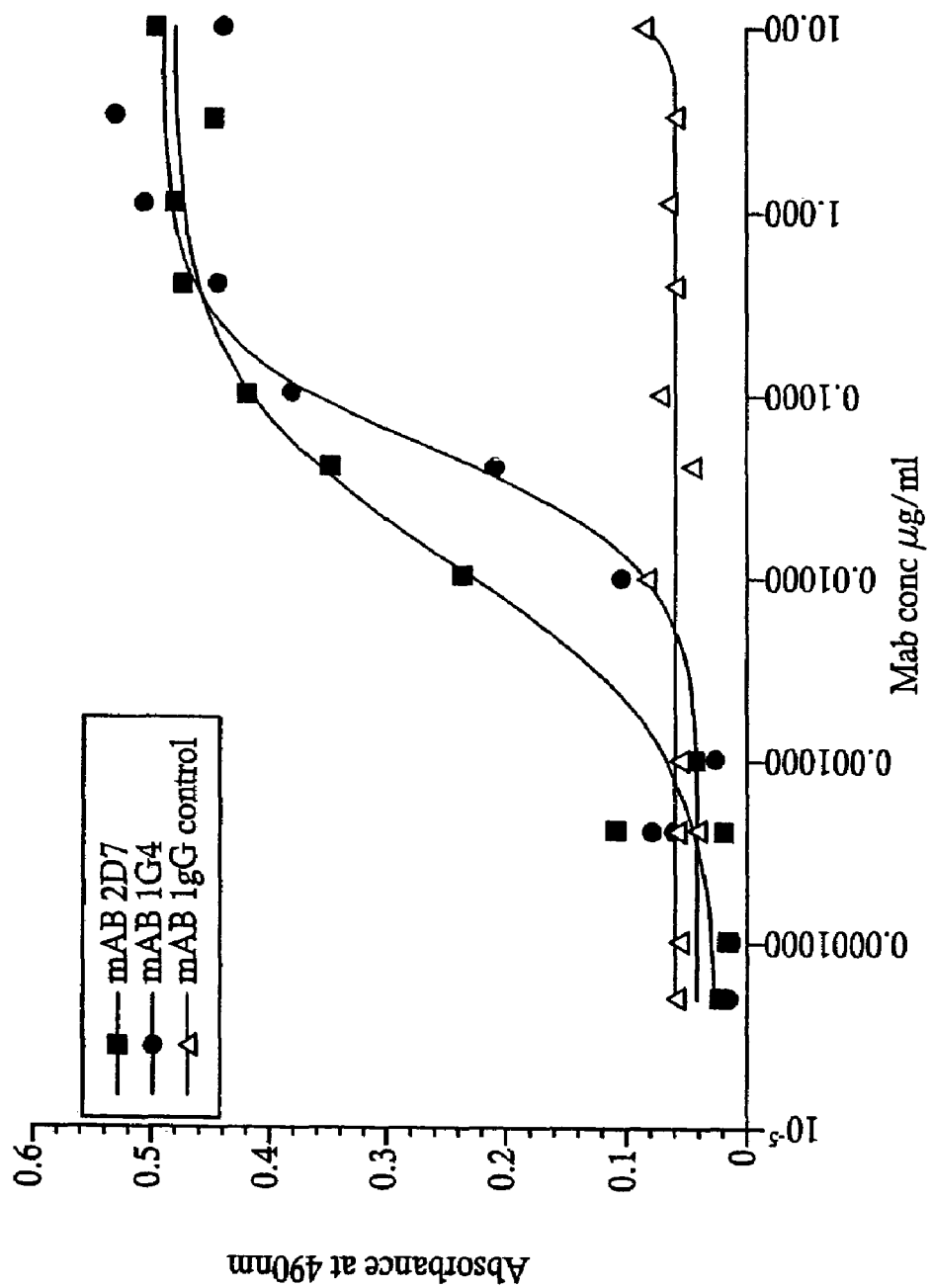
FIG. 17 shows binding of anti-WSX receptor agonist antibodies to human WSX receptor. The anti-WSX receptor agonist antibodies (2D7 and 1G4) produced as described in Example 13 and an IgG isotype control were evaluated for their ability to bind to human WSX receptor by capture ELISA.
Figure 18:
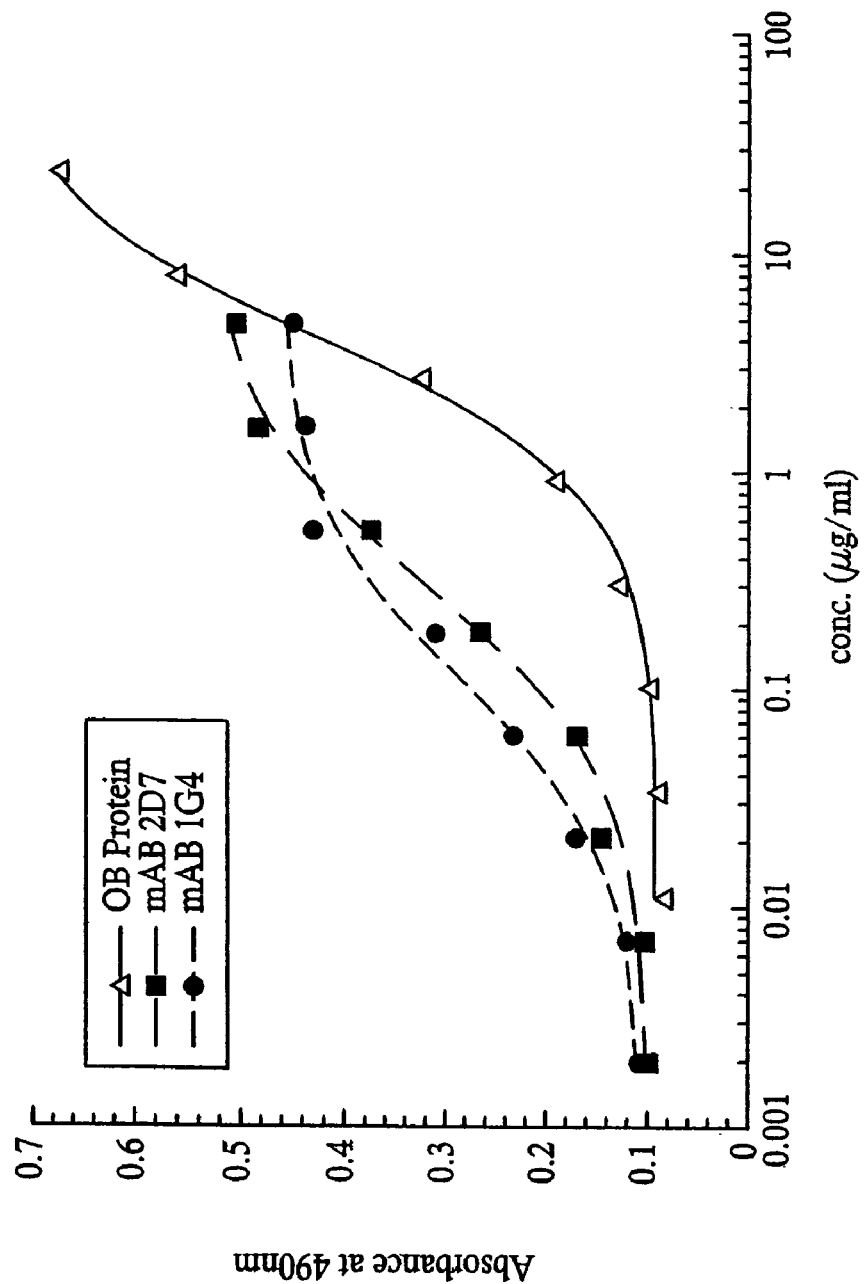
FIG. 18 shows the activity of mAbs 2D7 and 1G4 as well as OB protein in the KIRA ELISA (see Example 13). Absorbance at 490 nm versus concentration of antibody or ligand in this assay is shown.
Figure 19:
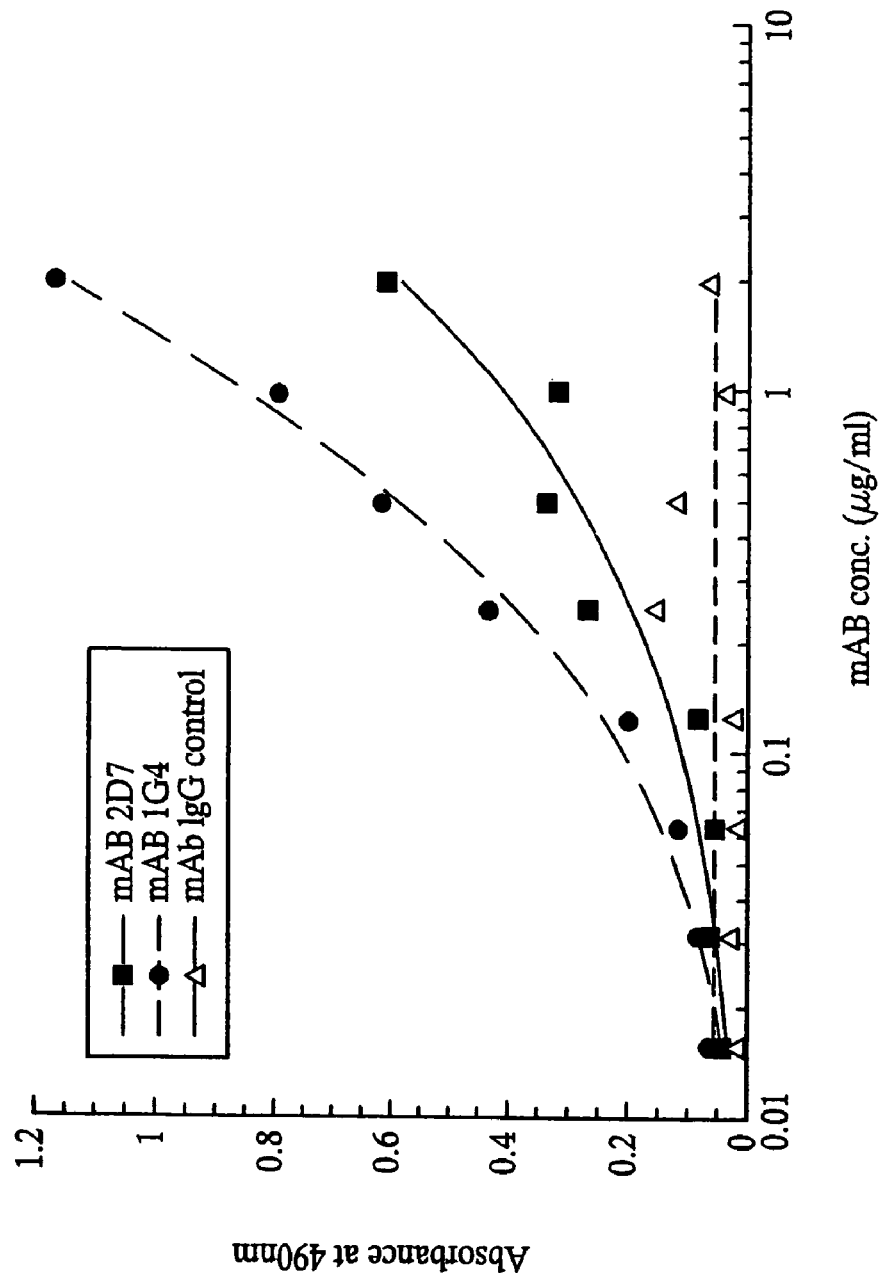
FIG. 19 depicts binding of anti-WSX receptor agonist antibodies to murine WSX receptor. The anti-WSX receptor agonist antibodies (2D7 and 1G4) and an IgG isotype control were evaluated for their ability to bind to murine WSX receptor by capture ELISA.
Figure 20B:
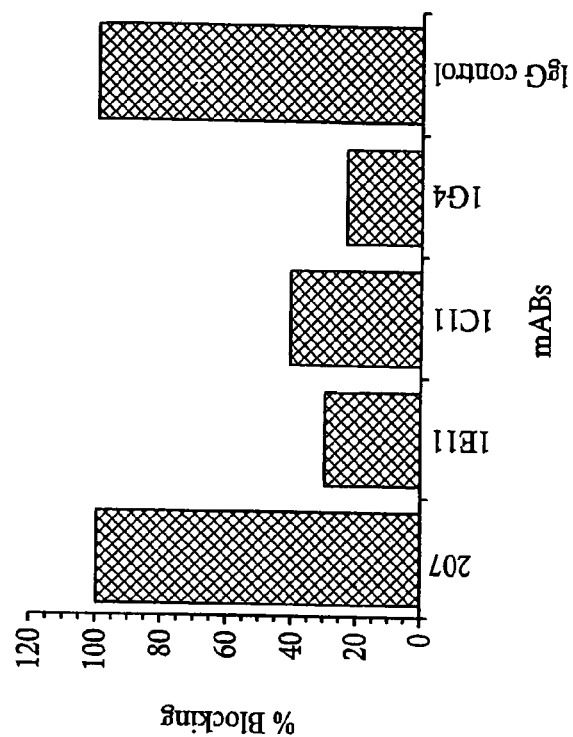
FIGS. 20A-B show the results of epitope mapping of the agonist anti-WSX receptor antibodies produced as described in Example 13.
Figure 20A:
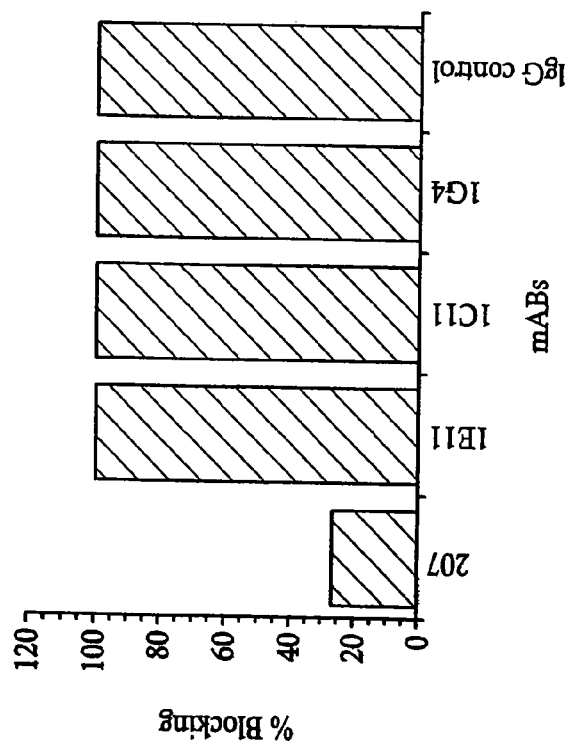

Hematopoietic analysis of the db/db mouse can be complicated by the onset of diabetes. Therefore, the impact of high glucose levels on lymphopoiesis was examined by comparing the peripheral blood profiles and blood glucose levels in two other diabetic models, the glucokinase knockout heterozygote mouse (Grupe et al., *Cell* 83:69-78 (1995)) and the IFN-α transgenic mouse (Stewart et al., *Science* 260:1942-6 (1993)). Comparison of peripheral lymphocytes and blood glucose in db/db mice, their appropriate controls and the high glucose models illustrated no relationship between blood-glucose and lymphocyte counts (FIG. 14). These results suggest therefore that the lymphoid defects observed in the db/db mouse are directly attributed to the hematopoietic function of the OB protein signalling pathway.

To test the capacity of the db/db hematopoietic compartment to respond to challenge, the db/db mice and controls were subjected to sub-lethal irradiation C57BLKS/J db/db, C57BLKS/Jm$^+$/db, and C57BLKS/J$^+$m/$^+$m mice were subjected to sub-lethal whole body irradiation (750 cGy, 190 cGy/min) as a single dose from a $^{137}$CS source. Ten animals were used per experimental group. The kinetics of hematopoietic recovery were then followed by monitoring the peripheral blood during the recovery phase. This experiment illustrated the inability of the db/db hematopoietic system to fully recover the lymphopoietic compartment of the peripheral blood 35 days post-irradiation. Platelet levels in these mice followed the same recovery kinetics as controls, however the reduction in erythrocytes lagged behind controls by 7-10 days. This finding may reflect the increased TER 119 population found in the marrow of the db/db mice (FIG. 12A).

Materials and Methods

Bone marrow, spleens and peripheral blood was harvested from the diabetic mouse strains: C57BLKS/J db/db (mutant), C57BLKS/J m+/db (lean heterozygote control littermate), C57BLKS/J+m/+m (lean homozygote misty gray coat control littermate) and the obese mouse strains: C57BL16J-ob/ob (mutant) and the C57BL/6J-ob/+ (lean littermate control). All strains from the Jackson Laboratory, Bar Harbor, Me. A minimum of five animals were used per experimental group. Femurs were flushed with Hank's balanced salt solution (HBSS) plus 2% FCS and a single cell suspension was made of the bone marrow cells. Spleens were harvested and the splenic capsule was ruptured and filtered through a nylon mesh. Peripheral blood was collected through the retro-orbital sinus in phosphate buffered saline (PBS) with 10 U/mL heparin and 1mmol EDTA and processed as previously described. The bone marrow, splenocytes and peripheral blood were then stained with the monoclonal antibodies against the following antigens: B220/CD45R (Pan B cell) FITC antimouse, TER-119/erythroid cell R-PE antimouse, CD4 (L3T4), FITC antimouse, CD8 (Ly 3.2), FITC antimouse, and sigM (Igh-6b), FITC antimouse (All monoclonals from Pharmigen, San Diego, Calif.). The appropriate isotype controls were included in each experiment. For methylcellulose assays, the bone marrow from five animals per group was pooled and 100,000 cell aliquots from each group used for each assay point.

EXAMPLE 11

Expression of OB-Immunoadhesin

Figure 16C:
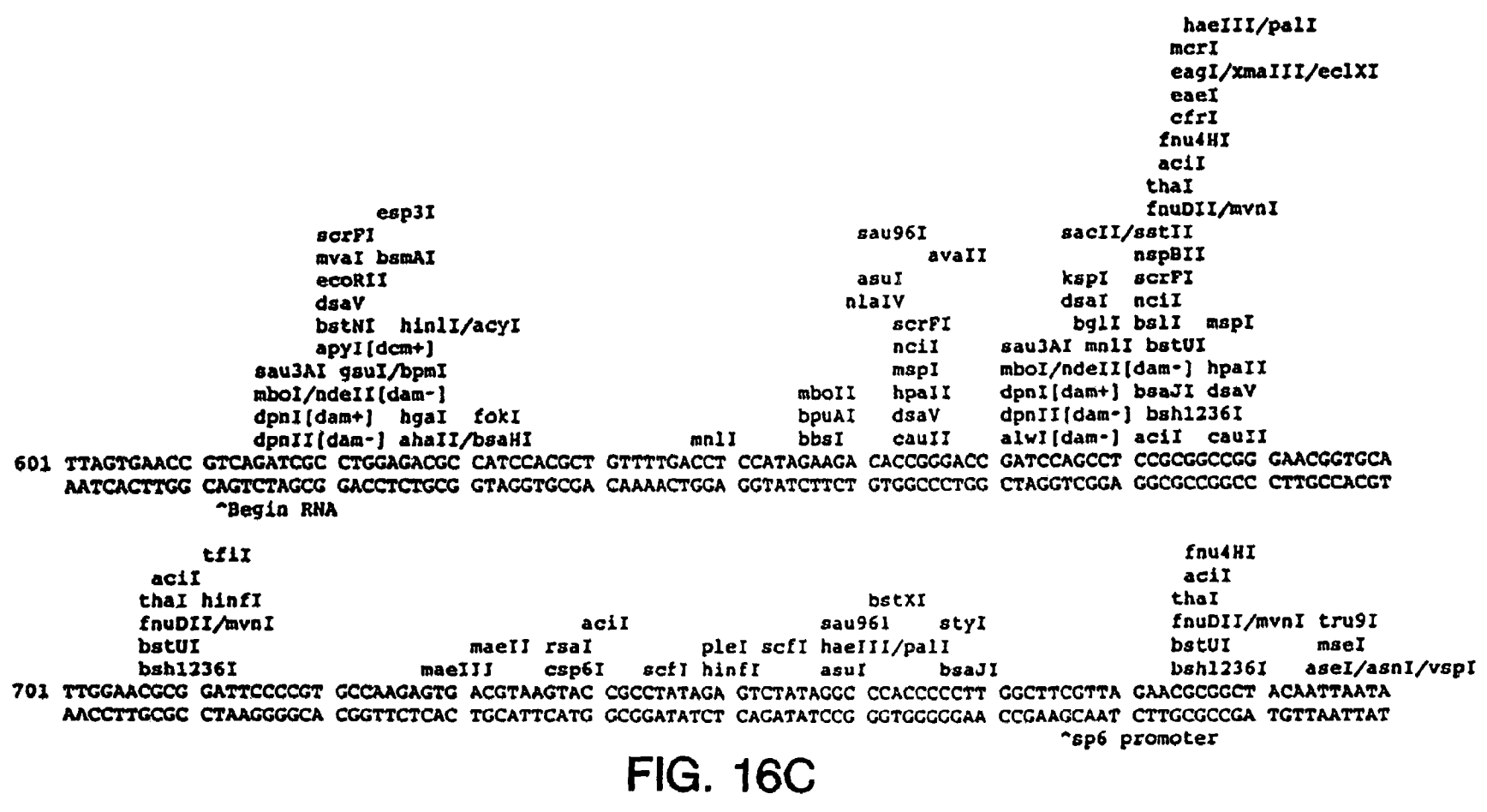
Figure 16D:
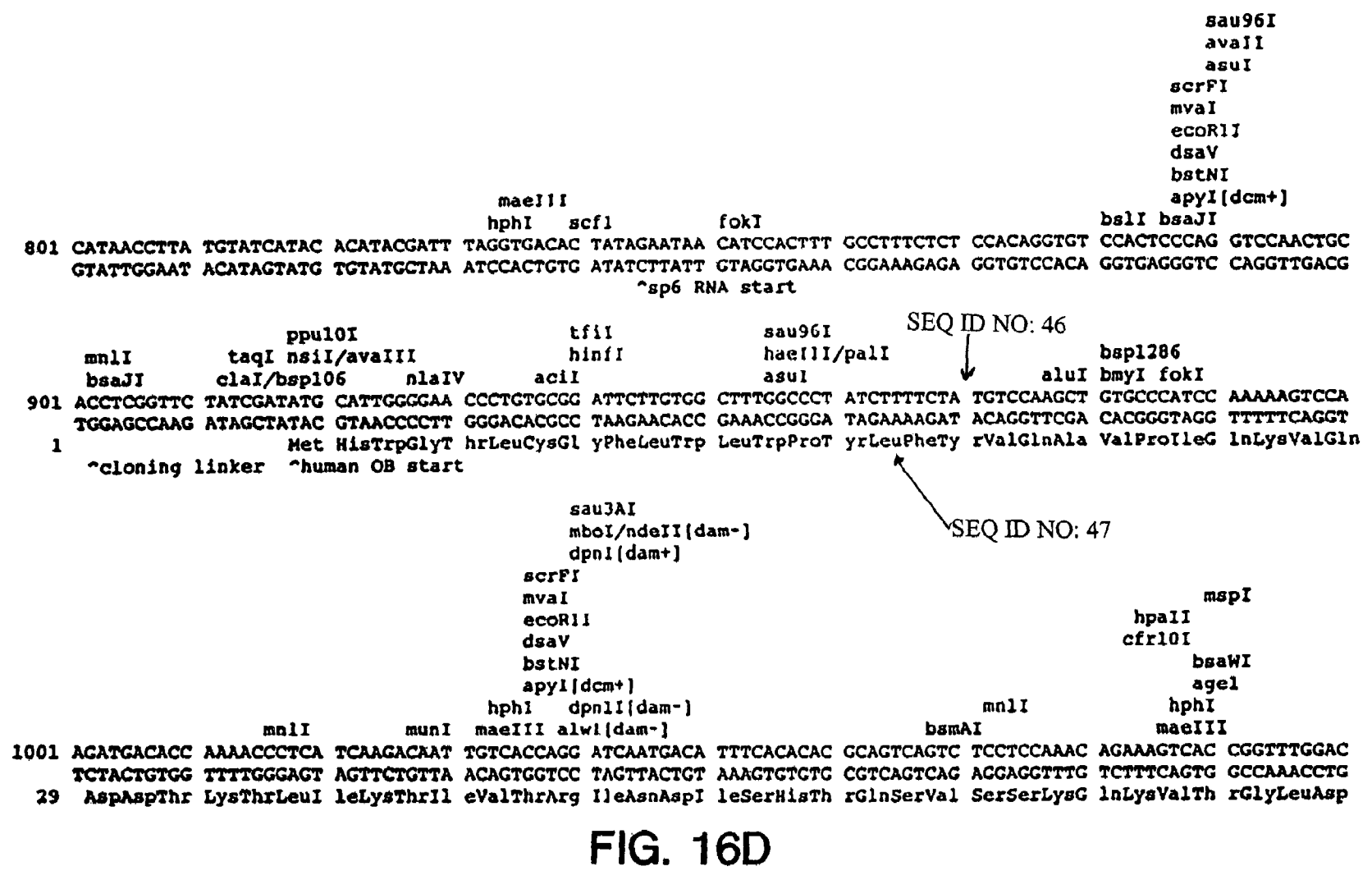
Figure 16E:
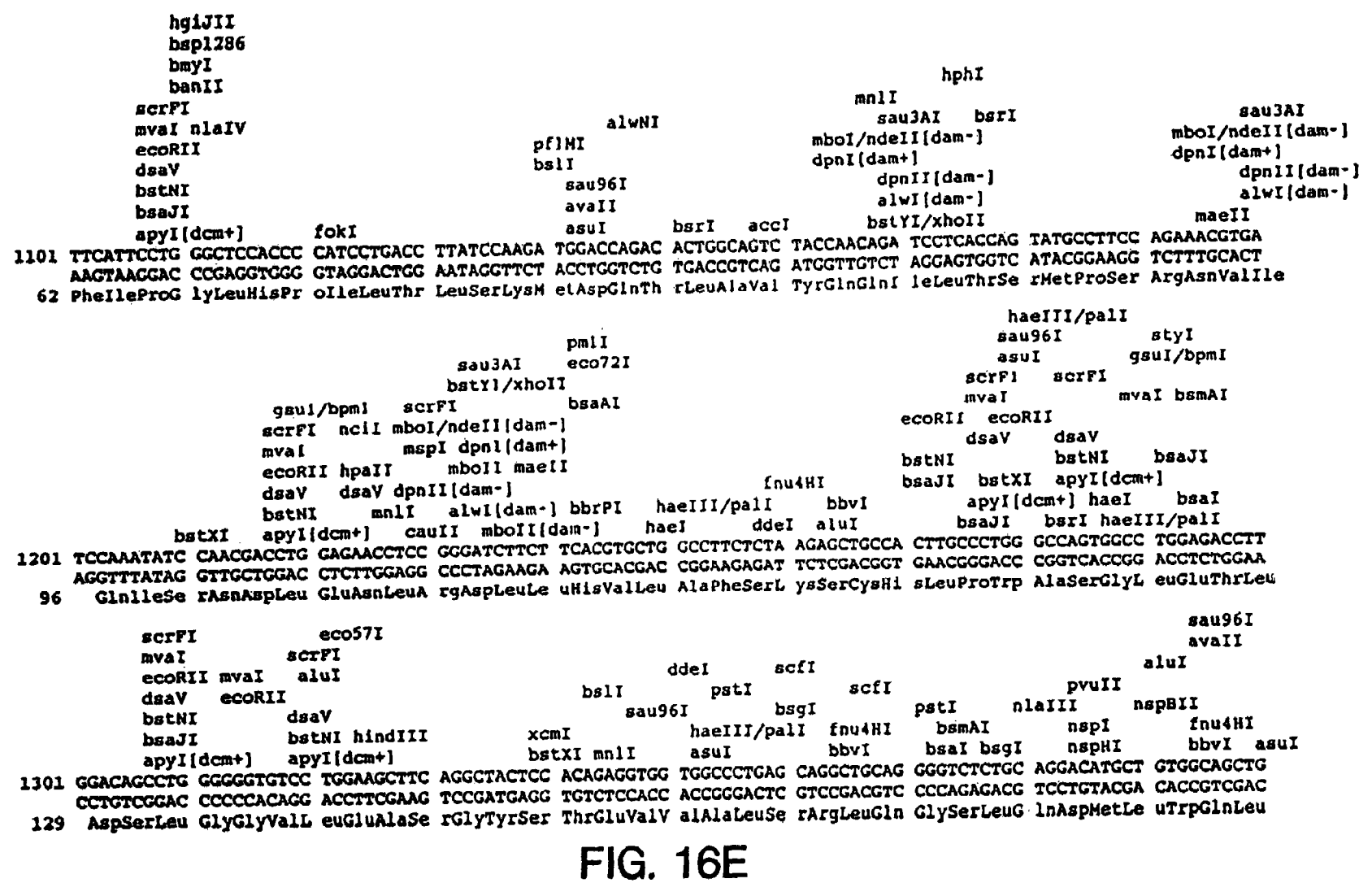
Figure 16G:
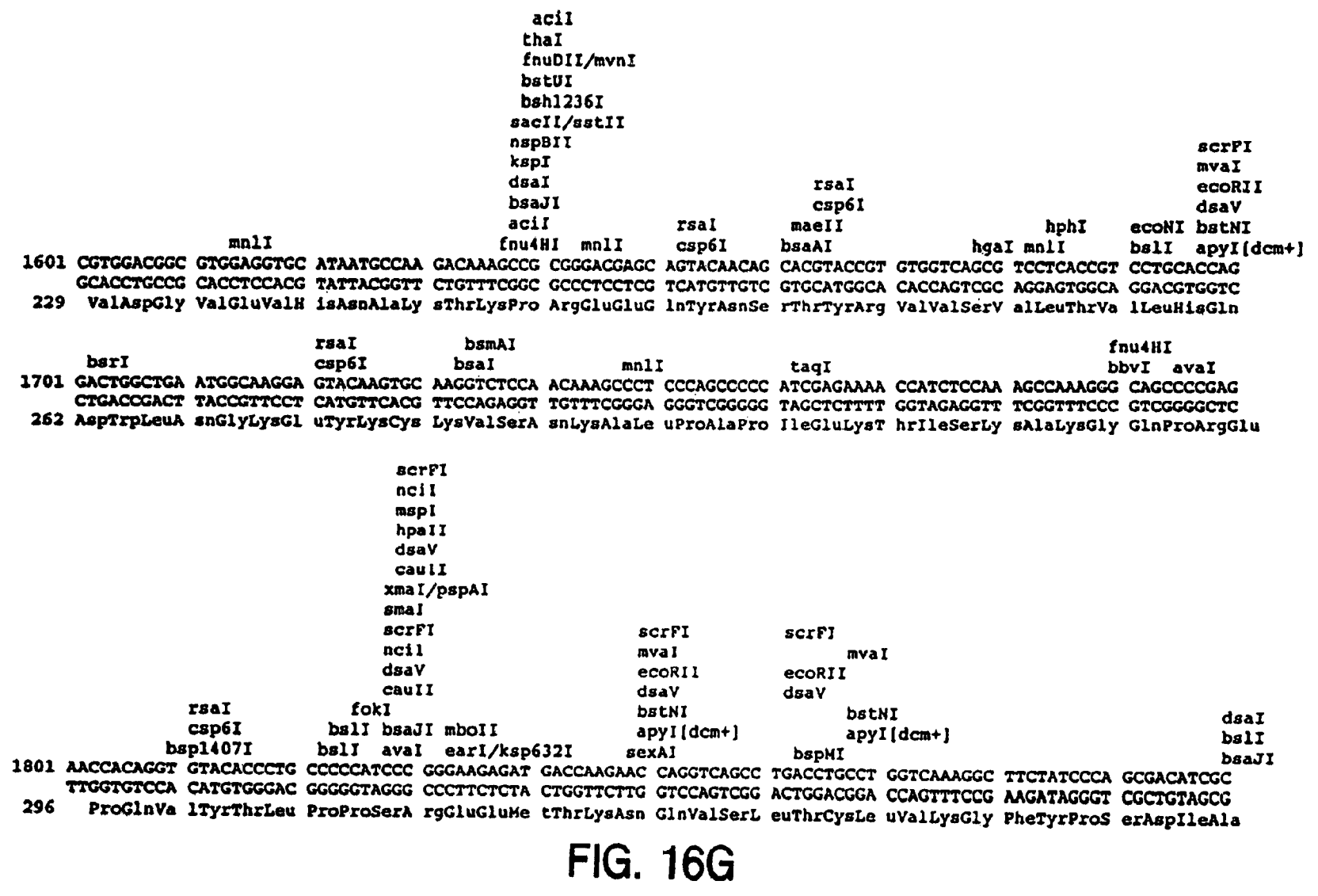
Figure 16I:
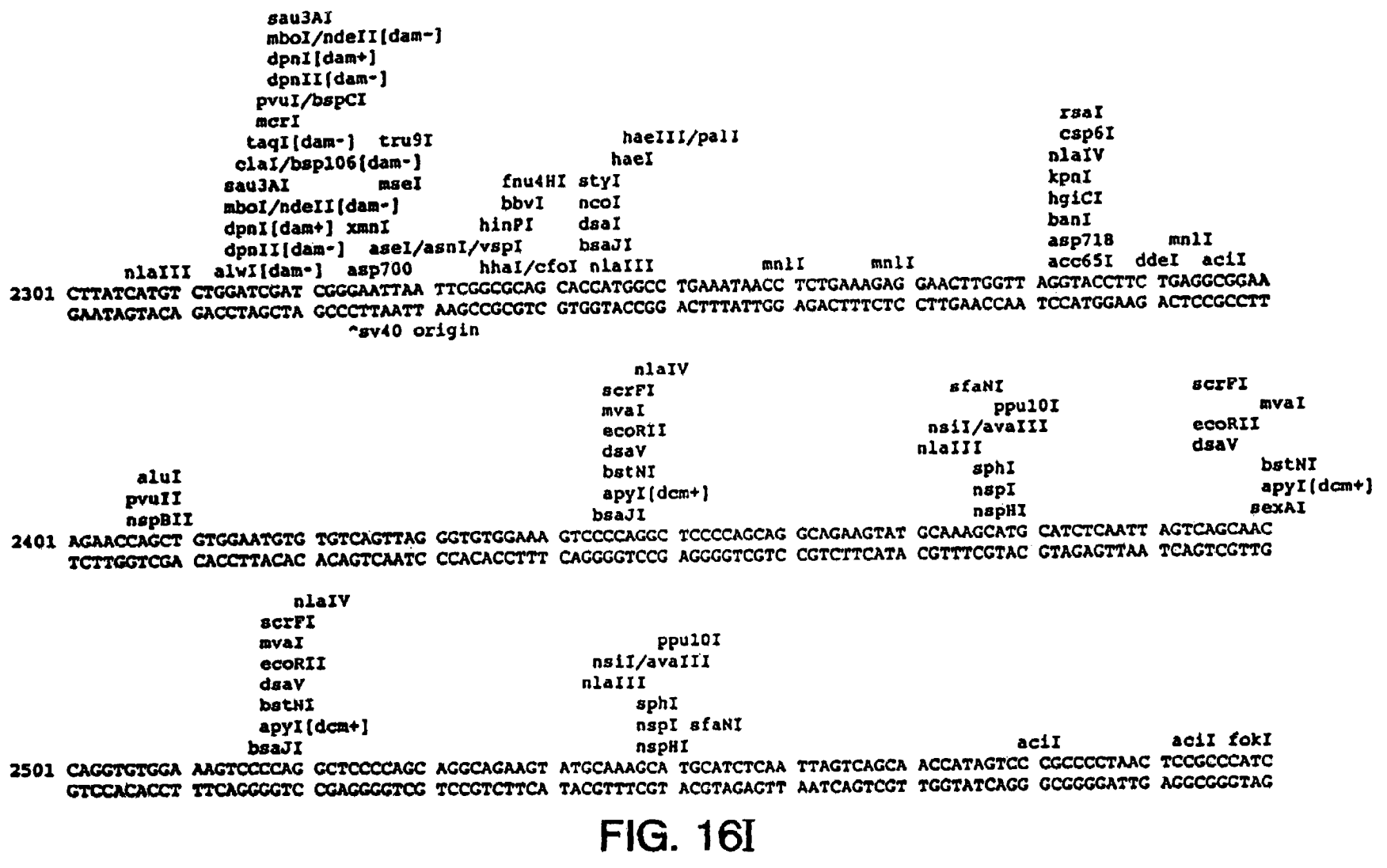
Figure 16J:
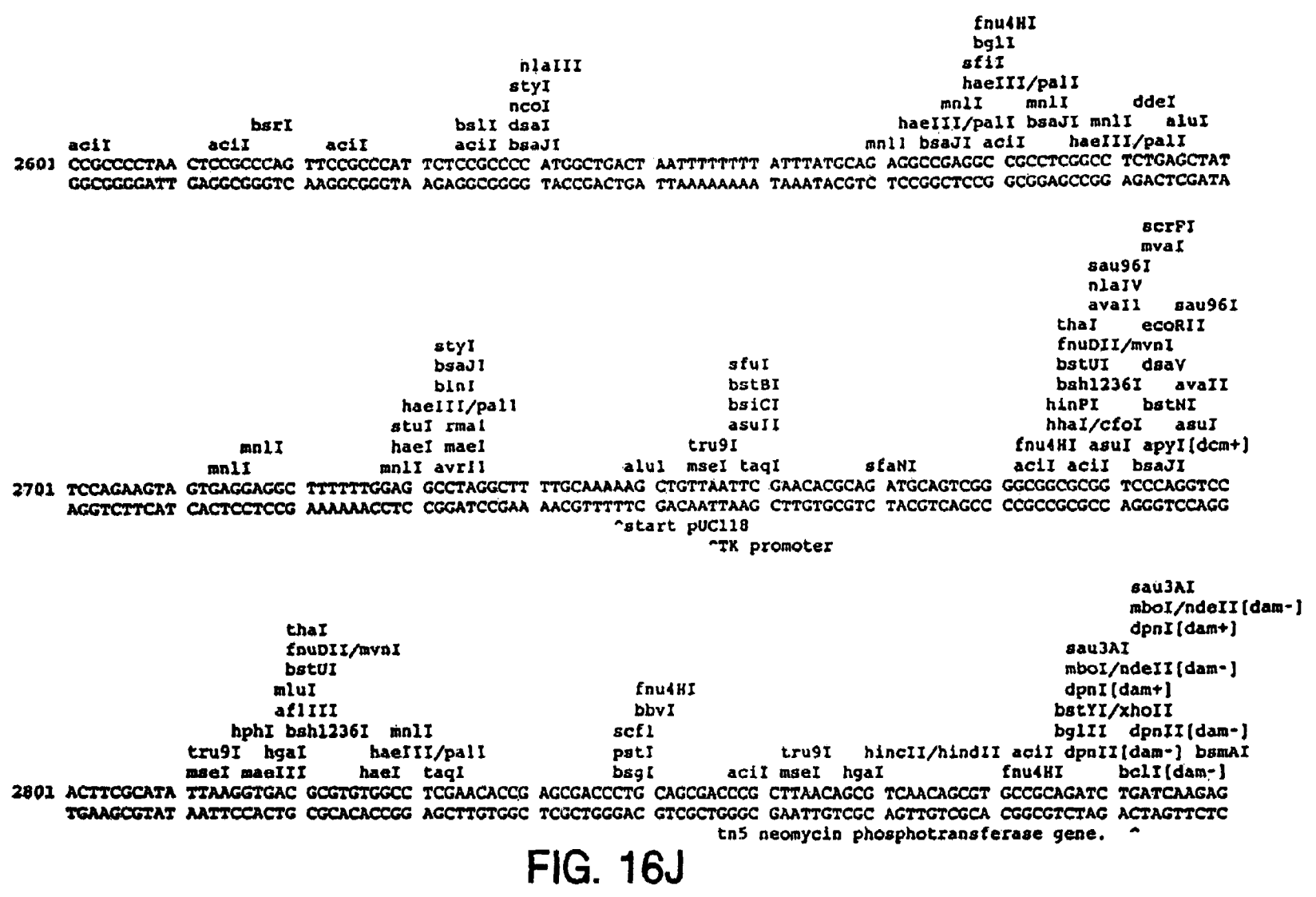
Figure 16K:
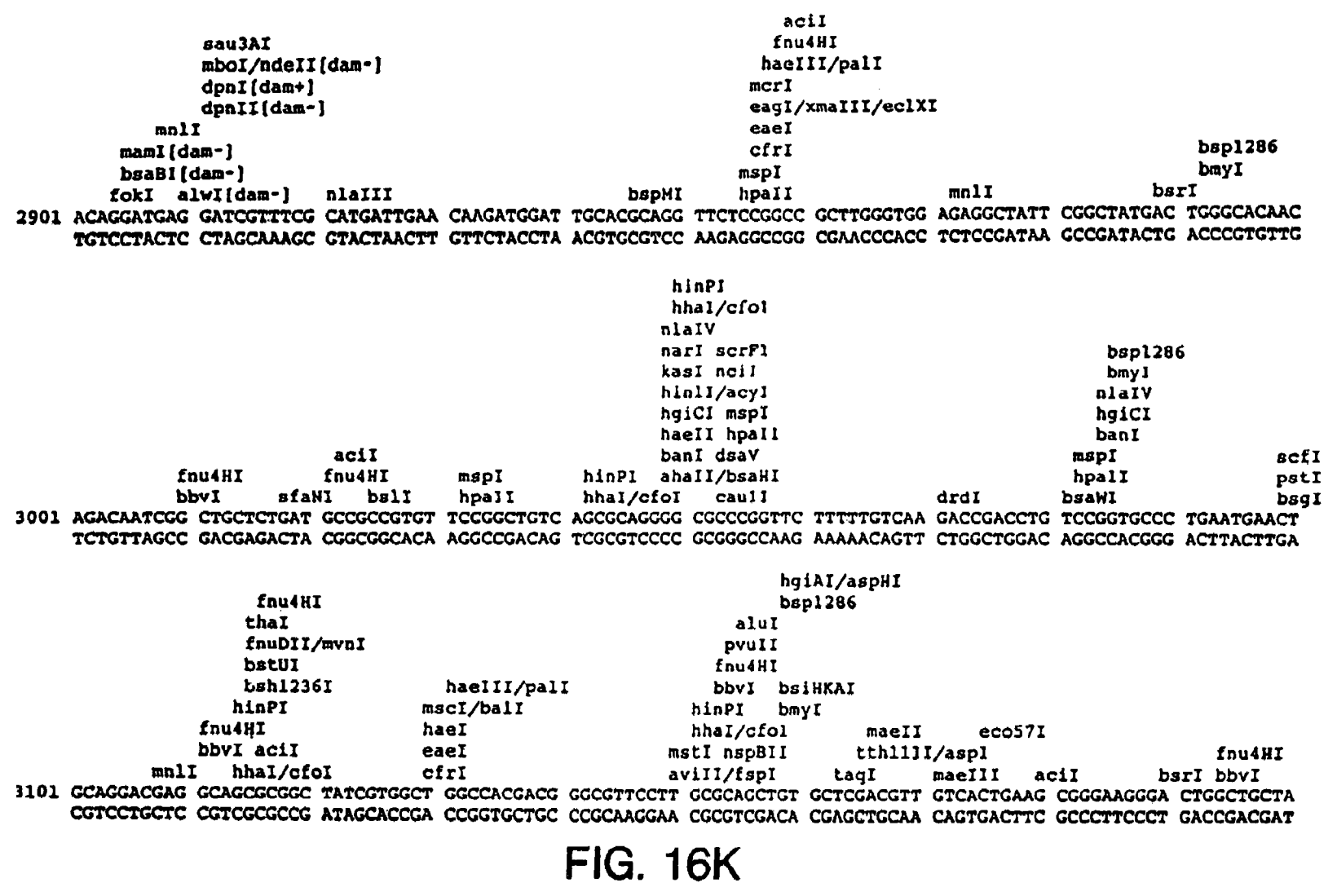
Figure 16N:
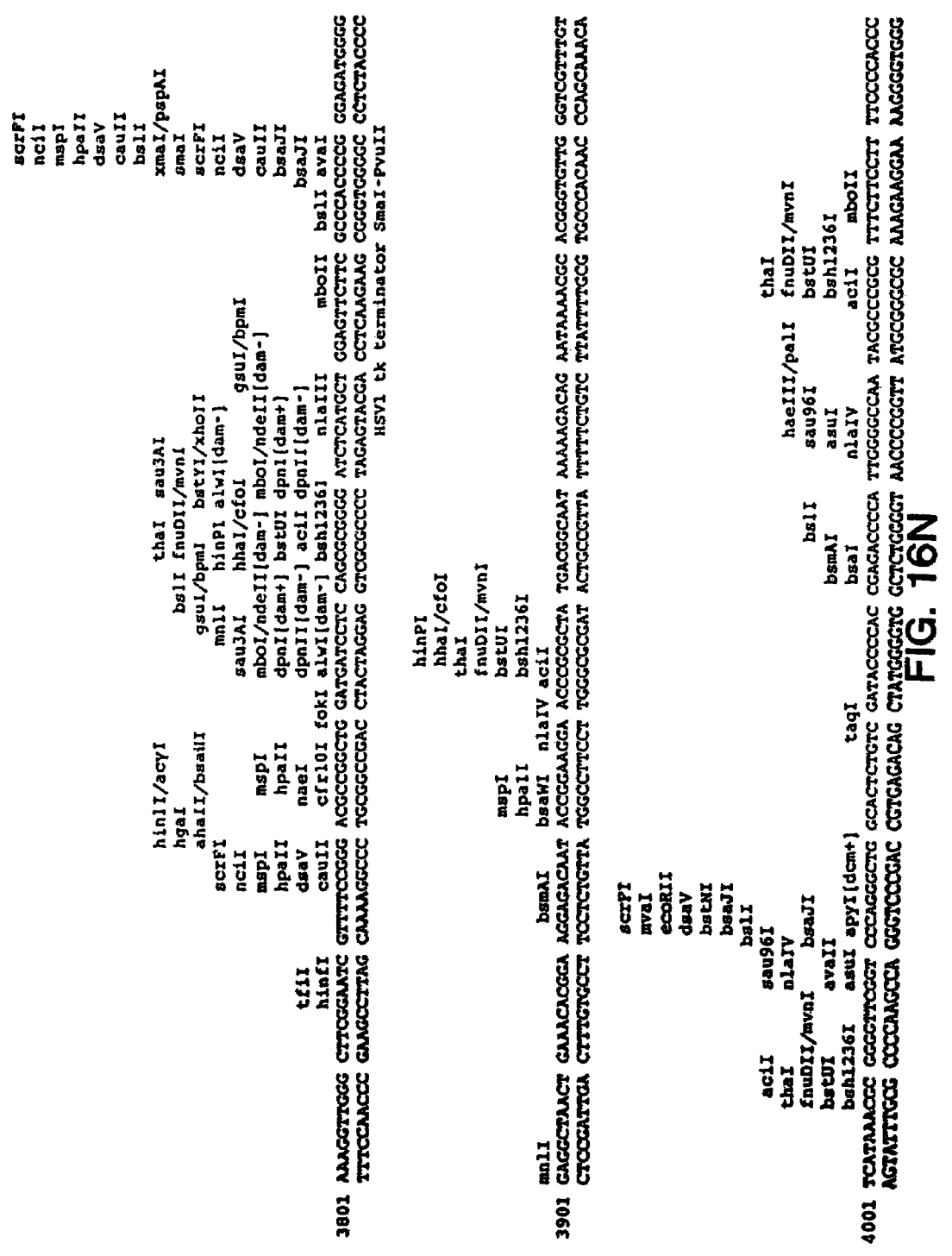
Figure 16Q:
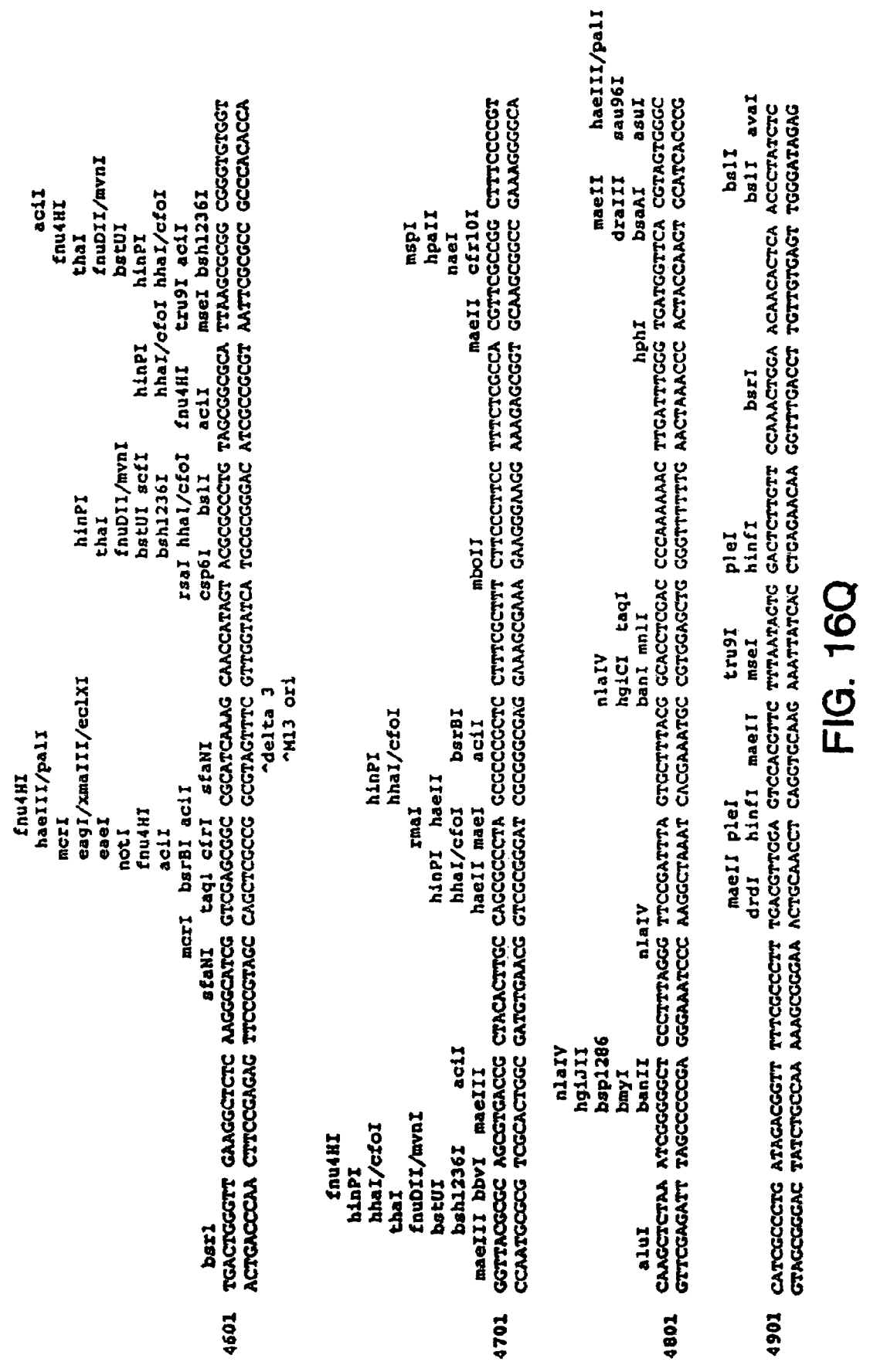
Figure 16T:
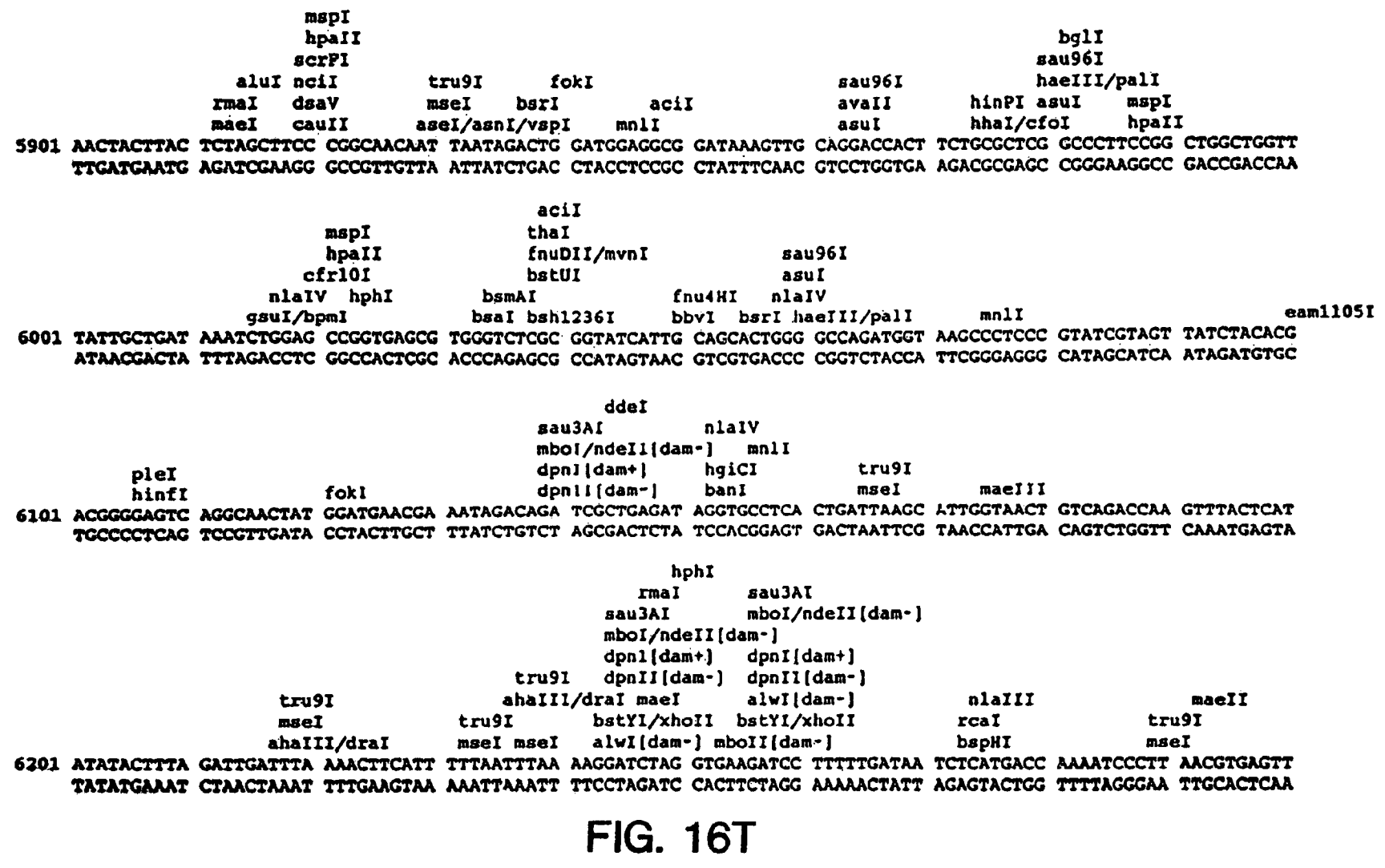

Using protein engineering techniques, the human OB protein was expressed as a fusion with the hinge, CH2 and CH3 domains of IgG1. DNA constructs encoding the chimera of the human OB protein and IgG1 Fc domains were made with the Fc region clones of human IgG1. Human OB cDNA was obtained by PCR from human fat cell dscDNA (Clontech Buick-Clone cDNA product). The source of the IgG1 cDNA was the plasmid pBSSK-CH2CH3. The chimera contained the coding sequence of the full length OB protein (amino acids 1-167 in FIG. 16A-V) and human IgG1 sequences beginning at aspartic acid 216 (taking amino acid 114 as the first residue of the heavy chain constant region (Kabat et al., *Sequences of proteins of Immunological Interest* 4th ed. (1987)), which is the first residue of the IgG1 hinge after the cysteine residue involved in heavy-light chain bonding, and ending with residues 441 to include the CH2 and CH3 Fc domains of IgG1. There was an insert of codons for three amino acids (GlyValThr) between the OB protein and IgG1 coding sequences. If necessary, this short linker sequence can easily be deleted, for example by site directed deletion mutagenesis, to create an exact junction between the coding sequences of the OB protein and the IgG1 hinge region. The coding sequence of the OB-IgG1 immunoadhesin was subcloned into the pRK5-based vector pRK5tk-neo which contains a neomycine selectable marker, for transient expression in 293 cells using the calcium phosphate technique (Suva et al., Science 237:893-896 (1987)). 293 cells were cultured in HAM's: Low Glucose DMEM medium (50:50), containing 10% FBS and 2 mM L-Gln. For purification of OB-IgG1 chimeras, cells were changed to serum free production medium PS24 the day after transfection and media collected after three days. The culture media was filtered.

The filtered 293 cell supernatant (400 ml) containing recombinant human OB-IgG1 was made 1 mM in phenylmethylsulfonyl fluoride and 2 µg/ml in aprotinin. This material was loaded at 4° C. onto a 1×4.5 cm Protein A agarose column (Pierce catalog #20365) equilibrated in 100 mM HEPES pH 8. The flow rate was 75 ml/h. Once the sample was loaded, the column was washed with equilibration buffer until the $A_{280}$ reached baseline. The OB-IgG1 protein was eluted with 3.5 M $MgCl_2$+2% glycerol (unbuffered) at a flow rate of 15 ml/h. The eluate was collected with occasional mixing into 10 ml of 100 mM HEPES pH 8 to reduce the $MgCl_2$ concentration by approximately one-half and to raise the pH. The eluted protein was then dialyzed into phosphate buffered saline, concentrated, sterile filtered and stored either at 4° C. or frozen at −70° C. The OB-IgG1 immunoadhesin prepared by this method is estimated by SDS-PAGE to be greater than 90% pure.

EXAMPLE 12

Preparation of PEG-OB

The PEG derivatives of the human OB protein were prepared by reaction of hOB protein purified by reverse phase chromatography with a succinimidyl derivative of PEG propionic acid (SPA-PEG) having a nominal molecular weight of 10 kD, which had been obtained from Shearwater Polymers, Inc. (Huntsville, Ala.). After purification of the hOB protein by reverse phase chromatography, an approximately 1-2 mg/ml solution of the protein in 0.1% trifluoroacetic acid and approximately 40% acetonitrile, was diluted with ⅓ to ½ volume of 0.2 M borate buffer and the pH adjusted to 8.5 with NaOH. SPA-PEG was added to the reaction mixture to make 1:1 and 1:2 molar ratios of protein to SPA-PEG and the mixture was allowed to incubate at room temperature for one hour. After reaction and purification by gel electrophoresis or ion exchange chromatography, the samples were extensively dialyzed against phosphate-buffered saline and sterilized by filtration through a 0.22 micron filter. Samples were stored at 4° C. Under these conditions, the PEG-hOB resulting from the 1:1 molar ratio protein to SPA-PEG reaction consisted primarily of molecules with one 10 kD PEG attached with minor amounts of the 2 PEG-containing species. The PEG-hOB from the 1:2 molar reaction consisted of approximately equal amounts of 2 and 3 PEGs attached to hOB, as determined by SDS gel electrophoresis. In both reactions, small amounts of unreacted protein were also detected. This unreacted protein can be efficiently removed by the gel filtration or ion exchange steps as needed. The PEG derivatives of the human OB protein can also be prepared essentially following the aldehyde chemistry described in EP 372,752 published Jun. 13, 1990.

EXAMPLE 13

Murine Agonist Antibodies

Mice were immunized five times with 20 µg of the WSX receptor immunoadhesin (see Example 2 above) resuspended in MPL-TDM (monophosphoryl lipid A/trehalose dicorynomycolate; Rabi, Immunochemical Research Inc.) into each foot pad. Three days after the last immunization, popliteal lymphoid cells were fused with mouse myeloma cells, X63-Ag8.8.653 cells, using 50% polyethylene glycol as described (Laskov et al. Cell. Immunol. 55:251 (1980)).

The initial screening of hybridoma culture supernatants was done using a capture ELISA. For the capture ELISA, microtiter plates (Maxisorb; Nunc, Kamstrup, Denmark) were coated with 50 µl/well of 2 µg/ml of goat antibodies specific to the Fc portion of human IgG (Goat anti-hIgG-Fc; Cappel), in PBS, overnight at 4° C. and blocked with 2× BSA for 1 hr at room temperature. Then, 50 µl/well of 2 µg/ml of WSX receptor immunoadhesin was added to each well for 1 hr. The remaining anti-Fc binding sites were blocked with PBS containing 3% human serum and 10 µg/ml of CD4-IgG for 1 hr. Plates were incubated with 50 µl/well of 2 µg/ml of anti-WSX receptor monoclonal antibody (or hybridoma culture supernatant) for 1 hr. Plates were then incubated with 50 µl/well of HRP-goat anti-mouse IgG. The bound enzyme was detected by the addition of the substrate (OPD) and the plates were read at 490 nM with an ELISA plate reader. Between each step, plates were washed in wash buffer (PBS containing 0.05% TWEEN 20™).

Agonist antibodies were screened for using the KIRA ELISA described in WO95/14930. A chimeric receptor comprising the extracellular domain of the WSX receptor and the transmembrane and intracellular domain of Rse receptor (Mark et al., Journal of Biological Chemistry 269(14): 10720-10728 (1994)) with a carboxyl-terminal herpes simplex virus glycoprotein D (gD) tag was produced and dp12.CHO cells were transformed therewith as described in Example 4 of WO95/14930.

The WSX/Rse.gD transformed dp12.CHO cells were seeded ($3 \times 10^4$ per well) in the wells of a flat-bottom-96 well culture plate in 100 µl media and cultured overnight at 37° C. in 5% $CO_2$. The following morning the well supernatants were removed and various concentrations of purified mAb were then added to separate wells. The cells were stimulated at 37° C. for 30 min. and the well supernatants were decanted. To lyse the cells and solubilize the chimeric receptors, 100 µl of lysis buffer was added to each well. The plate was then agitated gently on a plate shaker (Bellco Instruments, Vineland, N.J.) for 60 min. at room temperature.

While the cells were being solubilized, an ELISA microtiter plate (Nunc Maxisorp, Inter Med, Denmark) coated overnight at 4° C. with the 5B6 monoclonal anti-gD antibody (5.0 µg/ml in 50 mM carbonate buffer, pH 9.6, 100 µl/well) was decanted and blocked with 150 µl/well of Block Buffer containing 2% BSA for 60 min. at room temperature. After 60 minutes, the anti-gD 5B6 coated plate was washed 6 times with wash buffer (PBS containing 0.05% TWEEN 20™ and 0.01% thimerosal).

The lysate containing solubilized WSX/Rse.gD from the cell-culture microtiter well was transferred (85 µl/well) to anti-gD 5B6 coated and blocked ELISA well and was incubated for 2 h at room temperature. The unbound WSX/Rse.gD was removed by washing with wash buffer and 100 µl of biotinylated 4G10 (anti-phosphotyrosine) diluted 1:18000 in dilution buffer (PBS containing 0.5% BSA, 0.05% Tween-20, 5 mM EDTA, and 0.01% thimerosal), i.e. 56 ng/ml was added to each well. After incubation for 2 h at room temperature the plate was washed and HRPO-conjugated streptavidin (Zymed Laboratories, S. San Francisco, Calif.) was added to each well. The plate was incubated for 30 minutes at room temperature with gentle agitation. The free avidin-conjugate was washed away and 100 µl freshly prepared substrate solution (tetramethyl benzidine (TMB); 2-component substrate kit; Kirkegaard and Perry, Gaithersburg, Md.) was added to each well. The reaction was allowed to proceed for 10 minutes, after which the color development was stopped by the addition of 100 µl/well 1.0 M $H_3PO_4$. The absorbance at 450 nm was read with a reference wavelength of 650 nm ($ABS_{450/650}$), using a vmax plate reader (Molecular Devices, Palo Alto, Calif.) controlled with a Macintosh Centris 650 (Apple Computers, Cupertino, Calif.) and DeltaSoft software (BioMetallics, Inc, Princeton, N.J.).

Four of the 25 anti-WSX receptor monoclonal antibodies activated the chimeric WSX/Rse receptor in the KIRA ELISA. The antibodies were designated: 2D7, 1G4, 1E11 and 1C11.

To determine whether the four agonist anti-WSX receptor mAbs recognized the same or different epitopes, a competitive binding ELISA was performed as described in Kim et al. *J. Immunol. Method* 156:9-17 (1992) using biotinylated mAbs (Bio-mAb). Bio-mAb were prepared using N-hydroxyl succinimide as described in *Antibodies, A Laboratory Manual* Cold Spring Harbor Laboratory, Eds. Harlow E. and D. Lane, p. 341 (1988). Microtiter wells were coated with 50 µl of Goat anti-hIgG-Fc and kept overnight at 4° C., blocked with 2% BSA for 1 hr, and incubated with 25 µl/well of human WSX receptor immunoadhesin (1 µg/ml) for 1 hr at room temperature. After washing, a mixture of a predetermined optimal concentration of Bio-mAb bound and a thousand-fold excess of unlabeled mAb was added into each well. Following 1 hr incubation at room temperature, plates were washed and the amount of Bio-mAb was detected by the addition of HRP-streptavidin. After washing the plates, the bound enzyme was detected by the addition of the substrate o-phenylenediamine dihydrochloride (OPD), and the plates were read at 490 nm with an ELISA plate reader.

The ability of the mAbs to recognize murine WSX receptor was determined in a capture ELISA. Murine WSX receptor (FIG. 21) fused to a gD tag (see above) was captured by an anti-gD (5B6) coated ELISA plate. After washing, various concentrations of biotinylated mAbs were added into each well. Biotinylated mAbs bound to murine WSX receptor-gD were detected using HRP-streptavidin as described above.

To determine whether the antibodies bound membrane-bound receptor, FACS analysis was performed using 293 cells transfected with WSX receptor. $10^5$ WSX receptor-transfected 293 cells were resuspended in 100 µl of PBS plus 1% fetal calf serum (FSC) and incubated with 2D7 or 1G4 hybridoma cell supernatant for 30 min on ice. After washing, cells were incubated with 100 µl of FITC-goat anti-mouse IgG for 30 min at 4° C. Cells were washed twice and resuspended in 150 µl of PBS plus 1% FCS and analyzed by FACscan (Becton Dickinson, Mountain View, Calif.). The antibodies 2D7 and 1G4 bound to membrane WSX receptor according to the FACS analysis.

The properties of agonist antibodies 2D7 and 1G4 are summarized in the following table.

TABLE 3

| mAb | Isotype | epitope[a] | hWSXR[b] | mWSXR[b] | Agonist[c] |
|-----|---------|---------|--------|--------|---------|
| 2D7 | IgG1 | A | +++ | ++ | + |
| 1G4 | IgG1 | B | +++ | + | + |

[a]These mAbs are shown to recognize different epitopes by competitive binding ELISA.
[b]These results are determined by ELISA (hWSXR is human WSX receptor and mWSXR is murine WSX receptor).
[c]The agonistic activities were determined by KIRA ELISA.

EXAMPLE 14

Human Agonist Antibodies

Single-chain Fv (scFv) fragments binding to the human WSX receptor (hWSXR) were isolated from a large human scFv library (Vaughan et al. *Nature Biotechnology* 14:309-314 (1996)) using antigen coated on immunotubes or biotinylated antigen in conjunction with streptavidin-coated magnetic beads (Griffiths et al. *EMBO J.* 13:3245-3260 (1994); and Vaughan et al. (1996)). Briefly, immunotubes coated overnight with 10 µg/ml human WSX receptor immunoadhesin (see Example 2 above) in phosphate buffered saline (PBS) were used for three rounds of panning. The humanized antibody, huMAb4D5-8 (Carter et al. *Proc. Natl. Acad. Sci. USA* 89:4285-4289 (1992)) was used to counter-select for antibodies binding to the Fc of the immunoadhesin. This was done by using 1 mg/ml huMAb4D5-8 in solution for the panning steps. In addition, human WSX receptor extracellular domain (cleaved from the WSX receptor immunoadhesin with Genease (Carter et al. *Proteins: Structure, Function and Genetics* 6:240-248 (1989)) was biotinylated used for three rounds of panning. Individual phage following two or three rounds of panning were characterized by antigen-binding ELISA (Tables 4 and 5).

TABLE 4

Panning with human WSX receptor immunoadhesin-coated immunotubes

| Phage ELISA | | # clones | # BstNI |
|---|---|---|---|
| Round | hWSXR | Fc | characterized | fingerprints |
| 2 | 74/96 | 0/96 | 74 | 11[a] |
| 3 | 191/192 | 1/192 | 58 | 8[a] |

[a]Total of 11 different clones identified.

TABLE 5

Panning with biotinylated human WSX receptor

| Phage ELISA | | # clones | # BstNI |
|---|---|---|---|
| Round | hWSXR | Fc | characterized | fingerprints |
| 2 | 8/96 | 0/96 | 8 | 4[a] |
| 3 | 49/192 | 1/192 | 49 | 4[a] |

[a]Total of 7 different clones identified.

Clones binding to human WSX receptor were further characterized by BstNI fingerprinting of a PCR fragment encoding the scFv. A total of 18 clones were indentified: 11 from the panning using immunotubes and 7 from the panning using biotinlyated antigen (there was no overlap between these groups). The DNA for all 18 clones was sequenced.

Figure 22:
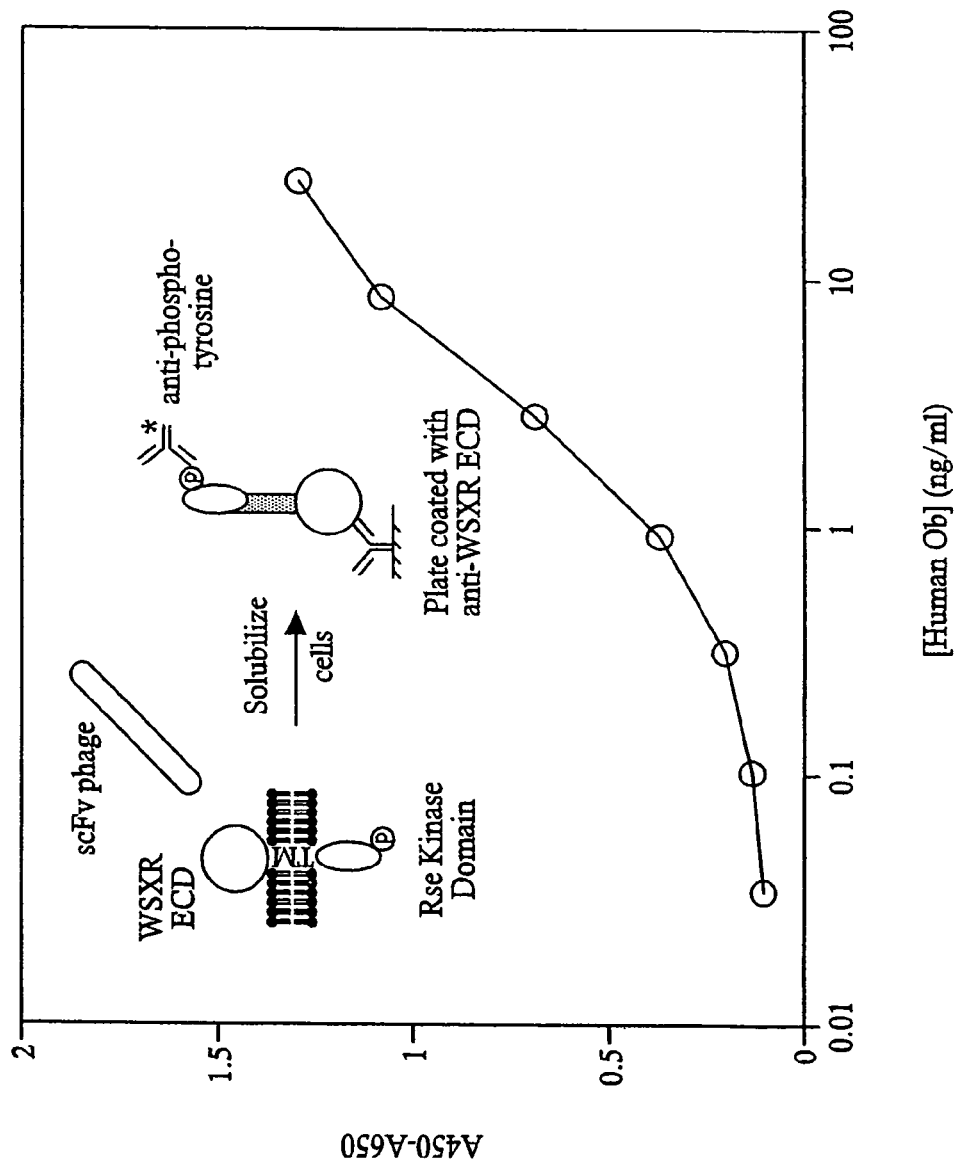
FIG. 22 is a standard curve for human OB protein in the KIRA ELISA, which illustrates schematically inside the graph WSX receptor KIRA ELISA panning with scFv phage as described in Example 14.

Anti-huWSXR clones obtained as described above were analyzed for agonist activity in a KIRA-ELISA assay (see above and FIG. 22) firstly as scFv phage and then as scFv. The scFv phage were PEG-precipitated (Carter et al., *Mutagenesis: A Practical Approach*, McPherson, M. ed. IRL Press, Oxford, UK, Chapter 1, pp 1-25 (1991)) and resuspended in PBS prior to screening. To prepare the scFv, DNA from the clones was transformed into 33D3 cells (a non-suppressor strain for expression of soluble protein). The cells were plated onto 2YT/2% glucose/50 µg per ml of carbenicillin and incubated at 37° C. overnight. A 5 ml culture (2YTG: 2YT, 2% glucose, 50 µg/ml carbenicillin) was inoculated and grown at 30° C. overnight. The next morning, the 5 ml culture was diluted into 500 ml 2YTG media and grown at 30° C. until OD550, 0.3. Then, the media was changed from 2YTG into 2YT/50 µg/ml carbenicillin/2 mM IPTG and grown at 30° C. for 4-5 hrs for scFv production. The culture was harvested and the cell pellet was frozen at −20° C. For purification, the cell pellet was resuspended in 10 ml shockate buffer (50 mM TrisHCl pH8.5, 20% sucrose, 1 mM EDTA) and agitated at 4° C. for 1 hr. The debris was spun down and supernatant was taken to be purified on Ni NTA Superose (Qiagen) column. MgCl$_2$ was added to the supernatant to 5 mM and loaded onto 0.5 ml Ni NTA Superose packed into a disposable column. The column was then washed with 2×5 ml wash buffer 1 (50 mM sodium phosphate, 300 mM NaCl, 25 mM imidazole pH 8.0) followed by 2×5 ml wash 2 buffer (50 mM sodium phosphate, 300 mM NaCl, 50 mM imidazole pH 8.0). The scFv was then eluted with 2.5 ml elution buffer (50 mM sodium phosphate, 300 mM NaCl, 250 mM imidazole, pH8.0). The eluted pool was buffer exchanged into PBS with a NAP5 column (Pharmacia) and stored at 4° C.

Figure 23:
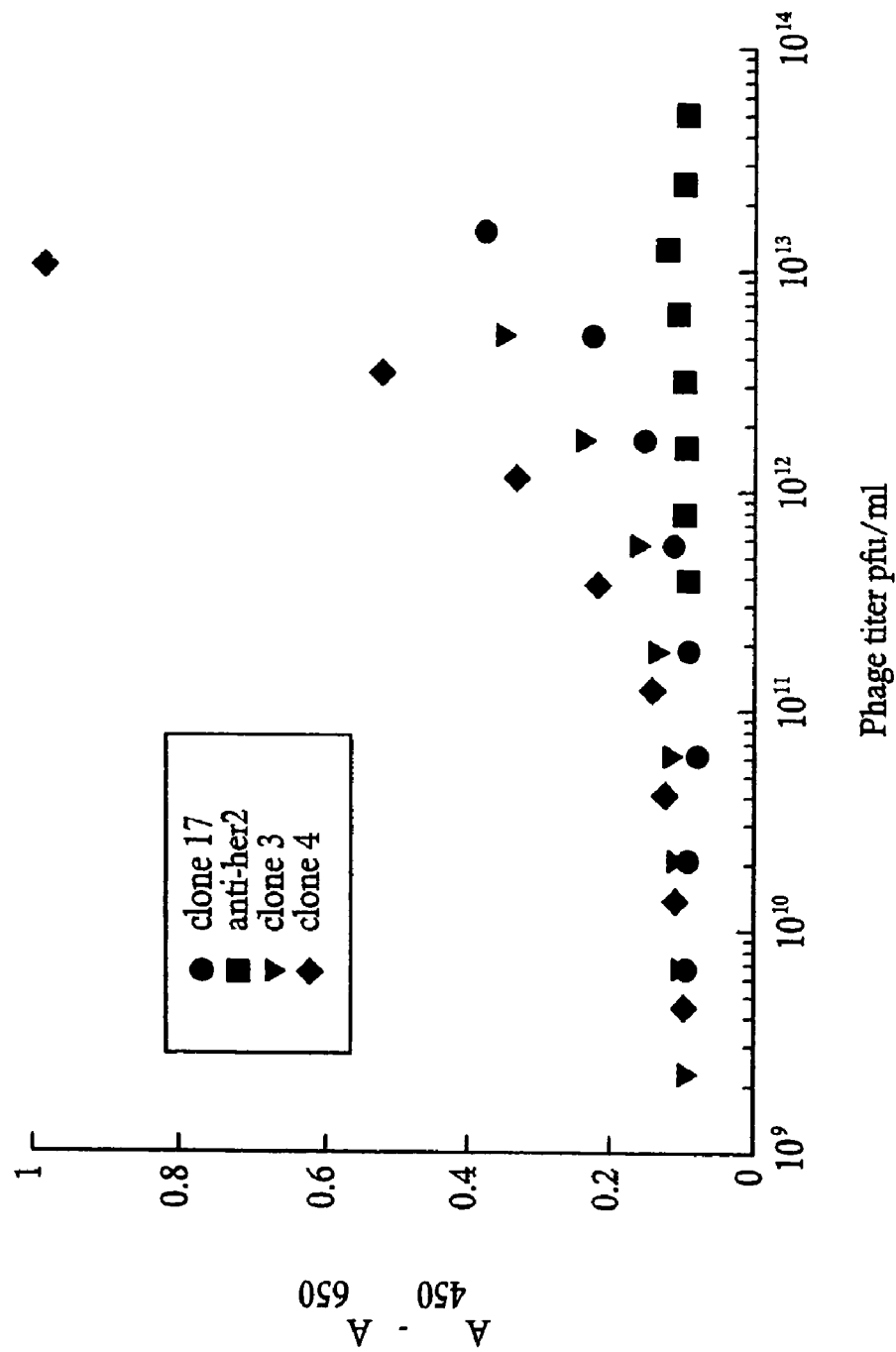
FIG. 23 shows the activity of clone #3, #4 and #17 scFv phage from Example 14 and anti-HER2 scFv phage control in the KIRA ELISA. Absorbance versus phage titer is shown.
Figure 24:
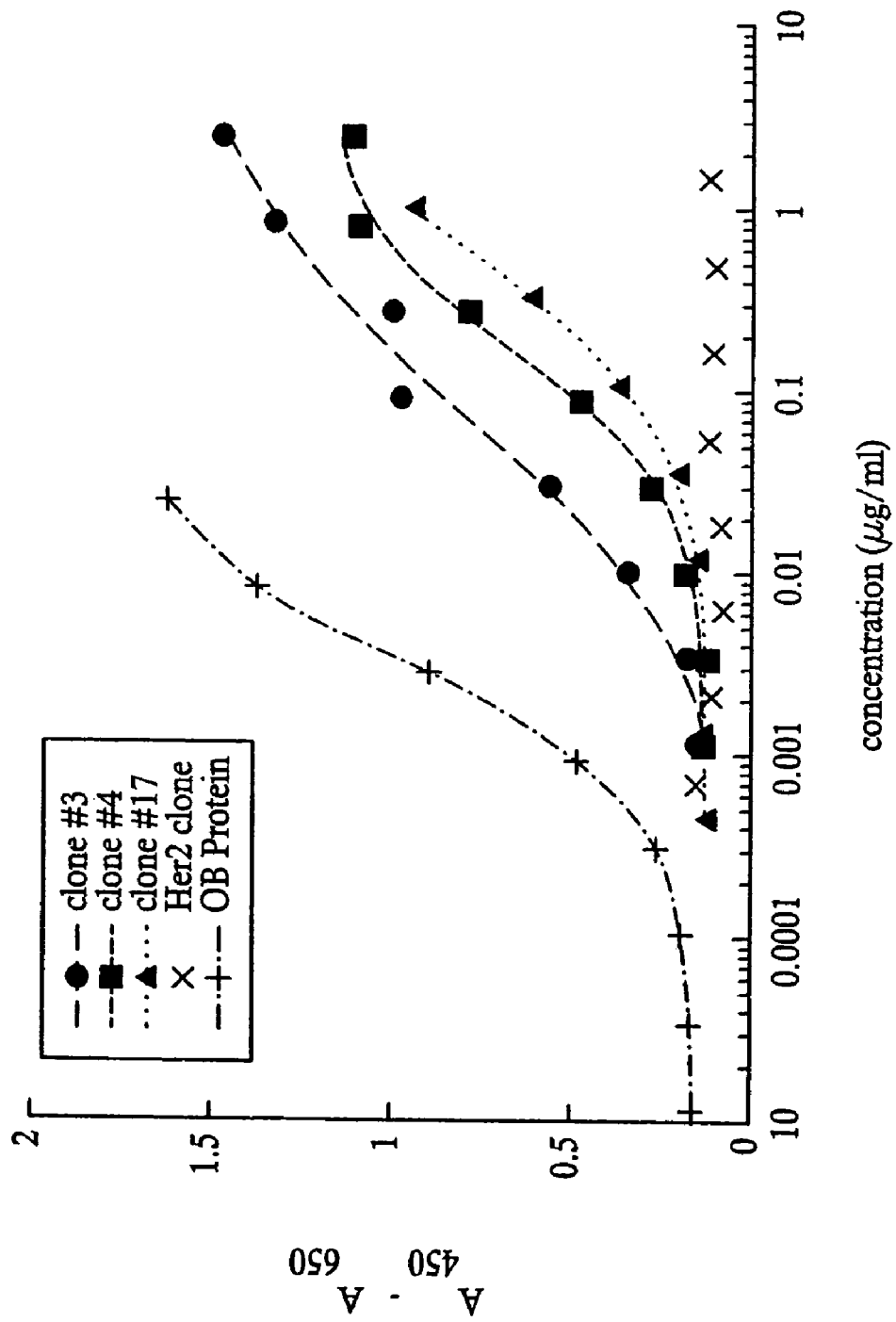
FIG. 24 shows the activity of clone #3, #4 and #17 scFv from Example 14, anti-HER2 scFv control (Her2 clone) and OB protein in the KIRA ELISA. Absorbance versus antibody concentration is shown.

Clones #3, #4 and #17 were found to have agonist activity as phage and as scFv (see FIGS. 23 and 24). The sequences of these agonist clones are shown in FIG. 25. The activity of the antibodies as F(ab')$_2$ in the KIRA ELISA was assessed, with clone #4 and clone #17 showing enhanced activity as F(ab')$_2$. The ability of the antibodies to bind murine WSX receptor in a capture ELISA (see Example 13) was assessed. Clone #4 and clone #17 bound murine WSX receptor in this assay.

What is claimed is:

1. An agonist antibody which specifically binds to a receptor having a WSX motif, wherein said receptor comprises an extracellular domain, wherein the extracellular domain comprises the extracellular domain sequence within SEQ ID NO: 2, and wherein said antibody comprises all 6 complementarity determining regions (CDRs) from antibody 2D7 (ATCC Accession Number HB-12249).

2. An agonist antibody which specifically binds to a receptor having a WSX motif, wherein said receptor comprises an extracellular domain, wherein the extracellular domain comprises the extracellular domain sequence within SEQ ID NO: 2, and wherein said antibody comprises all 6 complementarity determining regions (CDRs) from antibody 1G4 (ATCC Accession Number HB-12243).

3. An agonist antibody which specifically binds to a receptor having a WSX motif, wherein said receptor comprises an extracellular domain, wherein the extracellular domain comprises the extracellular domain sequence within SEQ ID NO: 2, and wherein said antibody comprises all 6 complementarity determining regions (CDRs) from antibody 1E11 (ATCC Accession Number HB-12248).

4. An agonist antibody which specifically binds to a receptor having a WSX motif, wherein said receptor comprises an extracellular domain, wherein the extracellular domain comprises the extracellular domain sequence within SEQ ID NO: 2, and wherein said antibody comprises all 6 complementarity determining regions (CDRs) residues from antibody 1C11 (ATCC Accession Number HB-12250).

5. An agonist antibody which specifically binds to a receptor having a WSX motif, wherein said receptor comprises an extracellular domain, wherein the extracellular domain comprises the extracellular domain sequence within SEQ ID NO: 2, and wherein said antibody comprises $V_H$ and $V_L$ hypervariable region residues of clone 3 antibody (SEQ ID NO:48).

6. An agonist antibody which specifically binds to a receptor having a WSX motif, wherein said receptor comprises an extracellular domain, wherein the extracellular domain comprises the extracellular domain sequence within SEQ ID NO: 2, and wherein said antibody comprises $V_H$ and $V_L$ hypervariable region residues of clone 4 antibody (SEQ ID NO:49).

7. An agonist antibody which specifically binds to a receptor having a WSX motif, wherein said receptor comprises an extracellular domain, wherein the extracellular domain comprises the extracellular domain sequence within SEQ ID NO: 2, and wherein said antibody comprises $V_H$ and $V_L$ hypervariable region residues of clone 17 antibody (SEQ ID NO:50).

8. An agonist antibody which specifically binds to a receptor having a WSX motif, wherein said receptor comprises an extracellular domain, wherein the extracellular domain comprises the extracellular domain sequence within SEQ ID NO: 2, wherein the antibody comprises a light chain and a heavy chain, and wherein the heavy chain comprises the heavy chain amino acid sequence from antibody 1G4 (ATCC Accession Number HB-12243).

9. An agonist antibody which specifically binds to a receptor having a WSX motif, wherein said receptor comprises an extracellular domain, wherein the extracellular domain comprises the extracellular domain sequence within SEQ ID NO: 2, wherein the antibody comprises a light chain and a heavy chain, and wherein the heavy chain comprises the heavy chain amino acid sequence from antibody 2D7 (ATCC Accession Number HB-12249).

10. An agonist antibody which specifically binds to a receptor having a WSX motif, wherein said receptor comprises an extracellular domain, wherein the extracellular domain comprises the extracellular domain sequence within SEQ ID NO: 2, wherein the antibody comprises a light chain and a heavy chain, and wherein the heavy chain comprises the heavy chain amino acid sequence from antibody 1E11 (ATCC Accession Number HB-12248).

11. An agonist antibody which specifically binds to a receptor having a WSX motif, wherein said receptor comprises an extracellular domain, wherein the extracellular domain comprises the extracellular domain sequence within SEQ ID NO: 2, wherein the antibody comprises a light chain and a heavy chain, and wherein the heavy chain comprises the heavy chain amino acid sequence from antibody 1C11 (ATCC Accession Number HB-12250).

12. An agonist antibody which specifically binds to a receptor having a WSX motif, wherein said receptor comprises an extracellular domain, wherein the extracellular domain comprises the extracellular domain sequence within SEQ ID NO: 2, wherein the antibody comprises a light chain and a heavy chain, and wherein the light chain comprises the light chain amino acid sequence from antibody 1G4 (ATCC Accession Number HB-12243).

13. An agonist antibody which specifically binds to a receptor having a WSX motif, wherein said receptor comprises an extracellular domain, wherein the extracellular domain comprises the extracellular domain sequence within SEQ ID NO: 2, wherein the antibody comprises a light chain and a heavy chain, and wherein the light chain comprises the light chain amino acid sequence from antibody 2D7 (ATCC Accession Number HB-12249).

14. An agonist antibody which specifically binds to a receptor having a WSX motif, wherein said receptor comprises an extracellular domain, wherein the extracellular domain comprises the extracellular domain sequence within SEQ ID NO: 2, wherein the antibody comprises a light chain and a heavy chain, and wherein the light chain comprises the light chain amino acid sequence from antibody 1E11 (ATCC Accession Number HB-12248).

15. An agonist antibody which specifically binds to a receptor having a WSX motif, wherein said receptor comprises an extracellular domain, wherein the extracellular domain comprises the extracellular domain sequence within SEQ ID NO: 2, wherein the antibody comprises a light chain and a heavy chain, and wherein the light chain comprises the light chain amino acid sequence from antibody 1C11 (ATCC Accession Number HB-12250).

16. An agonist antibody which specifically binds to a receptor having a WSX motif, wherein said receptor comprises an extracellular domain, wherein the extracellular domain comprises the extracellular domain sequence within SEQ ID NO: 2, and wherein the antibody comprises all 6 CDRs of clone 3 antibody (SEQ ID NO:48), or clone 17 antibody (SEQ ID NO: 50).

17. An agonist antibody which specifically binds to a receptor having a WSX motif, wherein said receptor comprises an extracellular domain, wherein the extracellular domain comprises the extracellular domain sequence within SEQ ID NO: 2, and wherein the antibody comprises a light chain and a heavy chain, and wherein the heavy chain comprises the heavy chain amino acid sequence from antibody 1G4(ATCC Accession Number HB-12243), 2D7 (ATCC Acession Number HB-12249), 1E11 (ATCC ACCESSION Number HB-12248), or 1C11 (ATCC Accession Number HB-12250).

18. An agonist antibody which specifically binds to a receptor having a WSX motif, wherein said receptor comprises an extracellular domain, wherein the extracellular domain comprises the extracellular domain sequence within SEQ ID NO:2, and wherein the antibody comprises a light chain and a heavy chain, and wherein the light chain comprises the light chain amino acid sequence from antibody 1G4 (ATCC Accession Number HB-12243), 2D7 (ATCC Acession Number HB-12249), 1E11 (ATCC Accession Number HB-12248), or 1C11 (ATCC Accession Number HB-12250).

* * * * *

UNITED STATES PATENT AND TRADEMARK OFFICE
CERTIFICATE OF CORRECTION

PATENT NO. : 7,524,937 B2  Page 1 of 3
APPLICATION NO. : 11/439325
DATED : April 28, 2009
INVENTOR(S) : Carter et al.

It is certified that error appears in the above-identified patent and that said Letters Patent is hereby corrected as shown below:

Title page 3, column 4, line 2, under Other Publications, change "407." to --407 (1994).--.

Title page 4, column 1, line 32, under Other Publications, change "Adminstration" to --Administration--.

Title page 4, column 2, line 4, under Other Publications, change "human" to --a human--.

Title page 4, column 2, line 7, under Other Publications, change "in" to --is--.

At column 2, line 19, change "P-sub" to --β-sub--.

At column 2, line 21, after "receptors" delete "1".

At column 5, line 51-52, change "lineage-4 specific" to --lineage-specific--.

At column 5, line 59, change "(LIEF)" to --(LIF)--.

At column 9, line 38, change "anti-TERI 19" to --anti-TER119--.

At column 11, line 1, change "WSk" to --WSX--.

At column 19, line 57, change "(e.g," to --(e.g.,--.

At column 23, line 23, change "4 ampicillin," to --ampicillin,--.

At column 24, line 16, change "No.44076" to --No. 44076--.

At column 24, line 25, change "Bianchietal.," to --Bianchi et al.,--.

At column 25, line 6, change "Shine-Dalgarno" to --Shine-Dalagarno--.

At column 25, line 66, change "etal.," to --et al.,--.

At column 26, line 18, change "(Banerdji" to --(Banerji--.

At column 26, line 27, change "29-7:" to --297:--.

At column 27, line 17, change "orpSVI6B." to --or pSVI6B.--.

At column 27, line 27, change "inarcescans," to --marcescans,--.

Signed and Sealed this

Twenty-first Day of December, 2010

David J. Kappos
*Director of the United States Patent and Trademark Office*

At column 27, line 46, change "No.4,946,783" to --No. 4,946,783--.

At column 27, line 64, change "marxianus," to --marxianus;--.

At column 28, line 7, change "Tilbum" to --Tilburn--.

At column 28, line 53, change "CVI" to --CV1--.

At column 28, line 61-62, change "monkeykidneycells" to --monkey kidney cells--.

At column 29, line 55, change "58:44." to --58:44--.

At column 31, line 1, change "DTAE;" to --DEAE;--.

At column 32, line 1, change "$^{125}$I," to --$^{125}$I--.

At column 32, line 36, change "ofthe" to --of the--.

At column 32, line 41, change "ofthe" to --of the--.

At column 34, line 24, change "epitopepeptide" to --epitope peptide--.

At column 37, line 51, change "delefional" to --deletional--.

At column 38, line 18, change "su ch" to --such--.

At column 38, line 63, change "LIEF," to --LIF,--.

At column 41, line 43, change "Such," to --Such--.

At column 43, line 27, change "Wu.et al.," to --Wu et al.,--.

At column 45, line 11, change "Pat," to --Pat.--.

At column 51, line 19, change "IL4," to --IL-4,--.

At column 52, line 12, change "maybe" to --may be--.

At column 52, line 30, change "J" to --J.--.

At column 52, line 67, change "IC11" to --1C11--.

At column 54, line 25, change "FLASK" to --flASK--.

At column 54, line 42, change "ofthe" to --of the--.

At column 59, line 66, before "Sustained" delete "103271".

At column 61, line 16, "Pat:" to --Pat.--.

At column 61, line 25, "pepfides;" to --peptides,--.

At column 61, line 35, change "with" to --with,--.

At column 64, line 65, change "ofthe" to --of the--.

At column 65, line 64, change "in," to --in--.

At column 66, line 57, change "ClaI" to --ClaI--.

At column 66, line 62, change "ofthe" to --of the--.

At column 68, line 10, change "ofthe" to --of the--.

At column 69, line 15, change "ofthe" to --of the--.

At column 72, line 3, change "$^{137}$CS" to --$^{137}$Cs--.

At column 72, line 21, change "C57BL16J" to --C57BL/6J--.

At column 76, line 32, "Genease" to --Genenase--.

At column 76, line 33, change "used" to --and used--.

At column 76, line 62, change "scFv.A" to --ScFv. A--.

At column 76, line 62, change "indentified:" to --identified:--.

At column 76, line 64, change "biotinlyated" to --biotinylated--.

At column 138, line 62, in Claim 16, change "(SEQ ID NO:48)," to --(SEQ ID NO:48), clone 4 antibody (SEQ ID NO:49),--.

At column 139, line 6, in Claim 17, change "Acession" to --Accession--.

At column 139, line 6, in Claim 17, change "ACCESSION" to --Accession--.

UNITED STATES PATENT AND TRADEMARK OFFICE
CERTIFICATE OF CORRECTION

PATENT NO. : 7,524,937 B2  
APPLICATION NO. : 11/439325  
DATED : April 28, 2009  
INVENTOR(S) : Carter et al.

Page 1 of 3

It is certified that error appears in the above-identified patent and that said Letters Patent is hereby corrected as shown below:

Title page 2, column 2, line 1, under Other Publications, change "a n" to --an--.

Title page 2, column 2, line 16, under Other Publications, change "Dematol" to --Dermatol--.

Title page 3, column 1, line 33, under Other Publications, change "Transcution,"" to --Transduction,"--.

Title page 3, column 1, line 48, under Other Publications, change "adiopocytes" to --adipocytes--.

Title page 3, column 2, line 16, under Other Publications, change ""Lodegment" to --"Lodgement--.

At sheet 82 of 83, below the X-axis on FIG. 24, change "10" to --$10^{-5}$--. The adjustment to the numbering is self-evident from the numbering and denoted log scale along the X-axis which is in the document as originally filed. A replacement sheet for FIG. 24 is also submitted herewith (and the adjusted version is also shown below).

Signed and Sealed this  
Twelfth Day of July, 2011

David J. Kappos  
*Director of the United States Patent and Trademark Office*

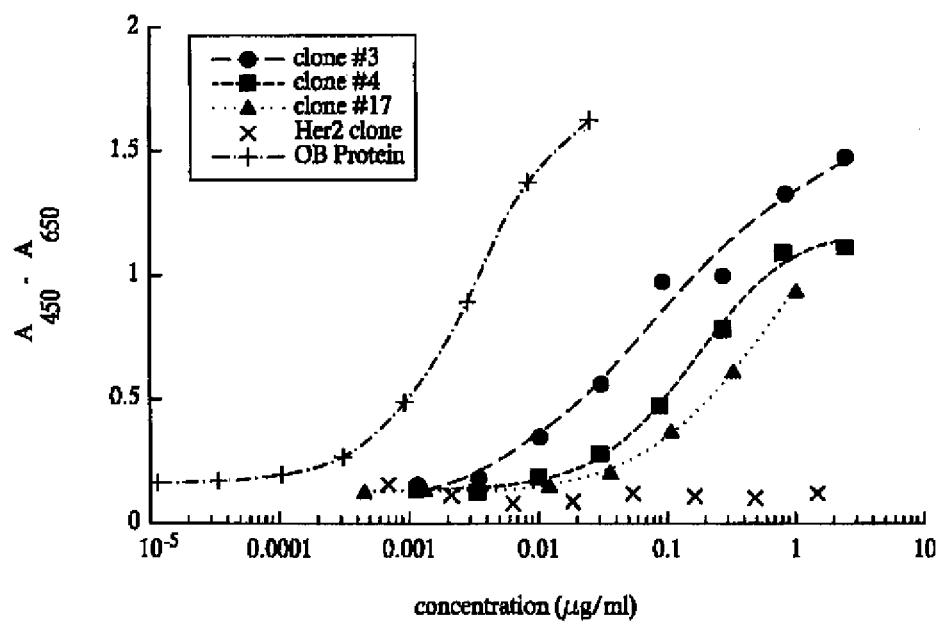

FIG. 24

At column 3, line 16, change "Diebetologia" to --Diabetologia--.

At column 3, line 17, change "Diebetologia" to --Diabetologia--.

At column 4, lines 39-40, change "hematopoeitic" to --hematopoietic--.

At column 4, line 63, change "ony" to --one--.

At column 5, line 12, change "Hodkin's" to --Hodgkin's--.

At column 5, line 17, change "erthrodegenerative" to --erythrodegenerative--.

At column 5, line 23, change "Faconi's" to --Fanconi's--.

At column 5, line 50, change "hematopoeitic" to --hematopoietic--.

At column 6, line 9, change "futher" to --further--.

At column 9, line 43, change "Serrono" to --Serono--.

At column 10, line 63, change "(e.g.,as" to --(e.g., as--.

At column 11, lines 22-23, change "(e.g.,alternatively" to --(e.g., alternatively--.

At column 12, line 23, change "(e.g.,the" to --(e.g., the--.

At column 12, line 31, change "polyeptides." to --polypeptides.--.

At column 17, lines 33-34, change "Vincreistine," to --Vincristine,--.

At column 18, line 24, change "lymphopoeisis" to --"lymphopoiesis"--.

At column 18, line 28, change "erythropoeisis" to --"erythropoiesis"--.

At column 19, line 53, change "(e.g.,controlled" to --(e.g., controlled--.

At column 21, line 49, change "specificed" to --specified--.

CERTIFICATE OF CORRECTION (continued)
U.S. Pat. No. 7,524,937 B2

At column 25, line 41, change "fowipox" to --fowlpox--.

At column 27, line 61, change "wickeramii" to --wickerhamii--.

At column 27, line 66, change "reesia" to --reesei--.

At column 32, lines 57-58, change "N-aceylgalactosamine," to --N-acetylgalactosamine,--.

At column 39, line 30, change "polyelkylenes" to --polyalkylenes--.

At column 39, line 41, change "dextrane" to --dextran--.

At column 40, line 20, change "trichlorophenylcloroformate" to --trichlorophenylchloroformate--.

At column 40, lines 20-21, change "P-nitrophenylcloroformate" to --P-nitrophenylchloroformate--.

At column 41, line 11, change "Cyanuronic" to --Cyanuric--.

At column 41, line 18, change "of"activated" to --of "activated--.

At column 41, line 23, change "of"activated" to --of "activated--.

At column 44, lines 15-16, change "(methylmethacylate)" to --(methylmethacrylate)--.

At column 45, line 39, change "pullullan;" to --pullulan;--.

At column 56, lines 54-55, change "Phytolaca" to --Phytolacca--.

At column 56, line 56, change "sapaonaria" to --saponaria--.

At column 56, line 58, change "tricothecenes." to --trichothecenes.--.

At columns 56-57, lines 67-1, change "glutareldehyde)," to --glutaraldehyde),--.

At column 58, line 59, change "adminstration" to --administration--.

At column 59, lines 8-9, change "intra-cerobrospinal," to --intra-cerebrospinal,--.

At column 69, line 55, change "fLASK" to --flASK--.

At column 71, line 33, change "Serrono" to --Serono--.

At column 72, line 19, change "C57BLKS/J m+/db" to --C57BLKS/Jm$^+$/db--.

At column 72, line 20, change "C57BLKS/J+m/+m" to --C57BLKS/J$^+$m/$^+$m--.

At column 76, line 67, change "KIRA-ELISA" to --KIRA ELISA--.